United States Patent [19]
Tang et al.

[11] Patent Number: 6,147,106
[45] Date of Patent: *Nov. 14, 2000

[54] INDOLINONE COMBINATORIAL LIBRARIES AND RELATED PRODUCTS AND METHODS FOR THE TREATMENT OF DISEASE

[75] Inventors: Peng Cho Tang, Moraga; Li Sun, Foster City; Gerald McMahon, San Francisco; Klaus Peter Hirth, San Francisco; Laura Kay Shawver, San Francisco, all of Calif.

[73] Assignee: Sugen, Inc., South San Francisco, Calif.

[ * ] Notice: This patent is subject to a terminal disclaimer.

[21] Appl. No.: 08/915,366

[22] Filed: Aug. 20, 1997

[51] Int. Cl.$^7$ .................. A61K 31/404; C07D 403/06
[52] U.S. Cl. .................. 514/414; 514/235.2; 514/323; 544/143; 544/144; 546/201; 548/455; 548/460
[58] Field of Search .................. 514/235.2, 323, 514/414; 544/143, 144; 546/201; 548/455, 460

[56] References Cited

U.S. PATENT DOCUMENTS

| | | | |
|---|---|---|---|
| Re. 36,256 | 7/1999 | Spada et al. | 514/249 |
| 4,002,749 | 1/1977 | Rovnyak | 424/246 |
| 4,053,613 | 10/1997 | Rovnyak et al. | 424/246 |

FOREIGN PATENT DOCUMENTS

| | | |
|---|---|---|
| 1398224 | 3/1965 | France . |
| 99/10325 | 3/1999 | WIPO . |

OTHER PUBLICATIONS

Beilstein Reg. No.: 252929 Beilstein, 1923.

*Primary Examiner*—Laura L. Stockton

[57] ABSTRACT

The present invention relates to organic molecules capable of modulating, regulating and/or inhibiting protein kinase signal transduction. Such compounds are useful for the treatment of diseases related to unregulated protein kinase signal transduction, including cell proliferative diseases such as cancer, atherosclerosis, arthritis and restenosis and metabolic diseases such as diabetes. The present invention features indolinone compounds that potently inhibit protein kinases and related products and methods. Inhibitors specific to the FLK protein kinase can be obtained by adding chemical substituents to the 3-[(indole-3-yl)methylene]-2-indolinone, in particular at the 1' position of the indole ring. Indolinone compounds that specifically inhibit the FLK and platelet derived growth factor protein kinases can harbor a tetrahydroindole or cyclopentano-b-pyrrol moiety. Indolinone compounds that are modified with substituents, particularly at the 5 position of the oxindole ring, can effectively activate protein kinases. This invention also features novel hydrosoluble indolinone compounds that are tyrosine kinase inhibitors and related products and methods.

15 Claims, 24 Drawing Sheets

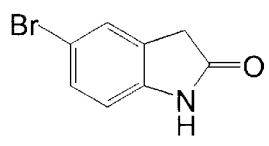
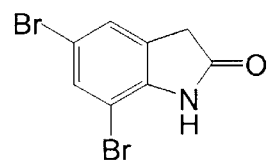
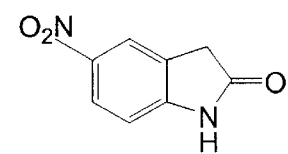
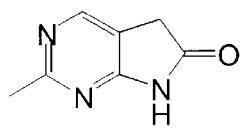
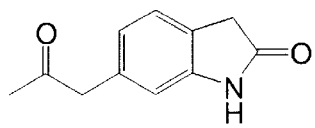
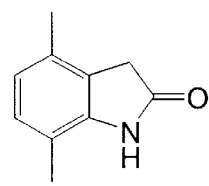
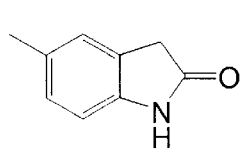
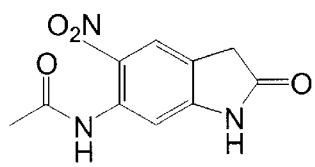
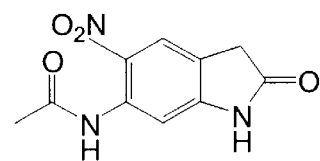
*Fig. 1  Sheet 1 of 12*

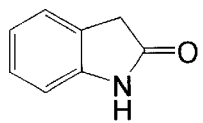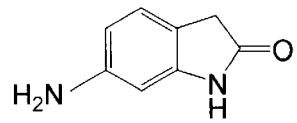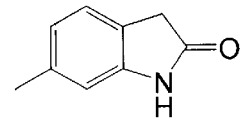
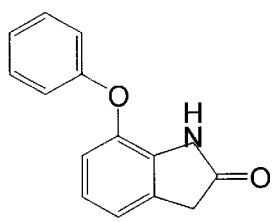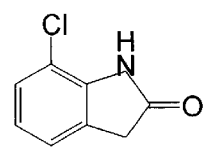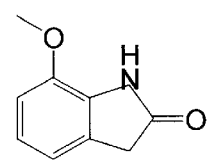
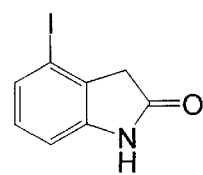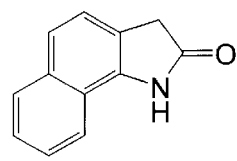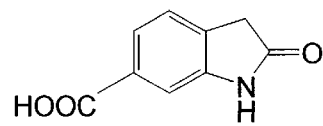
*Fig. 1  Sheet 2 of 12*

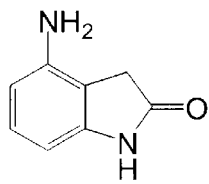 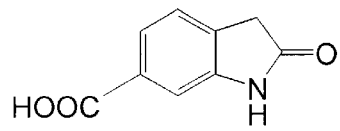 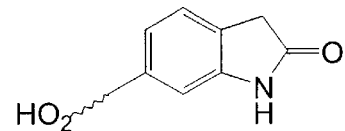
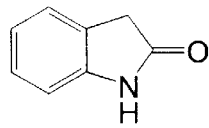 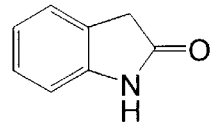 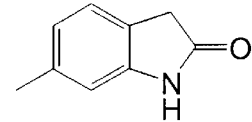
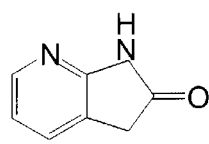 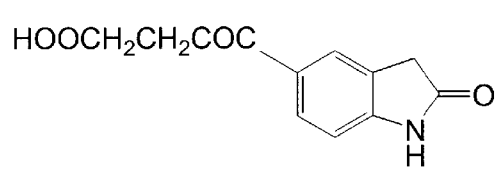 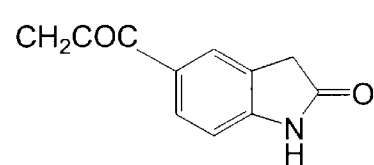
Fig. 1  Sheet 3 of 12

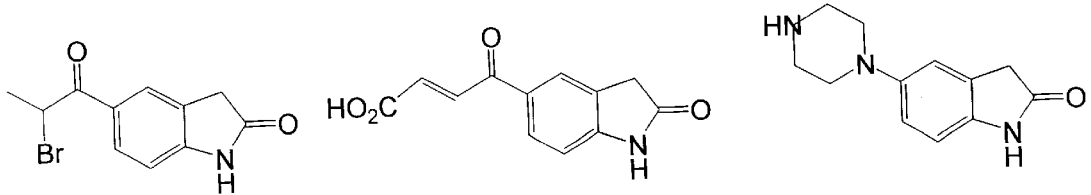
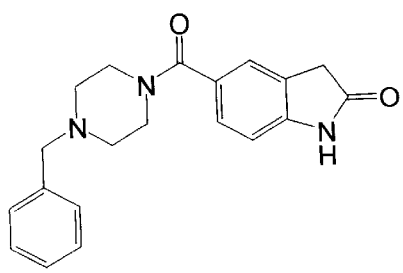
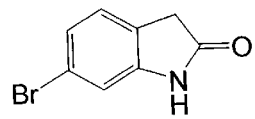
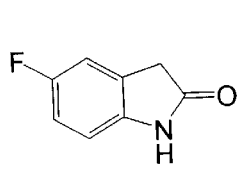
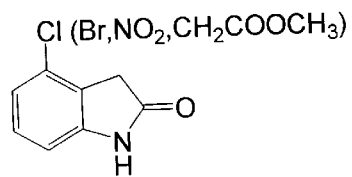
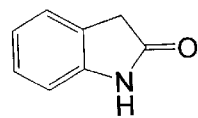
*Fig. 1  Sheet 4 of 12*

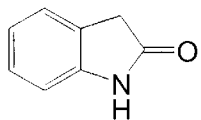 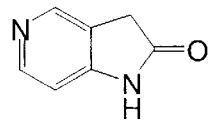 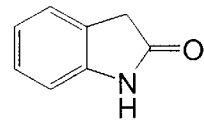
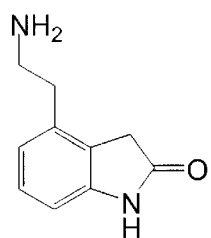 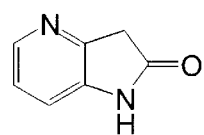 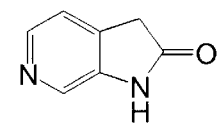
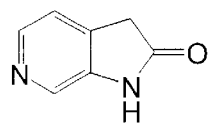 
Oxindole[4,5-b]pyrroic
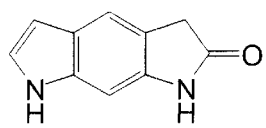 
Oxindole[6,5-b]pyrroic    Oxindole[5,4-b]pyrroic
*Fig. 1  Sheet 5 of 12*

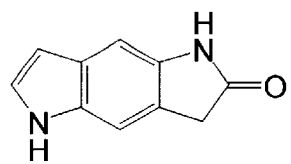
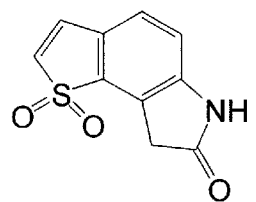
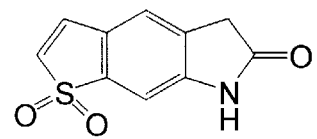
*Fig. 1  Sheet 6 of 12*

 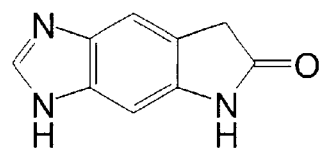
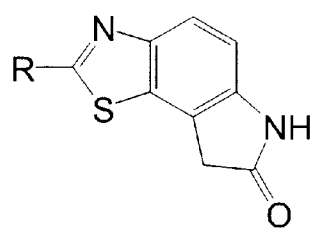 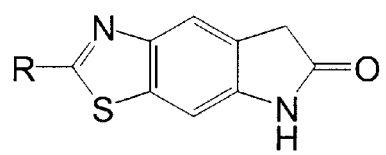
Fig. 1 Sheet 7 of 12

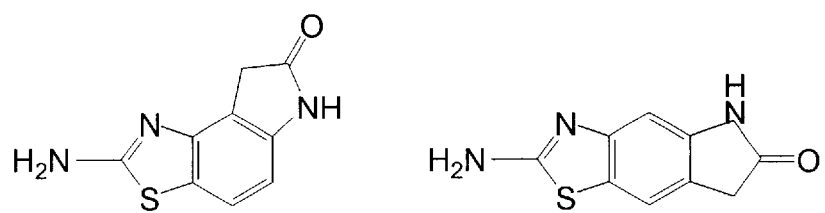
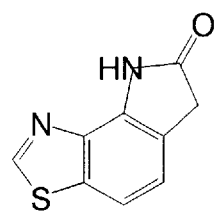
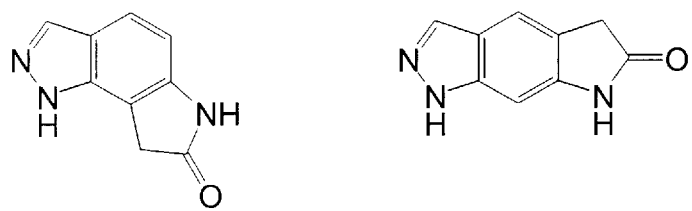
Fig. 1  Sheet 8 of 12

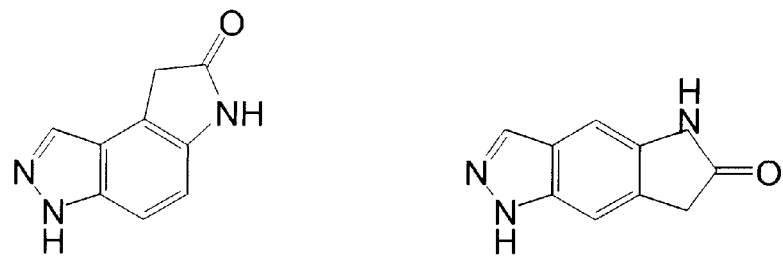
Fig. 1  Sheet 9 of 12

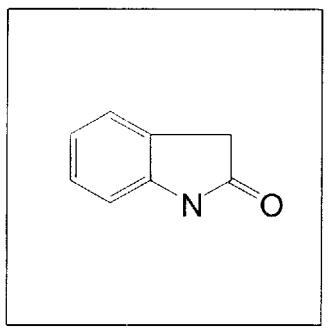
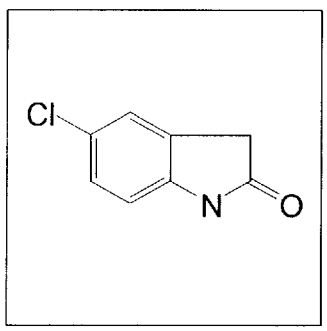
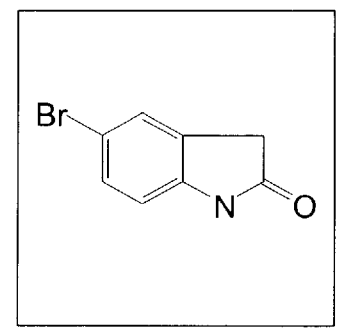
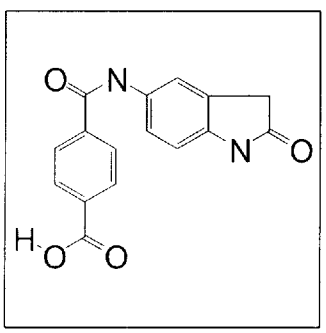
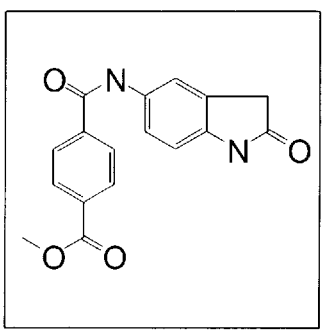
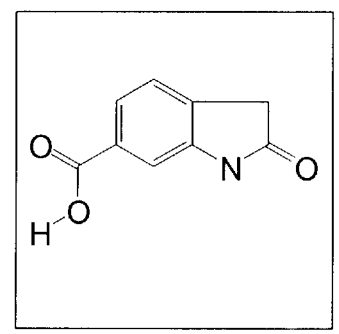
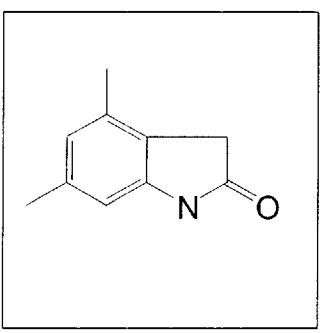
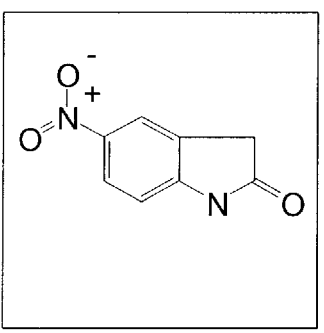
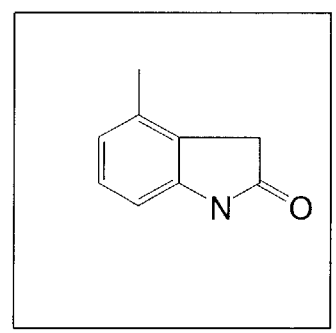
*Fig. 1  Sheet 10 of 12*

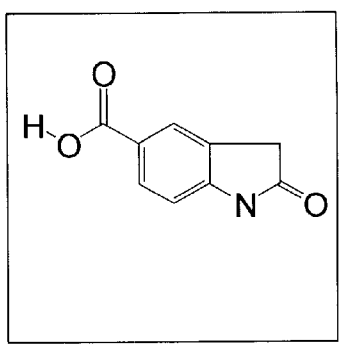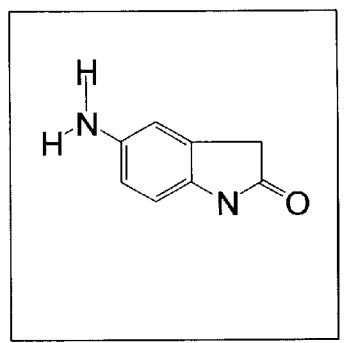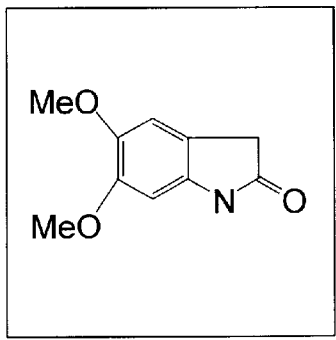
Fig. 1  Sheet 11 of 12

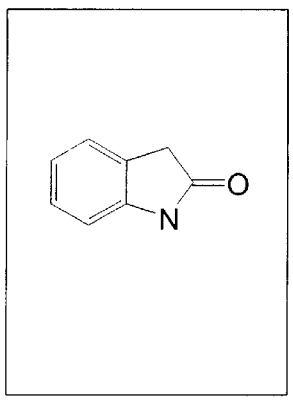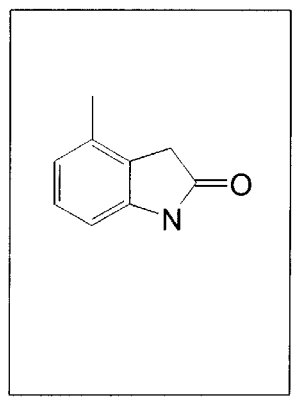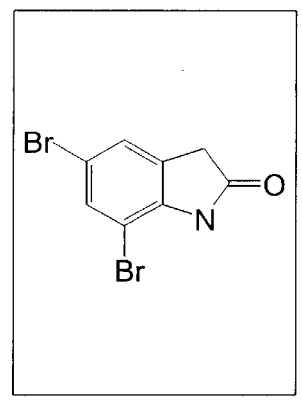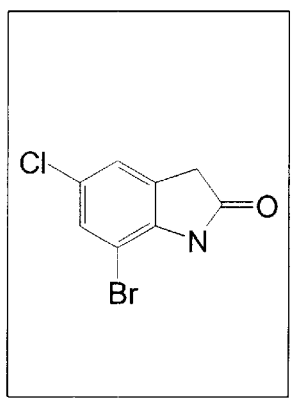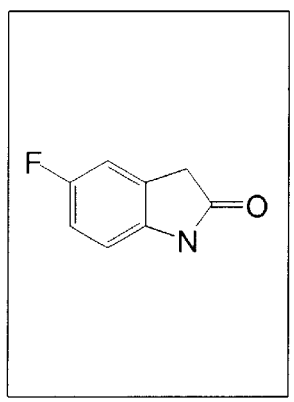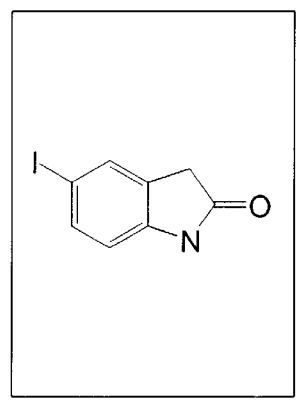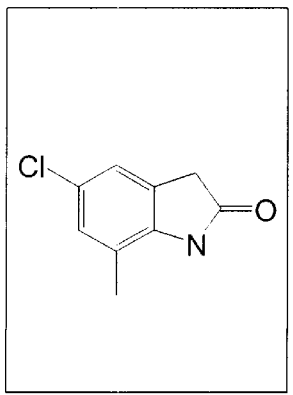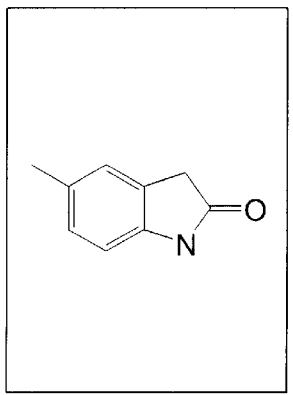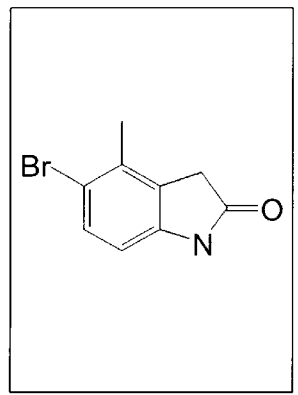
Fig. 1  Sheet 12 of 12

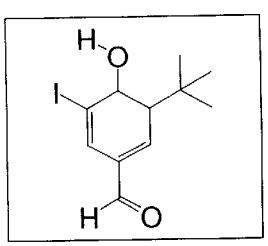 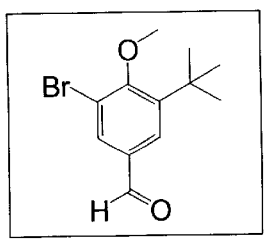 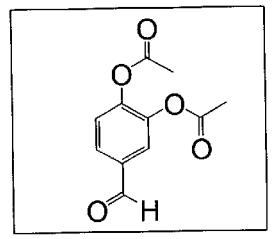 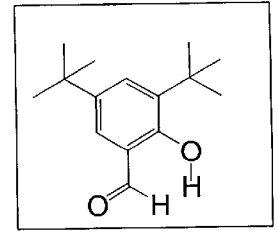
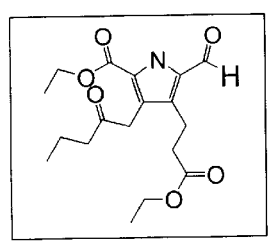 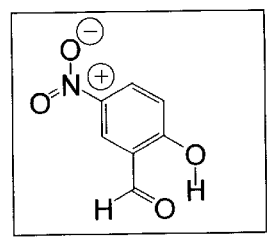 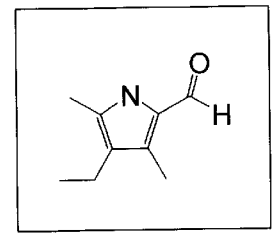 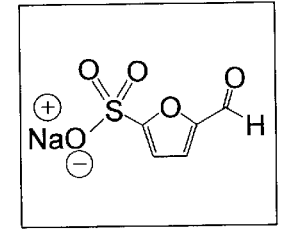
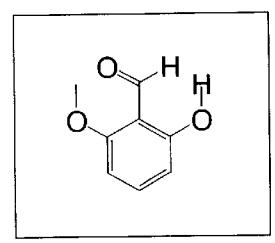 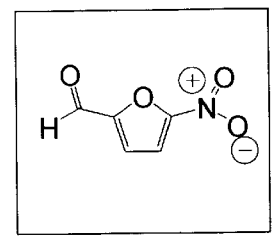 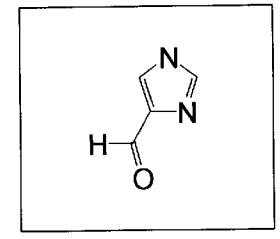 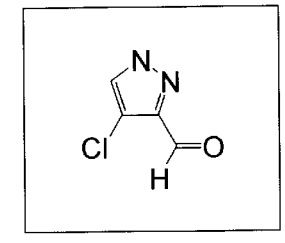
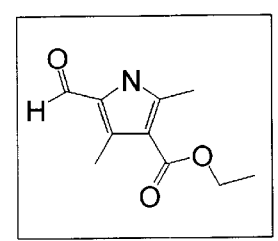 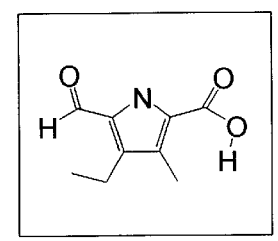 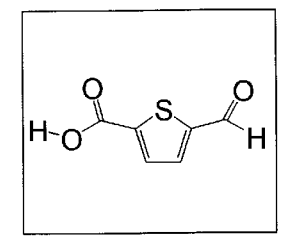 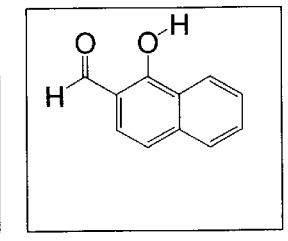
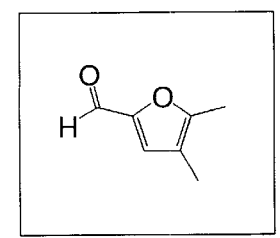 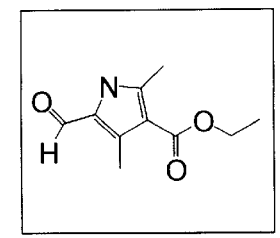 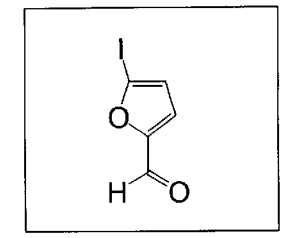 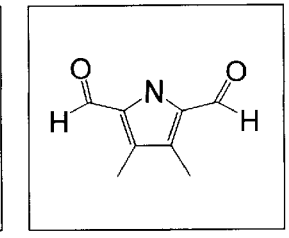
*Fig. 2 Sheet 1 of 12*

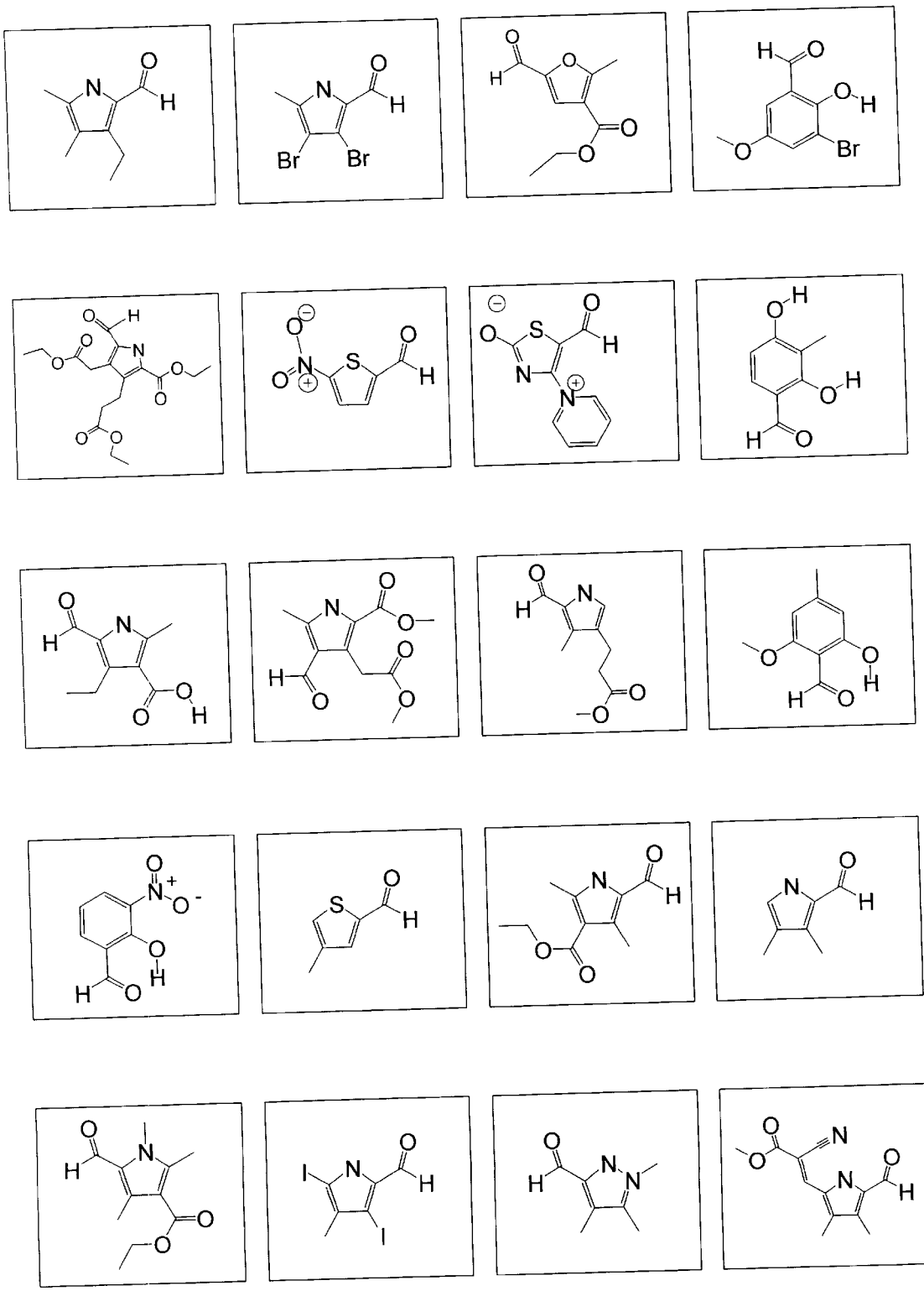
Fig. 2 Sheet 2 of 12

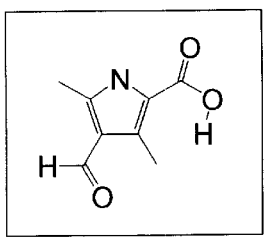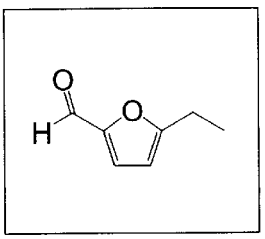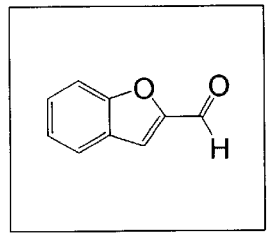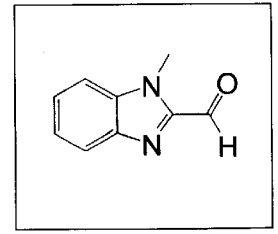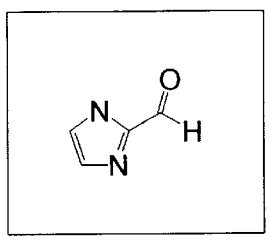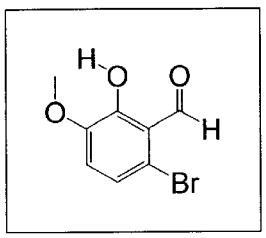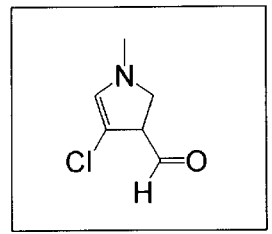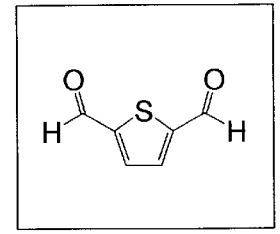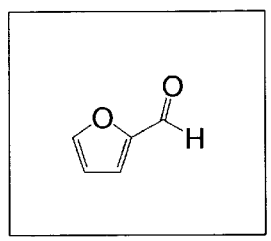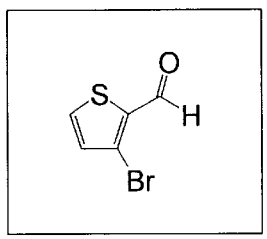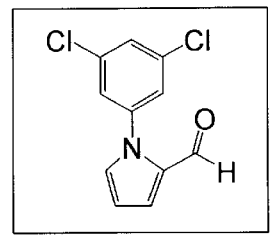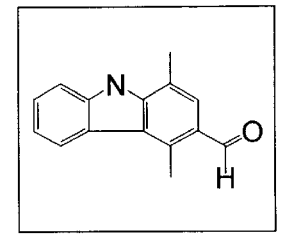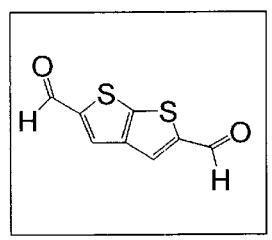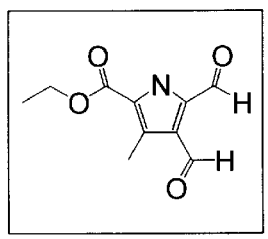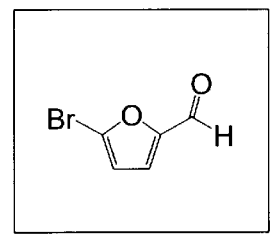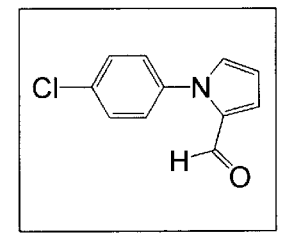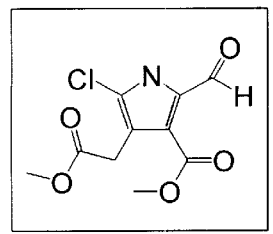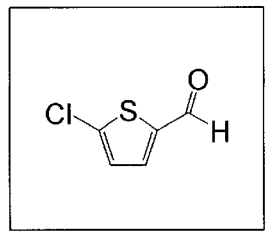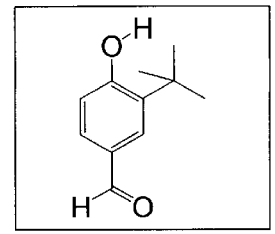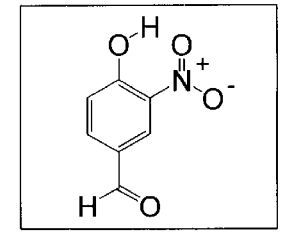
*Fig. 2  Sheet 3 of 12*

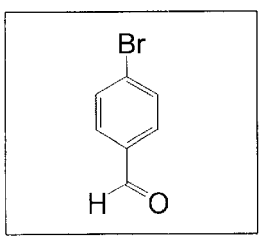
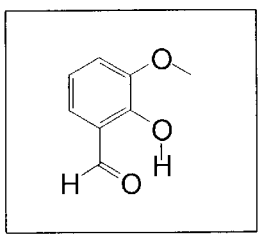
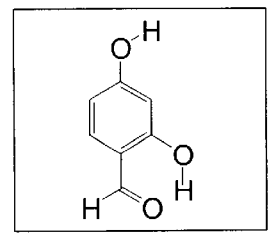
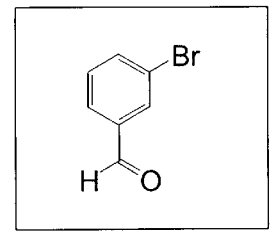
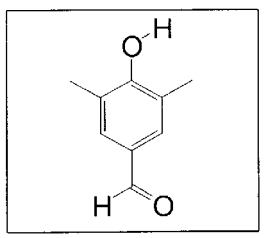
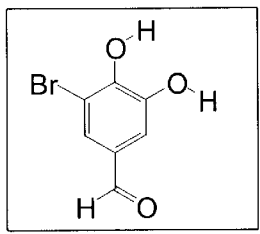
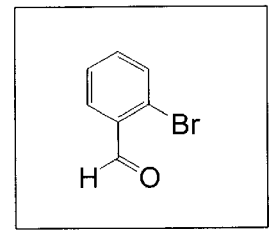
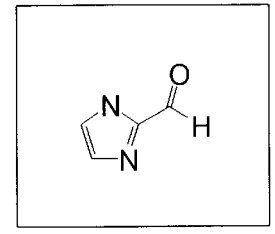
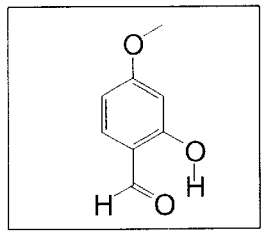
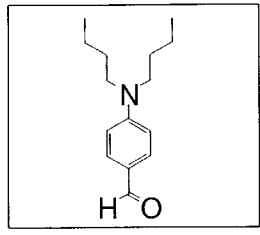
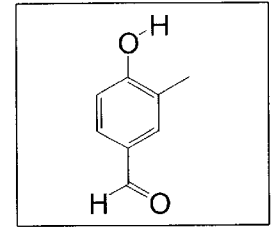
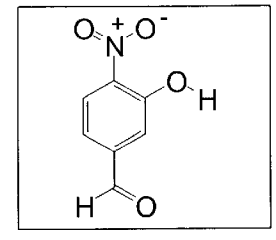
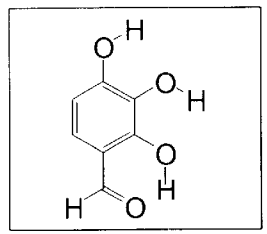
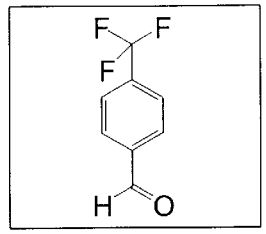
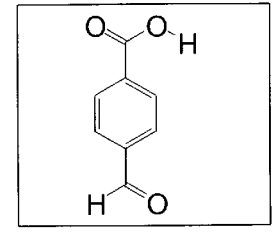
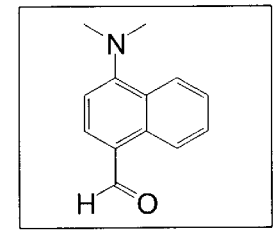
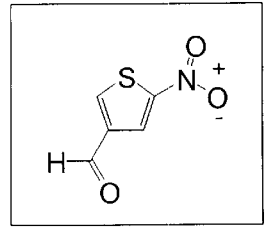
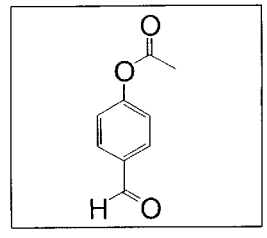
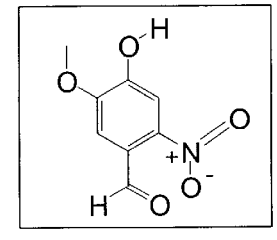
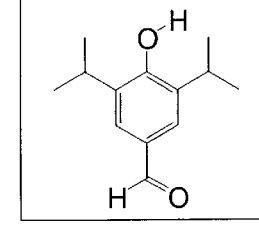
*Fig. 2  Sheet 4 of 12*

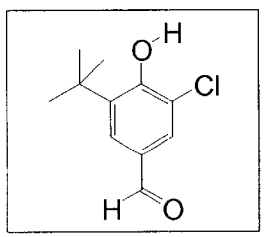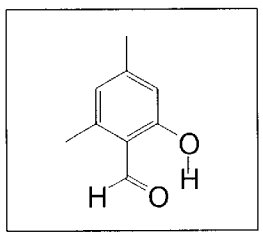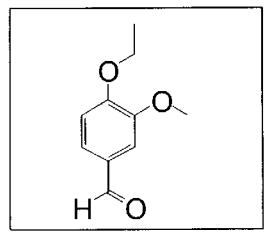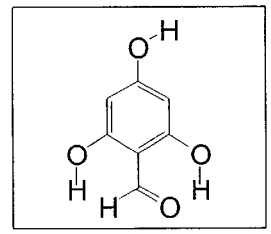
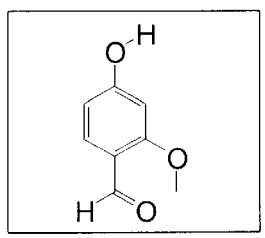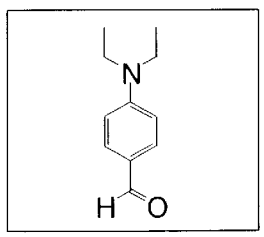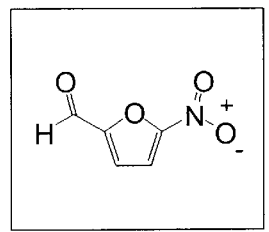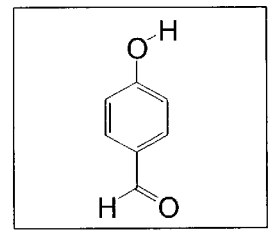
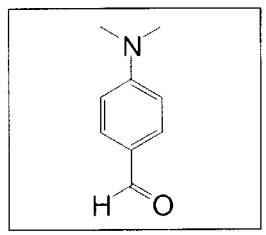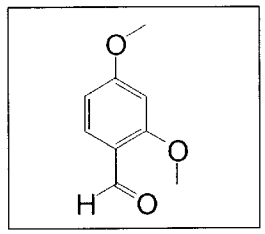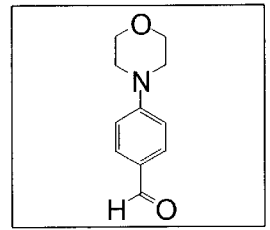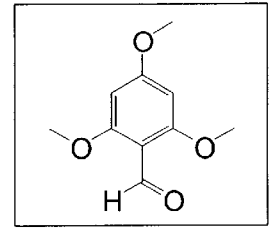
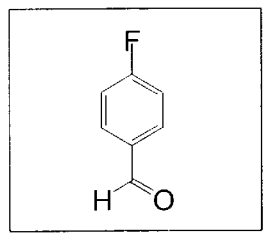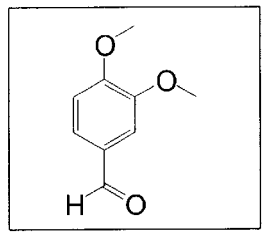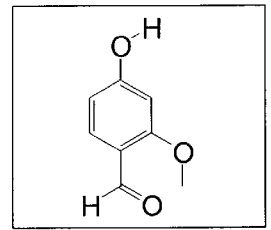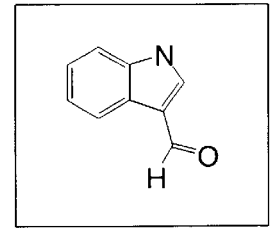
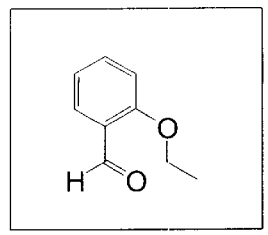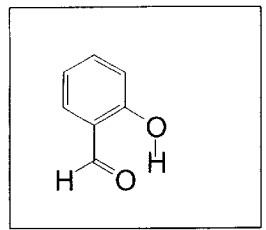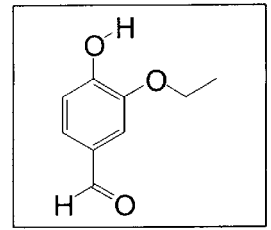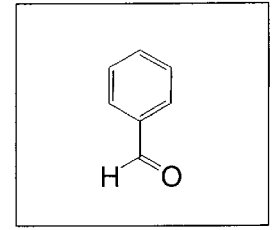
*Fig. 2  Sheet 5 of 12*

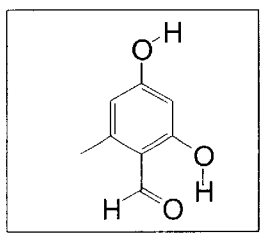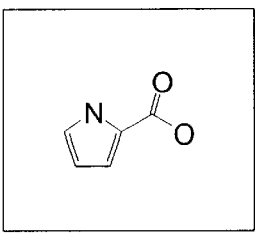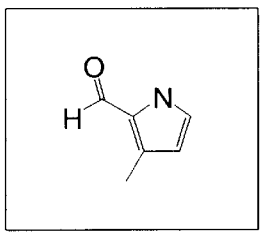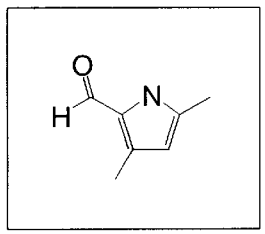
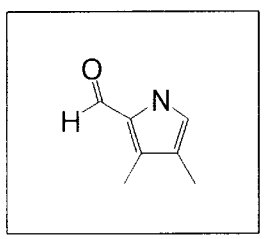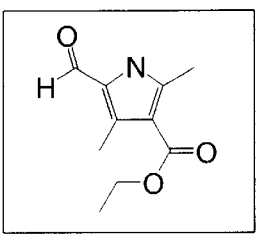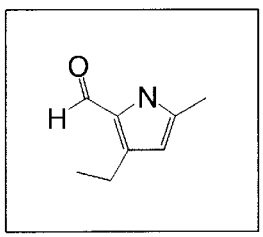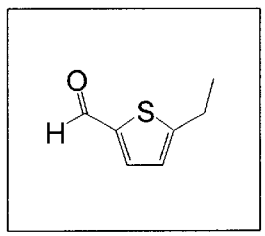
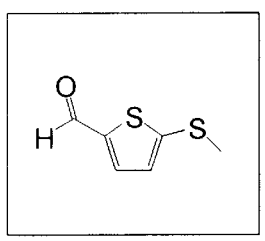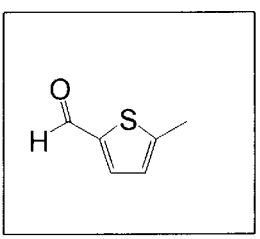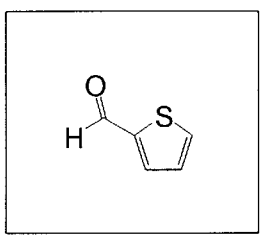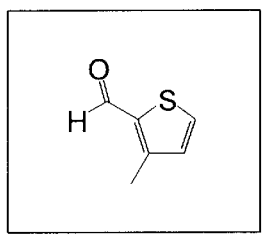
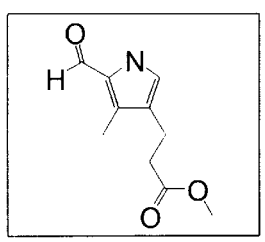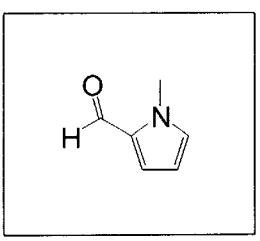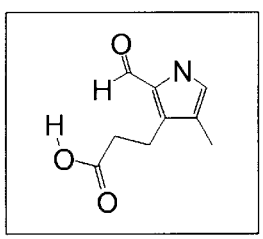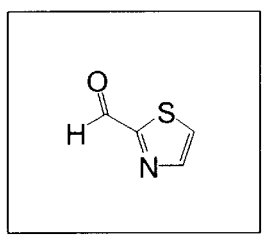
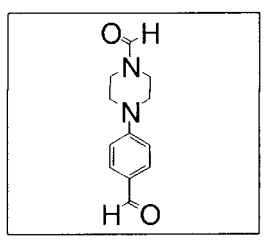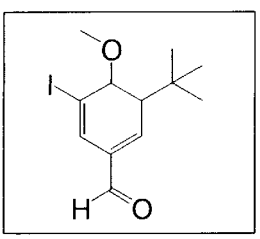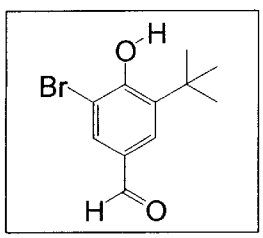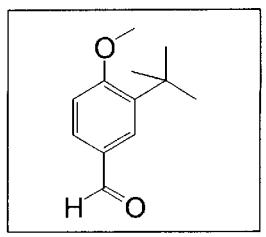
*Fig. 2  Sheet 6 of 12*

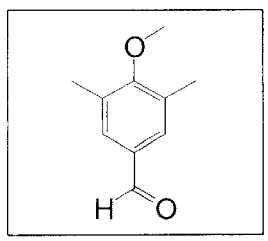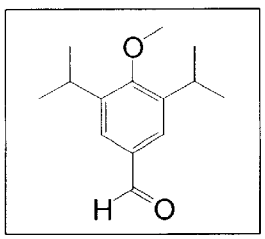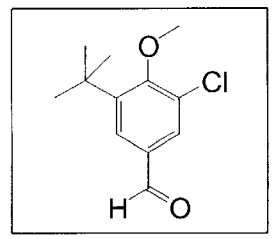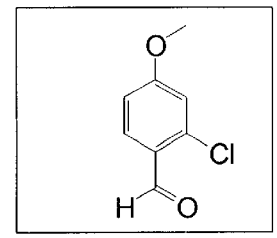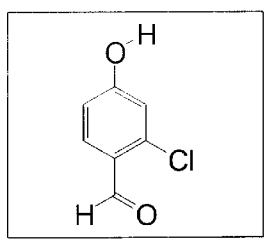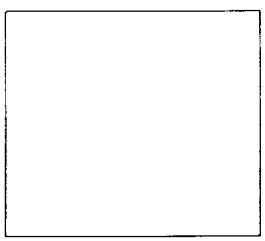
*Fig. 2 Sheet 7 of 12*

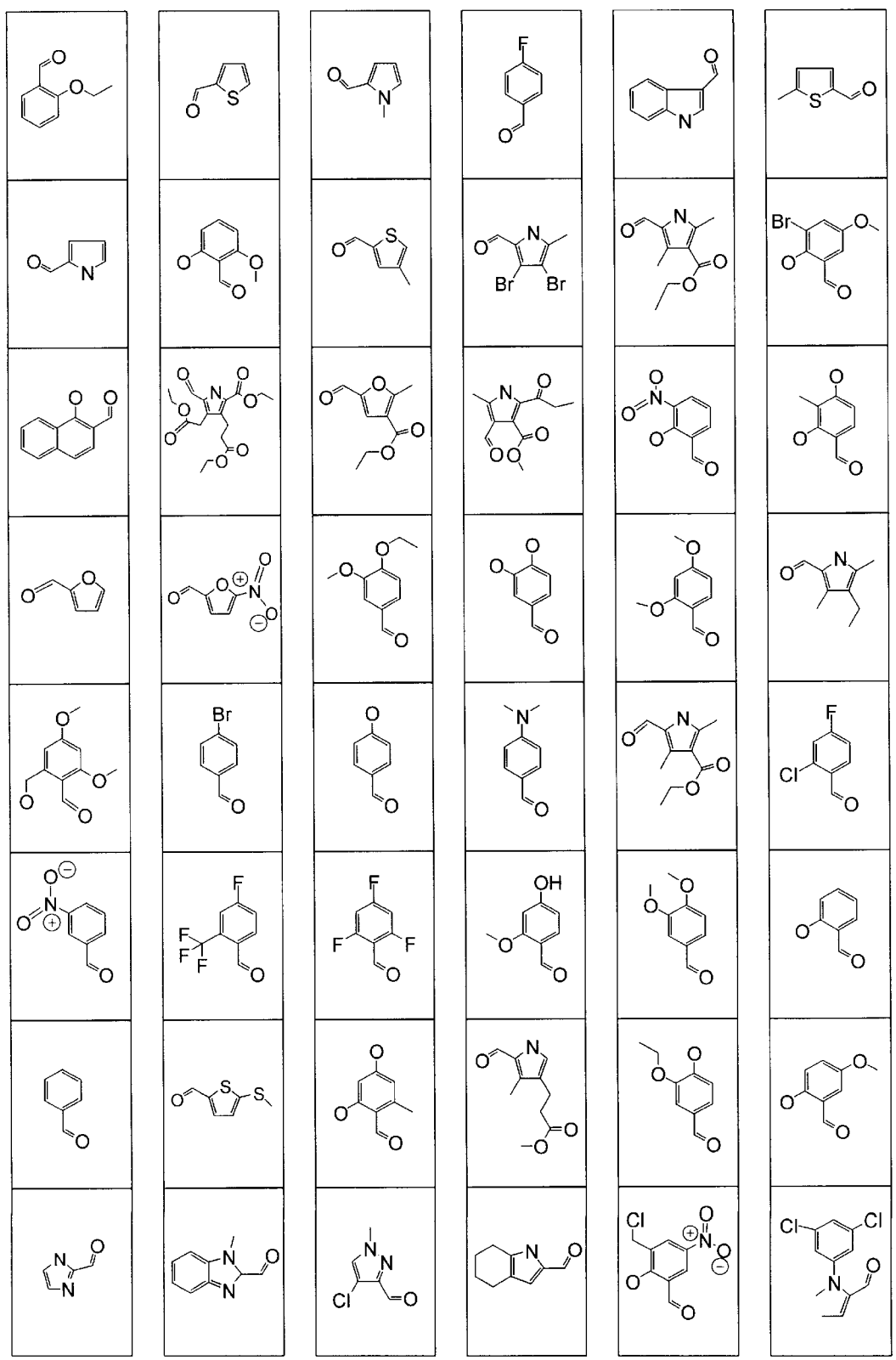
Fig. 2  Sheet 8 of 12

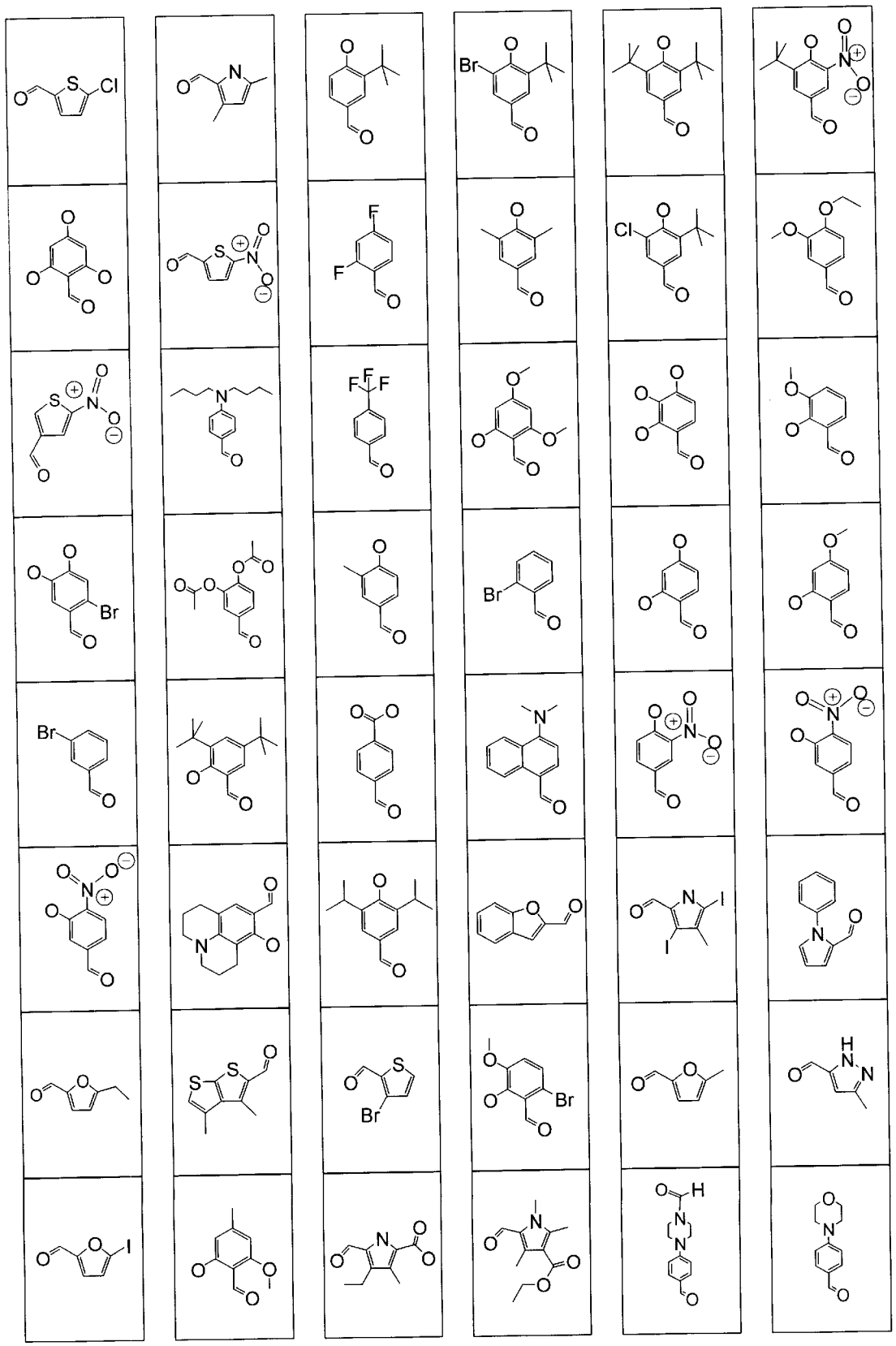
Fig. 2  Sheet 9 of 12

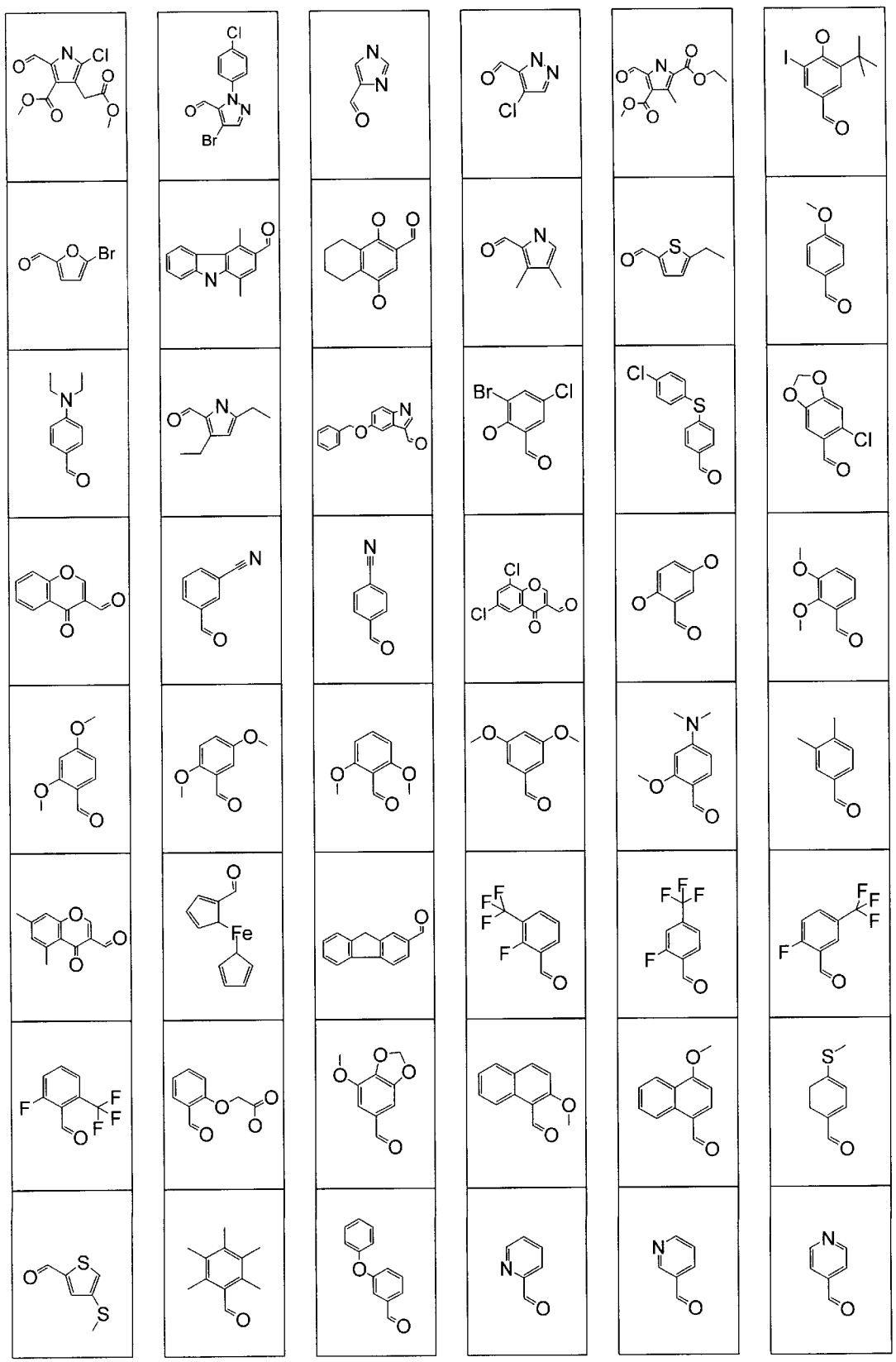
Fig. 2 Sheet 10 of 12

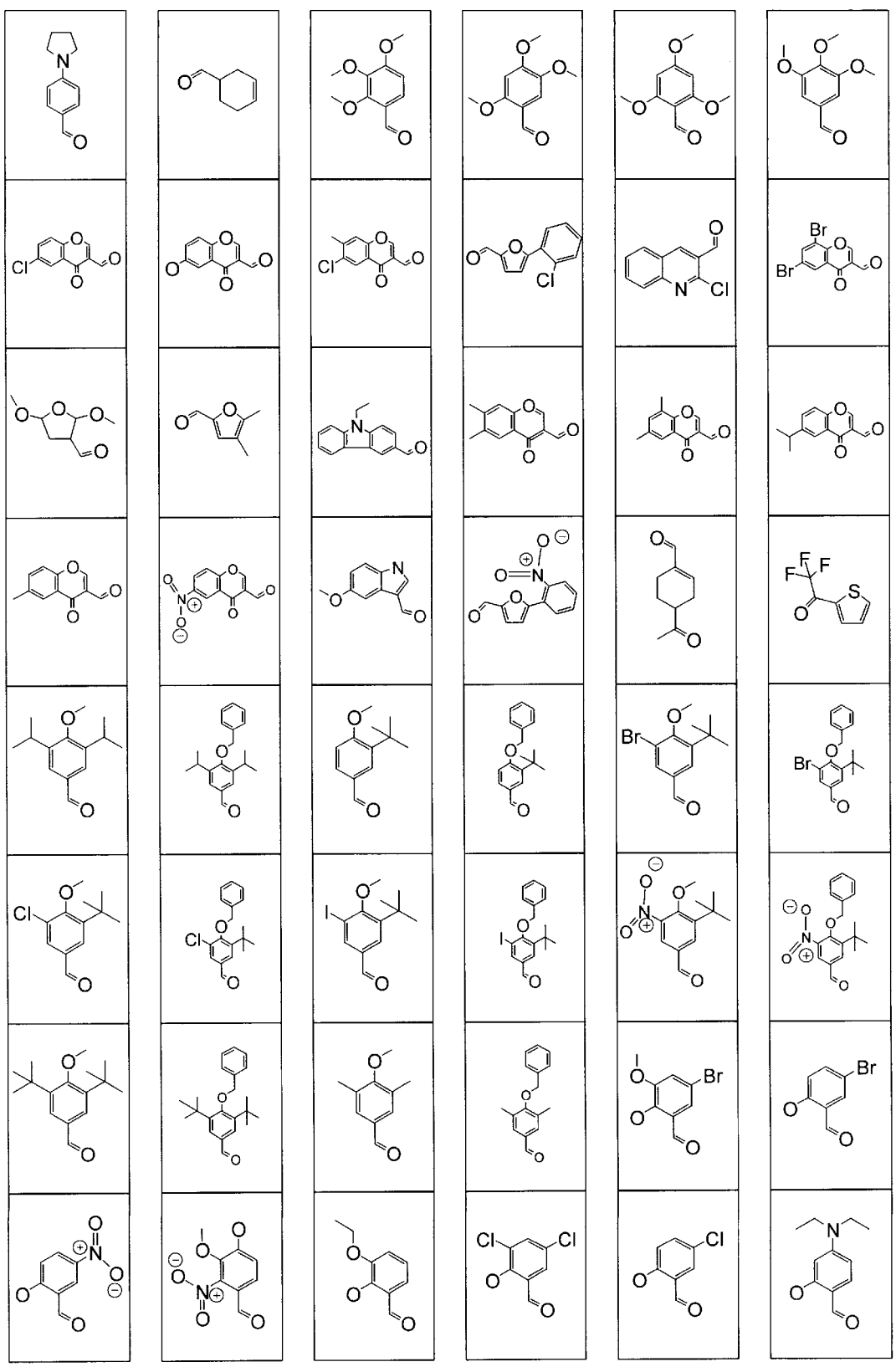
Fig. 2 Sheet 11 of 12

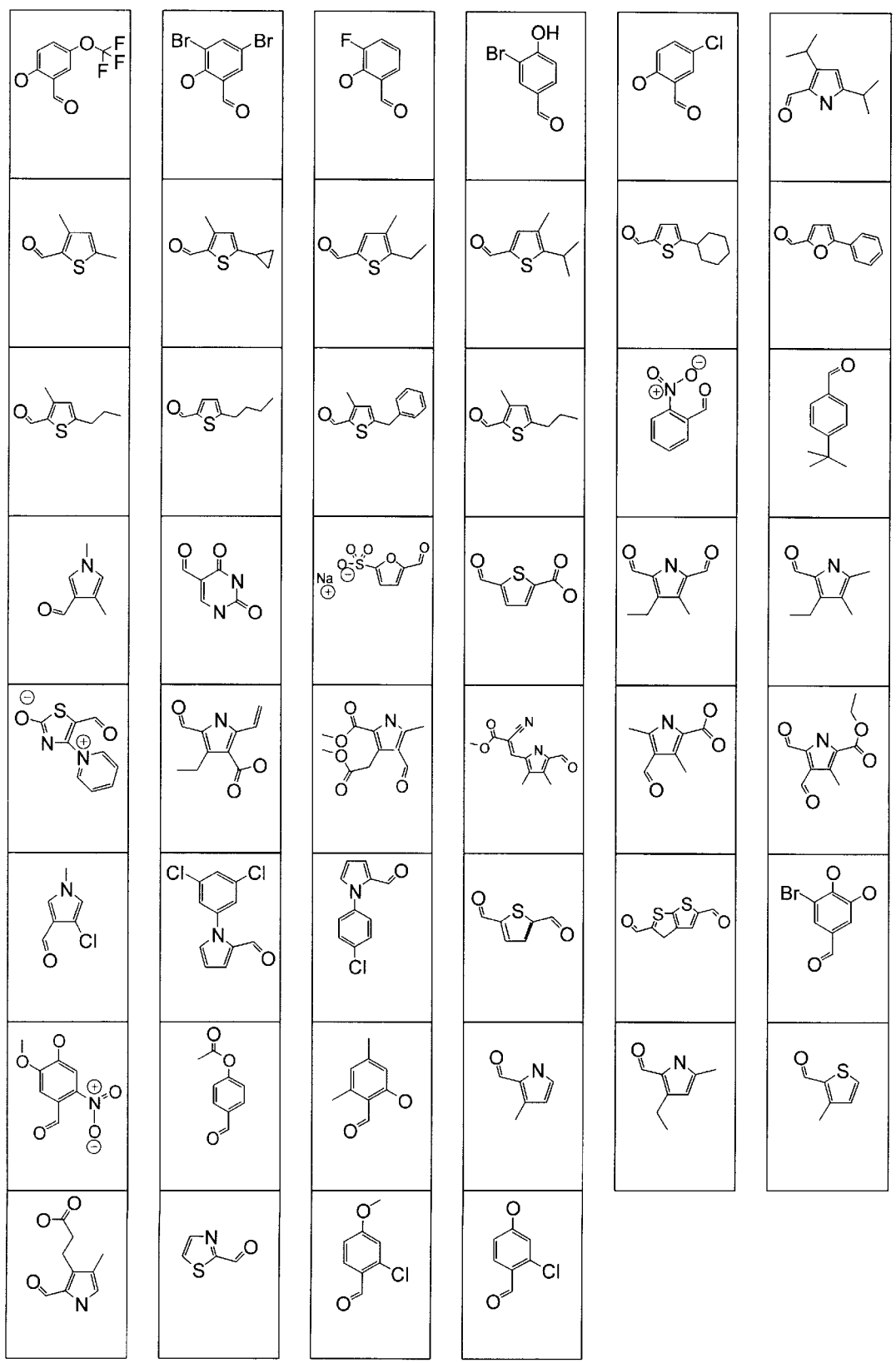

INDOLINONE COMBINATORIAL LIBRARIES AND RELATED PRODUCTS AND METHODS FOR THE TREATMENT OF DISEASE

RELATED APPLICATIONS

This application relates to U.S. patent applications Ser. No. 60/031,586, filed Dec. 5, 1996, entitled "FLK Specific Indolinone Compounds and Related Products and Methods for the Treatment of Disease" by McMahon et al.; Ser. No. 60/045,566, filed May 5, 1997, entitled "FLK Specific Indolinone Compounds and Related Products and Methods for the Treatment of Disease" by McMahon et al.; Ser. No. 60/032,546, filed Dec. 5, 1996, entitled "HYDROSOLUBLE INDOLINE TYROSINE KINASE INHIBITORS" by McMahon et al.; Ser. No. 60/045,715, filed Dec. 5, 1996, entitled "SUBSTITUTED 3-[(TETRAHYDROINDOLE-2-YL)METHYLENE]-2-INDOLINONE AND 3-[(CYCLOPENTANO-b-PYRROL-2-YL) METHYLENE]-2-INDOLINONE COMPOUNDS" by McMahon et al.; Ser. No. 60/031,588, filed Dec. 5, 1996, entitled "5-SUBSTITUTED INDOLINONE COMPOUNDS AS MODULATORS OF PROTEIN KINASE ACTIVITY" by McMahon et al.; Ser. No. 60/045,714, filed May 5, 1997, entitled "5-SUBSTITUTED INDOLINONE COMPOUNDS AS MODULATORS OF PROTEIN KINASE ACTIVITY" by McMahon et al.; Ser. No. 60/032, 547, filed Dec. 5, 1996, entitled "SUBSTITUTED 3-[(TETRAHYDROINDOLE-2-YL)METHYLENE]-2-INDOLINONE AND 3-[(CYCLOPENTANO-b-PYRROL-2-YL) METHYLENE]-2-INDOLINONE COMPOUNDS" by McMahon et al.; Ser. No. 60/046,843, filed May 5, 1997, entitled "HYDROSOLUBLE INDOLINE TYROSINE KINASE INHIBITORS" by McMahon et al.; Ser. No. 60/031,585, filed Dec. 5, 1996, entitled "SUBSTITUTED 3-[(INDOLE-3-YL)METHYLENE]-2-INDOLINONE COMPOUNDS" by McMahon et al.; Ser. No. 60/031,565, filed May 5, 1997, entitled "SUBSTITUTED 3-[(INDOLE-3-YL)METHYLENE]-2-INDOLINONE COMPOUNDS" by McMahon et al. and this application also relates to U.S. patent application Ser. No. 08/702,232, filed Aug. 23, 1996, entitled "Indolinone Combinatorial Libraries and Related Products and Methods for the Treatment of Disease" by Tang et al. which is a continuation-in-part application of U.S. patent applications Ser. No. 08/655,225, filed Jun. 5, 1996, now U.S. Pat. No. 5,834,504, entitled "3-(2'Halobenzylidenyl)-2-Indoline Compounds for the Treatment of Disease" by Tang et al.; Ser. No. 08/655,226, filed Jun. 5, 1996, now U.S. Pat. No. 5,886,020, entitled "3-(4'-Dimethylaminobenzylidenyl)-2-Indolinone and Analogues Thereof for the Treatment of Disease" by Tang et al.; Ser. No. 08/655,223, filed Jun. 5, 1996, now U.S. Pat. No. 5,792,783, entitled "3-Heteroaryl-2-Indolinone Compounds for the Treatment of Disease" by Tang et al.; Ser. No. 08/655,224, filed Jun. 5, 1996, now U.S. Pat. No. 5,883,116, entitled "3-(2'-Alkoxybenzylidenyl)-2-Indolinone and Analogues Thereof for the Treatment of Disease" by Tang et al.; and, Ser. No. 08/659,191, filed Jun. 5, 1996, now U.S. Pat. No. 5,883,113, entitled "3-(4'Bromobenzylindenyl)-2-Indolinone and Analogues Thereof for the Treatment of Disease" by Tang et al., all of which are continuations-in-part of U.S. patent application Ser. No. 08/485,323, filed Jun. 7, 1995, now U.S. Pat. No. 5,880,141 entitled "Benzylidene-Z-Indoline Compounds for the Treatment of Disease" by Tang et al. all of which are incorporated herein by reference in their entirety, including any drawings.

INTRODUCTION

The present invention relates to novel compounds capable of modulating, regulating and/or inhibiting protein kinase signal transduction. The present invention is also directed to methods of regulating, modulating or inhibiting protein kinases, whether of the receptor or non-receptor class, for the prevention and/or treatment of disorders related to unregulated protein kinase signal transduction, including cell proliferative and metabolic disorders.

BACKGROUND OF THE INVENTION

The following description of the background of the invention is provided to aid in understanding the invention, but is not admitted to be or describe prior art to the invention.

Protein kinases and protein phosphatases regulate a wide variety of cellular processes including metabolism, cell proliferation, cell differentiation, and cell survival by participating in signal transduction pathways. Alterations in the cellular function of a protein kinase or protein phosphatase can give rise to various diseased states in an organism. For example, many types of cancer tumors are associated with increases in the activity of specific protein kinases. Cell and tissue degeneration can also be associated with decreases in the activity of particular protein kinases.

Cellular signal transduction is a fundamental mechanism whereby extracellular stimuli are relayed to the interior of cells. One of the key biochemical mechanisms of signal transduction involves the reversible phosphorylation of proteins. Phosphorylation of amino acids regulates the activity of mature proteins by altering their structure and function.

Phosphate most often resides on the hydroxyl moiety of serine, threonine, or tyrosine amino acids in proteins. Enzymes that mediate phosphorylation of cellular effectors fall into two classes. While protein phosphatases hydrolyze phosphate moieties from phosphoryl protein substrates, protein kinases transfer a phosphate moiety from adenosine triphosphate to protein substrates. The converse functions of protein kinases and protein phosphatases balance and regulate the flow of signals in signal transduction processes.

Protein kinases are divided into two groups—receptor and non-receptor type proteins. Receptor protein kinases comprise an extracellular region, a transmembrane region, and an intracellular region. Part of the intracellular region of receptor protein kinases harbors a catalytic domain. While non-receptor protein kinases do not harbor extracellular or transmembrane regions, they do comprise a region similar to the intracellular regions of their receptor counterparts.

Protein kinases are divided further into three classes based upon the amino acids they act upon. Some incorporate phosphate on serine or threonine only, some incorporate phosphate on tyrosine only, and some incorporate phosphate on serine, threonine, and tyrosine.

In an effort to discover novel treatments for diseases, biomedical researchers and chemists have designed, synthesized, and tested molecules that inhibit the function of protein kinases. Some small organic molecules form a class of compounds that modulate the function of protein kinases.

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules that potently inhibit only specific protein kinases. Indolinone synthesis, methods of testing the biological activity of indolinones, and inhibition patterns of some indolinone derivatives are described in International Patent Publication No. WO96/40116, published Dec. 19, 1996 entitled "Benzylidene-Z-Indolinone Compounds for the Treatment of Disease" by Tang et al. (Lyon & Lyon Docket No. 223/298) and International Patent Publication No. WO 96/22976, published Aug. 1, 1996 by Ballinari et al., both of which are incorporated herein by reference in their entirety, including any drawings.

Despite the significant progress that has been made in developing indolinone based pharmaceuticals, there remains a need in the art to identify the particular structures and substitution patterns that cause inhibition of particular protein kinases and other specified biological activities.

SUMMARY OF THE INVENTION

The present invention relates to organic molecules capable of modulating, regulating and/or inhibiting protein kinase signal transduction. Such compounds are useful for the treatment of diseases related to unregulated protein kinase signal transduction, including cell proliferative diseases such as cancer, atherosclerosis, arthritis and restenosis and metabolic diseases such as diabetes. The protein kinases effected include, but are not limited to Flk, FGFR, PDGFR, and raf.

The present invention features indolinone compounds that potently inhibit protein kinases and related products and methods. Inhibitors specific to the FLK protein kinase can be obtained by adding chemical substituents to the 3-[(indole-3-yl)methylene]-2-indolinone, in particular at the 1' position of the indole ring. Indolinone compounds that specifically inhibit the FLK and platelet derived growth factor protein kinases can harbor a tetrahydroindole or cyclopentano-b-pyrrol moiety. Indolinone compounds that are modified with substituents, particularly at the 5 position of the oxindole ring, can effectively activate protein kinases. This invention also features novel hydrosoluble indolinone compounds that are tyrosine kinase inhibitors and related products and methods.

The compounds of the invention represent a new generation of potential therapeutics for diseases caused by one or more non-functional protein kinases. Neuro-degenerative diseases fall into this class of diseases, including, but not limited to Parkinson's Disease and Alzheimers disease. The compounds can be modified such that they are specific to their target or targets and will subsequently cause few side effects and thus represent a new generation of potential cancer therapeutics. These properties are significant improvements over the currently utilized cancer therapeutics that cause multiple side effects and deleteriously weaken patients.

It is believed the compounds of the invention will minimize and obliterate solid tumors by specifically inhibiting the activity of the FLK protein kinase, or will at least modulate or inhibit tumor growth and/or metastases. The FLK protein kinase regulates proliferation of blood vessels during angiogenesis. Increased rates of angiogenesis accompany cancer tumor growth in cells as cancer tumors must be nourished by oxygenated blood during growth. Therefore, inhibition of the FLK protein kinase and the corresponding decreases in angiogenesis will starve tumors of nutrients and most likely obliterate them.

While a precise understanding of the mechanism by which compounds inhibit PTKs (e.g., the fibroblast growth factor receptor 1 [FGFR1]) is not required in order to practice the present invention, the compounds are believed to interact with the amino acids of the PTKs' catalytic region. PTKs typically possess a bi-lobate structure, and ATP appears to bind in the cleft between the two lobes in a region where the amino acids are conserved among PTKs; inhibitors of PTKs are believed to bind to the PTKs through non-covalent interactions such as hydrogen bonding, Van der Waals interactions, and ionic bonding, in the same general region that ATP binds to the PTKs. More specifically, it is thought that the oxindole component of the compounds of the present invention binds in the same general space occupied by the adenine ring of ATP. Specificity of an indolinone PTK inhibitor for a particular PTK may be conferred by interactions between the constituents around the oxindole core with amino acid domains specific to individual PTKs. Thus, different indolinone substitutents may contribute to preferential binding to particular PTKs. The ability to select those compounds active at different ATP (or other nucleotide) binding sites makes them useful in targeting any protein with such a site, not only protein tyrosine kinases, but also serine/threonine kinases and protein phosphatases. Thus, such compounds have utility for in vitro assays on such proteins and for in vivo therapeutic effect through such proteins. In one aspect the invention features a combinatorial library of indolinone compounds. The library includes a series of at least ten (preferably at least 50–100, more preferably at least 100–500, and most preferably at least 500–5,000) indolinones that can be formed by reacting an oxindole compound with an aldehyde. In preferred embodiments the indolinones in the library can be formed by reacting a type A oxindole with a type B aldehyde. Type A oxindoles and type B aldehydes are shown in FIGS. 1 and 2 respectively (and Tables 11 and 12 respectively), as explained in detail below. As can be seen, in the figures the oxindoles are labeled 01, 02, 03, . . . and the aldehydes are named A1, A2, A3, . . . . Thus, one can readily appreciate that the combinatorial library could include any and all combinations of oxindoles and aldehydes, including the indolinones resulting from 01 and A1, 01 and A2, 01 and A3, 02 and A1, 02 and A2, 02 and A3, 03 and A1, 03 and A2, 03 and A3 and so on. Similarly, the indolinones in the library can be formed by any combination of the oxindoles in Table 11 with any of the aldehydes listed in FIG. 2 or Table 12. Finally, the indolinones may also, of course, come from any combination of aldehydes listed in Table 12 with any oxindoles from FIG. 1 or Table 11.

The term "combinatorial library" refers to a series of compounds. In the present case, the combinatorial library contains a series of indolinone compounds that can be formed by reacting an oxindole and an aldehyde. A wide variety of oxindoles and aldehydes may be used to create the library of indolinones.

The term "indolinone" is used as that term is commonly understood in the art and includes a large subclass of substituted or unsubstituted compounds that are capable of being synthesized from an aldehyde moiety and an oxindol moiety, such as the compounds shown below.

The term "type A oxindole" is meant to include any and all of the oxindoles set forth in FIG. 1 and Table 11. Oxindoles, as that term is used herein, typically have the structure set forth below:

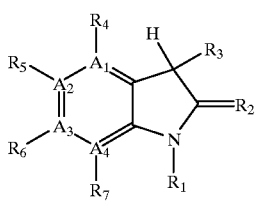

(I)

wherein, (a) $A_1$, $A_2$, $A_3$, and $A_4$ are independently carbon or nitrogen;

(b) $R_1$ is hydrogen or alkyl;

(c) $R_2$ is oxygen or sulfur;

(d) $R_3$ is hydrogen;

(e) $R_4$, $R_5$, $R_6$, and $R_7$ (i) are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' or (ii) any two adjacent $R_4$, $R_5$, $R_6$, and $R_7$ taken together form a fused ring with the aryl portion of the oxindole-based portion of the indolinone.

It is to be understood that when $A_1$, $A_2$, $A_3$, and $A_4$ is nitrogen or sulfur that the corresponding $R_4$, $R_5$, $R_6$, or $R_7$ is nothing and that the corresponding bond shown in structure I does not exist.

Examples of oxindoles having such fused rings (as described in (e) (ii) above) are shown in FIG. 1, compounds 044, 045, 047, 048, 050, 051, 052, 053, 055, 056, 058, 059, 061, 062, 064, 066, 067, 069, 070, and 073. Other examples of suitable fused rings include the following:

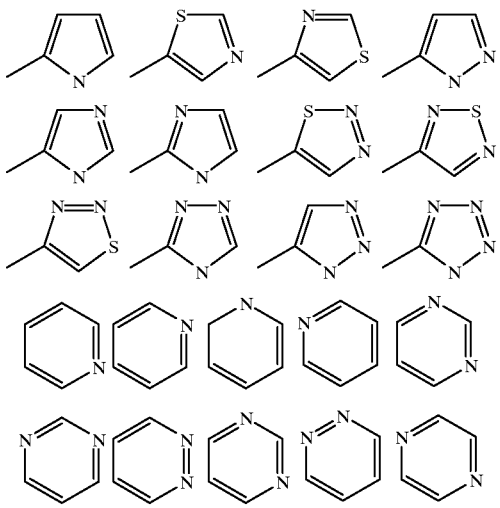

The six membered rings shown above also exemplify possible A rings in the structures II, III and IV.

The term "type B aldehyde" includes any and all of the aldehydes set forth in FIG. 2 and Table 11. The term "aldehyde" is used as is commonly understood in the art to include substituted and unsubstituted aldehydes of the structure $R_dCHO$ where $R_d$ can be a wide variety of substituted or unsubstituted groups such as alkyl and aryl.

In yet another aspect, the invention provides a method of synthesizing an indolinone by reacting a type A oxindole with a type B aldehyde. The method of making the indolinones of the present invention may involve creating a combinatorial library of compounds as described above, testing each compound in biological assays such as those described herein, selecting one or more suitable compounds and synthesizing the selected compound or compounds.

Also featured is an indolinone compound having formula II or III:

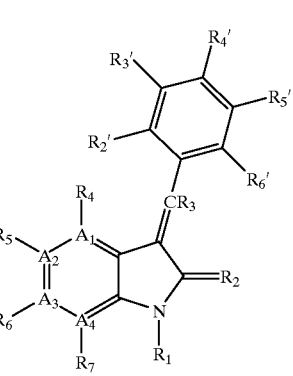

(II)

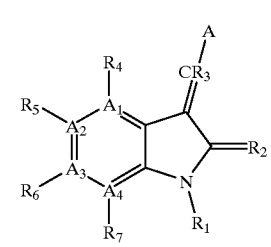

(III)

wherein:

(a) $A_1$, $A_2$, $A_3$, and $A_4$ are independently carbon or nitrogen;

(b) $R_1$ is hydrogen or alkyl;

(c) $R_2$ is oxygen or sulfur;

(d) $R_3$ is hydrogen;

(e) $R_4$, $R_5$, $R_6$, and $R_7$ (i) are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' or (ii) any two adjacent $R_4$, $R_5$, $R_6$, and $R_7$ taken together form a fused ring with the aryl ring of the oxindole-based portion of the indolinone;

(f) $R_2'$, $R_3'$, $R_4'$, $R_5'$, and $R_6'$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

(g) n is 0, 1, 2, or 3;

(h) R is hydrogen, alkyl or aryl;

(i) R' is hydrogen, alkyl or aryl; and (j) A is a five membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, optionally substituted at one or more positions with alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ or CONRR'.

As used herein, the term "compound" is intended to include pharmaceutically acceptable salts, esters, amides, prodrugs, isomers and metabolites of the base compound.

In preferred embodiments of structure III, the A substituent may be a five membered heterocycle of formula IV shown below:

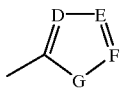

(IV)

wherein D, E, F, and G are nitrogen, carbon, or sulfur atoms. The specific juxtaposition of groups D–G is limited to examples of heterocyclic groups known in the chemistry arts, such as the fused rings referred to above and all of which may be optionally substituted as described above in paragraph (j).

In preferred embodiments, the aryl ring ("the A ring") of the oxindole-derived portion of the indolinone (i.e., the ring shown in structures II and III with $A_1$, $A_2$, $A_3$, and $A_4$) has a polar substituent, preferably selected from the group consisting of $NH_2$, COOH, $SO_3H$, Br, Cl, I, F, $COCH_2CH_2COOH$, $COCH_2Cl$, piperazine, and $CH_2CH_2NH_2$ at the 4, 5, 6, and 7 carbon atom positions (identified by substituents $R_4$, $R_5$, $R_6$, and $R_7$ respectively in structures V and VI), most preferably hydrophillic groups such as $NH_2$, COOH, $SO_3$, $COCH_2CH_2COOH$, piperazine and $CH_2CH_2NH_2$.

One approach to choosing target inhibitors of the FGFR (a protein kinase receptor linked to various disorders, such as Pfeiffer, Jackson-Weiss and Cruzon syndromes; dysplasias and hypochondroplasia; dwarfism; bone dysplasia; and developmental disorders involves selecting target compounds with a substituent on the A ring that mimics the triphosphate of ATP and thereby increases the affinity of target compounds for the active-site of the FGFR. Hydrophillic groups may act to mimic the triphosphate at ATP, and also to improve the solubility of the final inhibitor. Without being bound to any theory, it appears that the trans form of the indolinones is generally a more favorable form for FGFR inhibitors.

Amine-based substituents at positions 4, 5, and 6 at the A ring of structures II and III are a preferred class of substituents and an especially preferred class are amines of the structure:

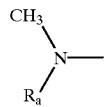

wherein $R_a$ is $CO(CH_2)_2COOH$, aryl, alkyl, or contains COOH, OH, or $NH_2$. These types of groups provide steric hindrance in order to force the isomer into a trans conformation which may be a favored property of FGFR inhibition and acts as a linker to a hydrophillic group.

Another favored class of substituents on the aryl ring of structures II and III includes piperazine type substituents of the structure:

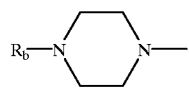

wherein $R_b$ is preferably a negatively charged group, such as a negatively charged alkyl or acyl.

Yet another preferred class of substituents for the aryl ring of structures II and III are C—COR groups of the formula:

wherein $R_c$ is a hydrophilic or negatively charged group, preferably at the 5 and/or 6 positions of the A ring of structures II and III, such as amide, ester, $CH_2CH_2COOH$, $CH_2Cl$, or piperazine. $R_c$ could also be linked to the aryl ring by a sp3 carbon or could be attached as $R_cO_3S$—.

Yet another preferred set of substituents on the aryl ring are fused heterocyclic rings which can be synthesized by acylation of the arylamine followed by alkylation of the heterocyclic ring systems. Examples of several such compounds are set forth in FIG. 1, compounds 044, 045, 047, 048, 050, 051, 052, 053, 055, 056, 058, 059, 061, 062, 064, 066, 067, 069, 070, and 073.

In another aspect, the invention features a 3-[(indole-3-yl)methylene]-2-indolinone compound having a substituent at the 1' position of the indole ring. The substituent at the 1' position of the indole ring is selected from the group consisting of (a) alkyl that is optionally substituted with a monocyclic or bicyclic five, six, eight, nine, or ten membered heterocyclic ring, where the ring is optionally substituted with one or more halogen, or trihalomethyl substituents;

(b) five, six, eight, nine, or ten membered monocyclic or bicyclic heterocyclic ring, where the ring is optionally substituted with one or more halogen or trihalomethyl substituents;

(c) an aldehyde or ketone of formula —CO—R12, where R12 is selected from the group consisting of hydrogen, alkyl, and a five or six membered heterocyclic ring;

(d) a carboxylic acid of formula -$(R_{13})_n$—COOH or ester of formula -$(R_{14})_m$—COO—$R_{15}$, where $R_{13}$, $R_{14}$, and $R_{15}$ are independently selected from the group consisting of alkyl and a five or six membered heterocyclic ring and m and n are independently 0 or 1;

(e) a sulfone of formula —$(SO_2)$—$R_{16}$, where $R_{16}$ is selected from the group consisting of alkyl and a five or six membered heterocyclic ring, where the ring is optionally substituted with an alkyl moiety;

(f) -$(R_{17})_n$-(indole-1-yl) or -$(R_{18})$m-CHOH—$(R_{19})$p-(indole-1-yl), where the indol moiety is optionally substituted where $R_{17}$, $R_{18}$, and $R_{19}$ are alkyl, and where m, n, and p are independently 0 or 1; and (g) taken together with a 2' substituent of the indole ring forms a five or six membered heterocyclic ring.

The term "alkyl" refers to a straight-chain, branched, or cyclic saturated aliphatic hydrocarbon. The alkyl group is preferably 1 to 10 carbons, more preferably a lower alkyl of from 1 to 7 carbons, and most preferably 1 to 4 carbons. Typical alkyl groups include methyl, ethyl, propyl, isopropyl, butyl, isobutyl, tertiary butyl, pentyl, hexyl and the like. The alkyl group may be substituted and some typical alkyl substituents include hydroxyl, cyano, alkoxy, oxygen, sulfur, nitroxy, halogen, —$N(CH_3)_2$, amino, and —SH.

The term "methyl" refers to a saturated alkyl moiety of one carbon. The term "ethyl" refers to a saturated alkyl moiety of two carbons. The term "propyl" refers to a saturated alkyl moiety of three carbons. The term "butyl" refers to a saturated alkyl moiety of four carbons. The term "pentyl" refers to a saturated alkyl moiety of five carbons.

The term "aryl" refers to an aromatic group which has at least one ring having a conjugated pi electron system and includes both carbocyclic aryl (e.g. phenyl) and heterocyclic aryl groups (e.g. pyridine). Aryl moieties include monocyclic, bicyclic, and tricyclic rings, where each ring has preferably five or six members. The aryl moiety may be substituted and typical aryl substituents include halogen, trihalomethyl, hydroxyl, —SH, —OH, —$NO_2$, amine, thioether, cyano, alkoxy, alkyl, and amino.

The terms "heterocycle" or "heterocyclic" refer to compounds that form a ring and contain up to four hetero atoms, the remainder of the atoms forming the ring being carbon. Thus, for example, each ring in the structure can contain zero, one, two, three, or four nitrogen, oxygen, or sulfur atoms within the ring. The ring can preferably be saturated with hydrogen atoms, more preferably harbor one or more unsaturations, and most preferably contain an aryl conjugated pi electron system. The rings are preferably eleven, twelve, thirteen, or fourteen membered rings, more preferably eight, nine, or ten membered rings, and most preferably five or six membered rings. Examples of such rings are furyl, thienyl, pyrrol, imidazolyl, indolyl, pyridinyl, thiadiazolyl, thiazolyl, piperazinyl, dibenzfuranyl, dibenzthienyl. The heterocyclic rings of the invention may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like. Structures of some preferred heterocyclic rings are the fused rings that have been shown above.

The term "aldehyde" refers to a chemical moiety with formula -(R)$_n$—CHO, where R is selected from the group consisting of alkyl or aryl and n is 0 or 1.

The term "ketone" refers to a chemical moiety with formula -(R)$_n$—CO—R', where R and R' are selected from the group consisting of alkyl or aryl and n is 0 or 1.

The term "carboxylic acid" refers to a chemical moiety with formula -(R)$_n$—COOH, where R is selected from the group consisting of alkyl or aryl and n is 0 or 1.

The term "ester" refers to a chemical moiety with formula -(R)$_n$—COOR', where R and R' are independently selected from the group consisting of alkyl or aryl and n is 0 or 1.

The term "sulfone" refers to a chemical moiety with formula —$SO_2$—R, where R is selected from the group consisting of alkyl or aryl.

The term "pharmaceutically acceptable salt" refers to a formulation of a compound that does not cause significant irritation to an organism and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

A preferred embodiment of the invention relates to compound of the following formula,

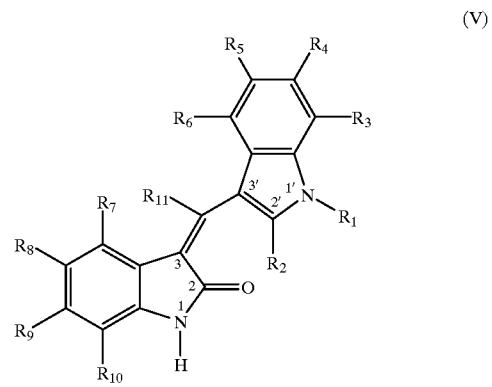

(V)

where (a) $R_1$ as is described above for the substituent at the 1' position of the indole ring;

(b) $R_2$, $R_3$, $R_4$, $R_5$, and $R_6$ are independently selected from the group consisting of, (i) hydrogen;

(ii) alkyl that is optionally substituted with a monocyclic or bicyclic five, six, eight, nine, or ten membered heterocyclic ring, where the ring is optionally substituted with one or more halogen, or trihalomethyl substituents;

(iii) five, six, eight, nine, or ten membered monocyclic or bicyclic heterocyclic ring, where the ring is optionally substituted with one or more halogen or trihalomethyl substituents;

(iv) a ketone of formula —CO—$R_{20}$, where $R_{20}$ is selected from the group consisting of hydrogen, alkyl, or a five or six membered heterocyclic ring (v) a carboxylic acid of formula -(R21)n-COOH or ester of formula -($R_{22}$)—COO—$R_{23}$, where $R_{21}$, $R_{22}$, and $R_{23}$ and are independently selected from the group consisting of alkyl or a five or six membered heterocyclic ring and m and n are independently 0 or 1;

(vi) halogen;

(vii) an alcohol of formula (R24)m-OH or an ether of formula -($R_{24}$)$_n$—O—$R_{25}$, where $R_{24}$ and $R_{25}$ are independently selected from the group consisting of alkyl and a five or six membered heterocyclic ring and m and n are independently 0 or 1;

(viii) —$NR_{26}R_{27}$, where $R_{26}$ and $R_{27}$ are independently selected from the group consisting of hydrogen, oxygen, alkyl, and a five or six membered heterocyclic ring;

(ix) —$NHCOR_{28}$, where $R_{28}$ is selected from the group consisting of hydroxyl, alkyl, and a five or six membered heterocyclic ring, where the ring is optionally substituted with alkyl, halogen, carboxylate, or ester;

(x) —$SO_2NR_{29}R_{30}$, where $R_{29}$ and $R_{30}$ are selected from the group consisting of hydrogen, oxygen, alkyl, and a five or six membered heterocyclic ring;

(xi) any two of $R_3$, $R_4$, $R_5$, or $R_6$ taken together form a bicyclic or tricyclic moiety fused to the six membered ring of the indole, where each ring in the multicyclic moiety is a five or six membered heterocyclic ring;

(c) $R_7$, $R_8$, $R_9$, and $R_{10}$ are independently selected from the group consisting of, (i) hydrogen;

(ii) alkyl that is optionally substituted with a monocyclic or bicyclic five, six, eight, nine, or ten membered heterocyclic ring, where the ring is optionally substituted with one or more halogen, aldehyde, or trihalomethyl substituents;

(iii) five, six, eight, nine, or ten membered monocyclic or bicyclic heterocyclic ring, where the ring is optionally substituted with one or more halogen or trihalomethyl substituents;

(iv) an aldehyde or ketone of formula —CO—$R_{31}$, where $R_{31}$ is selected from the group consisting of hydrogen, alkyl, or a five or six membered heterocyclic ring;

(v) a carboxylic acid of formula -(R32)n-COOH or ester of formula -$(R_{33})_m$—COO—$R_{34}$, where $R_{32}$, $R_{33}$, and $R_{34}$ and are independently selected from the group consisting of alkyl or a five or six membered heterocyclic ring and n and m are independently 0 or 1;

(vi) halogen;

(vii) an alcohol of formula $(R_{35})_m$—OH or an ether of formula -$(R_{35})$n-O—$R_{36}$, where $R_{35}$ and $R_{36}$ are independently chosen from the group consisting of alkyl or a five or six membered heterocyclic ring and m and n are independently 0 or 1;

(viii) —$NR_{37}R_{38}$, where $R_{37}$ and $R_{38}$ are independently selected from the group consisting of hydrogen, oxygen, alkyl, and a five or six membered heterocyclic ring;

(ix) —$NHCOR_{39}$, where $R_{39}$ is selected from the group consisting of hydroxyl, alkyl, and a five or six membered heterocyclic ring, where the ring is optionally substituted with alkyl, halogen, carboxylate, or ester;

(x) —$SO2NR_{40}R_{41}$, where $R_{40}$ and $R_{41}$ are selected from the group consisting of hydrogen, oxygen, alkyl, and a five or six membered heterocyclic ring;

(xi) any two of $R_7$, $R_8$, $R_9$, or $R_{10}$ taken together form a bicyclic or tricyclic heterocyclic moiety fused to the six membered ring of the indole, where each ring in the multicyclic moiety is a five or six membered heterocyclic ring; and (d) $R_{11}$ is hydrogen or alkyl;

provided that at least one of $R_1$, $R_2$, $R_3$, $R_4$, $R_5$, $R_6$, $R_7$, $R_8$, $R_9$, or $R_{10}$ is alkyl or provided that at least four of $R_1$, $R_2$, $R_3$, $R_4$, $R_5$, $R_6$, $R_7$, $R_8$, $R_9$, or $R_{10}$ are not hydrogen.

In preferred embodiments of the invention as shown in structure V above, $R_1$ is preferably a lower alkyl, branched or unbranched, more preferably an unbranched lower alkyl (e.g., ethyl, propyl, isopropyl, butyl, tertiary butyl, pentyl), and most preferably a methyl moiety.

In other preferred embodiments one or more of $R_1$, $R_2$, $R_3$, $R_4$, $R_5$, $R_6$, $R_7$, $R_8$, $R_9$, and $R_{10}$ of structure V are a heterocyclic ring. The heterocycle is preferably selected from the group consisting of five, six, eight, nine, ten, eleven, twelve, thirteen, and fourteen membered aryl or non-aryl rings. The heterocycles can be furyl, thienyl, pyrrol, imidazolyl, indolyl, pyridinyl, thiadiazolyl, thiazolyl, piperazinyl, dibenzfuranyl, dibenzthienyl, 2-aminothiazol-4-yl, 2-amino-5-chlorothiazol-4-yl, 2-amino-thiadiazol-4-yl, 2,3-dioxopiperazinyl, 4-alkylpiperazinyl, 2-iodo-3-dibenzfuranyl, and 3-hydroxy-4-dibenzthienyl. $R_2$ preferably is lower alkyl, more preferably methyl, or phenyl or biphenyl preferably mono-substituted with halogen. $R_3$, $R_4$, $R_5$ and mono-$R_6$ preferably are selected from the group consisting of hydrogen, unsubstituted lower alkyls, halogen, methoxy, carboncyclic and ether. R11 is preferably hydrogen.

In especially preferred embodiments of structure V, $R_1$ is methyl and $R_2$, $R_3$, $R_4$, $R_5$, $R_6$, $R_7$, $R_8$, $R_9$, $R_{10}$, and $R_{11}$ are hydrogen, or $R_1$ and $R_7$ are methyl and $R_2$, $R_3$, $R_4$, $R_6$, $R_9$, $R_{10}$, and $R_{11}$ are hydrogen. Other especially preferred compounds are set forth in the tables and examples set forth herein.

In another aspect, the invention features a method of synthesizing an indolinone compound, where the method comprises the steps of:

(a) reacting an aldehyde of formula VI with an oxindol of formula VII,

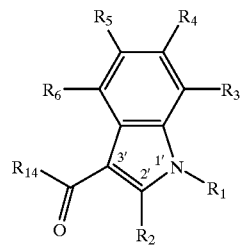

VI

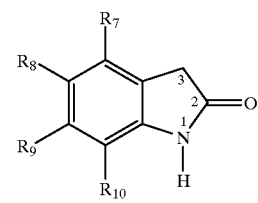

VII where $R_1$, $R_2$, $R_3$, $R_4$, $R_5$, $R_6$, $R_7$, $R_8$, $R_9$, $R_{10}$, and $R_{11}$ are described herein; and (b) separating the indolinone compound from the aldehyde and oxindol reactants.

The term "synthesizing" defines a method of combining multiple compounds together and/or chemically modifying the compound(s) in a controlled environment. A controlled environment preferably includes a glass vessel, a stirring rod or bar, a heating or cooling source, and specific organic solvents.

The term "reacting" refers to mixing two compounds together in a controlled environment. The compounds that are mixed together and reacted with one another are termed "reactants".

The term "separating" describes methods of segregating compounds from one or more other compounds. Compounds can be separated from one another by using techniques known in the art which include, but are not limited to, column chromatography techniques and solvent phase separation techniques.

In another aspect, the invention features optionally substituted 3-[(tetrahydroindole-2-yl)methylene]-2-indolinone and 3-[(cyclopentano-b-pyrrol-2-yl)methylene]-2-indolinone compounds.

The term "optionally substituted" refers, for example, to a benzene ring that either harbors a hydrogen at a particular position or optionally harbors another substituent at that position. The term "optionally substituted" refers to other molecules in addition to benzene. A ring structure, for example can be N-substituted or C-substituted.

The term "N-substituted" refers to a compound that harbors chemical substituents attached to a nitrogen atom in a ring of the indolinone.

The term "C-substituted" refers to a compound that harbors chemical substituents attached to a carbon atom in the indolinone.

The term "independently selected" refers to a molecule that harbors one substituent chosen from a group of substituents.

A preferred embodiment of the invention relates to an indolinone compound of the following formula,

VIII

IX where
(a) $R_1$ is selected from the group consisting of,
 (i) hydrogen;
 (ii) alkyl that is optionally substituted with a monocyclic or bicyclic five, six, eight, nine, or ten membered heterocyclic ring, where the ring is optionally substituted with one or more halogen, or trihalomethyl substituents;
 (iii) five, six, eight, nine, or ten membered monocyclic or bicyclic heterocyclic ring, where the ring is optionally substituted with one or more halogen or trihalomethyl substituents;
 (iv) ketone of formula —CO—$R_{11}$, where $R_{11}$ is selected from the group consisting of hydrogen, alkyl, or a five or six membered heterocyclic ring;
 (v) a carboxylic acid of formula -$(R_{12})_n$—COOH or ester of formula -$(R_{13})_m$—COO—$R_{14}$, where $R_{12}$, $R_{13}$, and $R_{14}$ and are independently selected from the group consisting of alkyl or a five or six membered heterocyclic ring and n and m are independently 0 or 1;
 (vi) a sulfone of formula —(SO2)—$R_{15}$, where $R_{15}$ is selected from the group consisting of alkyl or a five or six membered heterocyclic ring, where the ring is optionally substituted with an alkyl moiety;
 (vii) -$(R_{16})_n$-(indole-1-yl) or -$(R_{17})_m$—CHOH—$(R_{18})$p-(indole-1-yl), where the indole moiety is optionally substituted with an aldehyde and $R_{16}$, $R_{17}$, and $R_{18}$ are alkyl and n, m, and p are independently 0 or 1;
 (viii) taken together with a 2' substituent of the indole ring form a tricyclic moiety, where each ring in the tricyclic moiety is a five or six membered heterocyclic ring;

(b) $R_2$, $R_3$, $R_{3'}$, $R_4$, $R_{4'}$, $R_5$, $R_{5'}$, $R_6$, and $R_{6'}$ are independently selected from the group consisting of,
 (i) hydrogen;
 (ii) alkyl that is optionally substituted with a monocyclic or bicyclic five, six, eight, nine, or ten membered heterocyclic ring, where the ring is optionally substituted with one or more halogen, aldehyde, or trihalomethyl substituents;
 (iii) five, six, eight, nine, or ten membered monocyclic or bicyclic heterocyclic ring, where the ring is optionally substituted with one or more halogen or trihalomethyl substituents;
 (iv) ketone of formula —CO—$R_{20}$, where $R_{20}$ is selected from the group consisting of hydrogen, alkyl, or a five or six membered heterocyclic ring;
 (v) a carboxylic acid of formula -$(R_{21})_n$—COOH or ester of formula -$(R_{22})$—COO—$R_{23}$, where $R_{21}$, $R_{22}$, and $R_{23}$ and are independently selected from the group consisting of alkyl or a five or six membered heterocyclic ring and m and n are independently 0 or 1;
 (vi) halogen;
 (vii) an alcohol of formula $(R_{24})_m$—OH or an ether of formula -$(R_{24})_n$—O—$R_{25}$, where $R_{24}$ and $R_{25}$ are independently selected from the group consisting of alkyl and a five or six membered heterocyclic ring and m and n are independently 0 or 1;
 (viii) —$NR_{26}R_{27}$, where $R_{26}$ and $R_{27}$ are independently selected from the group consisting of hydrogen, oxygen, alkyl, and a five or six membered heterocyclic ring;
 (ix) —$NHCOR_{28}$, where $R_{28}$ is selected from the group consisting of hydroxyl, alkyl, and a five or six membered heterocyclic ring, where the ring is optionally substituted with alkyl, halogen, carboxylate, or ester;
 (x) —$SO2NR_{29}R_{30}$, where $R_{29}$ and $R_{30}$ are selected from the group consisting of hydrogen, oxygen, alkyl, and a five or six membered heterocyclic ring;
 (xi) any two of $R_3$, $R_{3'}$, $R_4$, $R_{4'}$, $R_5$, $R_{5'}$, $R_6$, or $R_{6'}$ taken together form a bicyclic or tricyclic hetercyclic moiety fused to the six membered ring of the indole, where each ring in the multicyclic moiety is a five or six membered heterocyclic ring;

(c) $R_7$, $R_8$, $R_9$, and $R_{10}$ are independently selected from the group consisting of,
 (i) hydrogen;
 (ii) alkyl that is optionally substituted with a monocyclic or bicyclic five, six, eight, nine, or ten membered heterocyclic ring, where the ring is optionally substituted with one or more halogen, or trihalomethyl substituents;
 (iii) five, six, eight, nine, or ten membered monocyclic or bicyclic heterocyclic ring, where the ring is optionally substituted with one or more halogen or trihalomethyl substituents;
 (iv) ketone of formula —CO—$R_{31}$, where $R_{31}$ is selected from the group consisting of hydrogen, alkyl, or a five or six membered heterocyclic ring;
 (v) a carboxylic acid of formula -$(R_{32})_n$—COOH or ester of formula -$(R_{33})_m$—COO—$R_{34}$, where $R_{32}$, $R_{33}$, and $R_{34}$ and are independently selected from the group consisting of alkyl or a five or six membered heterocyclic ring and n and m are independently 0 or 1;
 (vi) halogen;
 (vii) an alcohol of formula $(R_{35})_m$—OH or an ether of formula -$(R_{35})_n$—O—$R_{36}$, where $R_{35}$ and $R_{36}$ are independently chosen from the group consisting of alkyl or a five or six membered heterocyclic ring and m and n are independently 0 or 1;

(viii) —NR$_{37}$R$_{38}$, where R$_{37}$ and R$_{38}$ are independently selected from the group consisting of hydrogen, oxygen, alkyl, and a five or six membered heterocyclic ring;

(ix) —NHCOR$_{39}$, where R$_{39}$ is selected from the group consisting of hydroxyl, alkyl, and a five or six membered heterocyclic ring, where the ring is optionally substituted with alkyl, halogen, carboxylate, or ester;

(x) —SO2NR$_{40}$R$_{41}$, where R$_{40}$ and R$_{41}$ are selected from the group consisting of hydrogen, oxygen, alkyl, and a five or six membered heterocyclic ring;

(xi) any two of R$_7$, R$_8$, R$_9$, or R$_{10}$ taken together form a bicyclic or tricyclic hetercyclic moiety fused to the six membered ring of the indole, where each ring in the multicyclic moiety is a five or six membered heterocyclic ring; and (d) R$_{11}$ is hydrogen or alkyl.

Another preferred embodiment of the invention relates to indolinone compounds of structures VIII and IX, where R$_1$, R$_2$, R$_3$, R$_{3'}$, R$_4$, R$_{4'}$, R$_5$, R$_{5'}$, R$_6$, R$_{6'}$, R$_7$, R$_8$, R$_9$, R$_{10}$, and R$_{11}$ are hydrogen.

In another preferred embodiment, the invention relates to oxidolinone compounds of structures VIII and IX, where R$_8$ is bromine, chlorine, or NH2 and R$_2$, R$_{2'}$, R$_3$, R$_{3'}$, R$_4$, R$_{4'}$, R$_5$, R$_{5'}$, R$_6$, R$_{6'}$, R$_7$, R$_9$, R$_{10}$, and R$_{11}$ are hydrogen.

In yet another preferred embodiment, the invention relates to indolinone compounds of structures VIII and IX, where R$_7$ is methyl and R$_1$, R$_2$, R$_3$, R$_{3'}$, R$_4$, R$_{4'}$, R$_5$, R$_{5'}$, R$_6$, R$_{6'}$, R$_7$, R$_9$, R$_{10}$, and R$_{11}$ are hydrogen.

In another aspect, the invention features a method of synthesizing an indolinone compound, where the method comprises the steps of:

(a) reacting an aldehyde of formula X or XI with an oxindol of formula XII,

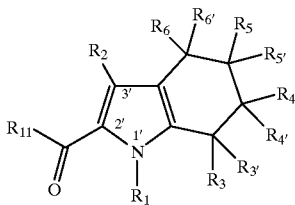

X

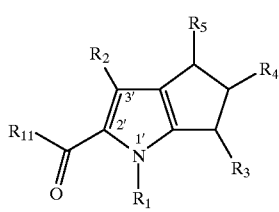

XI

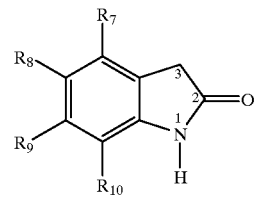

XII where R$_1$, R$_2$, R$_3$, R$_{3'}$, R$_4$, R$_{4'}$, R$_5$, R$_{5'}$, R$_6$, R$_{6'}$, R$_7$, R$_8$, R$_9$, R$_{10}$, and R$_{11}$ are described herein; and (b) separating the indolinone compound from the aldehyde and oxindole reactants.

In another aspect, the invention features an indolinone compound having a substituent at the 5 position of the oxindole ring, where the substituent at the 5 position of the oxindole ring is selected from the group consisting of:

(a) alkyl that is optionally substituted with a monocyclic or bicyclic five, six, eight, nine, or ten membered heterocyclic ring, where the ring is optionally substituted with one or more halogen, or trihalomethyl substituents;

(b) five, six, eight, nine, or ten membered monocyclic or bicyclic heterocyclic ring, where the ring is optionally substituted with one or more halogen or trihalomethyl substituents;

(c) a ketone of formula —CO—R$_{10}$, where R$_{10}$ is selected from the group consisting of hydrogen, alkyl, or a five or six membered heterocyclic ring;

(d) a carboxylic acid of formula -(R$_{11}$)n-COOH or ester of formula -(R$_{12}$)—COO—R$_{13}$, where R$_{11}$, R$_{12}$, and R$_{13}$ and are independently selected from the group consisting of alkyl or a five or six membered heterocyclic ring and m and n are independently 0 or 1;

(e) halogen;

(f) an alcohol of formula (R$_{14}$)$_m$—OH or an ether of formula -(R$_{14}$)n-O—R$_{15}$, where R$_{14}$ and R$_{15}$ are independently selected from the group consisting of alkyl and a five or six membered heterocyclic ring and m and n are independently 0 or 1;

(g) —NR$_{16}$R$_{17}$, where R$_{16}$ and R$_{17}$ are independently selected from the group consisting of hydrogen, alkyl, and a five or six membered heterocyclic ring;

(h) —NHCOR$_{18}$, where R$_{18}$ is selected from the group consisting of alkyl, and a five or six membered heterocyclic ring, where the ring is optionally substituted with alkyl, halogen, carboxylate, or ester;

(i) —SO$_2$NR$_{19}$R$_{20}$, where R$_{19}$ and R$_{20}$ are selected from the group consisting of hydrogen, alkyl, and a five or six membered heterocyclic ring;

(j) any two of R$_4$, R$_5$, R$_6$, or R$_7$ taken together form a bicyclic or tricyclic hetercyclic moiety fused to the six membered ring of the indole, where each ring in the multicyclic moiety is a five or six membered heterocyclic ring.

A preferred embodiment of the invention relates to a compound of the following formula,

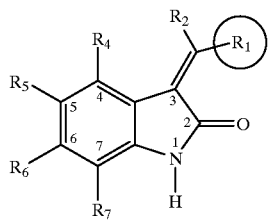

(XIII)

where
(a) $R_5$ is selected from the group consisting of,
(i) alkyl that is optionally substituted with a monocyclic or bicyclic five, six, eight, nine, or ten membered heterocyclic ring, where the ring is optionally substituted with one or more halogen, or trihalomethyl substituents;
(ii) five, six, eight, nine, or ten membered monocyclic or bicyclic heterocyclic ring, where the ring is optionally substituted with one or more halogen or trihalomethyl substituents;
(iii) a ketone of formula —CO—$R_{10}$, where $R_{10}$ is selected from the group consisting of hydrogen, alkyl, or a five or six membered heterocyclic ring;
(iv) a carboxylic acid of formula -($R_{11}$)n-COOH or ester of formula -($R_{12}$)—COO—$R_{13}$, where $R_{11}$, $R_{12}$, and $R_{13}$ and are independently selected from the group consisting of alkyl or a five or six membered heterocyclic ring and m and n are independently 0 or 1;
(v) halogen;
(vi) an alcohol of formula ($R_{14}$)$_m$—OH or an ether of formula -($R_{14}$)$_n$—O—$R_{15}$, where $R_{14}$ and $R_{15}$ are independently selected from the group consisting of alkyl and a five or six membered heterocyclic ring and m and n are independently 0 or 1;
(vii) —$NR_{16}R_{17}$, where $R_{16}$ and $R_{17}$ are independently selected from the group consisting of hydrogen, alkyl, and a five or six membered heterocyclic ring;
(viii) —$NHCOR_{18}$, where $R_{18}$ is selected from the group consisting of alkyl, and a five or six membered heterocyclic ring, where the ring is optionally substituted with alkyl, halogen, carboxylate, or ester;
(ix) —$SO_2NR_{19}R_{20}$, where $R_{19}$ and $R_{20}$ are selected from the group consisting of hydrogen, alkyl, and a five or six membered heterocyclic ring;
(x) any two of $R_4$, $R_5$, $R_6$, or $R_7$ taken together form a bicyclic or tricyclic hetercyclic moiety fused to the six membered ring of the oxindole, where each ring in the multicyclic moiety is a five or six membered heterocyclic ring;
(b) $R_1$ is selected from the group consisting of a five, six, eight, nine, and ten membered monocyclic or bicyclic heterocyclic ring, where the ring is optionally substituted with one or more substituents selected from the group consisting of
(i) hydrogen and alkyl that is optionally substituted with a monocyclic or bicyclic five, six, eight, nine, or ten membered heterocyclic ring, where the ring is optionally substituted with one or more halogen, or trihalomethyl substituents;
(ii) five, six, eight, nine, or ten membered monocyclic or bicyclic heterocyclic ring, where the ring is optionally substituted with one or more halogen or trihalomethyl substituents;
(iii) a ketone of formula —CO—$R_{21}$, where $R_{21}$ is selected from the group consisting of hydrogen, alkyl, or a five or six membered heterocyclic ring;
(iv) a carboxylic acid of formula -($R_{22}$)$_n$—COOH or ester of formula -($R_{23}$)—COO—$R_{24}$, where $R_{22}$, $R_{23}$, and $R_{24}$ and are independently selected from the group consisting of alkyl or a five or six membered heterocyclic ring and m and n are independently 0 or 1;
(v) halogen;
(vi) an alcohol of formula ($R_{25}$)m-OH or an ether of formula -($R_{25}$)$_n$—O—$R_{26}$, where $R_{25}$ and $R_{26}$ are independently selected from the group consisting of alkyl and a five or six membered heterocyclic ring and m and n are independently 0 or 1;
(vii) —$NR_{27}R_{28}$, where $R_{27}$ and $R_{28}$ are independently selected from the group consisting of hydrogen, alkyl, and a five or six membered heterocyclic ring;
(viii) —$NHCOR_{29}$, where $R_{29}$ is selected from the group consisting of alkyl, and a five or six membered heterocyclic ring, where the ring is optionally substituted with alkyl, halogen, carboxylate, or ester;
(ix) —$SO_2NR_{30}R_{31}$, where $R_{30}$ and $R_{31}$ are selected from the group consisting of hydrogen, alkyl, and a five or six membered heterocyclic ring;
(c) $R_4$, $R_6$, and $R_7$ are independently selected from the group consisting of,
(i) hydrogen and alkyl that is optionally substituted with a monocyclic or bicyclic five, six, eight, nine, or ten membered heterocyclic ring, where the ring is optionally substituted with one or more halogen, or trihalomethyl substituents;
(ii) five, six, eight, nine, or ten membered monocyclic or bicyclic heterocyclic ring, where the ring is optionally substituted with one or more halogen or trihalomethyl substituents;
(iii) a ketone of formula —CO—$R_{32}$, where $R_{32}$ is selected from the group consisting of hydrogen, alkyl, or a five or six membered heterocyclic ring;
(iv) a carboxylic acid of formula -($R_{33}$)n-COOH or ester of formula -($R_{34}$)—COO—$R_{35}$, where $R_{33}$, $R_{34}$, and $R_{35}$ and are independently selected from the group consisting of alkyl or a five or six membered heterocyclic ring and m and n are independently 0 or 1;
(v) halogen;
(vi) an alcohol of formula ($R_{36}$)m-OH or an ether of formula -($R_{36}$)$_n$—O—$R_{37}$, where $R_{36}$ and $R_{37}$ are independently selected from the group consisting of alkyl and a five or six membered heterocyclic ring and m and n are independently 0 or 1;
(vii) —$NR_{38}R_{39}$, where $R_{38}$ and $R_{39}$ are independently selected from the group consisting of hydrogen, alkyl, and a five or six membered heterocyclic ring;
(viii) —$NHCOR_{40}$, where $R_{40}$ is selected from the group consisting of alkyl, and a five or six membered heterocyclic ring, where the ring is optionally substituted with alkyl, halogen, carboxylate, or ester;
(ix) —$SO_2NR_{41}R_{42}$, where $R_{41}$ and $R_{42}$ are selected from the group consisting of hydrogen, alkyl, and a five or six membered heterocyclic ring; and
(d) $R_2$ is hydrogen or alkyl.
In preferred embodiments of the invention shown in structure XIII above one or more of $R_1$, $R_4$, $R_5$, $R_6$, or $R_7$ are a heterocyclic ring. Preferred heterocycles of the invention are described herein.

Another preferred embodiment of the invention shown in structure XIII above is an indolinone compound, where $R_1$ is (3,5-dimethylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-diethylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-diisopropylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-dimethylpyrrol)-2-yl, $R_5$ is —$(CH_2)_2$COOH, and $R_2$, $R_4$, $R_6$, and $R_7$ are hydrogen.

Another preferred embodiment of the invention shown in structure XIII above is an indolinone compound, where $R_1$ is (5-methylthiophene)-2-yl, $R_5$ is —COOH, and $R_2$, $R_4$, $R_6$, and $R_7$ are hydrogen.

In another aspect, the invention features a method of synthesizing an indolinone compound, where the method comprises the steps of:

(a) reacting an aldehyde of formula XIV with an oxindole of formula XV,

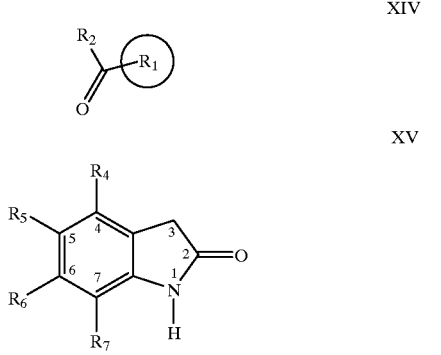

XIV

XV where $R_1$, $R_2$, $R_3$, $R_4$, $R_5$, $R_6$, $R_7$, $R_8$, $R_9$, $R_{10}$, and $R_{11}$ are as described herein; and (b) separating the indolinone compound from the aldehyde and oxindole reactants.

In another aspect, the invention features an indolinone compound having a substituent at the 3 position of the oxindole ring, where the substituent at the 3 position of the oxindole ring is selected from the group consisting of five-membered or six-membered heterocyclic rings. The oxindolonine is further substituted with groups enhancing hydrosolubility as set forth below.

A preferred embodiment of the invention relates to a compound of the following formula:

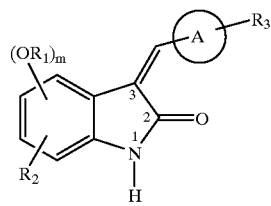

wherein (a) A is a five membered heterocyclic ring selected from the following group consisting of thiophene, pyrrole, pyrazole, imidazole, 1,2,3-triazole, 1,2,4-triazole, oxazole, isoxazole, thiazole, isothiazole, furan, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole (b) m is zero, 1, or 2;

(c) $R_1$ is hydrogen, $C_1$–$C_6$ alkyl or $C_2$–$C_6$ alkanoyl;

(d) one of $R_2$ and $R_3$ independently is hydrogen and the other is a substituent selected from:

(1) a $C_1$–$C_6$ alkyl group substituted by 1, 2 or 3 hydroxy groups;

(2) $SO_3R_4$ in which $R_4$ is hydrogen or $C_1$–$C_6$ alkyl unsubstituted or substituted by 1, 2 or 3 hydroxy groups;

(3) $SO_2NHR_5$ in which $R_5$ is as $R_4$ defined above or a —$(CH_2)_n$—$N(C_1$–$C_6$ alkyl$)_2$ group in which n is 2 or 3;

(4) $COOR_6$ in which $R_6$ is $C_1$–$C_6$ alkyl unsubstituted or substituted by phenyl or by 1, 2 or 3 hydroxy groups or phenyl;

(5) $CONHR_7$ in which $R_7$ is hydrogen, phenyl or $C_1$–$C_6$ alkyl substituted by 1, 2 or 3 hydroxy groups or by phenyl;

(6) $NHSO_2R_8$ in which $R_8$ is $C_1$–$C_6$ alkyl or phenyl unsubstituted or substituted by halogen or by $C_1$–$C_4$ alkyl;

(7) $N(R_9)_2$, $NHR_9$ or $OR_9$ wherein $R_9$ is $C_2$–$C_6$ alkyl substituted by 1, 2 or 3 hydroxy groups;

(8) $NHCOR_{10}$, $OOCR_{10}$ or $CH_2OOCR_{10}$ in which $R_{10}$ is $C_1$–$C_6$ alkyl substituted by 1, 2 or 3 hydroxy groups;

(9) $NHCONH_2$; $NH$—$C(NH_2)$=$NH$; $C(NH_2)$=$NH$; $CH_2NHC(NH_2)$=$NH$; $CH_2NH_2$; $OPO(OH)_2$; $CH_2OPO(OH)_2$; $PO(OH)_2$; or a

group wherein X is selected from the group consisting of $CH_2$, $SO_2$, CO, or $NHCO(CH_2)_p$ in which p is 1,2, or 3 and Z is CH2, O or N—$R_{11}$ in which $R_{11}$ is hydrogen or is as $R_9$ defined above.

The term "alkanoyl" refers to a chemical moiety with formula -(R)$_n$—CO—R', where R and R' are selected from the group consisting of alkyl or aryl and n is 0 or 1.

Inhibitors of protein kinase catalytic activity are known in the art. Small molecule inhibitors typically block the binding of substrates by tightly interacting with the protein kinase active-site. Indolinone compounds, for example, can bind to the active-site of a protein kinase and inhibit the molecule effectively, as measured by inhibition constants on the order of $10^{-6}$ M.

A preferred embodiment of the invention relates to an hydrosoluble indolinone compound that inhibits the catalytic activity of a FLK protein kinase. The indolinone preferably inhibits the catalytic activity of the FLK protein kinase with an $IC_{50}$ less than 50 $\mu$M, more preferably with an $IC_{50}$ less than 5 $\mu$M, and most preferably with an $IC_{50}$ less than 0.5 $\mu$M.

In another aspect, the invention features a method of synthesizing a hydrosoluble indolinone compound, where the method comprises the steps of:

(a) reacting an aldehyde of formula XVI with an oxindole of formula XVII,

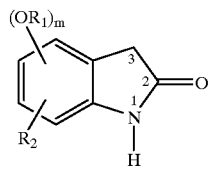

XVI

XVII

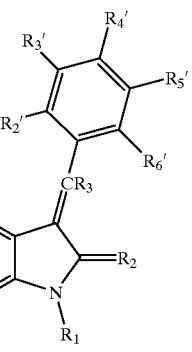

where (a) A is a five or six membered ring comprised of atoms selected from the group consisting of oxygen, carbon, sulfer and nitrogen (b) m is zero, 1, or 2;

(c) $R_1$ is hydrogen, $C_1$–$C_6$ alkyl or $C_2$–$C_6$ alkanoyl;

(d) one of $R_2$ and $R_3$ independently is hydrogen and the other is a substituent selected from:

(1) a $C_1$–$C_6$ alkyl group substituted by 1, 2 or 3 hydroxy groups;

(2) $SO_3R_4$ in which $R_4$ is hydrogen or $C_1$–$C_6$ alkyl unsubstituted or substituted by 1, 2 or 3 hydroxy groups;

(3) $SO_2NHR_5$ in which $R_5$ is as $R_4$ defined above or a —$(CH_2)_n$—$N(C_1$–$C_6$ alkyl$)_2$ group in which n is 2 or 3;

(4) $COOR_6$ in which $R_6$ is $C_1$–$C_6$ alkyl unsubstituted or substituted by phenyl or by 1, 2 or 3 hydroxy groups or phenyl;

(5) $CONHR_7$ in which $R_7$ is hydrogen, phenyl or $C_1$–$C_6$ alkyl substituted by 1, 2 or 3 hydroxy groups or by phenyl;

(6) $NHSO_2R_8$ in which $R_8$ is $C_1$–$C_6$ alkyl or phenyl unsubstituted or substituted by halogen or by $C_1$–$C_4$ alkyl;

(7) $N(R_9)_2$, $NHR_9$ or $OR_9$ wherein $R_9$ is $C_2$–$C_6$ alkyl substituted by 1, 2 or 3 hydroxy groups;

(8) $NHCOR_{10}$, $OOCR_{10}$ or $CH_2OOCR_{10}$ in which $R_{10}$ is $C_1$–$C_6$ alkyl substituted by 1, 2 or 3 hydroxy groups;

(9) $NHCONH_2$; NH—$C(NH_2)$=NH; C(NH)=$NH_2$; $CH_2NHC(NH_2)$=NH; $CH_2NH_2$; $OPO(OH)_2$; $CH_2OPO(OH)_2$; $PO(OH)_2$; or a

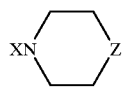

group wherein X is selected from the group consisting of $CH_2$, $SO_2$, CO, or $NHCO(CH_2)_p$ in which p is 1,2, or 3 and Z is CH2, O or N—$R_{11}$ in which $R_{11}$ is hydrogen or is as $R_9$ defined above; and (b) separating the indolinone compound from the aldehyde and oxindole reactants.

Another aspect of the invention features a pharmaceutical composition comprising an oxidolinone compound of the invention and a physiologically acceptable carrier or diluent.

In the embodiments set forth below, several preferred subclasses of compounds having activity against Flk are set forth. Thus, in one embodiment, the invention provides compounds having the formula:

wherein $R_1$ is hydrogen or alkyl (preferably lower alkyl, more preferably methyl);

$R_2$ is oxygen or sulfur;

$R_3$ is hydrogen or methyl;

$R_4$, $R_5$, $R_6$, and $R_7$ are each independently selected from the group consisting of hydrogen (preferably at least two or three of $R_4$, $R_5$, $R_6$ and $R_7$ are hydrogen), alkyl (preferably lower alkyl, more preferably methyl), halogen, $NO_2$, and NRR';

$R_{2'}$, $R_{3'}$, $R_{4'}$, $R_{5'}$, and $R_{6'}$ are each independently selected from the group consisting of hydrogen, alkyl, halogen, $NO_2$, NRR'(where taken together $NRR^1$ may form a five or six member non-aromatic heterocyc optionally substituted with COH), OH, $ORNRR^1$, and OR;

R is hydrogen, alkyl or aryl; and

R' is hydrogen, alkyl or aryl.

In another embodiment, the invention provides compounds having the formula:

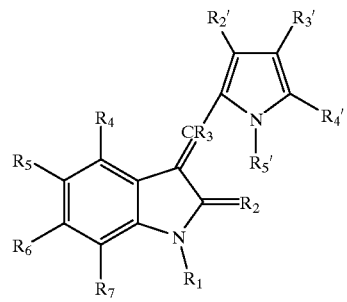

wherein $R_1$ is hydrogen or alkyl (preferably lower alkyl, more preferably methyl);

$R_2$ is oxygen or sulfer;

$R_3$ is hydrogen or methyl;

$R_4$, $R_5$, $R_6$, and $R_7$ are each independently selected from the group consisting of hydrogen, alkyl (preferably lower alkyl, more preferably methyl), halogen, and NRR';

$R_{2'}$, $R_{3'}$, $R_{4'}$, and $R_{5'}$, are each independently selected from the group consisting of hydrogen, alkyl, halogen, and (alkyl)$_n$$CO_2$R;

R is hydrogen, alkyl or aryl; and

R' is hydrogen, alkyl or aryl.

In another embodiment, the invention provides compounds having the formula:

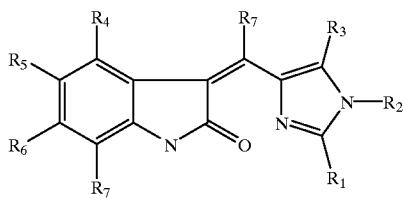

wherein $R_1$, $R_2$, and $R_3$, are each independently selected from the group consisting of hydrogen, alkyl, halogen, and (alkyl)$_n$CO$_2$R;

$R_4$, $R_5$, $R_6$, and $R_7$ are each independently selected from the group consisting of hydrogen, alkyl (preferably lower alkyl, more preferably methyl), halogen, and NRR';

$R_8$ and $R_9$ are independently hydrogen or alkyl;

R is hydrogen, alkyl or aryl; and

R' is hydrogen, alkyl or aryl.

In another embodiment, the invention provides compounds having the formula:

(XVIII)

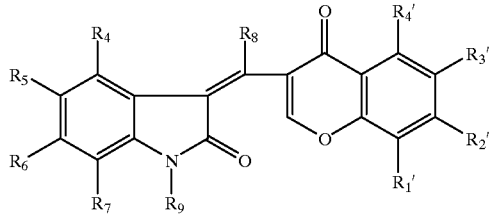

wherein $R_{1'}$, $R_{2'}$, $R_{3'}$, $R_{4'}$ and $R_7$ are each independently selected from the group consisting of hydrogen, alkyl (preferably lower alkyl, more preferably methyl), halogen and NRR';

$R_8$ and $R_9$ are independently hydrogen or alkyl;

R is hydrogen, alkyl or aryl; and

R' is hydrogen, alkyl or aryl.

In another aspect, the invention features a method of synthesizing an indolinone compound, where the method comprises the steps of:

(a) reacting an appropriate aldehyde with an appropriate oxindole, (b) separating the indolinone compound from the aldehyde and oxindole reactants.

In another aspect, the invention features an indolinone compound, salt, ester, amide, prodrug, isomer, or metabolite thereof that modulates the catalytic activity of a protein kinase.

The term "modulates" refers to the ability of a compound to alters the catalytic activity of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "protein kinase" defines a class of proteins that regulate a variety of cellular functions. Protein kinases regulate cellular functions by reversibly phosphorylating protein substrates which thereby changes the conformation of the substrate protein. The conformational change modulates catalytic activity of the substrate or its ability to interact with other binding partners.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

A preferred embodiment of the invention relates to an indolinone compound that inhibits the catalytic activity of a FLK protein kinase. The indolinone preferably inhibits the catalytic activity of the FLK protein kinase with an IC50 less than 50 $\mu$M, more preferably with an IC50 less than 5 $\mu$M, and most preferably with an IC50 less than 0.5 $\mu$M.

The term "FLK" refers to a protein kinase that phosphorylates protein substrates on tyrosine residues. The FLK protein kinase regulates cellular functions in response to the VEGF growth factor. These cellular functions include, but are not limited to, cellular proliferation, and in particular, blood vessel proliferation in tissues.

The term "IC$_{50}$", in the context of the invention, refers to a parameter that describes the concentration of a particular indolinone required to inhibit 50% of the FLK protein kinase catalytic activity. The IC$_{50}$ parameter can be measured using an assay described herein and by varying the concentration of a particular indolinone compound.

Another aspect of the invention features a pharmaceutical composition comprising, consisting essentially of, or consisting of an indolinone compound, salt, ester, amide, prodrug, isomer, or metabolite thereof of the invention and a physiologically acceptable carrier or diluent.

The term "pharmaceutical composition" refers to a mixture of an indolinone compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not cause significant irritation to an organism and does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

Another aspect of the invention features a method of preventing or treating an abnormal condition in an organism. The abnormal condition is associated with an aberration in a signal transduction pathway characterized by an interaction between a protein kinase and a natural binding partner. The method comprises the following steps: (a) administering a compound of the invention to an organism; and (b) promoting or disrupting the abnormal interaction.

The term "preventing" refers to a method of barring the organism from acquiring the abnormal condition.

The term "treating" refers to a method of alleviating or abrogating the abnormal condition in the organism.

The term "organism" relates to any living entity comprised of at least one cell. An organism can be as simple as one eukaryotic cell or as complex as a mammal.

The term "abnormal condition" refers to a function in the cells or tissues of an organism that deviates from their normal functions in that organism. An abnormal condition can relate to cell proliferation, cell differentiation, or cell survival.

Aberrant cell proliferative conditions include cancers such as fibrotic and mesangial disorders, abnormal angiogenesis and vasculogenesis, wound healing, psoriasis, diabetes mellitus, and inflammation.

Aberrant differentiation conditions include, but are not limited to neurodegenerative disorders, slow wound healing rates, and tissue grafting techniques.

Aberrant cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

Cell proliferation, differentiation, and survival are phenomena simply measured by methods in the art. These methods can involve observing the number of cells or the appearance of cells under a microscope with respect to time (days).

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The aberrant condition can also be prevented or treated by administering a group of cells having an aberration in a signal transduction process to an organism. The effect of administering a compound on organism function can then be monitored. The art contains multiple methods of introducing a group of cells to an organism as well as methods of administering a compound to an organism. The organism is preferably a frog, more preferably a mouse, rat, rabbit, guinea pig, or goat, and most preferably a monkey or ape.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein kinases, receptor and non-receptor protein phosphatases, nucleotide exchange factors, and transcription factors.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "natural binding partner" refers to a polypeptide that normally binds to the intracellular region of a protein kinase in a cell. These natural binding partners can play a role in propagating a signal in a protein kinase signal transduction process. The natural binding partner can bind to a protein kinase intracellular region with high affinity. High affinity represents an equilibrium binding constant on the order of $10^{-6}$ M or less. However, a natural binding partner can also transiently interact with a protein kinase intracellular region and chemically modify it. Protein kinase natural binding partners are chosen from a group consisting of, but not limited to, src homology 2 (SH2) or 3 (SH3) domains, other phosphoryl tyrosine binding (PTB) domains, and other protein kinases or protein phosphatases.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple amino acids at the complex interface. Alternatively, a compound can inhibit an interaction between a protein kinase and natural binding partners by compromising favorable interactions formed between amino acids at the complex interface.

A preferred embodiment of the invention relates to the method of treating an abnormal condition in an organism, where the organism is a mammal.

The term "mammal" refers preferably to such organisms as mice, rats, rabbits, guinea pigs, and goats, more preferably to monkeys and apes, and most preferably to humans.

Another preferred embodiment of the invention relates to a method of treating or preventing an abnormal condition associated with the FLK protein kinase.

Another preferred embodiment of the invention relates to an indolinone compound that inhibits the catalytic activity of a platelet derived growth factor protein kinase. The indolinone preferably inhibits the catalytic activity of the platelet derived growth factor protein kinase with an $IC_{50}$ less than 50 $\mu$M, more preferably with an $IC_{50}$ less than 5 $\mu$M, and most preferably with an $IC_{50}$ less than 0.5 $\mu$M.

The term "platelet derived growth factor" refers to a protein kinase that phosphorylates substrates on tyrosine residues. The platelet derived growth factor protein kinase regulates cellular functions in response to the PDGF growth factor. These cellular functions include, but are not limited to, cellular proliferation.

The chemical formulae referred herein may exhibit the phenomena of tautomerism or structural isomerism. For example, the compounds described herein may be adopt a cis or trans conformation about the double bond connecting the indolinone 3-substituent to the indolinone ring, or may be mixtures of cis and trans isomers. As the formulae drawing within this specification can only represent one possible tautomeric or structural isomeric form, it should be understood that the invention encompasses any tautomeric or structural isomeric form, or mixtures thereof, which possesses the ability to regulate, inhibit and/or modulate tyrosine kinase signal transduction or cell proliferation and is not limited to any one tautomeric or structural isomeric form utilized within the formulae drawing.

In addition to the above-described compounds, the invention is further directed, where applicable, to solvated as well as unsolvated forms of the compounds (e.g. hydrated forms) having the ability to regulate and/or modulate cell proliferation.

The compounds described herein may be prepared by any process known to be applicable to the preparation of chemically-related compounds. Suitable processes are illustrated in the examples. Necessary starting materials may be obtained by standard procedures of organic chemistry.

An individual compound's relevant activity and efficacy as an agent to affect receptor tyrosine kinase mediated signal transduction may be determined using available techniques. Preferentially, a compound is subjected to a series of screens to determine the compound's ability to modulate, regulate and/or inhibit cell proliferation. These screens, in the order in which they are conducted, include biochemical assays, cell growth assays and in vivo experiments.

The summary of the invention described above is not limiting and other features and advantages of the invention will be apparent from the following detailed description of the invention, and from the claims.

BRIEF DESCRIPTION OF THE DRAWINGS AND TABLES

FIG. 1 shows illustrative type A oxindoles.

FIG. 2 shows illustrative type B aldehydes.

Table 1 depicts examples of compounds of the invention. The table illustrates the molecular structure of each indolinone, the molecular weight of the compound, and the chemical formula of the compound.

Table 2 depicts the biological activity of select compounds of the invention. Listed are the chemical structure of the compound with $IC_{50}$ values measured in FLK-1 biological inhibition assays.

Table 3 shows preferred indole based aldehydes that can be used in the present invention.

Table 4 shows preferred oxindoles that can be used in the present invention.

Table 5 depicts examples of compounds of the invention. The table illustrates the molecular structure of each indolinone, the molecular weight of the compound, and the chemical formula of the compound.

Tables 6 and 7 depicts the biological activity of select compounds of the invention. Listed are the chemical structure of the compound with $IC_{50}$ values measured in FLK-1 and platelet derived growth factor protein kinase (PDGFR) biological inhibition assays.

Table 8 depicts examples of compounds of the invention. The table illustrates the molecular structure of exemplary indolinones and the biological activity of select compounds of the invention. Listed are the chemical structure of the compound with $IC_{50}$ values measured in FLK-1 biological inhibition assays.

Table 9 lists exemplary compounds of the invention.

Table 10 shows FLK activity data for illustrative compounds of the invention.

Table 11 shows type A oxindols.

Table 12 shows type B aldehydes.

Table 13 shows the names of several indolinone compounds of the present invention.

Table 14 shows kinase data for the compounds listed in Table 13 as determined using the assays described herein.

DETAILED DESCRIPTION OF THE INVENTION

The invention is directed in part towards designing protein kinase inhibitors that obliterate tumors by severing their sources of sustenance. The inhibitors are designed to specifically bind protein kinases over-expressed in the vasculature that supply tumors with sustenance. One such protein kinase target is FLK-1, which is over-expressed in the proliferating endothelial cells of a growing tumor, but not in the surrounding quiescent endothelial cells. Plate et al., 1992, *Nature* 359:845–848.

FLK-1 is activated upon binding VEGF, a strong regulator for endothelial cell proliferation as well as normal and pathological angiogenesis. Klagsburn and Soker, 1993, *Current Biology* 3:699–702. Thus, compounds that specifically inhibit the FLK protein kinase are potential anti-cancer agents as they may decrease the vasculature that nourishes tumors. These inhibitors will most likely result in minimizing and even obliterating solid tumors. In addition, compounds that specifically inhibit FLK will potentially represent a new generation of cancer therapeutics as they will most likely cause few side effects. These potential properties are a welcome improvement over the currently utilized cancer therapeutics that cause multiple side effects and deleteriously weaken patients.

Synthesis of Indolinone Compounds

The indolinone compounds of the invention are synthesized by reacting an aldehyde with an oxindol as shown in the examples provided herein. Descriptions of methods for synthesizing indolinone compounds are provided in the examples described herein. The examples fully describe the solvents, temperatures, separation techniques, and other conditions utilized for the invention. Other synthetic techniques, such as those described in International patent publications WO 96/22976, published Aug. 1, 1996 by Ballinari et al., and WO 96/40116, published Dec. 19, 1996 by Tang et al. may also be used or adapted by those skilled in the art to make the compounds of the present invention. Descriptions of the methods used to specifically synthesize the indolinone compounds of the invention, are disclosed herein.

Biological Activity of Indolinone Compounds

Indolinone compounds of the invention can be tested for their ability to activate or inhibit protein kinases in biological assays. The methods used to measure indolinone modulation of protein kinase function are described herein. Indolinone compounds of the invention were tested for their ability to inhibit the FLK protein kinase. The biological assay and results of these inhibition studies are reported herein.

Target Diseases to be Treated by Indolinone Compounds

Protein kinases are essential regulatory molecules that control a variety of cellular functions. For this reason, any alteration in the function of a protein kinase can cause an abnormal condition in an organism. One of the many functions controlled by protein kinases is cell proliferation.

Alterations in the function of a protein kinase that normally regulates cell proliferation can lead to enhanced or decreased cell proliferative conditions evident in certain diseases. Aberrant cell proliferative conditions include cancers such as fibrotic and mesangial disorders, abnormal angiogenesis and vasculogenesis, wound healing, psoriasis, restenosis, diabetes mellitus, and inflammation.

Fibrotic disorders and mesangial cell proliferative disorders are described in International Patent Publication No. WO 96/40116, published Dec. 19, 1996 by Tang et al.

Angiogenic and vasculogenic disorders result from excess proliferation of blood vessels. Blood vessel proliferation is necessary in a variety of normal physiological processes such as embryonic development, corpus luteum formation, wound healing and organ regeneration. However, blood vessel proliferation is also essential in cancer tumor development. Other examples of blood vessel proliferative disorders include arthritis, where new capillary blood vessels invade the joint and destroy cartilage. In addition, blood vessel proliferative diseases include ocular diseases, such as diabetic retinopathy, where new capillaries in the retina invade the vitreous, bleed and cause blindness. Conversely, disorders related to the shrinkage, contraction or closing of blood vessels, such as restenosis, are also implicated in adverse regulation of RPKs or RPPs.

Moreover, vasculogenesis and angiogenesis are associated with the growth of malignant solid tumors and metastasis. A vigorously growing cancer tumor requires a nutrient and oxygen rich blood supply to continue growing. As a consequence, an abnormally large number of capillary blood vessels often grow in concert with the tumor and act as supply lines to the tumor. In addition to supplying nutrients to the tumor, the new blood vessels embedded in a tumor provide a gateway for tumor cells to enter the circulation and metastasize to distant sites in the organism. Folkman, 1990, *J. Natl. Cancer Inst.* 82:4–6.

Angiogenic and vasculogenic disorders are closely linked to the FLK protein kinase. FLK-1 is activated upon binding VEGF, a strong regulator for endothelial cell proliferation as well as normal and pathological angiogenesis. Klagsburn and Soker, 1993, *Current Biology* 3:699–702. Thus, compounds that specifically inhibit the FLK protein kinase are potential anti-cancer agents as they may decrease the vasculature that nourishes tumors. These inhibitors will most likely result in minimizing and even obliterating solid tumors. In addition, compounds that specifically inhibit FLK will potentially represent a new generation of cancer therapeutics as they will most likely cause few side effects. These potential properties are a significant improvement over the currently utilized cancer therapeutics that cause multiple side effects and deleteriously weaken patients.

In addition to cell proliferation, some RPKs and RPPs regulate the penultimate cellular functions, cell survival and cell death. Glial derived growth factor (GDNF) activates c-ret, for example, by bringing multiple c-ret receptors together into close proximity and promoting cross phosphorylation of the intracellular regions. Signal transduction molecules that form a complex with c-ret as a result of these phosphoryl moieties, such as grb-2, sos, ras, and raf, propagate a signal in the cell that promotes neural survival. Thus, compounds that promote the interactions of these stimulatory molecules of c-ret would enhance the activity of c-ret. Alternatively, protein phosphatases can remove the phosphoryl moieties placed on the intracellular region of c-ret in response to GDNF, and thus inhibit the signaling capability of c-ret. Thus compounds that inhibit phosphatases of c-ret will enhance the signaling capacity of c-ret. In the context of the present invention, the c-ret protein kinase could be activated by indolinone compounds that are modified with substituents, particularly at the 5 position of the oxindole ring.

c-ret is implicated in the development and survival of enteric, synaptic, and sensory neurons and neurons of the renal system upon stimulation by GDNF. Lack of function mutations in c-ret can lead to Hirschsprung's disease, for example, which manifests itself as a decrease in intestinal tract innervation in patients. Thus, compounds that activate c-ret are potential therapeutic agents for the treatment of neurodegenerative disorders, including, but not limited to, Hirschsprung's disease, Parkinson's disease, Alzheimer's disease, and amyotrophic lateral sclerosis. Compounds that inhibit c-ret function are possible anti-cancer agents as over-expression of ret in cells is implicated in cancers, such as cancer of the thyroid.

Pharmaceutical Compositions and Administration of Indolinone Compounds

Methods of preparing pharmaceutical formulations of the compounds, methods of determining the amounts of compounds to be administered to a patient, and modes of administering compounds to an organism are disclosed in International Patent Publication No. WO 96/22976, published Aug. 1, 1996 by Ballinari et al., which is incorporated herein by reference in its entirety, including any drawings. Those skilled in the art will appreciate that such descriptions are applicable to the present invention and can be easily adapted to it. The mechanism of such action and possible uses for such compounds are described in International Patent Publication WO 96/40116, published Dec. 19, 1996 by Tang et al.

The compounds described herein can be administered to a human patient per se, or in pharmaceutical compositions where it is mixed with suitable carriers or excipient(s). Techniques for formulation and administration of the compounds of the instant application may be found in "Remington's Pharmaceutical Sciences," Mack Publishing Co., Easton, Pa., latest edition or in International Patent Publication No. WO 96/40116, published Dec. 19, 1996 by Tang et al.

Effective Dosage

Pharmaceutical compositions suitable for use in the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein and in International Patent Publication No. WO 96/40116, published Dec. 19, 1996 by Tang et al.

Packaging

The compositions may, if desired, be presented in a pack or dispenser device which may contain one or more unit dosage forms containing the active ingredient according to the description provided in International Patent Publication No. WO 96/40116, published Dec. 19, 1996 by Tang et al.

EXAMPLES

The examples below are not limiting and are merely representative of various aspects and features of the present invention. The examples demonstrate methods of synthesizing indolinone compounds of the invention. The examples also demonstrate the specificity as well as the potency with which these compounds inhibit protein kinase function in cells.

Example 1

Compound Synthesis

The compounds of the present invention may be synthesized according to known techniques such as those described in International Patent Publication No. WO 96/40116, published Dec. 19, 1996 by Tang et al. The following represent preferred methods for synthesizing the compounds of the claimed invention.

(a) Preparation of 4-Methyl-2-oxindole. Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternatively with 10% sodium hydroxide and 30% hydrogen peroxide until the dark color was no longer present. The solid was filtered off and the filtrate acidified with 6N hydrochloric acid. The resulting precipitate was collected by vacuum filtration, washed with water, and dried under vacuum to give 9.8 g (45% yield) of 1-methyl-6-nitrophenylacetic acid as an off-white solid. The sold was hydrogenated in methanol over 10% palladium on carbon to give 9.04 g of the title compound as a white solid.

(b) Preparation of 5-Nitro-2-oxindole. The 2-oxindole (6.5 g) was dissolved in 25 mL of concentrated sulfuric acid and the mixture maintained at −10–15° C. while 2.1 mL of fuming nitric acid was added dropwise. After the addition of the nitric acid the reaction mixture was stirred at 0° C. for 0.5 hr and poured into ice water. The precipitate was collected by filtration, washed with water and crystallized from 50% of the acetic acid. The final crystal was then filtered, washed with water and dried under vacuum to give 6.3 g (70%) of 5-nitro-2-oxindole.

(c) Preparation of 5-Amino-2-oxindole. The 5-nitro-2-oxindole (6.3 g) was hydrogenated in methanol over 10% palladium on carbon to give 3.0 g (60% yield) of the title compound as a white solid.

(d) Preparation of 5-Fluoro-2-oxindole. 5-Fluoroisatin (8.2 g) was dissolved in 50 mL of hydrazine hydrate and refluxed for 1 hr. The reaction mixtures were then poured in ice water. The precipitate was then filtered, washed with water and dried under vacuum oven to give 6.0 g of 5-fluoro-2-oxindole (79% yield).

(e) Preparation of 5-Bromo-2-oxindole. 2-Oxindole (1.3 g) in 20 mL of acetonitrile was cooled to −10° C. and 2.0 g of N-bromosuccinimide was slowly added with stirring. The reaction was stirred for 1 hour at −10° C. and 2 hours at 0° C. The precipitate was collected, washed with water and dried to give 1.9 g (90% yield) of the title compound.

(f) Preparation 5-Carboxy-2-oxindole

Step 1. Synthesis of 5-Methoxycarbonyl-2-oxindole. 5-Iodo-2-oxindole (17 g) was refluxed with 2 g of palladium diacetate, 18.15 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on a silica gel in 30% ethyl acetate in hexane. The fractions containing product were concentrated and allowed to stand. The precipitated product was collected by vacuum filtration to give 0.8 g (7%) of the title compound as an off-white solid.

Step 2: Synthesis of 5-Carboxy-2-oxindole. 5-Methoxycarbonyl-2-oxindole (1 g) and 1 g of sodium hydroxide in 20 mL of methanol was refluxed for 3 hours. The reaction mixture was cooled and concentrated to dryness. The residue was dissolved in water and extracted twice with ethyl acetate. The aqueous layer was acidified with 6 N hydrochloric acid and the precipitated solid collected, washed with water, and dried to give 0.7 g (78%) of the title compound as an off-white solid.

(g) Preparation of 5-Carboxyethyl-2-oxindole

Step 1: Synthesis of 5-Chloroacetyl-2-oxindole. Aluminum chloride (30.8 g) and 2-oxindole (5.0 g) were added to 200 ml of carbon disulfide at room temperature and the mixture stirred. Chloroacetyl chloride (3.8 mL) was added and the stirring continued for 1 hour. The mixture was heated to reflux for 3 hours, cooled and the solvent decanted. The residue was stirred in ice water until it became a solid suspension. The solid was collected by vacuum filtration, washed in water, and dried to give 7.0 g (90% yield) of the title compound.

Step 2: Synthesis of 5-Chloroethyl-2-oxindole. 5-Chloroacetyl-2-oxindole (7.0 g) was added to 25 mL of trifluoroacetic acid and the mixture cooled in an ice bath with stirring. Triethylsilane (12.3 mL) was added dropwise over 2 minutes. The reaction was then stirred at room temperature for 4 hours and poured into ice water. Hexane was added, the mixture stirred vigorously, and the solid collected by vacuum siltation and washed with hexane to give 5.9 g (91% yield) of the product as a white solid.

Step 3: Synthesis of 5-Cyanoethyl-2-oxindole. Potassium cyanide (2.02 g) was added to 15 mL of dimethylsulfoxide and heated to 90° C. 5-Chloroethyl-2-oxindole (3.0 g) dissolved in 5 mL of dimethylsulfoxide was added slowly with stirring, and the reaction heated to 150° C. for 2 hours. The mixture was cooled, poured into ice water and the precipitate collected by vacuum filtration, washed with water, and dried to give crude product. The crude material was chromatographed on silica gel in 5% methanol in chloroform to give 1.2 g (42% yield) of the title compound.

Step 4: Synthesis of 5-Carboxyethyl-2-oxindole. 5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

(h) Preparation of 3,5-Dimethylpyrrol-2-carboxaldehyde

5-Cyanoethly-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

(i) Preparation of 3,5-Dimethylpyrrol-2-carboaldehyde

To a solution dimethylformamide (80.4 g) and 1 L of dichloroethane at 0° C. was added phosphorous oxychoride (153.3 g) over a few minutes and the reaction stirred for 1–2 hr at 0° C. 2,4-Dimethylpyrrole (114.6 g) was added dropwise to the above solution at temperature below 5° C. After the addition was complete the reaction was heated and the aqueous layer isolated and saved. The organic layer was extracted again with 300 mL of water and the two aqueous layers combined. The aqueous phase was extracted with 200 mL of dichloroethane and the organic layer discarded. The aqueous phase was cooled to 10° C. and adjusted to pH 10 with 10% sodium hydroxide. The mixture was stirred at 10° C. for 2 hr. The yellow solid was collected by vacuum filtration and washed thoroughly with water. The solid was dried at room temperature under vacuum to give 110.8 g (90% yield of 2,4-dimethyl-5-formylpyrrole.

(j) Preparation of 3,5-Diethylpyrrol-2-carboxaldehyde:

The solution of 25.0 g of 3,5-heptanedione and 42.3 g of diethyl aminomalonate hydrochloride in 200 mL of acetic acid was heated to 95–10° C. for 1.25 hr. Sodium acetate was added and the reaction mixture was stirred for 5.35 hr and cooled down for 4 hr. The salt was filtered and washed with acetic acid. The acetic acid solution was then concentrated and the residue poured into 800 mL of water. The yellow solid was filtered and dried in a vacuum oven overnight to give 36.0 g of ethyl 3,5-diethlypyrrol-2-carboxalate as the orange liquid (92% yield).

Decarboxylation of ethyl 3,5-diethylpyrro-2-carboxalate upon hydrolysis gave 2,4-diethylpyrrole. The title compound was then synthesized via Vilsmeier formulation of 2,4-diethlpyrrole with the same condition used for the preparation of 3,5-dimethylpyrrol-5-carboxaldehyde.

(k) Preparation of 3,5-Diisopropylpyrrol-2-carboxaldehyde

The procedure was the same as the one for the preparation of 3,5-diethylpyrrol-2-carboxaldehyde except starting with 2,6-dimethyl-3,5-heptanedione.

Example 2

FLK Inhibition by Indolinone Compounds of the Invention

An enzyme linked immunosorbent assay (ELISA) was conducted to measure the catalytic activity of the FLK-1 receptor and more specifically, the inhibition or activation of indolinone compounds on the catalytic activity of the FLK-1 receptor. Specifically, the following assay was conducted to measure catalytic activity of the FLK-1 receptor in FLK-1/NIH3T3 cells.

The materials and protocol for the FLK-1 ELISA assay are as described in International Patent Publication No. WO 96/40116, published Dec. 19, 1996 by Tang et al.

Selected compounds were tested in the FLK-1 ELISA assay. IC50 measurements are reported in the tables. Derivatives of 3-[(indole-3-yl)methylene]-2-indolinone compounds with a methyl substituent at the 1' position proved to be the most potent inhibitors of the group of compounds tested in the assay.

Example 3

In Vitro RTK Assays

The following in vitro assays may be used to determine the level of activity and effect of the different compounds of the present invention on one or more of the RTKs. Similar assays can be designed along the same lines for any tyrosine kinase using techniques well known in the art.

(a) Enzyme Linked Immunosorbent Assay (ELISA)

Enzyme linked immunosorbent assays (ELISA) may be used to detect and measure the presence of tyrosine kinase activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific RTK. For example, the preferred protocols for conducting the ELISA experiments for specific RTKs is provided below. Adaptation of these protocols for determining a compound's activity for other members of the RTK family, as well as other receptor and non-receptor tyrosine kinases, are within the scope of those in the art.

(i) FLK-1 ELISA

An ELISA assay was conducted to measure the kinase activity of the FLK-1 receptor and more specifically, the inhibition or activation of protein tyrosine kinase activity on the FLK-1 receptor. Specifically, the following assay was conducted to measure kinase activity of the FLK-1 receptor in FLK-1/NIH3T3 cells.

Materials And Methods

Materials. The following reagents and supplies were used:
a. Corning 96-well ELISA plates (Corning Catalog No. 25805-96);
b. Cappel goat anti-rabbit IgG (catalog no. 55641);
c. PBS (Gibco Catalog No. 450-1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% glycerol);
g. EDTA (0.5 M (pH 7.0) as a 100× stock);
h. Sodium ortho vanadate (0.5 M as a 100× stock);
i. Sodium pyro phosphate (0.2M as a 100× stock);
j. NUNC 96 well V bottom polypropylene plates (Applied Scientific Catalog No. AS-72092);
k. NIH3T3 C7#3 Cells (FLK-1 expressing cells);
l. DMEM with 1× high glucose L Glutamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20) (kept as 1 μg/100 μl stock in Milli-Q dH$_2$O and stored at −20° C.;
p. Affinity purified anti-FLK-1 antiserum which can be obtained or purified as follows:
  1. Prepare a Tresyl-Activated Agarose/Flk-1-D column by incubating 10 ml of Tresyl-Activated Agarose with 20 mg of purified GST-Flk-1-D fusion protein in 100 mM sodium bicarbonate (pH 9.6) buffer overnight at 4° C.
  2. Wash the column once with PBS.
  3. Block the excess sites on the column with 2 M glycine for 2 hours at 4° C.
  4. Wash the column with PBS.
  5. Incubate the column with Rabbit anti-Flk-1D production bleed for 2 hours at 4° C.
  6. Wash the column with PBS.
  7. Elute antiserum with 100 mM Citric Acid, pH3.0 and neutralize the eluate immediately with 2 M Tris, pH 9.0.
  8. Dialyize the eluate against PBS overnight at 4° C. with 3 changes of buffer (sample to buffer ratio is 1:100).
  9. Adjust the dialyized antiserum to 5% glycerol and store at −80° C. in small aliquotes.
q. UB40 monoclonal antibody specific for phosphotyrosine, (see, Fendley, et al., 1990, *Cancer Research* 50:1550–1558);
r. EIA grade Goat anti-mouse IgG-POD (BioRad catalog no. 172-1011);
s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use;

t. H$_2$O$_2$ (30% solution) (Fisher catalog no. H325);

u. ABTS/H$_2$O$_2$ (15 ml ABTS solution, 2 μl H$_2$O$_2$) prepared 5 minutes before use and left at room temperature;

v. 0.2 M HCl stock in H$_2$O;

w. dimethylsulfoxide (100%) (Sigma Catalog No. D-8418); and x. Trypsin-EDTA (Gibco BRL Catalog No. 25200-049).

Protocol. The following protocol was used for conducting the assay:

1. Coat Corning 96-well elisa plates with 1.0 μg per well Cappel Anti-rabbit IgG antibody in 0.1M Na$_2$CO$_3$ pH 9.6. Bring final volume to 150 μl per well. Coat plates overnight at 4° C. Plates can be kept up to two weeks when stored at 4° C.

2. Grow cells in Growth media(DMEM, supplemental with 2.0 mM L-Glutamine, 10% FBS) in suitable culture dishes until confluent at 37° C., 5% CO$_2$.

3. Harvest cells by trypsinization and seed in Corning 25850 polystyrene 96-well roundbottom cell plates, 25.000 cells/well in 200 μl of growth media.

4. Grow cells at least one day at 37° C., 5% CO$_2$.

5. Wash cells with D-PBS 1×.

6. Add 200 μl/well of starvation media (DMEM, 2.0 mM 1-Glutamine, 0.1% FBS). Incubate overnight at 37° C., 5% CO$_2$.

7. Dilute Compounds/Extracts 1:20 in polypropylene 96 well plates using starvation media. Dilute dimethylsulfoxide 1:20 for use in control wells.

8. Remove starvation media from 96 well cell culture plates and add 162 μl of fresh starvation media to each well.

9. Add 18 μl of 1:20 diluted Compound/Extract dilution (from step 7) to each well plus the 1:20 dimethylsulfoxide dilution to the control wells (+/– VEGF), for a final dilution of 1:200 after cell stimulation. Final dimethylsulfoxide is 0.5%. Incubate the plate at 37° C., 5% CO$_2$ for two hours.

10. Remove unbound antibody from ELISA plates by inverting plate to remove liquid. Wash 3 times with TBSW+ 0.5% ethanolamine, pH 7.0. Pat the plate on a paper towel to remove excess liquid and bubbles.

11. Block plates with TBSW+0.5% Ethanolamine, pH 7.0, 150 μl per well. Incubate plate thirty minutes while shaking on a microtiter plate shaker.

12. Wash plate 3 times as described in step 10.

13. Add 0.5 μg/well affinity purified anti-FLU-1 polyclonal rabbit antiserum. Bring final volume to 150 μl/well with TBSW+0.5% ethanolamine pH 7.0. Incubate plate for thirty minutes while shaking.

14. Add 180 μl starvation medium to the cells and stimulate cells with 20 μl/well 10.0 mM sodium ortho vanadate and 500 ng/ml VEGF (resulting in a final concentration of 1.0 mM sodium ortho vanadate and 50 ng/ml VEGF per well) for eight minutes at 37° C., 5% CO$_2$. Negative control wells receive only starvation medium.

15. After eight minutes, media should be removed from the cells and washed one time with 200 μl/well PBS.

16. Lyse cells in 150 μl/well HNTG while shaking at room temperature for five minutes. HNTG formulation includes sodium ortho vanadate, sodium pyro phosphate and EDTA.

17. Wash ELISA plate three times as described in step 10.

18. Transfer cell lysates from the cell plate to elisa plate and incubate while shaking for two hours. To transfer cell lysate pipette up and down while scrapping the wells.

19. Wash plate three times as described in step 10.

20. Incubate ELISA plate with 0.02 μg/well UB40 in TBSW+05% ethanolamine. Bring final volume to 150 μl/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW+0.5% ethanolamine, pH 7.0. Bring final volume to 150 μl/well. Incubate while shaking for thirty minutes.

23. Wash plate as described in step 10.

24. Add 100 μl of ABTS/H$_2$O$_2$ solution to well. Incubate ten minutes while shaking.

25. Add 100 μl of 0.2 M HCl for 0.1 M HCl final to stop the color development reaction. Shake 1 minute at room temperature. Remove bubbles with slow stream of air and read the ELISA plate in an ELISA plate reader at 410 nm.

(ii) HER-2 ELISA

HER-2 ELISA assays are described in International Patent Publication No. WO 96/40116, published Dec. 19, 1996 by Tang et al.

(iii) PDGF-R ELISA

A PDGF-R ELISA is described in International Patent Publication No. WO 96/40116, published Dec. 19, 1996 by Tang et al.

(iv) IGF-I ELISA

The IGF-I ELISA protocol described in International Patent Publication No. WO 96/40116, published Dec. 19, 1996 by Tang et al. may be used to measure phosphotyrosine level on IGF-I receptor, which indicates IGF-I receptor tyrosine kinase activity.

(v) EGF Receptor ELISA

EGF Receptor kinase activity (EGFR-NIH3T3 assay) in whole cells was measured as described in International Patent Publication No. WO 96/40116, published Dec. 19, 1996 by Tang et al.

(vi) Cellular Insulin Receptor ELISA

The protocol described in International Patent Publication No. WO 96/40116, published Dec. 19, 1996 by Tang et al. was used to determine whether the compounds of the present invention possessed insulin receptor tyrosine kinase activity.

(vii) EGFR ELISA ASSAY

Purpose

To provide a consistent method for measuring the in vitro kinase activity of the EGFR in an Enzyme-linked immunosorbent assay (Elisa).

Scope. The following protocol describes the procedures used to analyze protein tyrosine kinase activity on the EGFR in an Elisa. The procedure also describes the protocol for the initial screening of drugs for inhibition or activation of protein tyrosine kinase activity.

Reagents and Supplies.

1. Corning 96-well Elisa plates

Corning Catalog # 25805-96
2. 05–101 monoclonal anti-EGFR antibody (commercially available from UB1)

–80° C., 1 ml aliquots
3. PBS (Dulbecco's Phosphate-Buffered Saline) Gibco Catalog # 450-1300 EB Formulation: 2.7 mM KCL
   1.1 mM KH$_2$PO$_4$
   0.5 mM MgCl$_2$ (anhydrous)
   138 mM NaCl
   8.1 mM Na$_2$HPO$_4$ -continued 4. TBST Buffer Formulation: 50 mM Tris pH 7.2
   150 mM NaCl
   0.1% Triton X-100
5. Blocking Buffer Formulation: 5% Carnation Instant Milk in PBS
6. A431 cell lysate A431 cells are available from a variety of commercial sources and may be used lysed using conventional methods known to those skilled in the art or as described for lysis of the 3T3 cells in the EGF cellular assay described herein. −80° C., 1 ml aliquots
7. TBS Buffer Formulation: 50 mM Tris pH 7.2
   150 mM NaCl
8. TBS + 10% DMSO Formulation: 10% DMSO in TBS Buffer
   (DMSO from Sigma, Catalog # D-2650)
9. ATP/MnCl$_2$ phosphorylation mix Formulation: 0.03 mM ATP
   (Adenosine-5'-triphosphate, Sigma Catalog # A-5394)
   50 mM MnCl$_2$
   Make fresh in autoclaved Milli-Q H$_2$O immediately before use
   Keep on ice until use
10. NUNC 96-well V bottom polypropylene plates
    Applied Scientific Catalog # AS-72092
11. EDTA Formulation: 200 mM EDTA pH 8.0
12. Rabbit polyclonal anti-phosphotyrosine serum or UB40 monoclonal antibody specific for phosphotyrosine or UBI's mab 4610, Upstate Biotechnology, Lake Placid, New York, Catalog # 05-321
    −80° C., 1 ml aliquots
    Thaw 1 ml vial and aliquot in smaller volumes to store at −80° C. Antiserum is stable for weeks when thawed and stored at 4 C.
13. Goat anti-rabbit IgG peroxidase conjugate Biosource Catalog # ALI0404
14. ABTS Solution Formulation: 100 mM Citric Acid (anhydrous)
    250 mM Na$_2$HPO$_4$ pH 4.0
    0.5 mg/ml ABTS
    (2,2'-azino-bis(3-ethylbenzthiazoline-6-sulfonic acid)
    (Sigma Catalog # A-1888)
    Keep solution in dark at 4 C. until ready to use
15. Hydrogen peroxide 30% solution Fisher Catalog # H325
    Store in the dark at 4 C. until ready to use
16. ABTS/H$_2$O$_2$ Formulation: 15 mls ABTS solution
    2 ul H$_2$O$_2$
    Prepare 5 minutes before use and room temperature
17. 0.2M HCL stock in H$_2$O Procedure 1. Coat Corning 96-well elisa plates with 0.5 ug per well 05-101 antibody.

Bring final volume to 100 ul per well with PBS.
   Coat plates overnight at 4° C.
2. Remove unbound 05-101 from wells by inverting plate to remove liquid.
   Wash 1× with distilled H2O by filling wells
   Pat the plate on a paper towel to remove excess liquid.
3. Block plates with 5% milk in PBS.
   150 ul per well.
   Incubate plate 30 minutes while shaking on a microtiter plate shaker.

4. Wash plate 3× with dionized water, then once with TBST
5. Add 7 ug A431 cell lysate per well (EGFR source).
   Add PBS to final volume of 100 ul per well
   Incubate 30 minutes while shaking.
6. Wash as described in step 4.
7. At this point, drugs or extracts are added to the wells.
   Dilute drugs/extracts 1:100 (unless specified otherwise) in TBS+10% DMSO in 96-well polypropylene plates.
   Add 120 ul TBS to ELISA plate containing captured EGFR.
   Add 13.5 ul diluted drugs/extracts to ELISA plate.
   To control wells (wells which do not receive any drug) add 135 ul TBS+1% DMSO.
   Incubate plate 30 minutes while shaking.
8. Add 15 ul of 0.03 mM ATP+50 mM MnCl$_2$ phosphorylation mix directly to all wells except negative control well which does not receive ATP/MnCl$_2$ (see diagram).
   (150 ul final volume in well with 3 uM ATP/5 mM MnCl2 final concentration in well.)
   Incubate 5 minutes while shaking vigorously.
   *NOTE: It is critical that ATP/MnCl2 phosphorylates the receptor for 5 minutes only.
   It is best to add the ATP/MnCl$_2$ with an 12 channel pipettor 1 row at a time leaving 20 seconds between each row so that the reaction may be stopped with EDTA exactly 5 minutes later (this depends on the number of plates being phosphorylated in one batch). Shake between each addition.
9. After 5 minutes, to stop reaction, add 16.5 ul of 200 mM EDTA pH 8.0 for 20 mM final in well, shaking continuously between each addition. This is done using the same timing method as above. After last row has received EDTA, shake plate an additional minute.
10. Wash 4× with deionized water, twice with TBST.
11. Add rabbit polyclonal anti-phosphotyrosine serum.
    Dilute 1:3000 in TBST.
    Add 100 ul per well.
    Incubate 30–45 minutes while shaking.
12. Wash as described above in step 4.
13. Add BioSource anti-rabbit peroxidase conjugate antibody.
    Dilute 1:2000 in TBST.
    Add 100 ul per well.
    Incubate 30 minutes while shaking.
14. Wash as described in step 4.
15. Add 100 ul of ABTS/H$_2$O$_2$ solution to well.
    Incubate 5 to 10 minutes while shaking.
    Remove bubbles
16. If necessary stop reaction with the addition of 100 ul of 0.2M HCl per well
17. Read assay on Dynatech MR7000 elisa reader.
    Test Filter: 410 nM
    Reference Filter: 630 nM (b) Cell Growth Assays The cell growth assays described in International Patent Publication No. WO 96/40116, published Dec. 19, 1996 by Tang et al. may be conducted to measure the effect of the claimed compounds upon cell growth as a result of the compound's interaction with one or more RTKs.

(vi) Assay Measuring Phosphorylating Function of Raf

The following assay reports the amount of RAF-catalyzed phosphorylation of its target protein MEK as well as MEK's target MAPK. The RAF gene sequence is described in Bonner et al., 1985, *Molec. Cell. Biol.* 5: 1400–1407, and is readily accessible in multiple gene sequence data banks. Construction of the nucleic acid vector and cell lines utilized for this portion of the invention are fully described in Morrison et al., 1988, *Proc. Natl. Acad. Sci. USA* 85: 8855–8859.

Materials and Reagents

1. Sf9 (*Spodoptera frugiperda*) cells; GIBCO-BRL, Gaithersburg, Md.

2. RIPA buffer: 20 mM Tris/HCl pH 7.4, 137 mM NaCl, 10% glycerol, 1 mM PMSF, 5 mg/L Aprotenin, 0.5% Triton X-100;

3. Thioredoxin-MEK fusion protein (T-MEK): T-MEK expression and purification by affinity chromatography were performed according to the manufacturer's procedures. Catalog# K 350-01 and R 350-40, Invitrogen Corp., San Diego, Calif.

4. His-MAPK (ERK 2); His-tagged MAPK was expressed in XL1 Blue cells transformed with pUC18 vector encoding His-MAPK. His-MAPK was purified by Ni-affinity chromatography. Cat# 27-4949-01, Pharmacia, Alameda, Calif.

5. Sheep anti mouse IgG: Jackson laboratories, West Grove, Pa. Catalog, # 515-006-008, Lot# 28563

6. RAF-1 protein kinase specific antibody: URP2653 from UBI.

7. Coating buffer: PBS; phosphate buffered saline, GIBCO-BRL, Gaithersburg, Md.

8. Wash buffer: TBST—50 mM Tris/HCL pH 7.2, 150 mM NaCl, 0.1% Triton X-100

9. Block buffer: TBST, 0.1% ethanolamine pH 7.4

10. DMSO, Sigma, St. Louis, Mo.

11. Kinase buffer (KB): 20 mM Hepes/HCl pH 7.2, 150 mM NaCl, 0.1% Triton X-100, 1 mM PMSF, 5 mg/L Aprotenin, 75 $\mu$M sodium ortho vanadate, 0.5 mM DTT and 10 mM $MgCl_2$.

12. ATP mix: 100 mM $MgCl_2$, 300 $\mu$M ATP, 10 $\mu$Ci $\gamma$-$^{33}$P ATP (Dupont-NEN)/mL.

13. Stop solution: 1% phosphoric acid; Fisher, Pittsburgh, Pa.

14. Wallac Cellulose Phosphate Filter mats; Wallac, Turku, Finland.

15. Filter wash solution: 1% phosphoric acid, Fisher, Pittsburgh, Pa.

16. Tomtec plate harvester, Wallac, Turku, Finland.

17. Wallac beta plate reader # 1205, Wallac, Turku, Finland.

18. NUNC 96-well V bottom polypropylene plates for compounds Applied Scientific Catalog # AS-72092.

Procedure

All of the following steps are conducted at room temperature unless specifically indicated.

1. ELISA plate coating: ELISA wells are coated with 100 $\mu$L of Sheep anti mouse affinity purified antiserum (1 $\mu$g/100 $\mu$L coating buffer) over night at 4° C. ELISA plates can be used for two weeks when stored at 4° C.

2. Invert the plate and remove liquid. Add 100 $\mu$L of blocking solution and incubate for 30 min.

3. Remove blocking solution and wash four times with wash buffer. Pat the plate on a paper towel to remove excess liquid.

4. Add 1 $\mu$g of purified Sumo 22 to each well and incubate for 1 hour. Wash as described in step 3.

5. Thaw lysates from RAS/RAF infected Sf9 cells and dilute with TBST to 10 $\mu$g/100 $\mu$L. Add 10 $\mu$g of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10 000×g). Aliquots of lysates are frozen in dry ice/ethanol and stored at −80° C. until use.

6. Remove non-bound material and wash as outlined above (step 3).

7. Add 2 $\mu$g of T-MEK and 2 $\mu$g of His-MAPK per well and adjust the volume to 40 $\mu$L with kinase buffer.

8. Predilute compounds (stock solution 10 mg/mL DMSO) or extracts 20 fold in TBST plus 1% DMSO. Add 5 $\mu$L of the prediluted compounds/extracts to the wells described in step 6. Incubate for 20 min. Controls receive no drug.

9. Start the kinase reaction by addition of 5 $\mu$L ATP mix; Shake the plates on an ELISA plate shaker during incubation.

10. Stop the kinase reaction after 60 min by addition of 30 $\mu$L stop solution to each well.

11. Place the phosphocellulose mat and the ELISA plate in the Tomtec plate harvestor. Harvest and wash the filter with the filter wash solution according to the manufacturers recommendation. Dry the filter mats. Seal the filter mats and place them in the holder. Insert the holder into radioactive detection apparatus and quantitate the radioactive phosphorous on the filter mats.

Alternatively, 40 $\mu$L aliquots from individual wells of the assay plate can be transferred to the corresponding positions on the phosphocellulose filter mat. After air-drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantitate the radioactive phosphorous on the filter mats.

(c) Toxicity and Animal Models

Measurement Of Cell Toxicity and In Vivo Animal Models are described in International Patent Publication No. WO 96/40116, published Dec. 19, 1996 by Tang et al.

(d) MET Biochemical Kinase Assay

A met biochemical kinase assay may be performed for met generally as described above for other kinases by substituting that or the other kinases. In particular, ELISA plates are coated with goat anti-rabbit Fc antibodies, which are used to capture commercially available (from Santa Cruz Biotechnology) rabbit polyclonal antibodies to the cytoplasmic domain of human MET. Lysates are made from 293T cells that have been transiently transfected with a chimeric receptor composed of the extracellular domain of the EGFr and the transmembrane and cytoplasmic domain of the MET receptor, or from NCI-H441 cells (a human lung adenocarcinoma cell line) which express high endogenous levels of MET. The chimeric receptors, or MET, from these lysates are captured on the antibody coated plates. After washing away extraneous proteins, test compounds are added and an in vitro kinase assay is performed by addition of an appropriate kinase buffer (containing ATP, divalent metal ions, etc.). Incorporation of phosphate into the captured receptors is detected with an anti-phosphotyrosine antibody conjugate with horse radish peroxidase using TMB as a substrate for calorimetric detection.

The present invention is not to be limited in scope by the exemplified embodiments which are intended as illustrations of single aspects of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

Other embodiments are within the following claims.

TABLE 1

TABLE 1-continued

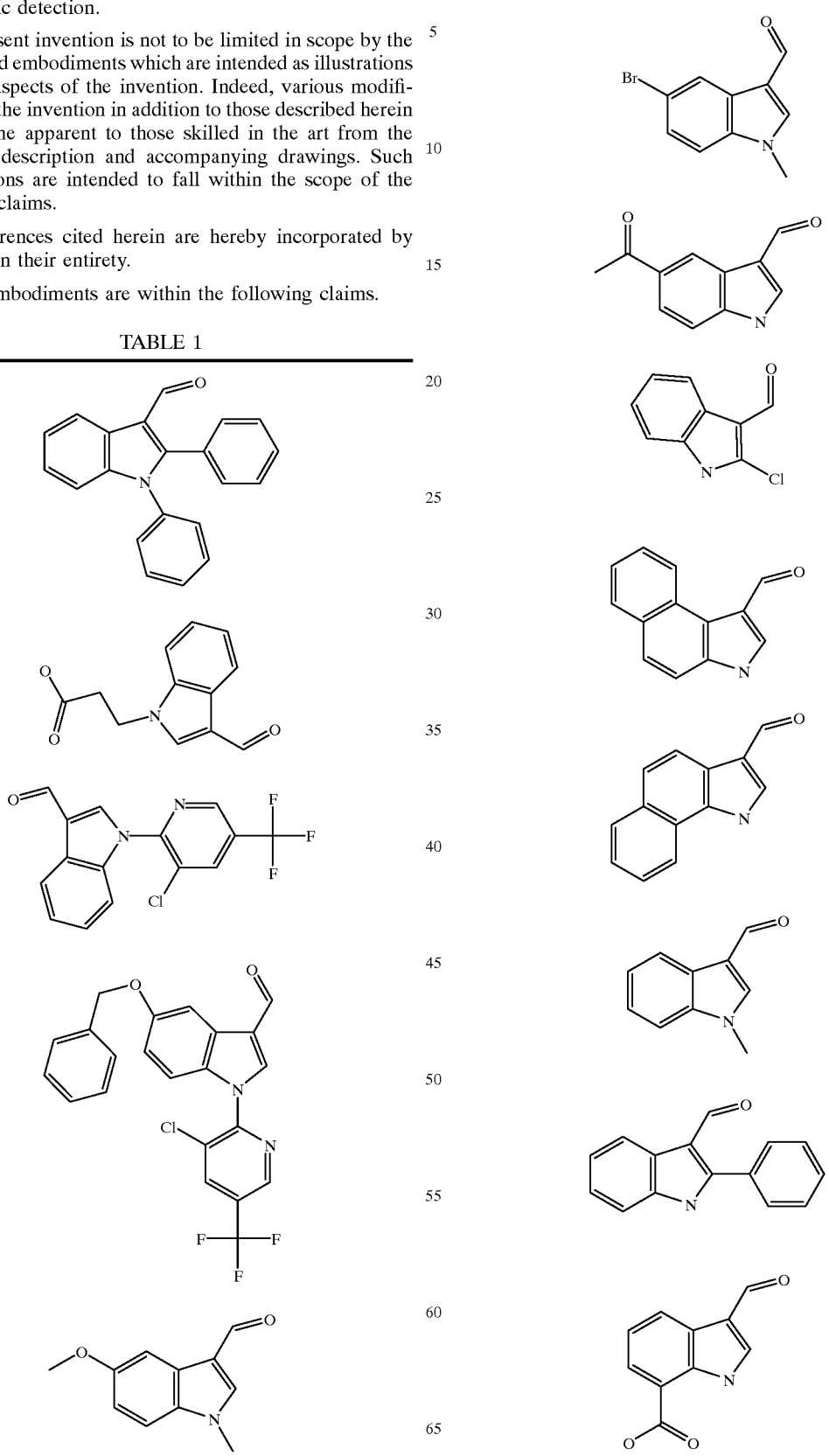

TABLE 1-continued
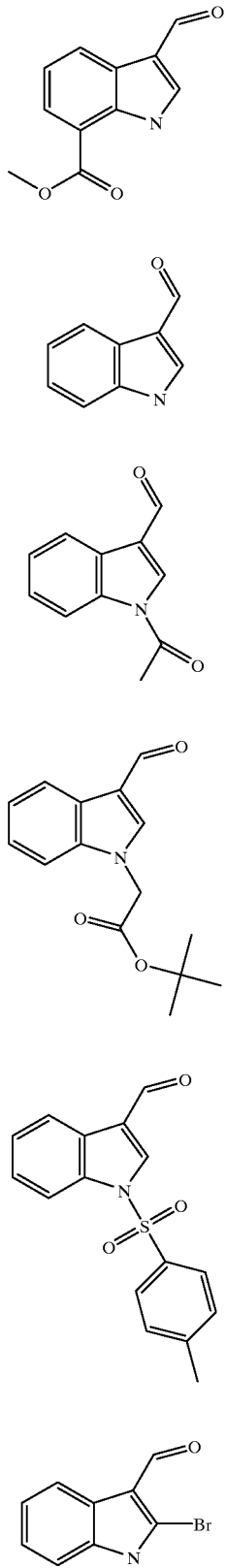
TABLE 1-continued
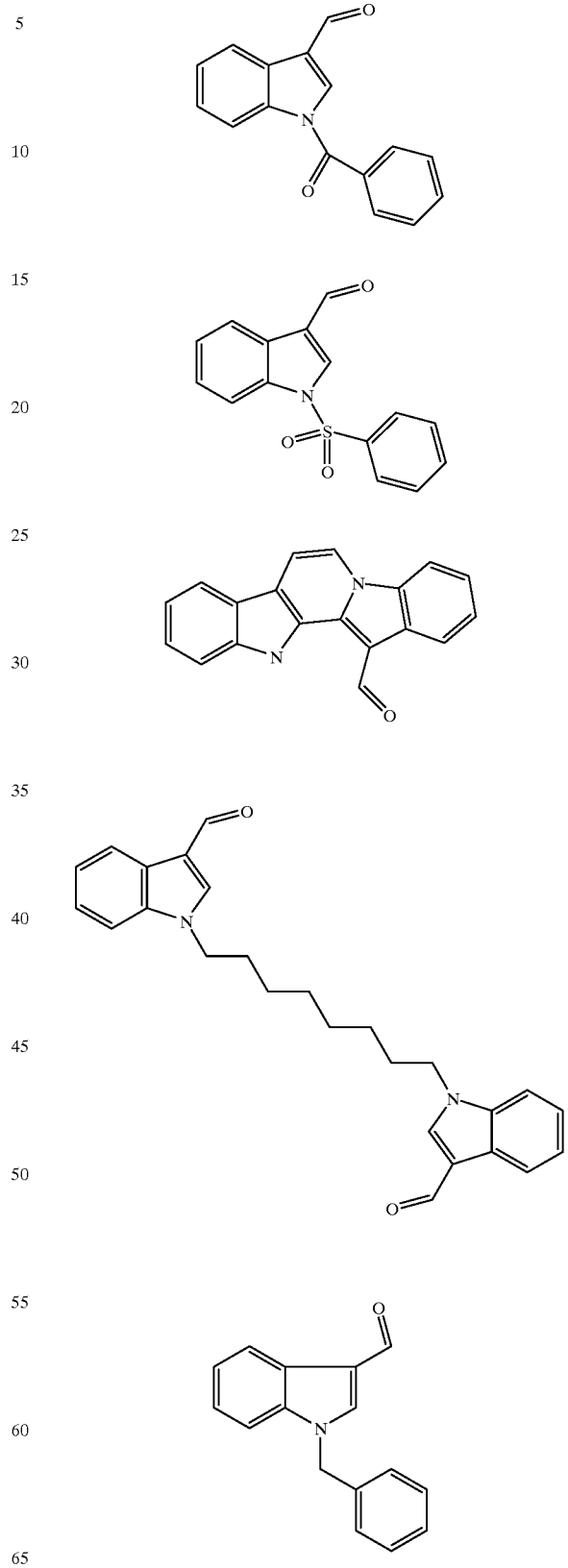

TABLE 1-continued
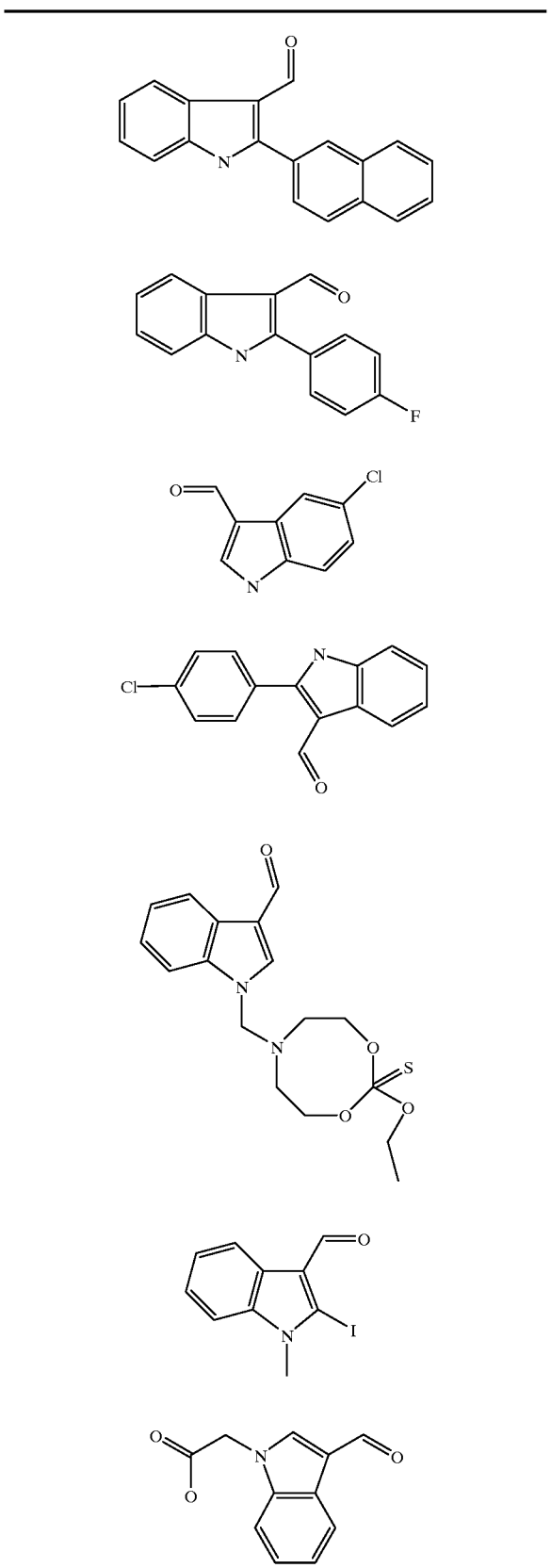
TABLE 1-continued
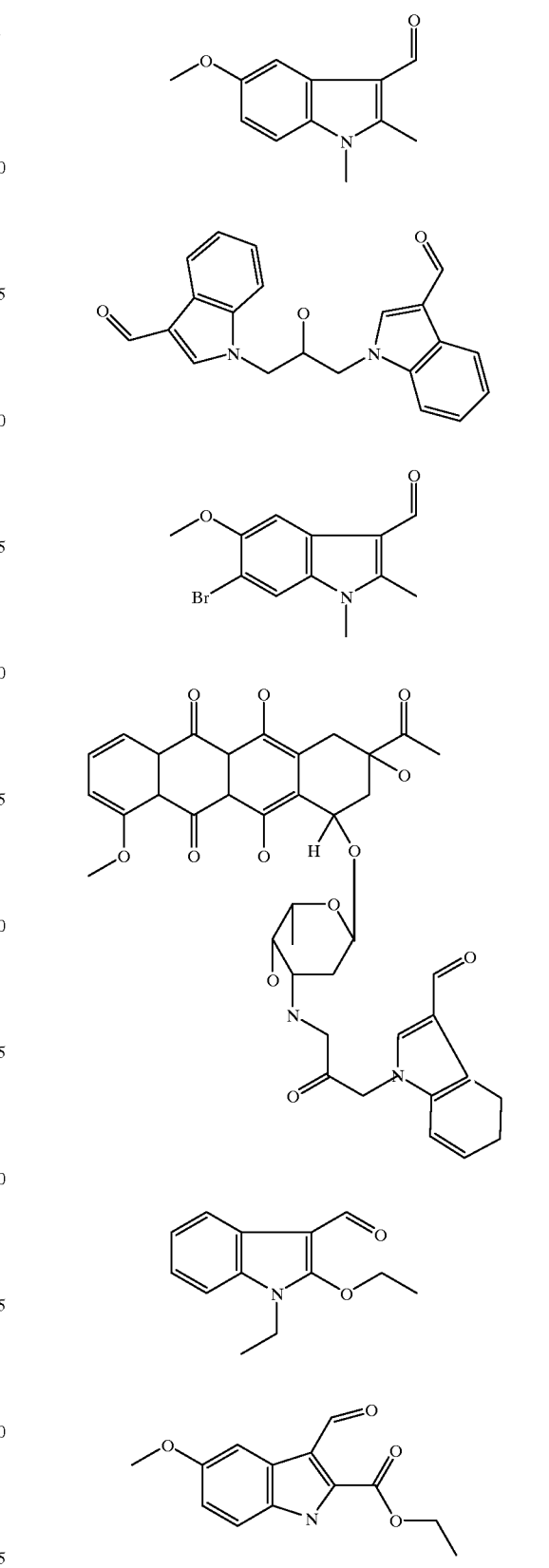

TABLE 1-continued
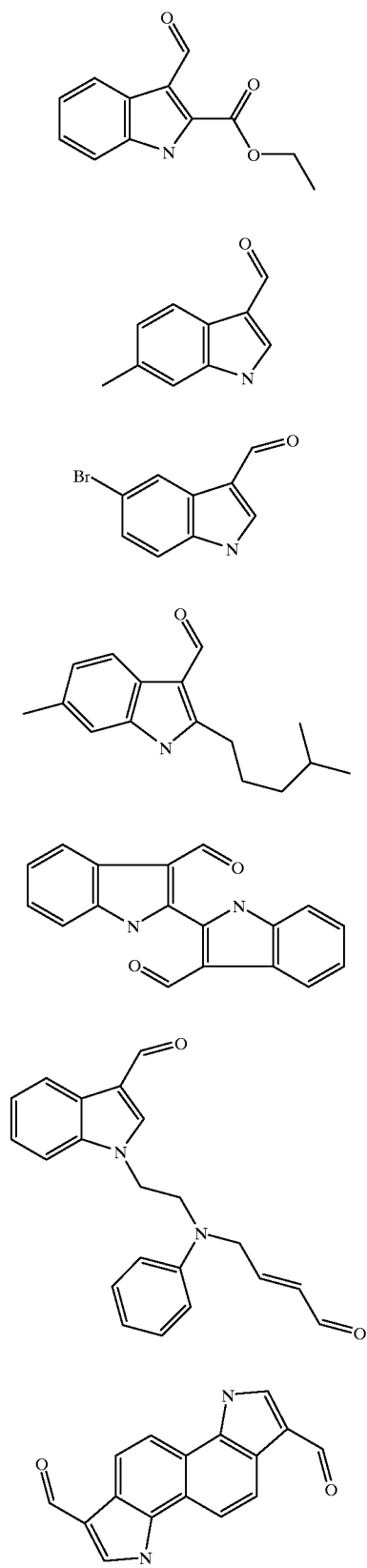
TABLE 1-continued
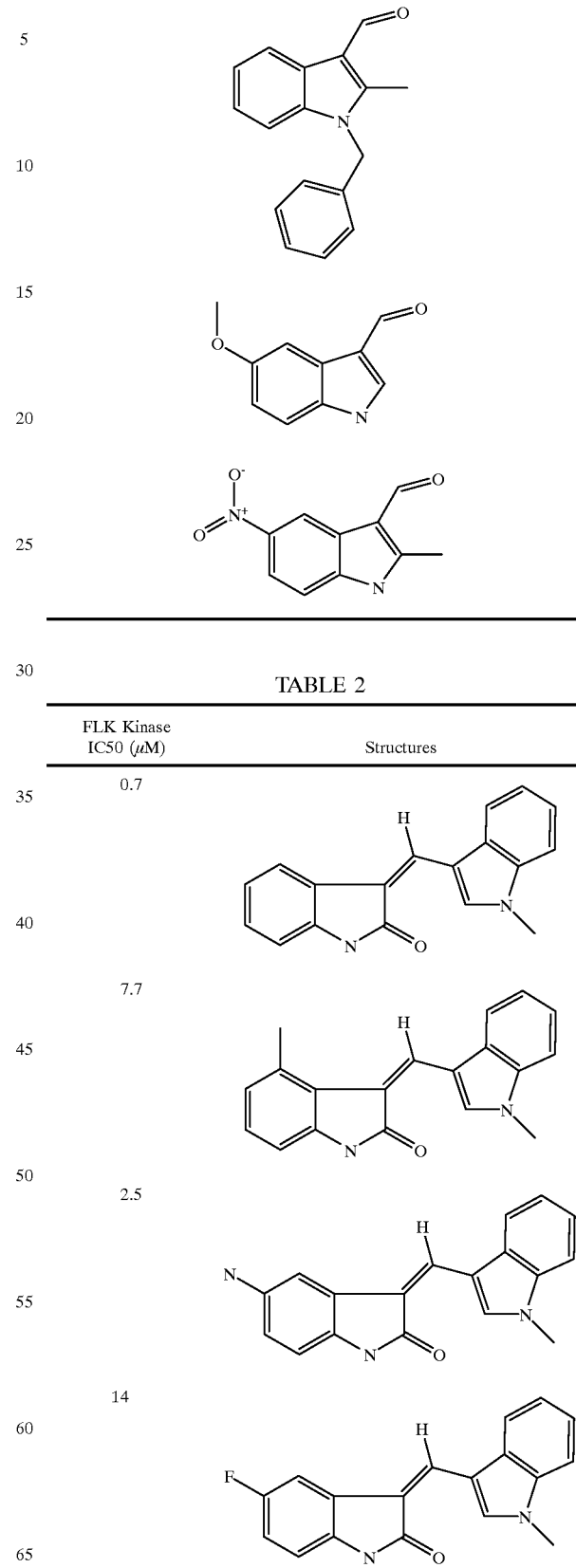
TABLE 2
| FLK Kinase IC50 (μM) | Structures |
|---|---|
| 0.7 | 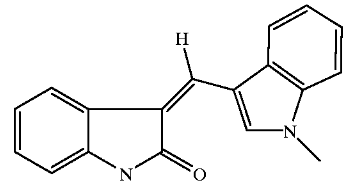 |
| 7.7 | 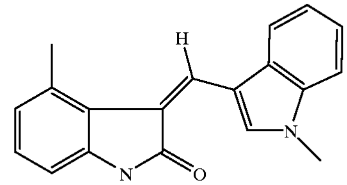 |
| 2.5 | 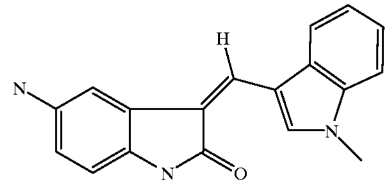 |
| 14 | 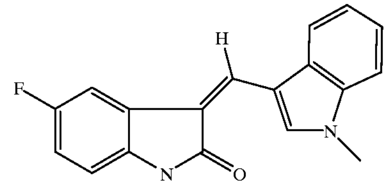 |
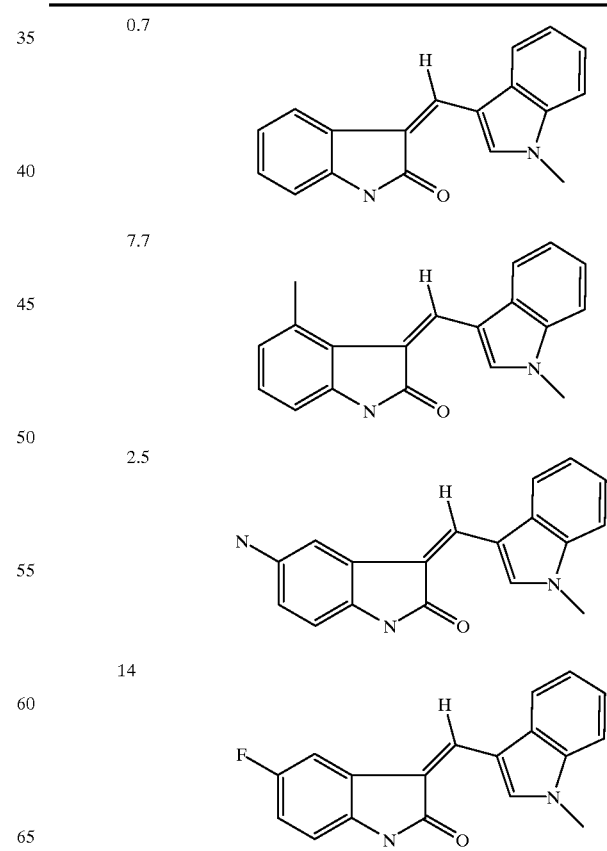

TABLE 2-continued

| FLK Kinase IC50 (μM) | Structures |
|---|---|
| 13 | (5-methoxyindol-3-ylmethylene oxindole) |
| 1.2 | (5-amino oxindole with tetrahydroindole) |
| 1.4 | (oxindole with tetrahydroindole) |
| 5 | (5-chloro oxindole with tetrahydroindole) |

TABLE 3

| NUMBER | ID | STRUCTURE |
|---|---|---|
| 1 | ind/ald-001 | (1-(2-carboxyethyl)indole-3-carbaldehyde) |
| 2 | ind/ald-002 | (1-methylindole-3-carbaldehyde) |
| 3 | ind/ald-003 | (1,2-diphenylindole-3-carbaldehyde) |
| 4 | ind/ald-004 | (1-benzylindole-3-carbaldehyde) |
| 5 | ind/ald-005 | (1-benzoylindole-3-carbaldehyde) |
| 6 | ind/ald-006 | (1-acetylindole-3-carbaldehyde) |
| 7 | ind/ald-007 | (1-tosylindole-3-carbaldehyde) |
| 8 | ind/ald-008 | (1-(3-chloro-5-trifluoromethylpyridin-2-yl)indole-3-carbaldehyde) |

TABLE 3-continued
| NUMBER | ID | STRUCTURE |
|---|---|---|
| 9 | ind/ald-009 | 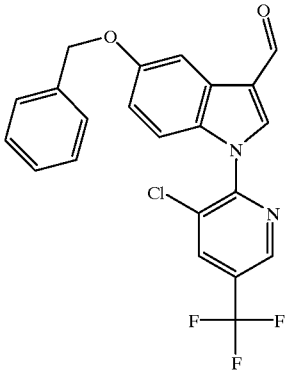 |
| 10 | ind/ald-010 | 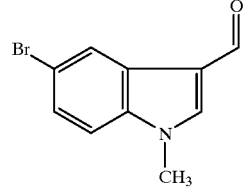 |
| 11 | ind/ald-011 | 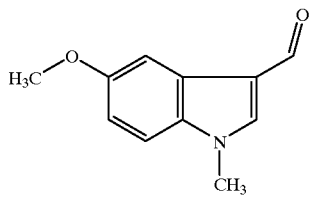 |
| 12 | ind/ald-012 | 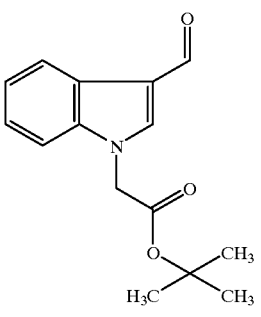 |
| 13 | ind/ald-013 | 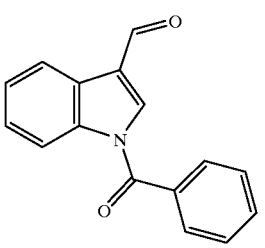 |
| 14 | ind/ald-014 | 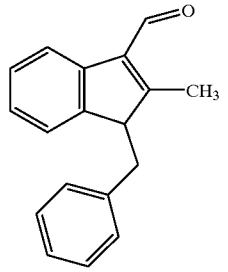 |
| 15 | ind/ald-015 | 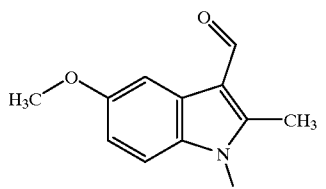 |
| 16 | ind/ald-016 | 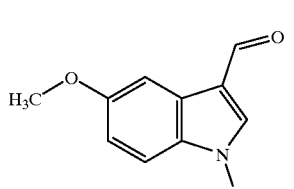 |
| 17 | ind/ald-017 | 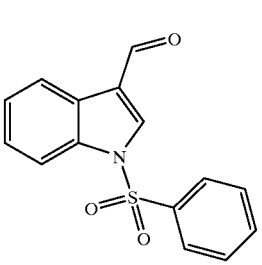 |
| 18 | ind/ald-018 | 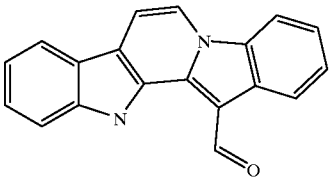 |
| 19 | ind/ald-019 | 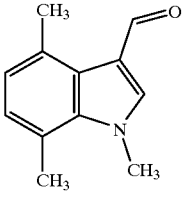 |
| 20 | ind/ald-020 | 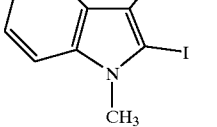 |

TABLE 3-continued

| NUMBER | ID | STRUCTURE |
|---|---|---|
| 21 | ind/ald-021 | 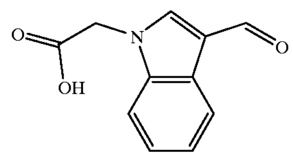 |
| 22 | ind/ald-022 | 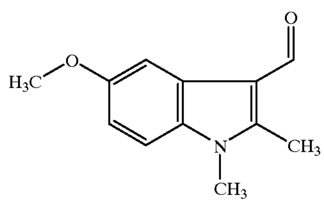 |
| 23 | ind/ald-023 | 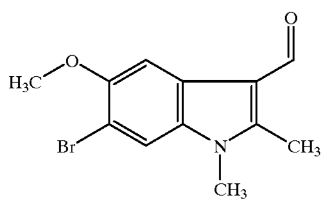 |
| 24 | ind/ald-024 | 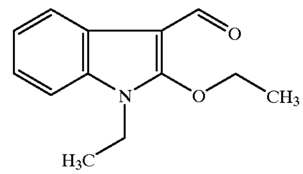 |
| 25 | ind/ald-025 | 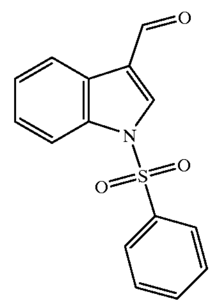 |

TABLE 4

| NUMBER | CORP ID | STRUCTURE |
|---|---|---|
| 1 | oxindole-001 | 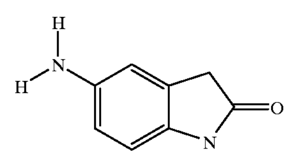 |
| 2 | oxindole-002 | 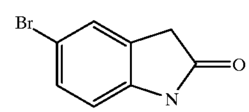 |
| 3 | oxindole-003 | 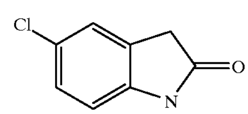 |
| 4 | oxindole-004 | 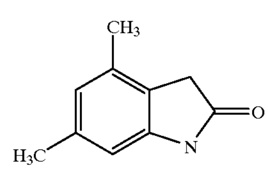 |

TABLE 4-continued

| NUMBER | CORP ID | STRUCTURE |
|---|---|---|
| 5 | oxindole-005 | 5,6-dimethoxy-2-oxindole |
| 6 | oxindole-006 | 2-oxindole |
| 7 | oxindole-007 | 4-methyl-2-oxindole |
| 8 | oxindole-008 | 5,7-dibromo-2-oxindole |
| 9 | oxindole-009 | 5-chloro-7-bromo-2-oxindole |
| 10 | oxindole-010 | 5-fluoro-2-oxindole |
| 11 | oxindole-011 | 5-nitro-2-oxindole |
| 12 | oxindole-012 | 5-iodo-2-oxindole |
| 13 | oxindole-013 | 5-chloro-7-methyl-2-oxindole |
| 14 | oxindole-014 | 5-methyl-2-oxindole |

TABLE 4-continued
| NUMBER | CORP ID | STRUCTURE |
|---|---|---|
| 15 | oxindole-015 | 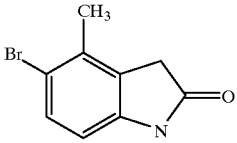 |
| 16 | oxindole-016 | 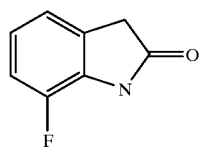 |
| 17 | oxindole-028 | 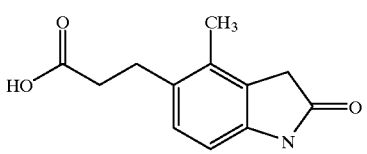 |
| 18 | oxindole-036 | 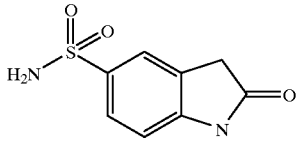 |
| 19 | oxindole-037 | 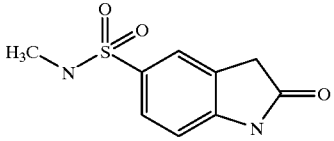 |
| 20 | oxindole-038 | 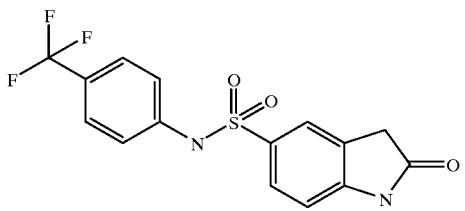 |
| 21 | oxindole-039 | 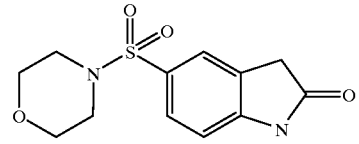 |
| 22 | oxindole-040 | 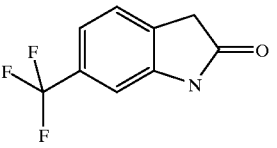 |
| 23 | oxindole-041 | 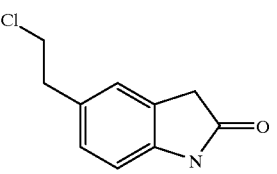 |

TABLE 4-continued

| NUMBER | CORP ID | STRUCTURE |
|---|---|---|
| 24 | oxindole-045 | methyl 2-oxoindoline-5-carboxylate |
| 25 | oxindole-048 | 2-oxoindoline-5-carboxylic acid |
| 26 | oxindole-050 | 3-(2-oxoindolin-5-yl)propanoic acid |
| 27 | oxindole-054 | 5-iodo-4-methylindolin-2-one |
| 28 | oxindole-056 | 5,7-dibromo-4-methylindolin-2-one |
| 29 | oxindole-057 | 5-butylindolin-2-one |
| 30 | oxindole-058 | 5-ethylindolin-2-one |
| 31 | oxindole-059 | 5-(2-morpholinoethyl)indolin-2-one |

TABLE 4-continued
| NUMBER | CORP ID | STRUCTURE |
|---|---|---|
| 32 | oxindole-060 | 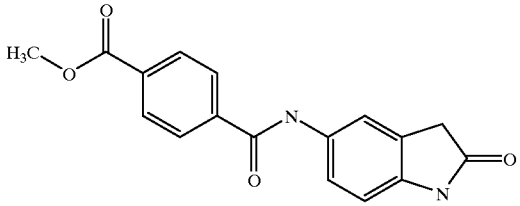 |
| 33 | oxindole-061 | 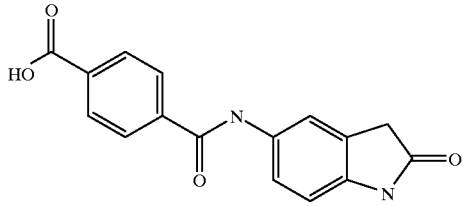 |
| 34 | oxindole-062 | 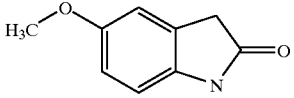 |
TABLE 5
| Structure | |
|---|---|
| 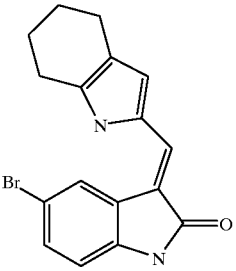 | Formula $C_{17}H_{15}BrN_2O$<br>M.W. 343.2230 |
| 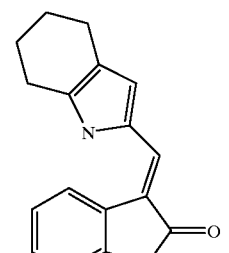 | Formula $C_{17}H_{16}N_2O$<br>M.W. 264.3260 |
| 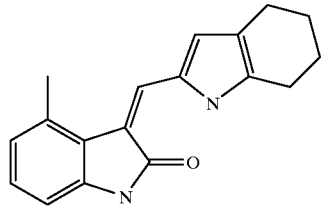 | Formula $C_{18}H_{18}N_2O$<br>M.W. 278.3530 |
TABLE 6
| FLK Kinase IC50 ($\mu$M) | STRUCTURES |
|---|---|
| 1.2 | 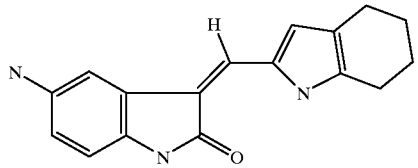 |
| 1.4 | 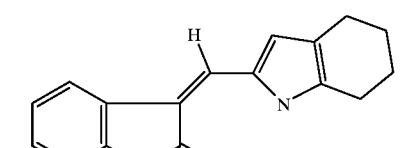 |
| 5 | 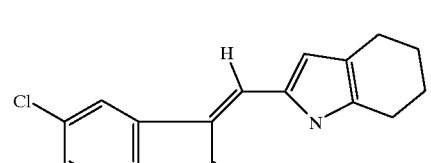 |

TABLE 7

| | Structure | | |
|---|---|---|---|
| Activity | 0128 | IC50 = 1.7 μm | FLK Kinase |
| | | IC50 = 6.8 μm | PDGF Kinase |
| Activity | 0129 | IC50 = 19.6 μm | FLK Kinase |
| | | IC50 = 0.8 μm | PDGF Kinase |

TABLE 8

| Structure | SU # |
|---|---|
| | EC₂₀₀ = 2.8 μm |
| | EC₂₀₀ = 2.8 μm |
| | EC₂₀₀ = 10 μm |

TABLE 8-continued

| Structure | SU # |
|---|---|
| | EC₂₀₀ = 32 μm |
| | EC₂₀₀ > 100 μm |
| | EC₂₀₀ = 46 μm |

TABLE 9

3-[(pyrrol-2-yl)methylidenyl]-5-sulfonyl-2-indolinone
3-[(2,4-dimethylpyrrol-5-yl)methylidenyl]-5-sulfonyl-2-indolinone
3-[(2,4-dimethyl-3-ethoxycarbonylpyrrol-5-yl)methylidenyl]-5-sulfonyl-2-indolinone
3-[(2-methylthien-5-yl)methylidenyl]-5-sulfonyl-2-indolinone
3-[(3-methylthien-2-yl)methylidenyl]-5-sulfonyl-2-indolinone
3-[(4,5,6,7-tetrahydroindol-3-yl)methylidenyl]-5-sulfonyl-2-indolinone
3-[(pyrrol-2-yl)methylidenyl]-5-aminosulfonyl-2-indolinone
3-[(2,4-dimethylpyrrol-5-yl)methylidenyl]-5-aminosulfonyl-2-indolinone
3-[(2,4-dimethyl-3-ethoxycarbonylpyrrol-5-yl)methylidenyl]-5-aminosulfonyl-2-indolinone
3-[(2-methylthien-5-yl)methylidenyl]-5-aminosulfonyl-2-indolinone
3-[(3-methylthien-2-yl)methylidenyl]-5-aminosulfonyl-2-indolinone
3-[(4,5,6,7-tetrahydroindol-3-yl)methylidenyl]-5-aminosulfonyl-2-indolinone
3-[(pyrrol-2-yl)methylidenyl]-5-methoxycarbonyl-2-indolinone
3-[(2,4-dimethylpyrrol-5-yl)methylidenyl]-5-methoxycarbonyl-2-indolinone
3-[(2,4-dimethyl-3-ethoxycarbonylpyrrol-5-yl)methylidenyl]-5-methoxycarbonyl-2-indolinone
3-[(2-methylthien-5-yl)methylidenyl]-5-methoxycarbonyl-2-indolinone
3-[(3-methylthien-2-yl)methylidenyl]-5-methoxycarbonyl-2-indolinone
3-[(4,5,6,7-tetrahydroindol-3-yl)methylidenyl]-5-methoxycarbonyl-2-indolinone
3-[(pyrrol-2-yl)methylidenyl]-5-diethanolamino-2-indolinone
3-[(2,4-dimethylpyrrol-5-yl)methylidenyl]-5-diethanolamino-2-indolinone
3-[(2,4-dimethyl-3-ethoxycarbonylpyrrol-5-yl)methylidenyl]-5-diethanolamino-2-indolinone
3-[(2-methylthien-5-yl)methylidenyl]-5-diethanolamino-2-indolinone
3-[(3-methylthien-2-yl)methylidenyl]-5-diethanolamino-2-indolinone
3-[(4,5,6,7-tetrahydroindol-3-yl)methylidenyl]-5-diethanolamino-2-indolinone
3-[(pyrrol-2-yl)methylidenyl]-5-(2,3-dihydroxypropylamino)-2-indolinone
3-[(2',4-dimethylpyrrol-5-yl)methylidenyl]-5-(2,3-dihydroxypropylamino)-2-indolinone
3-[(2,4-dimethyl-3-ethoxycarbonylpyrrol-5-yl)methylidenyl]-5-(2,3-dihydroxypropylamino)-2-indolinone
3-[(2-methylthien-5-yl)methylidenyl]-5-(2,3-dihydroxypropylamino)-2-indolinone
3-[(3-methylthien-2-yl)methylidenyl]-5-(2,3-dihydroxypropylamino)-2-indolinone
3-[(4,5,6,7-tetrahydroindol-3-yl)methylidenyl]-5-(2,3-dihydroxypropylamino)-2-
3-[(pyrrol-2-yl)methylidenyl]-5-ureido-2-indolinone
3-[(2,4-dimethylpyrrol-5-yl)methylidenyl]-5-ureido-2-indolinone
3-[(2,4-dimethyl-3-ethoxycarbonylpyrrol-5-yl)methylidenyl]-5-ureido-2-indolinone
3-[(2-methylthien-5-yl)methylidenyl]-5-ureido-2-indolinone
3-[(3-methylthien-2-yl)methylidenyl]-5-ureido-2-indolinone
3-[(4,5,6,7-tetrahydroindol-3-yl)methylidenyl]-5-ureido-2-indolinone
3-[(pyrrol-2-yl)methylidenyl]-5-guanidino-2-indolinone
3-[(2,4-dimethylpyrrol-5-yl)methylidenyl]-5-guanidino-2-indolinone
3-[(2,4-dimethyl-3-ethoxycarbonylpyrrol-5-yl)methylidenyl]-5-guanidino-2-indolinone
3-[(2-methylthien-5-yl)methylidenyl]-5-guanidino-2-indolinone
3-[(3-methylthien-2-yl)methylidenyl]-5-guanidino-2-indolinone
3-[(4,5,6,7-tetrahydroindol-3-yl)methylidenyl]-5-guanidino-2-indolinone
3-[(pyrrol-2-yl)methylidenyl]-5-glyceroylamido-2-indolinone
3-[(2,4-dimethylpyrrol-5-yl)methylidenyl]-5-glyceroylamido-2-indolinone
3-[(2,4-dimethyl-3-ethoxycarbonylpyrrol-5-yl)methylidenyl]-5-glyceroylamido-2-indolinone
3-[(2-methylthien-5-yl)methylidenyl]-5-glyceroylamido-2-indolinone
3-[(3-methylthien-2-yl)methylidenyl]-5-glyceroylamido-2-indolinone
3-[(4,5,6,7-tetrahydroindol-3-yl)methylidenyl]-5-glyceroylamido-2-indolinone
3-[(pyrrol-2-yl)methylidenyl]-5-[(3-piperidinyl)propanoylamino]-2-indolinone
3-[(2,4-dimethylpyrrol-5-yl)methylidenyl]-5-[(3-piperidinyl)propanoylamino]-2-indolinone
3-[(2,4-dimethyl-3-ethoxycarbonylpyrrol-5-yl)methylidenyl]-5-[(3-piperidjnyl)propanoylamino]-2-indolinone
3-[(2-methylthien-5-yl)methylidenyl]-5-[(3-piperidinyl)propanoylamino]-2-indolinone
3-[(3-methylthien-2-yl)methylidenyl]-5-[(3-piperidinyl)propanoylamino]-2-indolinone
3-[(4,5,6,7-tetrahydroindol-3-yl)methylidenyl]-5-[(3-piperidinyl)propanoylamino]-2-indolinone
3-[(pyrrol-2-yl)methylidenyl]-5-mesylamino-2-indolinone
3-[(2,4-dimethylpyrrol-5-yl)methylidenyl]-5-mesylamino-2-indolinone
3-[(2,4-dimethyl-3-ethoxycarbonylpyrrol-5-yl)methylidenyl]-5-mesylamino-2-indolinone
3-[(2-methylthien-5-yl)methylidenyl]-5-mesylamino-2-indolinone
3-[(3-methylthien-2-yl)methylidenyl]-5-mesylamino-2-indolinone
3-[(4,5,6,7-tetrahydroindol-3-yl)methylidenyl]-5-mesylamino-2-indolinone
3-[(pyrrol-2-yl)methylidenyl]-5-glycoloyloxy-2-indolinone
3-[(2,4-dimethylpyrrol-5-yl)methylidenyl]-5-glycoloyloxy-2-indolinone
3-[(2,4-dimethyl-3-ethoxycarbonylpyrrol-5-yl)methylidenyl]-5-glycoloyloxy-2-indolinone
3-[(2-methylthien-5-yl)methylidenyl]-5-glycoloyloxy-2-indolinone
3-[(3-methylthien-2-yl)methylidenyl]-5-glycoloyloxy-2-indolinone
3-[(4,5,6,7-tetrahydroindol-3-yl)methylidenyl]-5-glycoloyloxy-2-indolinone
3-[(pyrrol-2-yl)methylidenyl]-5-(2,3-dihydroxypropoxy)-2-indolinone
3-[(2,4-dimethylpyrrol-5-yl)methylidenyl]-5-(2,3-dihydroxypropoxy)-2-indolinone
3-[(2,4-dimethyl-3-ethoxycarbonylpyrrol-5-yl)methylidenyl]-5-(2,3-dihydroxypropoxy)-2-indolinone
3-[(2-methylthien-5-yl)methylidenyl]-5-(2,3-dihydroxypropoxy)-2-indolinone
3-[(3-methylthien-2-yl)methylidenyl]-5-(2,3-dihydroxypropoxy)-2-indolinone
3-[(4,5,6,7-tetrahydroindol-3-yl)methylidenyl]-5-(2,3-dihydroxypropoxy)-2-indolinone
3-[(pyrrol-2-yl)methylidenyl]-5-aminomethyl-2-indolinone
3-[(2,4-dimethylpyrrol-5-yl)methylidenyl]-5-aminomethyl-2-indolinone
3-[(2,4-dimethyl-3-ethoxycarbonylpyrrol-5-yl)methylidenyl]-5-aminomethyl-2-indolinone
3-[(2-methylthien-5-yl)methylidenyl]-5-aminomethyl-2-indolinone
3-[(3-methylthien-2-yl)methylidenyl]-5-aminomethyl-2-indolinone
3-[(4,5,6,7-tetrahydroindol-3-yl)methylidenyl]-5-aminomethyl-2-indolinone
3-[(pyrrol-2-yl)methylidenyl]-5-amidino-2-indolinone

TABLE 9-continued

3-[(2,4-dimethylpyrrol-5-yl)methylidenyl]-5-amidino-2-indolinone
3-[(2,4-dimethyl-3-ethoxycarbonylpyrrol-5-yl)methylidenyl]-5-amidino-2-indolinone
3-[(2-methylthien-5-yl)methylidenyl]-5-amidino-2-indolinone
3-[(3-methylthien-2-yl)methylidenyl]-5-amidino-2-indolinone
3-[(4,5,6,7-tetrahydroindol-3-yl)methylidenyl]-5-amidino-2-indolinone
3-[(pyrrol-2-yl)methylidenyl]-5-hydroxymethyl-2-indolinone
3-[(2,4-dimethylpyrrol-5-yl)methylidenyl] 5-hydroxymethyl-2-indolinone
3-[(2,4-dimethyl-3-ethoxycarbonylpyrrol-5-yl)methylidenyl-5-hydroxymethyl-2-indolinone
3-[(2-methylthien-5-yl)methylidenyl]-5-hydroxymethyl-2-indolinone
3-[(3-methylthien-2-yl)methylidenyl]-5-hydroxymethyl-2-indolinone
3-[(4,5,6,7-tetrahydroindol-3-yl)methylidenyl]-5-hydroxymethyl-2-indolinone
3-[(pyrrol-2-yl)methylidonyl]-5-phosphonooxy-2-indolinone
3-[(2,4-dimethylpyrrol-5-yl)methylidenyl]-5-phosphonooxy-2-indolinone
3-[(2,4-dimethyl-3-ethoxycarbonylpyrrol-5-yl)methylidenyl]-5-phosphonooxy-2-indolinone
3-[(2-methylthien-5-yl)methylidenyl]-5-phosphonooxy-2-indolinone
3-[(3-methylthien-2-yl)methylidenyl]-5-phosphonooxy-2-indolinone
3-[(4,5,6,7-tetrahydroindol-3-yl)methylidenyl]-5-phosphonooxy-2-indolinone
3-[(pyrrol-2-yl)methylidenyl]-5-ethoxycarbonyl-2-indolinone
3-[(2,4-dimethylpyrrol-5-yl)methylidenyl]-5-ethoxycarbonyl-2-indolinone
3-[(2,4-dimethyl-3-ethoxycarbonylpyrrol-5-yl)methylidenyl]-5-ethoxycarbonyl-2-indolinone
3-[(2-methylthien-5-yl)methylidenyl]-5-ethoxycarbonyl-2-indolinone
3-[(3-methylthien-2-yl)methylidenyl]-5-ethoxycarbonyl-2-indolinone
3-[(4,5,6,7-tetrahydroindol-3-yl)methylidenyl]-5-ethoxycarbonyl-2-indolinone
3-[(pyrrol-2-yl)methylidenyl]-5-benzyloxycarbonyl-2-indolinone
3-[(2,4-dimethylpyrrol-5-yl)methylidenyl]-5-benzyloxycarbonyl-2-indolinone
3-[(2,4-dimethyl-3-ethoxycarbonylpyrrol-5-yl)methylidenyl]-5-benzyloxycarbonyl-2-indolinone
3-[(2-methylthien-5-yl)methylidenyl]-5-benzyloxycarbonyl-2-indolinone 5-benzyloxycarbonyl-2-indolinone
3-[(3-methylthien-2-yl)methylidenyl]-5-benzyloxycarbonyl-2-indolinone
3-[(4,5,6,7-tetrahydroindol-3-yl)methylidenyl]-5-benzyloxycarbonyl-2-indolinone
3-[(pyrrol-2-yl)methylidenyl]-5-phenylaminocarbonyl-2-indolinone
3-[(2,4-dimethylpyrrol-5-yl)methylidenyl]-5-phenylaminocarbonyl-2-indolinone
3-[(2,4-dimethyl-3-ethoxycarbonylpyrrol-5-yl)methylidenyl]-5-phenylaminocarbonyl-2-indolinone
3-[(2-methylthien-5-yl)methylidenyl]-5-phenylaminocarbonyl-2-indolinone
3-[(3-methylthien-2-yl)methylidenyl]-5-phenylaminocarbonyl-2-indolinone
3-[(4,5,6,7-tetrahydroindol-3-yl)methylidenyl]-5-phenylaminocarbonyl-2-indolinone
3-[(pyrrol-2-yl)methylidenyl]-5-benzylaminocarbonyl-2-indolinone
3-[(2,4-dimethylpyrrol-5-yl)methylidenyl]-5-benzylaminocarbonyl-2-indolinone
3-[(2,4-dimethyl-3-ethoxycarbonylpyrrol-5-yl)methylidenyl]-5-benzylaminocarbonyl-2-indolinone
3-[(2-methylthien-5-yl)methylidenyl]-5-benzylaminocarbonyl-2-indolinone
3-[(3-methylthien-2-yl)methylidenyl]-5-benzylaminocarbonyl-2-indolinone
3-[(4,5,6,7-tetrahydroindol-3-yl)methylidenyl]-5-benzylaminocarbonyl-2-indolinone

TABLE 10

| FLK Kinase IC50 ($\mu$M) | STRUCTURES | METHOD |
|---|---|---|
| 1.6 | 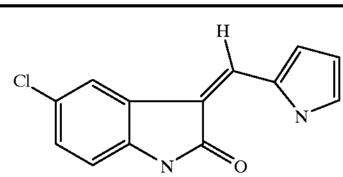 | A |
| 2.6 | 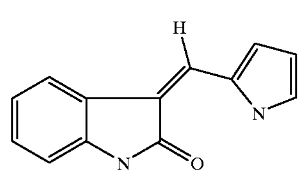 | A |
| 1.9 | 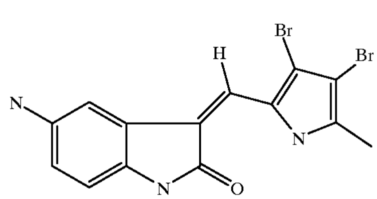 | B |

TABLE 10-continued
| FLK Kinase IC50 (μM) | STRUCTURES | METHOD |
|---|---|---|
| 4.7 | 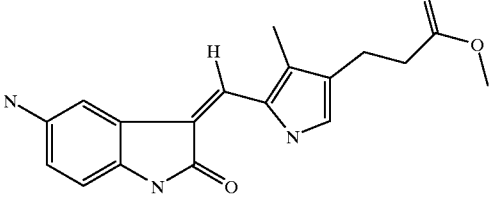 | B |
| 5.6 | 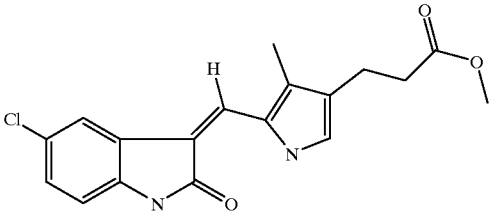 | B |
| 10.8 | 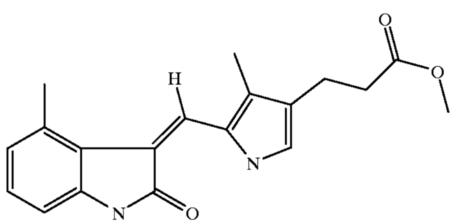 | B |
| 12.5 | 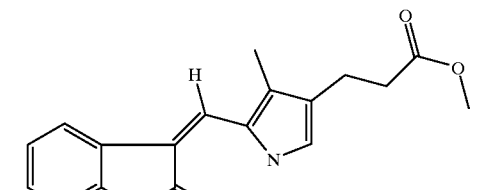 | A |
| 0.97 | 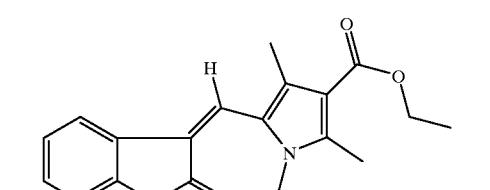 | B |
| 1.5 | 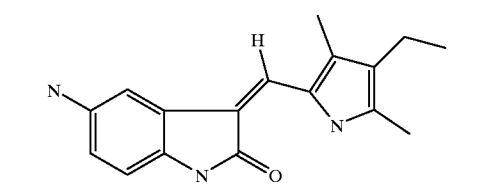 | B |

TABLE 10-continued

| FLK Kinase IC50 (μM) | STRUCTURES | METHOD |
|---|---|---|
| 1.1 | 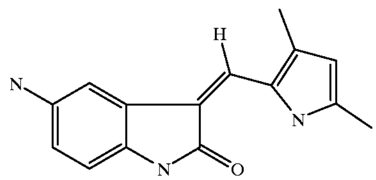 | B |
| 3.5 | 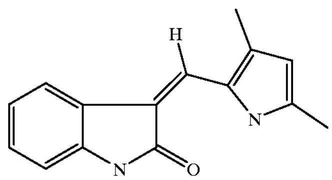 | A |
| 7.3 | 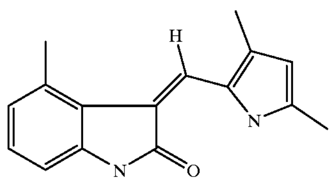 | A |
| 5.6 | 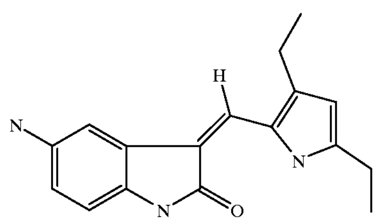 | B |
| 8.1 | 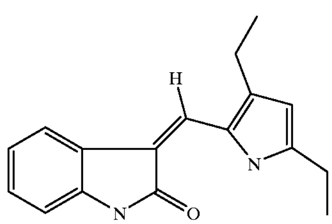 | A |
| 17.3 | 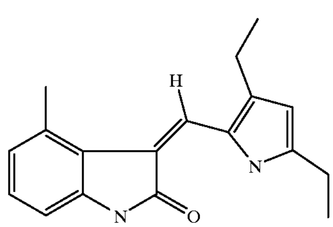 | A |
| 2.9 | 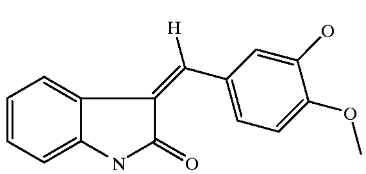 | B |

TABLE 10-continued

| FLK Kinase IC50 (μM) | STRUCTURES | METHOD |
|---|---|---|
| 5.2 | 5-Cl indolin-2-one with 3-bromo-4-hydroxy benzylidene | B |
| 18.5 | 5-Cl, 7-methyl indolin-2-one with 3-bromo-4,5-dihydroxy benzylidene | B |
| 8.8 | 5-Cl, 7-Br indolin-2-one with 3-bromo-4,5-dihydroxy benzylidene | B |
| 4 | indolin-2-one with 4-(3-dimethylaminopropoxy)benzylidene | B |
| 8 | 4-methyl indolin-2-one with 4-(3-dimethylaminopropoxy)benzylidene | B |
| 11.5 | 5-Cl indolin-2-one with 4-(3-dimethylaminopropoxy)benzylidene | B |

TABLE 10-continued
| FLK Kinase IC50 ($\mu$M) | STRUCTURES | METHOD |
|---|---|---|
| 13.7 | 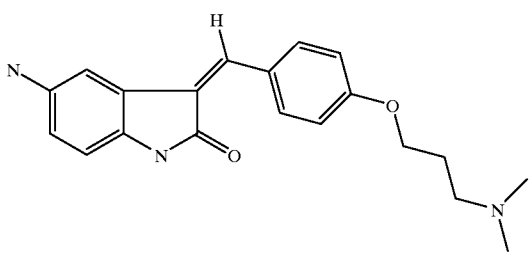 | B |
| 10.4 | 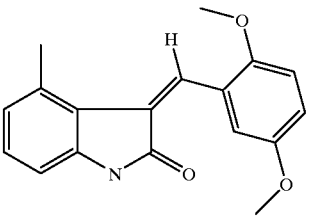 | B |
| 10.7 | 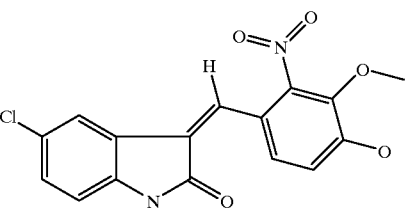 | B |
| 16.4 | 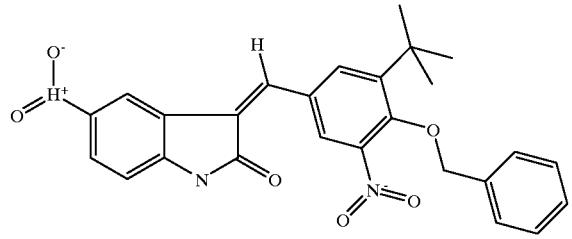 | B |
| 19.9 | 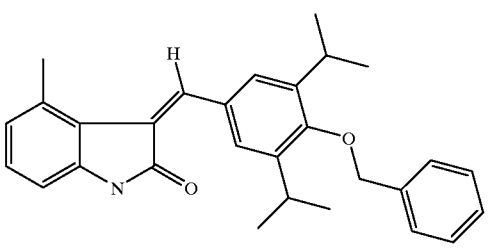 | B |
| 9.7 | 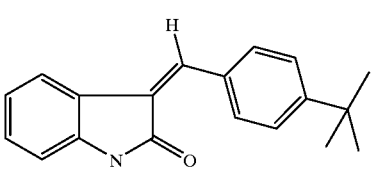 | B |

TABLE 10-continued

| FLK Kinase IC50 (μM) | STRUCTURES | METHOD |
|---|---|---|
| 20.3 | (3-(4-ethylbenzylidene)indolin-2-one) | B |
| 4.6 | (4,6-dimethyl-3-(1H-imidazol-5-ylmethylene)indolin-2-one) | B |
| 5.6 | (5-chloro-3-(1H-imidazol-5-ylmethylene)indolin-2-one) | B |
| 9.9 | (3-(4-(pyrrolidin-1-yl)benzylidene)indolin-2-one) | A |
| 12.3 | (5-chloro-3-(4-(pyrrolidin-1-yl)benzylidene)indolin-2-one) | B |
| 18.4 | (5-amino-3-(4-(pyrrolidin-1-yl)benzylidene)indolin-2-one) | B |
| 5.8 | (5-chloro-3-(4-(4-formylpiperazin-1-yl)benzylidene)indolin-2-one) | B |
| 6.2 | (3-(4-(4-formylpiperazin-1-yl)benzylidene)indolin-2-one) | A |

TABLE 10-continued

| FLK Kinase IC50 (μM) | STRUCTURES | METHOD |
|---|---|---|
| 17.1 | [structure: 5,6-dimethoxy oxindole condensed with 6-isopropyl-chromone] | B |

TABLE 11

5-aminooxindole
  oxindole-001
5-bromooxindole
  oxindole-002
5-chlorooxindole
  oxindole-003
4,5-dimethyloxindole
  oxindole-004
5,5-dimethoxyoxindole
  oxindole-005
oxindole
  oxindole-006
4-methyloxindole
  oxindole-007
5,7-dibromooxindole
  oxindole-008
7-bromo-5-chlorooxindole
  oxindole-009
5-fluorooxindone
  oxindole-010
5-nitrooxindole
  oxindole-011
5-iodooxindole
  oxindole-012
5-chloro-7-methyloxindole
  oxindole-013
5-methyloxindole
  oxindole-014
5-bromo-4-methyloxindole
  oxindole-015
7-fluorooxindole
  oxindole-016
7-chlorooxindole
  oxindole-017
4-fluorooxindole
  oxindole-018
6-fluorooxindole
  oxindole-019
4-chlorooxindole
  oxindole-020
5-chlorooxindole
  oxindole-021
5-bromo-7-methyloxindole
  oxindole-022
7-chloro-5-cyanooxindole
  oxindole-023
4-bromooxindole
  oxindole-024
7-methoxyoxindole
  oxindole-025
4-methyl-5-carboxyoxindole
  oxindole-026
4-methyl-5-carboxymethyloxindole
  oxindole-027
4-methyl-5-carboxyethyloxindole
  oxindole-028
4-methyl-5-(3-carboxy-n-propyl)oxindole
  oxindole-029
4-methyl-5-hydroxymethyloxindole
  oxindole-030
4-methyl-5-methoxymethyloxindole
  oxindole-031
4-methyl-5-(2-hydroxyethyl)oxindole
  oxindole-032
4-methyl-5-(2-methoxyethyl)oxindole
  oxindole-033
4-methyl-5-(3-hydroxy-n-propyl)oxindole
  oxindole-034
4-methyl-5-(3-methoxy-n-propyl)oxindole
  oxindole-035
5-aminosulfonyloxindole
  oxindole-036
5-methylaminosulfonyloxindole
  oxindole-037
5-(4-trifluoromethylanilinosulfonyl)oxindole
  oxindole-038
5-(morpholin-1-yl-sulfonyl)oxindole
  oxindole-039
5-trifluoromethyloxindole
  oxindole-040
5-(2-chloroethyl)oxindole
  oxindole-041
5-carboxymethyloxindole
  oxindole-042
5-carboxymethyloxindole
  oxindole-043
4-methoxycarbonyloxindole
  oxindole-044
5-methoxycarbonyloxindole
  oxindole-045
6-methoxycarbonyloxindole
  oxindole-046
4-carboxyoxindole
  oxindole-047
5-carboxyoxindole
  oxindole-048
6-carboxyoxindole
  oxindole-049
5-carboxyethyloxindole
  oxindole-050
5-hydroxyethyloxindole
  oxindole-051
4-methyl-5-aminooxindole
  oxindole-052
4-methyl-5-nitrooxindole
  oxindole-053
4-methyl-5-iodooxindole
  oxindole-054
4-methyl-5-chlorooxindole
  oxindole-055

TABLE 12

2-ethoxybenzaldehyde
CHO-001
2-thiophenecarboxaldehyde
CHO-002
1-methylpyrrole-2-carboxaldehyde
CHO-003
4-fluorobenzaldehyde
CHO-004
Indole-3-carboxaldehyde
CHO-005
5-methylthiophene-2-carboxaldehyde
CHO-006
4-bromobenzaldehyde
CHO-007
pyrrole-2-carboxaldehyde
CHO-008
2-Hydroxy-6-methoxybenzaldehyde
CHO-009
3-methyl-2-thiophenecarboxaldehyde
CHO-010
3,4-Dibromo-5-methyl-2-pyrrolecarboxaldehyde
CHO-011
Ethyl-2,4-Dimethyl-5-formyl-3-pyrrolecarboxylate
CHO-012
3-Bromo-2-hydroxy-5-methoxybenzaldehyde
CHO-013
1-Hydroxy-2-naphthaldehyde
CHO-014
Ethyl-2(ethoxycarbonyl)-4-(ethoxycarbonylmethyl)-
5-formyl-3-pyrrolepropionate
CHO-015
Ethyl-5-formyl-2-methyl-3-furancarboxylate
CHO-016
4-Formyl-3-methoxycarbonylmethyl-5-me-1H-
pyrrole-2-carboxylic acid methyl ester
CHO-017
2-Hydroxy-3-nitrobenzaldehyde
CHO-018
2,4-Dihydroxy-3-methylbenzaldehyde
CHO-019
Methyl5-formyl-4-methy-3-pyrrolepropionate
CHO-020
2-furaldehyde
CHO-021
5-Nitro-2-furaldehyde
CHO-022
4-Ethoxy-3-methoxybenzaldehyde
CHO-023
3,4-Dihydroxybenzaldehyde
CHO-024
2,4-Dimethoxybenzaldehyde
CHO-025
3,5-Dimethyl-4-ethyl-2-pyrrolcarboxaldehyde
CHO-026
2,4,6-trimethoxybenzaldehyde
CHO-027
4-Hydroxybenzaldehyde
CHO-028
4-(Dimethylamino)-benzaldehyde
CHO-029
2,4-Dimethyl-3-carbethoxypyrrole-5-carboxaldehyde
CHO-030
2-chloro-4-fluorobenzaldehyde
CHO-031
3-Nitrobenzaldehyde
CHO-032
4-Fluoro-2-(trifluromethyl)benzaldehyde
CHO-033
2,4,6-Trifluorobenzaldehyde
CHO-034
4-Hydroxy-2-methoxybenzaldehyde
CHO-035
3,4-Dimethoxybenzaldehyde
CHO-036
Salicylaldehyde
CHO-037
Benzaldehyde
CHO-038
3,5-diethylpyrrole-2-carboxaldehyde

TABLE 12-continued

CHO-038
5-(Methylthio)thiophene-2-carboxaldehyde
CHO-039
2,4-Dihydroxy-6-methylbenzaldehyde
CHO-040
Methyl-5-formyl-4-methyl-3-pyrrolepropionate
CHO-041
3-Ethoxy-4-hydroxybenzaldehyde
CHO-042
2-Hydroxy-5-methoxybenzaldehyde
CHO-043
2-imidazolecarboxaldehyde
CHO-044
1-Methyl-2-formylbenzimidazole
CHO-045
4-Chloro-1-methylpyrazole-3-carboxaldehyde
CHO-046
2,3-dimethyl-5-formylthiophene
CHO-047
2-Formyl-4,5,6,7-tetrahydroindole
CHO-048
3-Chloromethyl-5-nitrosalicylaldehyde
CHO-049
1-(3,5-Dichlorophenyl)pyrrole-2-carboxaldehyde
CHO-050
5-Chlorothiophene-2-carboxaldehyde
CHO-051
3,5-dimethyl-5-formylpyrrole
CHO-052
3-t-Butyl-4-hydroxybenzaldehyde
CHO-053
3-t-ethyl-6-bromo-4-hydroxybenzaldehyde
CHO-054
3,5-Di-tert-butyl-4-hydroxybenzaldehyde
hemihydrate
CHO-055
3-t-Butyl-4-hydroxy-5-nitrobenzaldehyde
CHO-056
2,4,6-Trihydroxybenzaldehyde
CHO-057
2-formyl-5-nitrothiophene
CHO-058
4-Carboxybenzaldehyde
CHO-059
2,4-difluorobenzaldehyde
CHO-060
3,5-Dimethyl-4-hydroxybenzaldehyde
CHO-061
3-Chloro-4-hydroxy-5-t-butylbenzaldehyde
CHO-062
4-Ethoxy-3-methoxybenzaldehyde
CHO-063
2-Nitrothiophene-4-carboxaldehyde
CHO-064
4-(Dibutylamino)benzaldehyde
CHO-065
4-(Trifluoromethyl)benzaldehyde
CHO-066
4,6-Dimethoxy-salicyladehyde
CHO-067
2,3,4-Trihydroxybenzaldehyde
CHO-068
2-Hydroxy-3-methoxybenzaldehyde
CHO-069
5-Bromo-3,4-dihydroxybenzaldehyde
CHO-070
3,4-Diacetoxybenzaldehyde
CHO-071
4-Hydroxy-3-methylbenzaldehyde
CHO-072
2-Bromobenzaldehyde
CHO-073
2,4-Dihydroxybenzaldehyde
CHO-074
2-Hydroxy-4-methoxybenzaldehyde
CHO-075
3-Bromobenzaldehyde
CHO-076
3,5-Di-tert-cutyl-2-hydroxybenzaldehyde

TABLE 12-continued

CHO-077
4-Carboxybenzaldehyde
CHO-078
4-Dimethylamino-1-naphthaldehyde
CHO-079
4-Hydroxy-3-nitrobenzaldehyde
CHO-080
2-Hydroxy-4-methyloxybenzaldehyde
CHO-081
3-Hydroxy-4-nitrobenzaldehyde
CHO-082
3-Bromobenzaldehyde
CHO-083
2,3,5,7-Tetrahydro-8-hydroxy-1H,5H-benzo-
[ij]quinolizine.9 carboxaldehyde
CHO-084
3,5-Diisopropyl-4-hydroxybenzaldehyde
CHO-085
Benzo[b]furan-2-carboxaldehyde
CHO-086
3,5-Diiodo-4-methyl-2-pyrrolecarboxaldehyde
CHO-087
1-(4-chlorophenyl)pyrrole-2-carboxaldehyde
CHO-088
5-Ethyl-2-furaldehyde
CHO-089
3,4-Dimethylthieno[b]thiophene-2-carboxaldehyde
CHO-090
3-Bromothiophene-2-carboxaldehyde
CHO-091
6-Bromo-2-hydroxy-3-methoxybenzaldehyde
CHO-092
5-Methylfurfural
CHO-093
3-Methyl-1H-Pyrazole-5-carboxaldehyde
CHO-094
4-Iodo-2-furaldehyde
CHO-095
6-Methoxy-4-methylsalicylaldehyde
CHO-096
Ethyl 2,4-Dimethyl-5-formy-3-pyrrolecarboxylate
CHO-097
4-Ethyl-5-formy-3-methyl-2-pyrrolecarboxylic acid
CHO-098
Ethyl-5-formy-1,2,4-trimethyl-3-pyrrolecarboxylate
CHO-099
4-(4-Formylpiperazine-1-yl)benzaldehyde
CHO-100
4-(4-Formylmorphonino-1-yl)benzaldehyde
CHO-101
5-Chloro-3-methoxycarbonyl-4-methoxy-
carbonylmethyl-pyrrole-2-carboxaldehyde
CHO-102
1-(4-chlorobenzyl)-4-bromo-pyrazole-5-carboxaldehyde
CHO-103
Imidazole-4-carboxaldehyde
CHO-104
4-Chloro-pyrazole-5-carboxaldehyde
CHO-105
5-Ethoxycarbonyl-4-methyl-3-methylcarbonyl-
pyrrole-2-carboxaldehyde
CHO-106
5-t-Butyl-4-hydroxy-3-iodobenzaldehyde
CHO-107
5-Bromofuran-2-carboxaldehyde
CHO-108
1,4-Dimethyl-3-formylcarbazole
CHO-109
1,4-Dihydroxy-2-formyl-5,6,7,8-tetrahydronaphthalene
CHO-110
5-fluoroisatin
CHO-111
3,4-dimethyl-2-formylpyrrole
CHO-112
isatin
CHO-113
5-ethyl-2-formylthiophene
CHO-114
4-methoxybenzaldehyde

TABLE 12-continued

CHO-115
4-diethylaminobenzaldehyde
CHO-116
3,5-diethylpyrrole-2-carboxaldehyde
CHO-117
5-Benzyloxyindole-3-carboxaldehyde
CHO-118
3-Bromo-5-chloro-2-hydroxybenzaldehyde
CHO-119
2-(4-chlorophenylthio)benzaldehyde
CHO-120
6-Chloropiperonal
CHO-121
Chromone-3-carboxaldehyde
CHO-122
3-Cyanobenzaldehyde
CHO-123
4-Cyanobenzaldehyde
CHO-124
6,8-Dichlorochromone-3-carboxyaldehyde
CHO-125
2,5-dihydroxybenzaldehyde
CHO-126
2,3-Dimethoxybenzaldehyde
CHO-127
2,4-Dimethoxybenzaldehyde
CHO-128
2,5-Dimethoxybenzaldehyde
CHO-129
2,6-Dimethoxybenzaldehyde,
CHO-130
3,5-Dimethoxybenzaldehyde
CHO-131
4-Dimethylamino-2-methoxybenzaldehyde
CHO-132
3,4-Dimethylbenzaldehyde
CHO-133
5,7-Dimethylchromone-3-carboxaldehyde
CHO-134
5-Ethylfurfural
CHO-135
Ferrocenecarboxaldehyde
CHO-136
Fluorene-2-carboxaldehyde
CHO-137
2-Fluoro-3-(trifluoromethyl)benzaldehyde
CHO-138
2-Fluoro-4-(trifluoromethyl)benzaldehyde
CHO-139
2-Fluoro-5-(trifluoromethyl)benzaldehyde
CHO-140
2-Fluoro-6-(trifluoromethyl)benzaldehyde
CHO-141
2-Formylphenoxyacetic acid
CHO-142
3-Methoxy-5,-methylenedioxybenzaldehyde
CHO-143
2-Methoxy-1-naphthaldehyde
CHO-144
4-Methoxy-1-naphthaldehyde
CHO-145
4-(Methylthio)benzaldehyde
CHO-146
3-Methylthionene-2-carboxaldehyde
CHO-147
5-Methylthiophene-2-carboxaldehyde
CHO-148
pentamethylbenzaldehyde
CHO-149
3-Phenoxybenzaldehyde
CHO-150
Pyridine-2-carboxaldehyde
CHO-151
Pyridine-3-carboxaldehyde
CHO-152
Pyridine-4-carboxaldehyde
CHO-153
4-Pyrrolidoinooenzaldehyde, 98+%
CHO-154

TABLE 12-continued 1,2,3,6-Tetrahydrobenzaldehyde
CHO-155
2,3,4-Trimethoxybenzaldehyde
CHO-156
2,4,5-Trimethoxybenzaldehyde
CHO-157
2,4,6-Trimethoxybenzaldehyde
CHO-158
3,4,5-Trimethoxybenzaldehyde
CHO-159
1-Acetyl-3-indolecarboxaldehyde
CHO-160
6-Chloro-3-formylchromone
CHO-161
6-Chloro-3-formyl-7-methylchromone
CHO-162
5-(2-Chlorophenyl)furfural
CHO-163
2-Chloro-3-quinolinecarboxaldehyde
CHO-164
6,8-Dibromo-3-formylchromone
CHO-165
2,5-Dimethoxy-3-tetranydrofuracarboxaldehyde
CHO-166
4,5-Dimethyl-2-furaldehyde
CHO-167
9-Ethyl-3-carbazolecarboxaldehyde
CHO-168
3-Formyl-6,7-dimethylchromone
CHO-169
3-formyl-6,8-dimethylchromone
CHO-170
3-formyl-6-isopropylchromone
CHO-171
3-formyl-6-methylchromone
CHO-172
3-formyl-6-nitrochromone
CHO-173
5-Formyluracil
CHO-174
5-Methoxyindole-3-carboxaldehyde
CHO-175
1-Methylisatin
CHO-176
5-(2-Nitrophenyl)furfural
CHO-177
(S)-(−)-Perillaldehyde
CHO-178
2-(Trifluoroacetyl)thiophene
CHO-179
3,5-diisopropyl-4-methoxybenzaldehyde
CHO-180
4-benzyloxy-3,5-diisopropylbenzaldehyde
CHO-181
3-t-butyl-4-methoxybenzaldehyde
CHO-182
4-benzyloxy-3-t-butylbenzaldehyde
CHO-183
3-bromo-5-t-butyl-4-methoxybenzaldehyde
CHO-184
4-benzyloxy-3-bromo-5-t-butylbenzaldehyde
CHO-185
3-t-butyl-5-chloro-4-methoxybenzaldehyde
CHO-186
4-benzyloxy-3-t-butyl-5-chlorobenzaldehyde
CHO-187
3-t-butyl-5-iodo-4-methoxybenzaldehyde
CHO-188
4-benzyloxy-3-t-butyl-5-iodobenzaldehyde
CHO-189
3-t-butyl-4-methoxy-5-nitrobenzaldehyde
CHO-190
4-benzyloxy-3-t-butyl-5-nitrobenzaldehyde
CHO-191
3,5-di-t-butyl-4-methoxybenzaldehyde
CHO-192
4-benzyloxy-3,5-di-t-butylbenzaldehyde
CHO-193
3,5-dimethyl-4-methoxybenzaldehyde
CHO-194
4-benzyloxy-3,5-dimethoxybenzaldehyde
CHO-195
5-bromo-2-hydroxy-3-methoxy-benzaldehyde
CHO-196
5-bromosalicyaldehyde 201
CHO-197
2-hydroxy-5-nitrobenzaldehyde
CHO-198
4-hydroxy-2-nitro-3-methoxybenzaldehyde
CHO-199
3-ethoxysalicylaldehyde
CHO-200
3,5-dichlorosalicylaldehyde
CHO-201
5-chlorosalicylaldehyde
CHO-202
4-(diethylamino)salicylaldehyde
CHO-203
5-(trifluoromethoxy)salicylaldehyde
CHO-204
3,5-dibromosalicylaldehyde
CHO-205
3-fluorosalicylaldehyde
CHO-206
3-bromo-4-hydroxybenzaldehyde
CHO-207
5-chlorosalicylaldehyde
CHO-208
2-4,dimethyl-5-formylpyrrole
CHO-209
3,5-diisopropyl-2-formylpyrrole
CHO-210
3,5-dimethylthiophene-2-carboxaldehyde
CHO-211
3-methyl-5-ethylthiophene-2-carboxaldehyde
CHO-212
3-methyl-5-isopropylthiophene-2-
carboxaldehyde
CHO-213
3-methyl-5-cyclopentylmethylthiophene-2-
carboxaldehyde
CHO-214
3-methyl-5-cyclopropylthiophene-2-carboxaldehyde
CHO-215
4-methyl-5-ethylthiophene-2-carboxaldehyde
CHO-216
4-methyl-5-isopropylthiophene-2-carboxaldehyde
CHO-217
4-methyl-5-cyclopentylmethylthiophene-2-carboxaldehyde
CHO-218
4-methyl-5-cyclopropylmethylthiophene-2-carboxaldehyde
CHO-219
5-isopropylthiophene-2-carboxaldehyde
CHO-220
5-phenylmethylthiophene-2-carboxaldehyde
CHO-221
5-cyclohexylmethylthiophene-2-carboxaldehyde
CHO-222
5-cyclohexylthiophene-2-carboxaldehyde
CHO-223
5-phenylthiophene-2-carboxaldehyde
CHO-224
3-methyl-5-propylthiophene-2-carboxaldehyde
CHO-225
3-methyl-5-cyclohexylmethylthiophene-2-carboxaldehyde
CHO-226
4-methyl-5-propylthiophene-2-carboxaldehyde
CHO-227
4-methyl-5-cyclohexylmethylthiophene-2-carboxaldehyde
CHO-228
5-n-butylthiophene-2-carboxaldehyde
CHO-229
5-cyclopropylmethylthiophene-2-carboxaldehyde
CHO-230
5-cyclopropylthiophene-2-carboxaldehyde
CHO-231
3-methyl-5-phenylmethylthiophene-2-carboxaldehyde
CHO-232

TABLE 12-continued

| | |
|---|---|
| 4-methyl-5-phenylmethylthiophene-2-carboxaldehyde | CHO-233 |
| 5-cyclopentylmethylthiophene-2-carboxaldehyde | CHO-234 |
| 5-cyclopentylthiophene-2-carboxaldehyde | CHO-235 |
| 4,5-dimethylthiophene-2-carboxaldehyde | CHO-236 |
| 5-n-propylthiophene-2-carboxaldehyde | CHO-237 |

TABLE 13

| MASTER BARCODE | PLATE ROW | PLATE COLUMN | NAME |
|---|---|---|---|
| 10717 | A | 2 | 3-(2-ethoxybenzylidenyl)-5,7-dibromo-2-indolinone |
| 10717 | A | 3 | 3-[(thien-2-yl)methylidenyl]-5,7-dibromo-2 indolinone |
| 10717 | A | 4 | 3-[(1-methylpyrrol-2-yl)methylidenyl]-5,7-dibromo-2 indolinone |
| 10717 | A | 5 | 3-(4-fluorobenzylidenyl)-5,7-dibromo-2-indolinone |
| 10717 | A | 6 | 3-[(indol-3-yl)methylidenyl]-5,7-dibromo-2 indolinone |
| 10717 | A | 7 | 3-[(2-methylthien-5-yl)methylidenyl]-5,7-dibromo-2-indolinone |
| 10717 | A | 8 | 3-(4-bromobenzylidenyl)-5,7-dibromo-2-indolinone |
| 10717 | A | 9 | 3-[(pyrrol-2-yl)methylidenyl]-5,7-dibromo-2 indolinone |
| 10717 | A | 10 | 3-(2-hydroxy-6-methoxybenzylidenyl)-5,7-dibromo-2-indolinone |
| 10717 | A | 11 | 3-[(3,4-dibromo-2-methylpyrrol-5-yl)methylidenyl]-5,7-dibromo-2-indolinone |
| 10717 | B | 2 | 3-(2-ethoxybenzylidenyl)-5-iodo-2-indolinone |
| 10717 | B | 3 | 3-[(thien-2-yl)methylidenyl]-5-iodo-2-indolinone |
| 10717 | B | 4 | 3-[(1-methylpyrrol-2-yl)methylidenyl]-5-iodo-2-indolinone |
| 10717 | B | 5 | 3-(4-fluorobenzylidenyl)-5-iodo-2-indolinone |
| 10717 | B | 6 | 3-[(indol-3-yl)methylidenyl]-5-iodo-2-indolinone |
| 10717 | B | 7 | 3-[(2-methylthien-5-yl)methylidenyl]-5-iodo-2 indolinone |
| 10717 | B | 8 | 3(4-bromobenzylidenyl)-5-iodo-2-indolinone |
| 10717 | B | 9 | 3-[(pyrrol-2-yl)methylidenyl]-5-iodo-2-indolinone |
| 10717 | B | 10 | 3-(2-hydroxy-6-methoxybenzylidenyl)-5-iodo-2 indolinone |
| 10717 | B | 11 | 3-[(3,4-dibromo-2-methylpyrrol-5-yl)methylidenyl]-5-iodo-2-indolinone |
| 10717 | C | 2 | 3-(2-thoxybenzylidenyl)-5-bromo-4-methyl-2-indolinone |
| 10717 | C | 3 | 3-[(thien-2-yl)methylidenyl]-5-bromo-4-methyl-2-indolinone |
| 10717 | C | 4 | 3-[(1-methylpyrrol-2-yl)methylidenyl]-5-bromo-4-methyl-2-indolinone |
| 10717 | C | 5 | 3-(4-fluorobenzylidenyl)-5-bromo-4-methyl-2-indolinone |
| 10717 | C | 6 | 3-[(indol-3-yl)methylidenyl]-5-bromo-4-methyl-2-indolinone |
| 10717 | C | 7 | 3-[(2-methylthien-5-yl)methylidenyl]-5-bromo-4-methyl-2-indolinone |
| 10717 | C | 8 | 3-(4-bromobenzylidenyl)-5-bromo-4-methyl-2-indolinone |
| 10717 | C | 9 | 3-[(pyrrol-2-yl)methylidenyl]-5-bromo-4-methyl-2-indolinone |
| 10717 | C | 10 | 3-(2-hydroxy-6-methoxybenzylidenyl)-5-bromo-4-methyl-2-indolinone |
| 10717 | C | 11 | 3-[(3,4-dibromo-2-methylpyrrol-5-yl)methylidenyl]-5-bromo-4-methyl-2-indolinone |
| 10717 | D | 2 | 3-(2-ethoxybenzylidenyl)-5-methylaminosulfonyl-2-indolinone |
| 10717 | D | 3 | 3-[(thien-2-yl)methylidenyl]-5-methylaminosulfonyl-2-indolinone |
| 10717 | D | 4 | 3-[(1-methylpyrrol2-yl)methylidenyl]-5-methylaminosulfonyl-2-indolinone |
| 10717 | D | 5 | 3-(4-fluorobenzylidenyl)-5-methylaminosulfonyl-2-indolinone |
| 10717 | D | 6 | 3-[(indol-3-yl)methylidenyl]-5-methylaminosulfonyl-2-indolinone |

TABLE 13-continued

| MASTER BARCODE | PLATE ROW | PLATE COLUMN | NAME |
|---|---|---|---|
| 10717 | D | 7 | 3-[(2-methylthien-5-yl)methylidenyl]-5-methylaminosulfonyl-2-indolinone |
| 10717 | D | 8 | 3-(4-brornobenzylidenyl)-5-methylaminosulfonyl-2 indolinone |
| 10717 | D | 9 | 3-[(pyrrol-2-yl)methylidenyl]-5-methylaminosulfonyl-2-indolinone |
| 10717 | D | 10 | 3-(2-hydroxy-6-methoxybenzylidenyl)-5-methylaminosulfonyl-2-iddolinone |
| 10717 | D | 11 | 3-[(3,4-dibromo-2-methylpyrrol-5-yl)methylidenyl]-5-methylaminosulfonyl-2-indolinone |
| 10717 | E | 2 | 3-(2-ethoxybenzylidenyl)-5-(4-(trifluoromethyl)phenylaminosulfonyl]-2-indolinone |
| 10717 | E | 3 | 3-[(thien-2-yl)methylidenyl]-5-[4-(trifluoromethyl)phenylaminosulfonyl]-2-indolinone |
| 10717 | E | 4 | 3-[(1-methylpyrrol-2-yl)methylidenyl]-5-(4-(trifluoromethyl)phenylaminosulfonyl]-2-indolinone |
| 10717 | E | 5 | 3-(4-fluorobenzylidenyl)-5-(4-(trifluoromethyl)phenylaminosulfonyl]-2-indolinone |
| 10717 | E | 6 | 3-[(indol-3-yl)methylidenyl]-5-[4-(trifluoromethyl)phenylaminosulfonyl]-2-indolinone |
| 10717 | E | 7 | 3-[(2-methylthien-5-yl)methylidenyl]-5-(4-(trifluoromethyl)phenylaminosulfonyl]-2-indolinone |
| 10717 | E | 8 | 3-(4-bromobenzylidenyl)-5-[4-(trifluoromethyl)phenylaminosulfonyl]-2-indolinone |
| 10717 | E | 9 | 3-[(pyrrol-2-yl)methylidenyl]-5-[4 (trifluoromethyl)phenylaminosulfonyl]-2-indolinone |
| 10717 | E | 10 | 3-(2-hydroxy-6-methoxybenzylidenyl)-5-[4-(trifluoromethyl)phenylaminosulfonyl]-2-indolinone |
| 10717 | E | 11 | 3-[(3,4-dibromo-2-methylpyrrol-5-yl)methylidenyl]-5-[4-(trifluoromethyl)phenylaminosulfonyl]-2 indolinone |
| 10717 | F | 2 | 3-(2-ethoxybenzylidenyl)-5-(morpholin-1-yl)sulfonyl-2-indolinone |
| 10717 | F | 3 | 3-[(thien-2-yl)methylidenyl]-5-(morpholin-1-yl)sulfonyl-2-indolinone |
| 10717 | F | 4 | 3-[(1-methylpyrrol-2-yl)methylidenyl]-5-(morpholin 1-yl)sulfonyl-2-indolinone |
| 10717 | F | 5 | 3-(4-fluorobenzylidenyl)-5-(morpholin-1-yl)sulfonyl-2-indolinone |
| 10717 | F | 6 | 3-[(indo)-3-yl)methylidenyl]-5-(morpholin-1-yl)sulfonyl-2-indolinone |
| 10717 | F | 7 | 3-[(2-methylthien-5-yl)methylidenyl]-5-(morpholin-1-yl)sulfonyl-2-indolinone |
| 10717 | F | 8 | 3-(4-bromobenzylidenyl)-5-(morpholin-1-yl)sulfonyl-2-indolinone |
| 10717 | F | 9 | 3-[(pyrrol-2-yl)methylidenyl]-5-(morpholin-1-yl)sulfonyl-2-indolinone |
| 10717 | F | 10 | 3-(2-hydroxy-6-methoxybenzylidenyl)-5-(morpholin-1-yl)sulfonyl-2-indolinone |
| 10717 | F | 11 | 3-[(3,4-dibromo-2-methylpyrrol-5-yl)methylidenyl]-5-(morpholin-1-yl)sulfonyl-2-indolinone |
| 10717 | G | 2 | 3-(2-ethoxybenzylidenyl)-5-(2-chloroethyl)-2-indolinone |
| 10717 | G | 3 | 3-[(thien-2-yl)methylidenyl]-5-(2-chloroethyl)-2-indolinone |
| 10717 | G | 4 | 3-[(1-methylpyrrol-2-yl)methylidenyl]-5-(2-chloroethyl)-2-indolinone |
| 10717 | G | 5 | 3-(4-fluorobenzylidenyl)-5-(2-chloroethyl)-2 indolinone |
| 10717 | G | 6 | 3-[(indol-3-yl)methylidenyl]-5-(2-chloroethyl)-2 indolinone |
| 10717 | G | 7 | 3-[(2-methylthien-5-yl)methylidenyl]-5-(2-chloroethyl)-2-indolinone |
| 10717 | G | 8 | 3-(4-bromobenzylidenyl)-5-(2-chloroethyl)-2-indolinone |
| 10717 | G | 9 | 3-[(pyrrol-2-yl)methylidenyl]-5-(2-chloroethyl)-2-indolinone |
| 10717 | G | 10 | 3-(2-hydroxy-6-methoxybenzylidenyl)-5-(2-chloroethyl)-2-indolinone |
| 10717 | G | 11 | 3-[(3,4-dibromo-2-methylpyrrol-5-yl)methylidenyl]-5-(2-chloroethyl)-2-indolinone |
| 10718 | A | 2 | 3-[(2,4-dimethyl-3-ethoxycarbonylpyrrol-5-yl)methylidenyl]-5,7-dibromo-2-indolinone |
| 10718 | A | 3 | 3-(3-bromo-2-hydroxy-5-methoxybenzylidenyl)-5,7-dibromo-2-indolinone |

TABLE 13-continued

| MASTER BARCODE | PLATE ROW | PLATE COLUMN | NAME |
|---|---|---|---|
| 10718 | A | 4 | 3-[(1-hydroxynapth-2-yl)methylidenyl]-5,7-dibromo-2-indolinone |
| 10718 | A | 5 | 3-[[2-ethoxycarbonyl-3-(2-ethoxycarbonyl)ethyl-4-(ethoxycarbonylmethyl)pyrrol-5-yl]methylidenyl]-5,7-dibromo-2-indolinone |
| 10718 | A | 6 | 3-[(2-methyl-3-ethoxycarbonylfuran-5-yl)methylidenyl]-5,7-dibromo-2-indolinone |
| 10718 | A | 7 | 3-[(2,3-dimethoxycarbonyl-5-methylpyrrol-4-yl)methylidenyl]-5,7-dibromo-2-indolinone |
| 10718 | A | 8 | 3-(4-chloro-3-nitrobenzylidenyl)-5,7-dibromo-2-indolinone |
| 10718 | A | 9 | 3-(2,4-dihydroxy-3-methylbenzylidenyl)-5,7-dibromo-2-indolinone |
| 10718 | A | 10 | 3-[(furan-2-yl)methylidenyl]-5,7-dibromo-2-indolinone |
| 10718 | A | 11 | 3-[(2-nitrofuran-5-yl)methylidenyl]-5,7-dibromo-2-indolinone |
| 10718 | B | 2 | 3-[(2,4-dimethyl-3-ethoxycarbonylpyrrol-5-yl)methylidenyl]-5-iodo-2-indolinone |
| 10718 | B | 3 | 3-(3-bromo-2-hydroxy-5-methoxybenzylidenyl)-5-iodo-2-indolinone |
| 10718 | B | 4 | 3-[(1-hydroxynapth-2-yl)methylidenyl]-5-iodo-2-indolinone |
| 10718 | B | 5 | 3-[[2-ethoxycarbonyl-3-(2-ethoxycarbonyl)ethyl-4-(ethoxycarbonylmethyl)pyrrol-5-yl]methylidenyl]-5-iodo-2-indolinone |
| 10718 | B | 6 | 3-[(2-methyl-3-ethoxycarbonylfuran-5-yl)methylidenyl]-5-iodo-2-indolinone |
| 10718 | B | 7 | 3-[(2,3-dimethoxycarbonyl-5-methylpyrrol-4-yl)methylidenyl]-5-iodo-2-indolinone |
| 10718 | B | 8 | 3-(4-chloro-3-nitrobenzylidenyl)-5-iodo-2-indolinone |
| 10718 | B | 9 | 3-(2,4-dihydroxy-3-methylbenzylidenyl)-5-iodo-2-indolinone |
| 10718 | B | 10 | 3-[(furan-2-yl)methylidenyl]-5-iodo-2-indolinone |
| 10718 | B | 11 | 3-[(2-nitrofuran-5-yl)methylidenyl]-5-iodo-2-indolinone |
| 10718 | C | 2 | 3-[(2,4-dimethyl-3-ethoxycarbonylpyrrol-5-yl)methylidenyl]-5-bromo-4-methyl-2-indolinone |
| 10718 | C | 3 | 3-(3-bromo-2-hydroxy-5-methoxybenzylidenyl)-5-bromo-4-methyl-2-indolinone |
| 10718 | C | 4 | 3-[(1-hydroxynapth-2-yl)methylidenyl]-5-bromo-4-methyl-2-indolinone |
| 10718 | C | 5 | 3-[[2-ethoxycarbonyl-3-(2-ethoxycarbonyl)ethyl-4-(ethoxycarbonylmethyl)pyrrol-5-yl]methylidenyl]-5-bromo-4-methyl-2-indolinone |
| 10718 | C | 6 | 3-[(2-methyl-3-ethoxycarbonylfuran-5-yl)methylidenyl]-5-bromo-4-methyl-2-indolinone |
| 10718 | C | 7 | 3-[(2,3-dimethoxycarbonyl-5-methylpyrrol-4-yl)methylidenyl]-5-bromo-4-methyl-2-indolinone |
| 10718 | C | 8 | 3-(4-chloro-3-nitrobenzylidenyl)-5-bromo-4-methyl-2-indolinone |
| 10718 | C | 9 | 3-(2-4-dihydroxy-3-methylbenzylidenyl)-5-bromo-4-methyl-2-indolinone |
| 10718 | C | 10 | 3-[(furan-2-yl)methylidenyl]-5-bromo-4-methyl-2-indolinone |
| 10718 | C | 11 | 3-[(2-nitrofuran-5-yl)methylidenyl]-5-bromo-4-methyl-2-indolinone |
| 10718 | D | 2 | 3-[(2,4-dimethyl-3-ethoxycarbonylpyrrol-5-yl)methylidenyl]-5-methylaminosulfonyl-2-indolinone |
| 10718 | D | 3 | 3-(3-bromo-2-hydroxy-5-methoxybenzylidenyl)-5-methylaminosulfonyl-2-indolinone |
| 10718 | D | 4 | 3-[(1-hydroxynapth-2-yl)methylidenyl]-5-methylaminosulfonyl-2-indolinone |
| 10718 | D | 5 | 3-[[2-ethoxycarbonyl-3-(2-ethoxycarbonyl)ethyl-4-(ethoxycarbonylmethyl)pyrrol-5-yl]methylidenyl]-5-methylaminosulfonyl-2-indolinone |
| 10718 | D | 6 | 3-[(2-methyl-3-ethoxycarbonylfuran-5-yl)methylidenyl]-5-methylaminosulfonyl-2-indolinone |
| 10718 | D | 7 | 3-[(2,3-dimethoxycarbonyl-5-methylpyrrol-4-yl)methylidenyl]-5-methylaminosulfonyl-2-indolinone |
| 10718 | D | 8 | 3-(4-chloro-3-nitrobenzylidenyl)-5-methylaminosulfonyl-2-indolinone |

TABLE 13-continued

| MASTER BARCODE | PLATE ROW | PLATE COLUMN | NAME |
|---|---|---|---|
| 10718 | D | 9 | 3-(2-4-dihydroxy-3-methylbenzylidenyl)-5-methylaminosulfonyl-2-indolinone |
| 10718 | D | 10 | 3-[(furan-2-yl)methylidenyl]-5-methylaminosulfonyl-2-indolinone |
| 10718 | D | 11 | 3-[(2-nitrofuran-5-yl)methylidenyl]-5-methylaminosulfonyl-2-indolinone |
| 10718 | E | 2 | 3-[(2,4-dimethyl-3-ethoxycarbonylpyrrol-5-yl)methylidenyl]-5-[4-(trifluoromethyl)phenylaminosulfonyl]-2-indolinone |
| 10718 | E | 3 | 3-(3-bromo-2-hydroxy-5-methoxybenzylidenyl)-5-[4-(trifluoromethyl)phenylaminosulfonyl]-2-indolinone |
| 10718 | E | 4 | 3-[(1-hydroxynapth-2-yl)methylidenyl]-5-[4-(trifluoromethyl)phenylaminosulfonyl]-2-indolinone |
| 10718 | E | 5 | 3-[(2-ethoxycarbonyl-3-(2-ethoxycarbonyl)ethyl-4-ethoxycarbonylmethyl-pyrrol-5-yl)methylidenyl]-5-[4-(trifluoromethyl)phenylaminosulfonyl]-2-indolinone |
| 10718 | E | 6 | 3-[(2-methyl-3-ethoxycarbonylfuran-5-yl)methylidenyl]-5-[4-(trifluoromethyl)phenylaminosulfonyl]-2-indolinone |
| 10718 | E | 7 | 3-[(2-3-dimethoxycarbonyl-5-methylpyrrol-4-yl)methylidenyl]-5-[4-(trifluoromethyl)phenylaminosulfonyl]-2-indolinone |
| 10718 | E | 8 | 3-(4-chloro-3-nitrobenzylidenyl)-5-[4-(trifluoromethyl)phenylaminosulfonyl]-2-indolinone |
| 10718 | E | 9 | 3-(2,4-dihydroxy-3-methylbenzylidenyl)-5-[4-(trifluoromethyl)phenylaminosulfonyl]-2-indolinone |
| 10718 | E | 10 | 3-[(furan-2-yl)methylidenyl]-5-[4-(trifluoromethyl)phenylaminosulfonyl]-2-indolinone |
| 10718 | E | 11 | 3-[(2-nitrofuran-5-yl)methylidenyl]-5-[4-(trifluoromethyl)phenylaminosulfonyl]-2-indolinone |
| 10718 | F | 2 | 3-[(2,4-dimethyl-3-ethoxycarbonylpyrrol-5-yl)methylidenyl]-5-(morpholin-1-yl)sulfonyl-2-indolinone |
| 10718 | F | 3 | 3-(3-bromo-2-hydroxy-5-methoxybenzylidenyl)-5-(morpholin-1-yl)sulfonyl-2-indolinone |
| 10718 | F | 4 | 3-[(1-hydroxynapth-2-yl)methylidenyl]-5-(morpholin-1-yl)sulfonyl-2-indolinone |
| 10718 | F | 5 | 3-[[2-ethoxycarbonyl-3-(2-ethoxycarbonyl)ethyl-4-(ethoxycarbonylmethyl)pyrrol-5-yl]methylidenyl]-5-(morpholin-1-yl)sulfonyl-2-indolinone |
| 10718 | F | 6 | 3-[(2-methyl-3-ethoxycarbonylfuran-5-yl)methylidenyl]-5-(morpholin-1-yl)sulfonyl-2-indolinone |
| 10718 | F | 7 | 3-[(2,3-dimethoxycarbonyl-5-methyl-pyrrol-4-yl)methylidenyl)-5-(morpholin-1-yl)sulfonyl-2-indolinone |
| 10718 | F | 8 | 3-(4-chloro-3-nitrobenzylidenyl)-5-(morpholin-1-yl)sulfonyl-2-indolinone |
| 10718 | F | 9 | 3-(2,4-dihydroxy-3-methylbenzylidenyl)-5-(morpholin-1-yl)sulfonyl-2-indolinone |
| 10718 | F | 10 | 3-[(furan-2-yl)methylidenyl]-5-(morpholin-1-yl)sulfonyl-2-indolinone |
| 10718 | F | 11 | 3-[(2-nitrofuran-5-yl)methylidenyl]-5-(morpholin-1-yl)sulfonyl-2-indolinone |
| 10718 | G | 2 | 3-[(2,4-dimethyl-3-ethoxycarbonylpyrrol-5-yl)methylidenyl]-5-(2-chloroethyl)-2-indolinone |
| 10718 | G | 3 | 3-(3-bromo-2-hydroxy-5-methoxybenzylidenyl)-5-(2-chloroethyl)-2-indolinone |
| 10718 | G | 4 | 3-[(1-hydroxynapth-2-yl)methyldenyl]-5-(2 chloroethyl)-2-indolinone |
| 10718 | G | 5 | 3-[[2-ethoxycarbonyl-3-(2-ethoxycarbonyl)ethyl-4(ethoxycarbonylmethyl)pyrrol-5-yl]methylidenyl]-5-(2-chloroethyl)-2-indolinone |
| 10718 | G | 6 | 3-[(2-methyl-3-ethoxycarbonylfuran-5-yl)methylidenyl]-5-(2-chloroethyl)-2-indolinone |
| 10718 | G | 7 | 3-[(2,3-dimethoxycarbonyl-5-methylpyrrol-4-yl)methylidenyl]-5-(2-chloroethyl)-2-indolinone |
| 10718 | G | 8 | 3-(4-chloro-3nitrobenzylidenyl)-5-(2-chloroethyl)-2-indolinone |
| 10718 | G | 9 | 3-(2,4-dihydroxy-3-methylbenzylidenyl)-5-(2-chloroethyl)-2-indolinone |
| 10718 | G | 10 | 3-[(furan-2-yl)methylidenyl]-5-(2-chloroethyl)-2-indolinone |
| 10718 | G | 11 | 3-[(2-nitrofuran-5-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10719 | A | 2 | 3-(4-ethoxy-3-methoxybenzylidenyl)-5,7-dibromo-2-indolinone |
| 10719 | A | 3 | 3-(3,4-dihydoxybenzylidenyl)-5,7-dibromo-2-indolinone |
| 10719 | A | 4 | 3-(2,4-dimethoxybenzylidenyl)-5,7-dibromo-2-indolinone |
| 10719 | A | 5 | 3-[(2,4-dimethyl-3-ethylpyrrol-5-yl)methylidenyl]5,7-dibromo-2-indolinone |
| 10719 | A | 6 | 3-(2,4,6-trimethoxybenzylidenyl)-5,7-dibromo-2-indolinone |
| 10719 | A | 7 | 3-(4-hydroxybenzylidenyl)-5,7-dibromo-2-indolinone |
| 10719 | A | 8 | 3-(4-dimethylaminobenzylidenyl)-5,7-dibromo-2-indolinone |
| 10719 | A | 9 | 3-(2-chloro-4-fluorobenzylidenyl)-5,7-dibromo-2-indolinone |
| 10719 | A | 10 | 3-(3-nitrobenzylidenyl)-5,7-dibromo-2-indolinone |
| 10719 | A | 11 | 3-[4-fluoro-2-(trifluoromethyl)benzylidenyl]-5,7-dibromo-2-indolinone |
| 10719 | B | 2 | 3-(4-ethoxy-3-methoxybenzylidenyl)-5-iodo-2-indolinone |
| 10719 | B | 3 | 3-(3,4-dihydoxybenzylidenyl)-5-iodo-2-indolinone |
| 10719 | B | 4 | 3-(2,4-dimethoxybenzylidenyl)-5-iodo-2-indolinone |
| 10719 | B | 5 | 3-[(2,4-dimethyl-3-ethylpyrrol-5-yl)methylidenyl]-5-iodo-2-indolinone |
| 10719 | B | 6 | 3-(2,4,6-trimethoxybenzylidenyl)-5-iodo-2-indolinone |
| 10719 | B | 7 | 3-(4-hydroxybenzylidenyl)-5-iodo-2-indolinone |
| 10719 | B | 8 | 3-(4-dimethylaminobenzylidenyl)-5-iodo-2-indolinone |
| 10719 | B | 9 | 3-(2-chloro-4-fluorobenzylidenyl)-5-iodo-2-indolinone |
| 10719 | B | 10 | 3-(3-nitrobenzylidenyl)-5-iodo-2-indolinone |
| 10719 | B | 11 | 3-[4-fluoro-2-(trifluoromethyl)benzylidenyl]-5-iodo-2-indolinone |
| 10719 | C | 2 | 3-(4-ethoxy-3-methoxybenzylidenyl)-5-bromo-4-methyl-2-indolinone |
| 10719 | C | 3 | 3-(3,4-dihydoxybenzylidenyl)-5-bromo-4-methyl-2-indolinone |
| 10719 | C | 4 | 3-(2,4-dimethoxybenzylidenyl)-5-bromo-4-methyl-2 indolinone |
| 10719 | C | 5 | 3-[(2,4-dimethyl-3-ethylpyrrol-5-yl)methylidenyl]-5-bromo-4-methyl-2-indolinone |
| 10719 | C | 6 | 3-(2,4,6-tnmethoxybenzylidenyl)-5-bromo-4-methyl-2-indolinone |
| 10719 | C | 7 | 3-(4-hydroxybenzylidenyl)-5-bromo-4-methyl-2-indolinone |
| 10719 | C | 8 | 3-(4-dimethylaminobenzylidenyl)-5-bromo-4-methyl-2-indolinone |
| 10719 | C | 9 | 3-(2-chloro-4-fluorobenzylidenyl)-5-bromo-4-methyl-2-indolinone |
| 10719 | C | 10 | 3-(3-nitrobenzylidenyl)-5-bromo-4-methyl-2-indolinone |
| 10719 | C | 11 | 3-[4-fluoro-2-(trifluoromethyl)benzylidenyl]-5-bromo 4-methyl-2-indolinone |
| 10719 | D | 2 | 3-(4-ethoxy-3-methoxybenzylidenyl)-5-methylaminosulfonyl-2-indolinone |
| 10719 | D | 3 | 3-(3,4-dihydoxybenzylidenyl)-5-methylaminosulfonyl-2-indolinone |
| 10719 | D | 4 | 3-(2,4-dimethoxybenzylidenyl)-5-methylaminosulfonyl-2-indolinone |
| 10719 | D | 5 | 3-[(2,4-dimethyl-3-ethylpyrrol-5-yl)methylidenyl]-5-methylaminosulfonyl-2-indolinone |
| 10719 | D | 6 | 3-(2,4,6-tnmethoxybenzylidenyl)-5-methylaminosulfonyl-2-indolinone |
| 10719 | D | 7 | 3-(4-hydroxybenzylidenyl)-5-methylaminosulfonyl-2-indolinone |
| 10719 | D | 8 | 3-(4-dimethylaminobenzylidenyl)-5-methylaminosulfonyl-2-indolinone |
| 10719 | D | 9 | 3-(2-chloro-4-fluorobenzylidenyl)-5-methylaminosulfonyl-2-indolinone |
| 10719 | D | 10 | 3-(3-nitrobenzylidenyl)-5-methylaminosulfonyl-2-indolinone |
| 10719 | D | 11 | 3-[4-fluoro-2-(trifluoromethyl)benzylidenyl]-5-methylaminosulfonyl-2-indolinone |
| 10719 | E | 2 | 3-(4-ethoxy-3-methoxybenzylidenyl)-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10719 | E | 3 | 3-(3,4-dihydoxybenzylidenyl)-5-[4-(trifluoromethyl)phenylaminosulfonyl]-2-indolinone |
| 10719 | E | 4 | 3-(2,4-dimethoxybenzylidenyl)-5-[4-(trifluoromethyl)phenylaminosulfonyl]-2-indolinone |
| 10719 | E | 5 | 3-[(2-4-dimethyl3-ethylpyrrol-5-yl)methylidenyl]-5-[4-(trifluoromethyl)phenylaminosulfonyl]-2-indolinone |
| 10719 | E | 6 | 3-(2,4,6-trimethoxybenzylidenyl)-5-[4-(trifluoromethyl)phenylaminosulfonyl]-2-indolinone |
| 10719 | E | 7 | 3-(4-hydroxybenzylidenyl)-5-[4-(trifluoromethyl)phenylaminosulfonyl]-2-indolinone |
| 10719 | E | 8 | 3-(4-dimethylaminobenzylidenyl)-5-[4-(trifluoromethyl)phenylaminosulfonyl]-2-indolinone |
| 10719 | E | 9 | 3-(2-chloro-4-fluorobenzylidenyl)-5-[4-(trifluoromethyl)phenylaminosulfonyl]-2-indolinone |
| 10719 | E | 10 | 3-(3-nitrobenzylidenyl)-5-[4-(trifluoromethyl)phenylaminosulfonyl]-2-indolinone |
| 10719 | E | 11 | 3-[4-fluoro-2-(trifluoromethyl)benzylidenyl]-5-[4-(trifluoromethyl)phenylaminosulfonyl]-2-indolinone |
| 10719 | F | 2 | 3-(4-ethoxy-3-methoxybenzylidenyl)-5-(morpholin-1-yl)sulfonyl-2-indolinone |
| 10719 | F | 3 | 3-(3,4-dihydoxybenzylidenyl)-5-(morpholin-1-yl)sulfonyl-2-indolinone |
| 10719 | F | 4 | 3-(2,4-dimethoxybenzylidenyl)-5-(morpholin-1-yl)sulfonyl-2-indolinone |
| 10719 | F | 5 | 3-[(2,4-dimethyl-3-ethylpyrrol-5-yl)methylidenyl]-5-(morpholin-1-yl)sulfonyl-2-indolinone |
| 10719 | F | 6 | 3-(2,4,6-trimethoxybenzylidenyl)-5-(morpholin-1-yl)sulfonyl-2-indolinone |
| 10719 | F | 7 | 3-(4-hydroxybenzylidenyl)-5-(morpholin-1-yl)sulfonyl-2-indolinone |
| 10719 | F | 8 | 3-(4-dimethylaminobenzylidenyl)-5-(morpholin-1-yl)sulfonyl-2-indolinone |
| 10719 | F | 9 | 3-(2-chloro-4-fluorobenzylidenyl)-5-(morpnolin-1-yl)sulfonyl-2-indolinone |
| 10719 | F | 10 | 3-(3-nitrobenzylidenyl)-5-(morpholin-1-yl)sulfonyl-2-indolinone |
| 10719 | F | 11 | 3-[4-fluoro-2-(trifluoromethyl)benzylidenyl]-5-(morpholin-1-yl)sulfonyl-2-indolinone |
| 10719 | G | 2 | 3-(4-ethoxy-3-methoxybenzylidenyl)-5-(2-chloroethyl)-2-indolinone |
| 10719 | G | 3 | 3-(3,4-dihydoxybenzylidenyl)-5-(2-chloroethyl)-2-indolinone |
| 10719 | G | 4 | 3-(2,4-dimethoxybenzylidenyl)-5-(2-chloroethyl)-2-indolinone |
| 10719 | G | 5 | 3-[(2,4-dimethyl-3-ethylpyrrol-5-yl)methylidenyl]-5-(2-chloroethyl)-2-indolinone |
| 10719 | G | 6 | 3-(2,4,6-trimethoxybenzylidenyl)-5-(2-chloroethyl)-2-indolinone |
| 10719 | G | 7 | 3-(4-hydroxybenzylidenyl)-5-(2-chloromethyl)-2-indolinone |
| 10719 | G | 8 | 3-(4-dimethylaminobenzylidenyl)-5-(2-chloroethyl)-2-indolinone |
| 10719 | G | 9 | 3-(2-chloro-4-fluorobenzylidenyl)-5-(2-chloroethyl)-2-indolinone |
| 10719 | G | 10 | 3-(3-nitrobenzylidenyl)-5-(2-chloroethyl)-2-indolinone |
| 10719 | G | 11 | 3-[4-fluoro-2-(trifluoromethyl)benzylidenyl]-5-(2-chloroethyl)-2-indolinone |
| 10720 | A | 2 | 3-(2,4,6-trifluorobenzylidenyl)-5,7-dibromo-2-indolinone |
| 10720 | A | 3 | 3-(4-hydroxy-2-methoxybenzylidenyl)-5,7-dibromo-2-indolinone |
| 10720 | A | 4 | 3-(3,4-dimethoxybenzylidenyl)-5,7-dibromo-2-indolinone |
| 10720 | A | 5 | 3-(2-hydroxybenzylidenyl)-5,7-dibromo-2-indolinone |
| 10720 | A | 6 | 3-benzylidenyl-5,7-dibromo-2-indolinone |
| 10720 | A | 7 | 3-[(2-methylmercaptothien-5-yl)methylidenyl]-5,7-dibromo-2-indolinone |
| 10720 | A | 8 | 3-(2,4-dihydroxy-methylbenzylidenyl)-5,7-dibromo-2-indolinone |
| 10720 | A | 9 | 3-(3-ethoxy-4-hydroxybenzylidenyl)-5,7-dibromo-2-indolinone |
| 10720 | A | 10 | 3-(2-hydroxy-5-methoxybenzylidenyl)-5,7-dibromo-2-indolinone |

TABLE 13-continued

| MASTER BARCODE | PLATE ROW | PLATE COLUMN | NAME |
| --- | --- | --- | --- |
| 10720 | A | 11 | 3-[(imidazol-2-yl)methylidenyl]-5,7-dibromo-2-indolinone |
| 10720 | B | 2 | 3-(2,4,6-trifluorobenzylidenyl)-5-iodo-2-indolinone |
| 10720 | B | 3 | 3-(4-hydroxy-2-methoxybenzylidenyl)-5-iodo-2-indolinone |
| 10720 | B | 4 | 3-(3,4-dimethoxybenzylidenyl)-5-iodo-2-indolinone |
| 10720 | B | 5 | 3-(2-hydroxybenzylidenyl)-5-iodo-2-indolinone |
| 10720 | B | 6 | 3-benzylidenyl-5-iodo-2-indolinone |
| 10720 | B | 7 | 3-[(2-methylmercaptothien-5-yl)methylidenyl]-5-iodo-2-indolinone |
| 10720 | B | 8 | 3-(2,4-dihydroxy-5-methylbenzylidenyl)-5-iodo-2-indolinone |
| 10720 | B | 9 | 3-(3-ethoxy-4-hydroxybenzylidenyl)-5-iodo-2-indolinone |
| 10720 | B | 10 | 3-(2-hydroxy-5-methoxybenzylidenyl)-5-iodo-2-indolinone |
| 10720 | B | 11 | 3-[(imidazol-2-yl)methylidenyl]-5-iodo-2-indolinone |
| 10720 | C | 2 | 3-(2,4,6-trifluorobenzylidenyl)-5-bromo-4-methyl-2-indolinone |
| 10720 | C | 3 | 3-(4-hydroxy-2-methoxybenzylidenyl)-5-bromo-4-methyl-2-indolinone |
| 10720 | C | 4 | 3-(3,4-dimethoxybenzylidenyl)-5-bromo-4-methyl-2-indolinone |
| 10720 | C | 5 | 3-(2-hydroxybenzylidenyl)-5-bromo-4-methyl-2-indolinone |
| 10720 | C | 6 | 3-benzylidenyl-5-bromo-4-methyl-2-indolinone |
| 10720 | C | 7 | 3-[(2-methylmercaptothien-5-yl)methylidenyl]-5-bromo-4-methyl-2-indolinone |
| 10720 | C | 8 | 3-(2,4-dihydroxy-6-methylbenzylidenyl)-5-bromo-4-methyl-2-indolinone |
| 10720 | C | 9 | 3-(3-ethoxy-4-hydroxybenzylidenyl)-5-bromo-4-methyl-2-indolinone |
| 10720 | C | 10 | 3-(2-hydroxy-5-methoxybenzylidenyl)-5-bromo-4-methyl-2-indolinone |
| 10720 | C | 11 | 3-[(imidazol-2-yl)methylidenyl]-5-bromo-4-methyl-2-indolinone |
| 10720 | D | 2 | 3-(2,4,6-trifluorobenzylidenyl)-5-methylaminosulfonyl-2-indolinone |
| 10720 | D | 3 | 3-(4-hydroxy-2-methoxybenzylidenyl)-5-methylaminosulfonyl-2-indolinone |
| 10720 | D | 4 | 3-(3,4-dimethoxybenzylidenyl)-5-methylaminosulfonyl-2-indolinone |
| 10720 | D | 5 | 3-(2-hydroxybenzylidenyl)-5-methylaminosulfonyl-2-indolinone |
| 10720 | D | 6 | 3-benzylidenyl-5-methylaminosulfonyl-2-indolinone |
| 10720 | D | 7 | 3-[(2-methylmercaptothien-5-yl)methylidenyl]-5-methylaminosulfonyl-2-indolinone |
| 10720 | D | 8 | 3-(2,4-dihydroxy-6-methylbenzylidenyl)-5-methylaminosulfonyl-2-indolinone |
| 10720 | D | 9 | 3-(3-ethoxy-4-hydroxybenzylidenyl)-5-methylaminosulfonyl-2-indolinone |
| 10720 | D | 10 | 3-(2-hydroxy-5-methoxybenzylidenyl)-5-methylaminosulfonyl-2-indolinone |
| 10720 | D | 11 | 3-[(imidazol-2-yl)methylidenyl]-5-methylaminosulfonyl-2-indolinone |
| 10720 | E | 2 | 3-(2,4,6-trifluorobenzylidenyl)-5-[4-(trifluoromethyl)phenylaminosulfonyl]-2-indolinone |
| 10720 | E | 3 | 3-(4-hydroxy-2-methoxybenzylidenyl)-5-[4-(trifluoromethyl)phenylaminosulfonyl]-2-indolinone |
| 10720 | E | 4 | 3-(3,4-dimethoxybenzylidenyl)-5-[4-(trifluoromethyl)phenylaminosulfonyl]-2-indolinone |
| 10720 | E | 5 | 3-(2-hydroxybenzylidenyl)-5-]4-(trifluoromethyl)phenylaminosulfonyl]-2-indolinone |
| 10720 | E | 6 | 3-benzylidenyl-5-[4-(trifluoromethyl)phenylaminosulfonyl]-2-indolinone |
| 10720 | E | 7 | 3-[(2-methylmercaptothien-5-yl)methylidenyl]-5-[4-(trifluoromethyl)phenylaminosulfonyl]-2-indolinone |
| 10720 | E | 8 | 3-(2,4-dihydroxy-6-methylbenzylidenyl)-5-[4-(trifluoromethyl)phenylaminosulfonyl]-2-indolinone |
| 10720 | E | 9 | 3-(3-ethoxy-4-hydroxybenzylidenyl)-5-[4-(trifluoromethyl)phenylaminosulfonyl]-2-indolinone |
| 10720 | E | 10 | 3-(2-hydroxy-5-methoxybenzylidenyl)-5-[4-(trifluoromethyl)phenylaminosulfonyl]-2-indolinone |
| 10720 | E | 11 | 3-[(imidazol-2-yl)methylidenyl]-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10720 | F | 2 | 3-(2,4,6-trifluorobenzylidenyl)-5-(morpholin-1-yl)sulfonyl-2-indolinone |
| 10720 | F | 3 | 3-(4-hydroxy-2-methoxybenzylidenyl)-5-(morpholin-1-yl)sulfonyl-2-indolinone |
| 10720 | F | 4 | 3-(3,4-dimethoxybenzylidenyl)-5-(morpholin-1-yl)sulfonyl-2-indolinone |
| 10720 | F | 5 | 3-(2-hydroxybenzylidenyl)-5-(morpholin-1-yl)sulfonyl-2-indolinone |
| 10720 | F | 6 | 3-benzylidenyl-5-(morpholin-1-yl)sulfonyl-2-indolinone |
| 10720 | F | 7 | 3-[(2-methylmercaptothien-5-yl)methylidenyl]-5-(morpholin-1-yl)sulfonyl-2-indolinone |
| 10720 | F | 8 | 3-(2,4-dihydroxy-6-methylbenzylidenyl)-5-(morpholin-1-yl)sulfonyl-2-indolinone |
| 10720 | F | 9 | 3-(3-ethoxy-4-hydroxybenzylidenyl)-5-(morpholin-1-yl)sulfonyl-2-indolinone |
| 10720 | F | 10 | 3-(2-hydroxy-5-methoxybenzylidenyl)-5-(morpholin-1-yl)sulfonyl-2-indolinone |
| 10720 | F | 11 | 3-[(imidazol-2-yl)methylidenyl]-5-(morpholin-1-yl)sulfonyl-2-indolinone |
| 10720 | G | 2 | 3-(2,4,6-trifluorobenzylidenyl)-5-(2-chloroethyl)-2-indolinone |
| 10720 | G | 3 | 3-(4-hydroxy-2-methoxybenzylidenyl)-5-(2-chloroethyl)-2-indolinone |
| 10720 | G | 4 | 3-(3,4-dimethoxybenzylidenyl)-5-(2-chloroethyl)-2-indolinone |
| 10720 | G | 5 | 3-(2-hydroxybenzylidenyl)-5-(2-chloroethyl)-2-indolinone |
| 10720 | G | 6 | 3-benzylidenyl-5-(2-chloroethyl)-2-indolinone |
| 10720 | G | 7 | 3-[(2-methylmercaptothien-5-yl)methylidenyl]-5-(2-chloroethyl)-2-indolinone |
| 10720 | G | 8 | 3-(2,4-dihydroxy-6-methylbenzylidenyl)-5-(2-chloroethyl)-2-indolinone |
| 10720 | G | 9 | 3-(3-ethoxy-4-hydroxybenzylidenyl)-5-(2-chloroethyl)-2-indolinone |
| 10720 | G | 10 | 3-(2-hydroxy-5-methoxybenzylidenyl)-5-(2-chloroethyl)-2-indolinone |
| 10720 | G | 11 | 3-[(imidazol-2-yl)methylidenyl]-5-(2-chloroethyl)-2-indolinone |
| 10721 | A | 2 | 3-[(1-methylbenzimidazol-2-yl)methylidenyl]-5,7-dibromo-2-indolinone |
| 10721 | A | 3 | 3-[(4-chloro-1-methylpyrazol-3-yl)methylidenyl]-5,7-dibromo-2-indolinone |
| 10721 | A | 4 | 3-[(2,3-dimethylthien-5-yl)methylidenyl]-5,7-dibromo-2-indolinone |
| 10721 | A | 5 | 3-[(4,5,6,7-tetrahydroindol-2-yl)methylidenyl]-5,7-dibromo-2-indolinone |
| 10721 | A | 6 | 3-(3-chloromethyl-2-hydroxy-5-nitrobenzylidenyl)-5,7-dibromo-2-indolinone |
| 10721 | A | 7 | 3-[(2-chlorothien-5-yl)methylidenyl]-5,7-dibromo-2-indolinone |
| 10721 | A | 8 | 3-[(2,4-dimethylpyrrol-5-yl)methylidenyl]-5,7-dibromo-2-indolinone |
| 10721 | A | 9 | 3-(3-t-butyl-4-hydroxybenzylidenyl)-5,7-dibromo-2-indolinone |
| 10721 | A | 10 | 3-(3-bromo-5-t-butyl-4-hydroxybenzylidenyl)-5,7-dibromo-2-indolinone |
| 10721 | A | 11 | 3-(3,5-di-t-butyl-4-hydroxybenzylidenyl)-5,7-dibromo-2-indolinone |
| 10721 | B | 2 | 3-[(1-methylbenzimidazol-2-yl)methylidenyl]-5-iodo-2-indolinone |
| 10721 | B | 3 | 3-[(4-chloro-1-methylpyrazol-3-yl)methylidenyl]-5-iodo-2-indolinone |
| 10721 | B | 4 | 3-[(2,3-dimethylthien-5-yl)methylidenyl]-5-iodo-2-indolinone |
| 10721 | B | 5 | 3-[(4,5,6,7-tetrahydroindol-2-yl)methylidenyl]-5-iodo-2-indolinone |
| 10721 | B | 6 | 3-(3-chloromethyl-2-hydroxy-5-nitrobenzylidenyl)-5-iodo-2-indolinone |
| 10721 | B | 7 | 3-[(2-chlorothien-5-yl)methylidenyl]-5-iodo-2-indolinone |
| 10721 | B | 8 | 3-[(2,4-dimethylpyrrol-5-yl)methylidenyl]-5-iodo-2-indolinone |
| 10721 | B | 9 | 3-(3-t-butyl-4-hydroxybenzylidenyl)-5-iodo-2-indolinone |

TABLE 13-continued

| MASTER BARCODE | PLATE ROW | PLATE COLUMN | NAME |
|---|---|---|---|
| 10721 | B | 10 | 3-(3-bromo-5-t-butyl-4-hydroxybenzylidenyl)-5-iodo-2-indolinone |
| 10721 | B | 11 | 3-(3,5-di-t-butyl-4-hydroxybenzylidenyl)-5-iodo-2-indolinone |
| 10721 | C | 2 | 3-[(1-methylbenzimidazol-2-yl)methylidenyl]-5-bromo-4-methyl-2-indolinone |
| 10721 | C | 3 | 3-[(4-chloro-1-methylpyrazol-3-yl)methylidenyl]-5-bromo-4-methyl-2-indolinone |
| 10721 | C | 4 | 3-[(2,3-dimethylthien-5-yl)methylidenyl]-5-bromo-4-methyl-2-indolinone |
| 10721 | C | 5 | 3-[(4,5,6,7-tetrahydroindol-2-yl)methylidenyl]-5-bromo-4-methyl-2-indolinone |
| 10721 | C | 6 | 3-(3-chloromethyl-2-hydroxy-5-nitrobenzylidenyl)-5-bromo-4-methyl-2-indolinone |
| 10721 | C | 7 | 3-[(2-chlorothien-5-yl)methylidenyl]-5-bromo-4-methyl-2-indolinone |
| 10721 | C | 8 | 3-[(2,4-dimethylpyrrol-5-yl)methylidenyl]-5-bromo-4-methyl-2-indolinone |
| 10721 | C | 9 | 3-(3-t-butyl-4-hydroxybenzylidenyl)-5-bromo-4-methyl-2-indolinone |
| 10721 | C | 10 | 3-(3-bromo-5-t-butyl-4-hydroxybenzylidenyl)-5-bromo-4-methyl-2-indolinone |
| 10721 | C | 11 | 3-(3,5-di-t-butyl-4-hydroxybenzylidenyl)-5-bromo-4-methyl-2-indolinone |
| 10721 | D | 2 | 3-[(1-methylbenzimidazol-2-yl)methylidenyl]-5-methylaminosulfonyl-2-indolinone |
| 10721 | D | 3 | 3-[(4-chloro-1-methylpyrazol-3-yl)methylidenyl]-5-methylaminosulfonyl-2-indolinone |
| 10721 | D | 4 | 3-[(2,3-dimethylthien-5-yl)methylidenyl]-5-methylaminosulfonyl-2-indolinone |
| 10721 | D | 5 | 3-[(4,5,6,7-tetrahydroindol-2-yl)methylidenyl]-5-methylaminosulfonyl-2-indolinone |
| 10721 | D | 6 | 3-(3-chloromethyl-2-hydroxy-5-nitrobenzylidenyl)-5-methylaminosulfonyl-2-indolinone |
| 10721 | D | 7 | 3-[(2-chlorothien-5-yl)methylidenyl]-5-methylaminosulfonyl-2-indolinone |
| 10721 | D | 8 | 3-[(2,4-dimethylpyrrol-5-yl)methylidenyl]-5-methylaminosulfonyl-2-indolinone |
| 10721 | D | 9 | 3-(3-t-butyl-4-hydroxybenzylidenyl)-5-methylaminosulfonyl-2-indolinone |
| 10721 | D | 10 | 3-(3-bromo-5-t-butyl-4-hydroxybenzylidenyl)-5-methylaminosulfonyl-2-indolinone |
| 10721 | D | 11 | 3-(3,5-di-t-butyl-4-hydroxybenzylidenyl)-5-methylaminosulfonyl-2-indolinone |
| 10721 | E | 2 | 3-[(1-methylbenzimidazol-2-yl)methylidenyl]-5-[4-(trifluoromethyl)phenylaminosulfonyl]-2-indolinone |
| 10721 | E | 3 | 3-[(4-chloro-1-methylpyrazol-3-yl)methylidenyl]-5-[4-(trifluoromethyl)phenylaminosulfonyl]-2-indolinone |
| 10721 | E | 4 | 3-[(2,3-dimethythien-5-yl)methylidenyl]-5-[4-(trifluoromethyl)phenylaminosulfonyl]-2-indolinone |
| 10721 | E | 5 | 3-[(4,5,6,7-tetrahydroindol-2-yl)methylidenyl]-5-[4-(trifluoromethyl)phenylaminosulfonyl]-2-indolinone |
| 10721 | E | 6 | 3-(3-chloromethyl-2-hydroxy-5-nitrobenzylidenyl)-5-[4-(trifluoromethyl)phenylaminosulfonyl]-2-indolinone |
| 10721 | E | 7 | 3-[(2-chlorothien-5-yl)methylidenyl]-5-[4-(trifluoromethyl)phenylaminosulfonyl]-2-indolinone |
| 10721 | E | 8 | 3-[(2,4-dimethylpyrrol-5-yl)methylidenyl]-5-[4-(trifluoromethyl)phenylaminosulfonyl]-2-indolinone |
| 10721 | E | 9 | 3-(3-t-butyl-4-hydroxybenzylidenyl)-5-[4-(trifluoromethyl)phenylaminosulfonyl]-2-indolinone |
| 10721 | E | 10 | 3-(3-bromo-5-t-butyl-4-hydroxybenzylidenyl)-5-[4-(trifluoromethyl)phenylaminosulfonyl]-2-indolinone |
| 10721 | E | 11 | 3-(3,5-di-t-butyl-4-hydroxybenzylidenyl)-5-[4-(trifluoromethyl)phenylaminosulfonyl]-2-indolinone |
| 10721 | F | 2 | 3-[(1-methylbenzimidazol-2-yl)methylidenyl]-5-(morpholin-1-yl)sulfonyl]-2-indolinone |
| 10721 | F | 3 | 3-[(4-chloro-1-methylpyrazol-3-yl)methylidenyl]-5-(morpholin-1-yl)sulfonyl]-2-indolinone |
| 10721 | F | 4 | 3-[(2,3-dimethylthien-5-yl)methylidenyl]-5-(morpholin-1-yl)sulfonyl]-2-indolinone |
| 10721 | F | 5 | 3-[(4,5,6,7-tetrahydroindol-2-yl)methylidenyl]-5-(morpholin-1-yl)sulfonyl]-2-indiinone |
| 10721 | F | 6 | 3-(3-chloromethyl-2-hydroxy-5-nitrobenzylidenyl)-5-(morpholin-1-yl)sulfonyl]-2-indolinone |

TABLE 13-continued

| MASTER BARCODE | PLATE ROW | PLATE COLUMN | NAME |
|---|---|---|---|
| 10721 | F | 7 | 3-[(2-chlorothien-5-yl)methylidenyl]-5-(morpholin-1-yl)sulfonyl]-2-indolinone |
| 10721 | F | 8 | 3-[(2,4-dimethylpyrrol-5-yl)methylidenyl]-5-(morpholin-1-yl)sulfonyl]-2-indolinone |
| 10721 | F | 9 | 3-(3-t-butyl-4-hydroxybenzylidenyl)-5-(morpholin-1-yl)sulfonyl]-2-indolinone |
| 10721 | F | 10 | 3-(3-bromo-5-t-butyl-4-hydroxybenzylidenyl)-5-(morpholin-1-yl)sulfonyl]-2-indolinone |
| 10721 | F | 11 | 3-(3,5-di-t-butyl-4-hydroxybenzylidenyl)-5-(morpholin-1-yl)sulfonyl]-2-indolinone |
| 10721 | G | 2 | 3-[(1-methylbenzimidazol-2-yl)methylidenyl]-5-(2-chloroethyl)-2-indolinone |
| 10721 | G | 3 | 3-[(4-chloro-1-methylpyrazol-3-yl)methylidenyl]-5-(2-chloroethyl)-2-indolinone |
| 10721 | G | 4 | 3-[(2,3-dimethylthien-5-yl)methylidenyl]-5-(2-chloroethyl)-2-indolinone |
| 10721 | G | 5 | 3-[(4,5,6,7-tetrahydroindol-2-yl)methylidenyl]-5-(2-chloroethyl)-2-indolinone |
| 10721 | G | 6 | 3-(3-chloromethyl-2-hydroxy-5-nitrobenzylidenyl)-5-(2-chloroethyl)-2-indolinone |
| 10721 | G | 7 | 3-[(2-chlorothien-5-yl)methylidenyl]-5-(2-chloroethyl)-2-indolinone |
| 10721 | G | 8 | 3-[(2,4-dimethylpyrrol-5-yl)methylidenyl]-5-(2-chloroethyl)-2-indolinone |
| 10721 | G | 9 | 3-(3-t-butyl-4-hydroxybenzylidenyl)-5-(2-chloroethyl)-2-indolinone |
| 10721 | G | 10 | 3-(3-bromo-5-t-butyl-4-hydroxybenzylidenyl)-5-(2-chloroethyl)-2-indolinone |
| 10721 | G | 11 | 3-(3,5-di-ti-butyl-4-hydroxybenzylidenyl)-5-(2-chloroethyl)-2-indolinone |
| 10722 | A | 2 | 3-(3-t-butyl-4-hydroxy-5-nitrobenzylidenyl)-5,7-dibromo-2-indolinone |
| 10722 | A | 3 | 3-(2,4,6-trihydroxybenzylidenyl)-5,7-dibromo-2-indolinone |
| 10722 | A | 4 | 3-[(2-nitrothien-5-yl)methylidenyl]-5,7-dibromo-2-indolinone |
| 10722 | A | 5 | 3-(4-carboxybenzylidenyl)-5,7-dibromo-2-indolinone |
| 10722 | A | 6 | 3-(2,4-difluorobenzylidenyl)-5,7-dibromo-2-indolinone |
| 10722 | A | 7 | 3-(3,5-dimethyl-4-hydroxybenzylidenyl)-5,7-dibromo-2-indolinone |
| 10722 | A | 8 | 3-(3-t-butyl-5-chloro-4-hydroxybenzylidenyl)-5,7-dibromo-2-indolinone |
| 10722 | A | 9 | 3-[(2-nitrothien-4-yl)methylidenyl]-5,7-dibromo-2-indolinone |
| 10722 | A | 10 | 3-(4-di-n-butylaminobenzylidenyl)-5,7-dibromo-2-indolinone |
| 10722 | A | 11 | 3-[4-(trifluoromethyl)benzylidenyl]-5,7-dibromo-2-indolinone |
| 10722 | B | 2 | 3-(3-t-butyl-4-hydroxy-5-nitrobenzylidenyl)-5-iodo-2-indolinone |
| 10722 | B | 3 | 3-(2,4,6-trihydroxybenzylidenyl)-5-iodo-2-indolinone |
| 10722 | B | 4 | 3-[(2-nitrothien-5-yl)methylidenyl]-5-iodo-2-indolinone |
| 10722 | B | 5 | 3-(4-carboxybenzylidenyl)-5-iodo-2-indolinone |
| 10722 | B | 6 | 3-(2,4-difluorobenzylidenyl)-5-iodo-2-indolinone |
| 10722 | B | 7 | 3-(3,5-dimethyl-4-hydroxybenzylidenyl)-5-iodo-2-indolinone |
| 10722 | B | 8 | 3-(3-t-butyl-5-chloro-4-hydroxybenzylidenyl)-5-iodo-2-indolinone |
| 10722 | B | 9 | 3-[(2-nitrothien-4-yl)methylidenyl]-5-iodo-2-indolinone |
| 10722 | B | 10 | 3-(4-di-n-butylaminobenzylidenyl)-5-iodo-2-indolinone |
| 10722 | B | 11 | 3-[4-(trifluoromethyl)benzylidenyl]-5-iodo-2-indolinone |
| 10722 | C | 2 | 3-(3-t-butyl-4-hydroxy-5-nitrobenzylidenyl)-5-dibromo-4-methyl-2-indolinone |
| 10722 | C | 3 | 3-(2,4,6-trihydroxybenzylidenyl)-5-dibromo-4-methyl-2-indolinone |
| 10722 | C | 4 | 3-[(2-nitrothien-5-yl)methylidenyl]-5-dibromo-4-methyl-2-indolinone |
| 10722 | C | 5 | 3-(4-carboxybenzylidenyl)-5-dibromo-4-methyl-2-indolinone |
| 10722 | C | 6 | 3-(2,4-difluorobenzylidenyl)-5-dibromo-4-methyl-2-indolinone |

TABLE 13-continued

| MASTER BARCODE | PLATE ROW | PLATE COLUMN | NAME |
| --- | --- | --- | --- |
| 10722 | C | 7 | 3-(3,5-dimethyl-4-hydroxybenzylidenyl)-5-dibromo-4-methyl-2-indolinone |
| 10722 | C | 8 | 3-(3-t-butyl-5-chloro-4-hydroxybenzylidenyl)-5-dibromo-4-methyl-2-indolinone |
| 10722 | C | 9 | 3-[(2-nitrothien-4-yl)methylidenyl]-5-dibromo-4-methyl-2-indolinone |
| 10722 | C | 10 | 3-(4-di-n-butylaminobenzylidenyl)-5-dibromo-4-methyl-2-indolinone |
| 10722 | C | 11 | 3-[4-(trifluoromethyl)benzylidenyl]-5-dibromo-methyl-2-indolinone |
| 10722 | D | 2 | 3-(3-t-butyl-4-hydroxy-5-nitrobenzylidenyl)-5-methylaminosulfonyl-2-indolinone |
| 10722 | D | 3 | 3-(2,4,6-trihydroxybenzylidenyl)-5-methylaminosulfonyl-2-indolinone |
| 10722 | D | 4 | 3-[(2-nitrothien-5-yl)methylidenyl]-5-methylaminosulfonyl-2-indolinone |
| 10722 | D | 5 | 3-(4-carboxybenzylidenyl)-5-methylaminosulfonyl-2-indolinone |
| 10722 | D | 6 | 3-(2,4-difluorobenzylidenyl)-5-methylaminosulfonyl-2-indolinone |
| 10722 | D | 7 | 3-(3,5-dimethyl-4-hydroxybenzylidenyl)-5-methylaminosulfonyl-2-indolinone |
| 10722 | D | 8 | 3-(3-t-butyl-5-chloro-4-hydroxybenzylidenyl)-5-methylaminosulfonyl-2-indolinone |
| 10722 | D | 9 | 3-[(2-nitrothien-4-yl)methylidenyl)-5-methylaminosulfonyl-2-indolinone |
| 10722 | D | 10 | 3-(4-di-n-butylaminobenzylidenyl)-5-methylaminosulfonyl-2-indolinone |
| 10722 | D | 11 | 3-[4-(trifluoromethyl)benzylidenyl]-5-methylaminosulfonyl-2-indolinone |
| 10722 | E | 2 | 3-(3-t-butyl-4-hydroxy-5-nitrobenzylidenyl)-5-[4-(trifluoromethyl)phenylaminosulfonyl]-2-indolinone |
| 10722 | E | 3 | 3-(2,4,6-trihydroxybenzylidenyl)-5-[4-(trifluoromethyl)phenylaminosulfonyl]-2-indolinone |
| 10722 | E | 4 | 3-[(2-nitrothien-5-yl)methylidenyl]-5-[4-(trifluoromethyl)phenylaminosulfonyl]-2-indolinone |
| 10722 | E | 5 | 3-(4-carboxybenzylidenyl)-5-[4-(trifluoromethyl)phenylaminosulfonyl]-2-indolinone |
| 10722 | E | 6 | 3-(2,4-difluorobenzylidenyl)-5-[4-(trifluoromethyl)phenylaminosulfonyl]-2-indolinone |
| 10722 | E | 7 | 3-(3,5-dimethyl-4-hydroxybenzylidenyl)-5-[4-(trifluoromethyl)phenylaminosulfonyl]-2-indolinone |
| 10722 | E | 8 | 3-(3-t-butyl-5-chloro-4-hydroxybenzylidenyl)-5-[4-(trifluoromethyl)phenylaminosulfonyl]-2-indolnone |
| 10722 | E | 9 | 3-[(2-nitrothien-4-yl)methylidenyl]-5-[4-(trifluoromethyl)phenylaminosulfonyl]-2-indolinone |
| 10722 | E | 10 | 3-(4-di-n-butylaminobenzylidenyl)-5-[4-(trifluoromethyl)phenylaminosulfonyl]-2-indolinone |
| 10722 | E | 11 | 3-[4-(trifluoromethyl)benzylidenyl]-5-[4-(trifluoromethyl)phenylaminosulfonyl]-2-indolinone |
| 10722 | F | 2 | 3-(3-t-butyl-4-hydroxy-5-nitrobenzylidenyl)-5-(morpholin-1-yl)aminosulfonyl-2-indolinone |
| 10722 | F | 3 | 3-(2,4,6-trihydroxybenzylidenyl)-5-(morpholin-1-yl)aminosulfonyl-2-indolinone |
| 10722 | F | 4 | 3-[(2-nitrothien-5-yl)methylidenyl]-5-(morpholin-1-yl)aminosulfonyl-2-indolinone |
| 10722 | F | 5 | 3-(4-carboxybenzylidenyl)-5-(morpholin-1-yl)aminosulfonyl-2-indolinone |
| 10722 | F | 6 | 3-(2,4-difluorobenzylidenyl)-5-(morpholin-1-yl)aminosulfonyl-2-indolinone |
| 10722 | F | 7 | 3-(3,5-dimethyl-4-hydroxybenzylidenyl)-5-(morpholin-1-yl)aminosulfonyl-2-indolinone |
| 10722 | F | 8 | 3-(3-t-butyl-5-chloro-4-hydroxybenzylidenyl)-5-(morpholin-1-yl)aminosulfonyl-2-indolinone |
| 10722 | F | 9 | 3-[(2-nitrothien-4-yl)methylidenyl]-5-(morpholin-1-yl)aminosulfonyl-2-indolinone |
| 10722 | F | 10 | 3-(4-di-n-butylaminobenzylidenyl)-5-(morpholin-1-yl)aminosulfonyl-2-indolinone |
| 10722 | F | 11 | 3-[4-(trifluoromethyl)benzylidenyl]-5-(morpholin-1-yl)aminosulfonyl-2-indolinone |
| 10722 | G | 2 | 3-(3-t-butyl-4-hydroxy-5-nitrobenzylidenyl)-5-(2-chloroethyl)-2-indolinone |
| 10722 | G | 3 | 3-(2,4,6-trihydroxybenzylidenyl)-5-(2-chloroethyl)-2-indolinone |
| 10722 | G | 4 | 3-[(2-nitrothien-5-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10722 | G | 5 | 3-(4-carboxybenzylidenyl)-5-(2-chloroethyl)-2-indolinone |
| 10722 | G | 6 | 3-(2,4-difluorobenzylidenyl)-5-(2-chloroethyl)-2-indolinone |
| 10722 | G | 7 | 3-(3,5-dimethyl-4-hydroxybenzyl-denyl)-5-(2-chloroethyl)-2-indolinone |
| 10722 | G | 8 | 3-(3-t-butyl-5-chloro-4-hydroxybenzylidenyl)-5-(2 chloroethyl)-2-indolinone |
| 10722 | G | 9 | 3-[(2-nitrothien-4-yl)methylidenyl]-5-(2-chloroethyl)-2-indolinone |
| 10722 | G | 10 | 3-(4-di-n-butylaminobenzylidenyl)-5-(2-chloroethyl)-2-indolinone |
| 10722 | G | 11 | 3-[4-(trifluoromethyl)benzylidenyl]-5-(2-chloroethyl)-2-indolinone |
| 10723 | A | 2 | 3-(2,3,4-trihydroxybenzylidenyl)-5,7-dibromo-2-indolinone |
| 10723 | A | 3 | 3-(2-hydroxy-3-methoxybenzylidenyl)-5,7-dibromo-2-indolinone |
| 10723 | A | 4 | 3-(3-bromo-4,5-dihydroxybenzylidenyl)-5,7-dibromo-2-indolinone |
| 10723 | A | 5 | 3-(3,4-diacetoxybenzylidenyl)-5,7-dibromo-2-indolinone |
| 10723 | A | 6 | 3-(4-hydroxy-3-methylbenzylidenyl)-5,7-dibromo-2-indolinone |
| 10723 | A | 7 | 3-(2-bromobenzylidenyl)-5-7-dibromo-2-indolinone |
| 10723 | A | 8 | 3-(2,4-dihydroxybenzylidenyl)-5,7-dibromo-2-indolinone |
| 10723 | A | 9 | 3-(2-hydroxy-4-methoxybenzylidenyl)-5,7-dibromo-2-indolinone |
| 10723 | A | 10 | 3-(3-bromobenzylidenyl)-5,7-dibromo-2-indolinone |
| 10723 | A | 11 | 3-(3,5-di-t-butyl-2-hydroxybenzylidenyl)-5,7-dibromo-2-indolinone |
| 10723 | B | 2 | 3-(2,3,4-trihydroxybenzylidenyl)-5-iodo-2-indolinone |
| 10723 | B | 3 | 3-(2-hydroxy-3-methoxybenzylidenyl)-5-iodo-2-indolinone |
| 10723 | B | 4 | 3-(3-bromo-4,5-dihydroxybenzylidenyl)-5-iodo-2-indolinone |
| 10723 | B | 5 | 3-(3,4-diacetoxybenzylidenyl)-5-iodo-2-indolinone |
| 10723 | B | 6 | 3-(4-hydroxy-3-methylbenzylidenyl)-5-iodo-2-indolinone |
| 10723 | B | 7 | 3-(2-bromobenzylidenyl)-5-iodo-2-indolinone |
| 10723 | B | 8 | 3-(2,4-dihydroxybenzylidenyl)-5-iodo-2-indolinone |
| 10723 | B | 9 | 3-(2-hydroxy-4-methoxybenzylidenyl)-5-iodo-2-indolinone |
| 10723 | B | 10 | 3-(3-bromobenzylidenyl)-5-iodo-2-indolinone |
| 10723 | B | 11 | 3-(3,5-di-t-butyl-2-hydroxybenzylidenyl)-5-iodo-2-indolinone |
| 10723 | C | 2 | 3-(2,3,4-trihydroxybenzylidenyl)-5-bromo-4-methyl-2-indolinone |
| 10723 | C | 3 | 3-(2-hydroxy-3-methoxybenzylidenyl)-5-bromo-4-methyl-2-indolinone |
| 10723 | C | 4 | 3-(3-bromo-4,5-dihydroxybenzylidenyl)-5-bromo-4-methyl-2-indolinone |
| 10723 | C | 5 | 3-(3,4-diacetoxybenzylidenyl)-5-bromo-4-methyl-2-indolinone |
| 10723 | C | 6 | 3-(4-hydroxy-3-methylbenzylidenyl)-5-bromo-4-methyl-2-indolinone |
| 10723 | C | 7 | 3-(2-bromobenzylidenyl)-5-bromo-4-methyl-2 indolinone |
| 10723 | C | 8 | 3-(2,4-dihydroxybenzylidenyl)-5-bromo-4-methyl-2-indolinone |
| 10723 | C | 9 | 3-(2-hydroxy-4-methoxybenzylidenyl)-5-bromo-4-methyl-2-indolinone |
| 10723 | C | 10 | 3-(3-bromobenzylidenyl)-5-bromo-4-methyl-2-indolinone |
| 10723 | C | 11 | 3-(3,5-di-t-butyl-2-hydroxybenzylidenyl)-5-bromo-4-methyl-2-indolinone |
| 10723 | D | 2 | 3-(2,3,4-trihydroxybenzylidenyl)-5-methylaminosulfonyl-2-indolinone |
| 10723 | D | 3 | 3-(2-hydroxy-3-methoxybenzylidenyl)-5-methylaminosulfonyl-2-indolinone |
| 10723 | D | 4 | 3-(3-bromo-4,5-dihydroxybenzylidenyl)-5-methylaminosulfonyl-2-indolinone |
| 10723 | D | 5 | 3-(3,4-diacetoxybenzylidenyl)-5-methylaminosulfonyl-2-indolinone |

TABLE 13-continued

| MASTER BARCODE | PLATE ROW | PLATE COLUMN | NAME |
|---|---|---|---|
| 10723 | D | 6 | 3-(4-hydroxy-3-methylbenzylidenyl)-5-methylaminosulfonyl-2-indolinone |
| 10723 | D | 7 | 3-(2-bromobenzylidenyl)-5-methylaminosulfonyl-2-indolinone |
| 10723 | D | 8 | 3-(2,4-dihydroxybenzylidenyl)-5-methylaminosulfonyl-2-indolinone |
| 10723 | D | 9 | 3-(2-hydroxy-4-methoxybenzylidenyl)-5-methylaminosulfonyl-2-indolinone |
| 10723 | D | 10 | 3-(3-bromobenzylidenyl)-5-methylaminosulfonyl-2-indolinone |
| 10723 | D | 11 | 3-(3,5-di-t-butyl-2-hydroxybenzylidenyl)-5-methylaminosulfonyl-2-indolinone |
| 10723 | E | 2 | 3-(2,3,4-trihydroxybenzylidenyl)-5-[4-(trifluoromethyl)phenylaminosulfonyl]-2-indolinone |
| 10723 | E | 3 | 3-(2-hydroxy-3-methoxybenzylidenyl)-5-[4-(trifluoromethyl)phenylaminosulfonyl]-2-indolinone |
| 10723 | E | 4 | 3-(3-bromo-4,5-dihydroxybenzylidenyl)-5-[4-(trifluoromethyl)phenylaminosulfonyl]-2-indolinone |
| 10723 | E | 5 | 3-(3,4-diacetoxybenzylidenyl)-5-[4-(trifluoromethyl)phenylaminosulfonyl]-2-indolinone |
| 10723 | E | 6 | 3-(4-hydroxy-3-methylbenzylidenyl)-5-[4-(trifluoromethyl)phenylaminosulfonyl]-2-indolinone |
| 10723 | E | 7 | 3-(2-bromobenzylidenyl)-5-[4-(trifluoromethyl)phenylaminosulfonyl]-2-indolinone |
| 10723 | E | 8 | 3-(2,4-dihydroxybenzylidenyl)-5-[4-(trifluoromethyl)phenylaminosulfonyl]-2-indolinone |
| 10723 | E | 9 | 3-(2-hydroxy-4-methoxybenzylidenyl)-5-[4-(trifluoromethyl)phenylaminosulfonyl]-2-indolinone |
| 10723 | E | 10 | 3-(3-bromobenzylidenyl)-5-[4-(trifluoromethyl)phenylaminosulfonyl]-2-indolinone |
| 10723 | E | 11 | 3-(3,5-di-t-butyl-2-hydroxybenzylidenyl)-5-[4-(trifluoromethyl)phenylaminosulfonyl]-2-indolinone |
| 10723 | F | 2 | 3-(2,3,4-trihydroxybenzylidenyl)-5-(morpholin-1-yl)aminosulfonyl-2-indolinone |
| 10723 | F | 3 | 3-(2-hydroxy-3-methoxybenzylidenyl)-5-(morpholin-1-yl)aminosulfonyl-2-indolinone |
| 10723 | F | 4 | 3-(3-bromo-4,5-dihydroxybenzylidenyl)-5-(morpholin-1-yl)aminosulfonyl-2-indolinone |
| 10723 | F | 5 | 3-(3,4-diacetoxybenzylidenyl)-5-(morpholin-1-yl)aminosulfonyl-2-indolinone |
| 10723 | F | 6 | 3-(4-hydroxy-3-methylbenzylidenyl)-5-(morpholin-1-yl)aminosulfonyl-2-indolinone |
| 10723 | F | 7 | 3-(2-bromobenzylidenyl)-5-(morpholin-1-yl)aminosulfonyl-2-indolinone |
| 10723 | F | 8 | 3-(2,4-dihydroxybenzylidenyl)-5-(morpholin-1-yl)aminosulfonyl-2-indolinone |
| 10723 | F | 9 | 3-(2-hydroxy-4-methdxybenzylidenyl)-5-(morpholin-1-yl)aminosulfonyl-2-indolinone |
| 10723 | F | 10 | 3-(3-bromobenzylidenyl)-5-(morpholin-1-yl)aminosulfonyl-2-indolinone |
| 10723 | F | 11 | 3-(3,5-di-t-butyl-2-hydroxybenzylidenyl)-5-(morpholin-1-yl)aminosulfonyl-2-indolinone |
| 10723 | G | 2 | 3-(2,3,4-trihydroxybenzylidenyl)-5-(2-chloroethyl)-2-indolinone |
| 10723 | G | 3 | 3-(2-hydroxy-3-methoxybenzylidenyl)-5-(2-chloroethyl)-2-indolinone |
| 10723 | G | 4 | 3-(3-bromo-4,5-dihydroxybenzylidenyl)-5-(2-chloroethyl)-2-indolinone |
| 10723 | G | 5 | 3-(3,4-diacetoxybenzylidenyl)-5-(2-chloroethyl)-2-indolinone |
| 10723 | G | 6 | 3-(4-hydroxy-3-methylbenzylidenyl)-5-(2-chloroethyl)-2-indolinone |
| 10723 | G | 7 | 3-(2-bromobenzylidenyl)-5-(2-chloroethyl)-2-indolinone |
| 10723 | G | 8 | 3-(2,4-dihydroxybenzylidenyl)-5-(2-chloroethyl)-2-indolinone |
| 10723 | G | 9 | 3-(2-hydroxy-4-methoxybenzylidenyl)-5-(2-chloroethyl)-2-indolinone |
| 10723 | G | 10 | 3-(3-bromobenzylidenyl)-5-(2-chloroethyl)-2-indolinone |
| 10723 | G | 11 | 3-(3,5-di-t-butyl-2-hydroxybenzylidenyl)-5-(2-chloroethyl)-2-indolinone |
| 10724 | A | 2 | 3-[(1-dimethylaminonapth-4-yl)methylidenyl]-5,7-dibromo-2-indolinone |
| 10724 | A | 3 | 3-(4-hydroxy-3-nitrobenzylidenyl)-5,7-dibromo-2-indolinone |

TABLE 13-continued

| MASTER BARCODE | PLATE ROW | PLATE COLUMN | NAME |
|---|---|---|---|
| 10724 | A | 4 | 3-(3-hydroxy-4-nitrobenzylidenyl)-5,7-dibromo-2-indolinone |
| 10724 | A | 5 | 3-[(8-hydroxy-2,3,6,7-tetrahydro-1H,5H-benzo[ij]quinolizin-9-yl)methylidenyl]-5,7-dibromo-2-indolinone |
| 10724 | A | 6 | 3-(3,5-diisopropyl-4-hydroxybenzylidenyl)-5,7-dibromo-2-indolinone |
| 10724 | A | 7 | 3-[(benzo[b]furan-2-yl)methylidenyl]-5,7-dibromo-2-indolinone |
| 10724 | A | 9 | 3-[[1-(4-chlorophenyl)pyrrol-2-yl]methylidenyl]-5,7-dibromo-2-indolinone |
| 10724 | A | 10 | 3-[(2-ethylfuran-5-yl)methylidenyl]-5,7-dibromo-2-indolinone |
| 10724 | A | 11 | 3-[(3,4-dimethylthieno[2,3-b]thien-2-yl)methylidenyl]-5,7-dibromo-2-indolinone |
| 10724 | B | 2 | 3-[(1-dimethylaminonapth-4-yl)methylidenyl]-5-iodo-2-indolinone |
| 10724 | B | 3 | 3-(4-hydroxy-3-nitrobenzylidenyl)-5-iodo-2-indolinone |
| 10724 | B | 4 | 3-(3-hydroxy-4-nitrobenzylidenyl)-5-iodo-2-indolinone |
| 10724 | B | 5 | 3-[(8-hydroxy-2,3,7-tetrahydro-1H,5H-benzo[ij]quinolizin-9-yl)methylidenyl]-5-iodo-2-indolinone |
| 10724 | B | 6 | 3-(3,5-diisopropyl-4-hydroxybenzylidenyl)-5-iodo-2-indolinone |
| 10724 | B | 7 | 3-[(benzo[b]furan-2-yl)methylidenyl]-5-iodo-2-indolinone |
| 10724 | B | 9 | 3-[[1-(4-chlorophenyl)pyrrol-2-yl]methylidenyl]-5-iodo-2-indolinone |
| 10724 | B | 10 | 3-[(2-ethylfuran-5-yl)methylidenyl]-5-iodo-2-indolinone |
| 10724 | B | 11 | 3-[(3,4-dimethylthieno[2,3-b]thien-2-yl)methylidenyl]-5-iodo-2-indolinone |
| 10724 | C | 2 | 3-[(1-dimethylaminonapth-4-yl)methylidenyl]-5-bromo-4-methyl-2-indolinone |
| 10724 | C | 3 | 3-(4-hydroxy-3-nitrobenzylidenyl)-5-bromo-4-methyl-2-indolinone |
| 10724 | C | 4 | 3-(3-hydroxy-4-nitrobenzylidenyl)-5-bromo-4-methyl-2-indolinone |
| 10724 | C | 5 | 3-[(8-hydroxy-2,3,6,7-tetrahydro-1H,5H-benzo[ij]quinolizin-9-yl)methylidenyl]-5-bromo-4-methyl-2-indolinone |
| 10724 | C | 6 | 3-(3,5-diisopropyl-4-hydroxybenzylidenyl)-5-bromo-4-methyl-2-indolinone |
| 10724 | C | 7 | 3-[(benzo[b]furan-2-yl)methylidenyl]-5-bromo-4-methyl-2-indolinone |
| 10724 | C | 9 | 3-[[1-(4-chlorophenyl)pyrrol-2-yl]methylidenyl]-5-bromo-4-methyl-2-indolinone |
| 10724 | C | 10 | 3-[(2-ethylfuran-5-yl)methylidenyl]-5-bromo-4-methyl-2-indolinone |
| 10724 | C | 11 | 3-[(3,4-dimethylthieno[2,3-b]thien-2-yl)methylidenyl]-5-bromo-4-methyl-2-indolinone |
| 10724 | D | 2 | 3-[(1-dimethylaminonapth-4-yl)methylidenyl]-5-methylaminosulfonyl-2-indolinone |
| 10724 | D | 3 | 3-(4-hydroxy-3-nitrobenzylidenyl)-5-methylaminosulfonyl-2-indolinone |
| 10724 | D | 4 | 3-(3-hydroxy-4-nitrobenzylidenyl)-5-methylaminosulfonyl-2-indolinone |
| 10724 | D | 5 | 3-[(8-hydroxy-2,3,6,7-tetrahydro-1H,5H-benzo[ij]quinolizin-9-yl)methylidenyl]-5-methylaminosulfonyl-2-indolinone |
| 10724 | D | 6 | 3-(3,5-diisopropyl-4-hydroxybenzylidenyl)-5-methylaminosulfonyl-2-indolinone |
| 10724 | D | 7 | 3-[(benzo[b]furan-2-yl)methylidenyl]-5-methylaminosulfonyl-2-indolinone |
| 10724 | D | 9 | 3-[1-(4-chlorophenyl)pyrrol-2-yl]methylidenyl]-5-methylaminosulfonyl-2-indolinone |
| 10724 | D | 10 | 3-[(2-ethylfuran-5-yl)methylidenyl]-5-methylaminosulfonyl-2-indolinone |
| 10724 | D | 11 | 3-[(3,4-dimethylthieno[2,3-b]thien-2-yl)methylidenyl]-5-methylaminosulfonyl-2-indolinone |
| 10724 | E | 2 | 3-[(1-dimethylaminonapth-4-yl)methylidenyl]-5-[4-(trifluoromethyl)phenylaminosulfonyl]-2-indolinone |
| 10724 | E | 3 | 3-(4-hydroxy-3-nitrobenzylidenyl)-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10724 | E | 4 | 3-(3-hydroxy-4-nitrobenzylidenyl)-5-[4-(trifluoromethyl)phenylaminosulfonyl]-2-indolinone |
| 10724 | E | 5 | 3-[(8-hydroxy-2,3,6,7-tetrahydro-1H,5H-benzo[ij]quinolizin-9-yl)methylidenyl]-5-[4-(trifluoromethyl)phenylaminosulfonyl]-2-indolinone |
| 10724 | E | 6 | 3-(3,5-diisopropyl-4-hydroxybenzylidenyl)-5-[4-(trifluoromethyl)phenylaminosulfonyl]-2-indolinone |
| 10724 | E | 7 | 3-[(benzo[b]furan-2-yl)methylidenyl]-5-[4-(trifluoromethyl)phenylaminosulfonyl]-2-indolinone |
| 10724 | E | 9 | 3-[[1-(4-chlorophenyl)pyrrol-2-yl]methylidenyl]-5-[4-(trifluoromethyl)phenylaminosulfonyl]-2-indolinone |
| 10724 | E | 10 | 3-[(2-ethylfuran-5-yl)methylidenyl]-5-[4-(trifluoromethyl)phenylaminosulfonyl]-2-indoinone |
| 10724 | E | 11 | 3-[(3,4-dimethylthieno[2,3-b]thien-2-yl)methylidenyl]-5-[4-(trifluoromethyl)phenylaminosulfonyl]-2-indolinone |
| 10724 | F | 2 | 3-[(1-dimethylaminonapth-4-yl)methylidenyl]-5-(morpholin-lyl)aminosulfonyl-2-indolinone |
| 10724 | F | 3 | 3-(4-hydroxy-3-nitrobenzylidenyl)-5-(morpholin-1yl)aminosulfonyl-2-indolinone |
| 10724 | F | 4 | 3-(3-hydroxy-4-nitrobenzylidenyl)-5-(morpholin-1yl)aminosulfonyl-2-indolinone |
| 10724 | F | 5 | 3-[(8-hydroxy-2,3,6,7-tetrahydro-1H,5H-benzol[ij]quinolizin-9-yl)methylidenyl]-5-(morpholin-1yl)aminosulfonyl-2-indolinone |
| 10724 | F | 6 | 3-(3,5-diisopropyl-4-hydroxybenzylidenyl)-5-(morpholin-1yl)aminosulfonyl-2-indolinone |
| 10724 | F | 7 | 3-[(benzo[b]furan-2-yl)methylidenyl]-5-(morpholin-1yl)aminosulfonyl-2-indolinone |
| 10724 | F | 9 | 3-[[1-(4-chlorophenyl)pyrrol-2-yl]methylidenyl]-5-(morpholin-1yl)aminosulfonyl-2-indolinone |
| 10724 | F | 10 | 3-[(2-ethylfuran-5-yl)methylidenyl]-5-(morpholin-1yl)aminosulfonyl-2-indolinone |
| 10724 | F | 11 | 3-[(3,4-dimethylthieno[2,3-b]thien-2-yl)methylidenyl]-5-(morpholin-1yl)aminosulfonyl-2-indolinone |
| 10724 | G | 2 | 3-[(1-dimethylaminonapth-4-yl)methylidenyl]-5-(2-chloroethyl)-2-indolinone |
| 10724 | G | 3 | 3-(4-hydroxy-3-nitrobenzylidenyl)-5-(2-chloroethyl)-2-indolinone |
| 10724 | G | 4 | 3-(3-hydroxy-4-nitrobenzylidenyl)-5-(2-chloroethyl)-2-indolinone |
| 10724 | G | 5 | 3-[(8-hydroxy-2,3,6,7-tetrahydro-1H,5H-benzol[ij]quinolizin-9-yl)methylidenyl]-5-(2-chloroethyl)-2-indolinone |
| 10724 | G | 6 | 3-(3,5-diisopropyl-4-hydroxybenzylidenyl)-5-(2-chloroethyl)-2-indolinone |
| 10724 | G | 7 | 3-[(benzo[b]furan-2-yl)methylidenyl]-5-(2-chloroethyl)-2-indolinone |
| 10724 | G | 9 | 3-[[1-(4-chlorophenyl)pyrrol-2-yl]methylidenyl]-5-(2-chloroethyl)-2-indolinone |
| 10724 | G | 10 | 3-[(2-ethylfuran-5-yl)methylidenyl]-5-(2-chloroethyl)-2-indolinone |
| 10724 | G | 11 | 3-[(3,4-dimethylthieno[2,3-b]thien-2-yl)methylidenyl]-5-(2-chloroethyl)-2-indolinone |
| 10725 | A | 2 | 3-[(3-bromothien-2-yl)methylidenyl]-5,7-dibromo-2-indolinone |
| 10725 | A | 3 | 3-(2-bromo-6-hydroxy-5-methoxybenzylidenyl)-5,7-dibromo-2-indolinone |
| 10725 | A | 4 | 3-[(2-methylfuran-5-yl)methylidenyl]-5,7-dibromo-2-indolinone |
| 10725 | A | 5 | 3-[(3-methylpyrazol-5-yl)methylidenyl]-5,7-dibromo-2-indolinone |
| 10725 | A | 6 | 3-(2-hydroxy-6-methoxy-4-methylbenzylidenyl)-5,7-dibromo-2-indolinone |
| 10725 | A | 7 | 3-[4-(4-formylpiperazin-1-yl)benzylidenyl]-5,7-dibromo-2-indolinone |
| 10725 | A | 8 | 3-[4-(morpholin-1-yl)benzylidenyl]-5,7-dibromo-2-indolinone |
| 10725 | A | 9 | 3-[[2-chloro-4-methoxycarbonyl-3-(methoxycarbonylmethyl)pyrrol-5-yl]methylidenyl]-5,7-dibromo-4-methyl-2-indolinone |
| 10725 | A | 10 | 3-[[4-bromo-2-(4-chlorophenyl)pyrazol-3-yl]methylidenyl]-5,7-dibromo-4-methyl-2-indolinone |
| 10725 | A | 11 | 3-[(imidazol-4-yl)methylidenyl]-5,7-ibromo-4-methyl-2-indolinone |

TABLE 13-continued

| MASTER BARCODE | PLATE ROW | PLATE COLUMN | NAME |
|---|---|---|---|
| 10725 | B | 2 | 3-[(3-bromothien-2-yl)methylidenyl]-5-iodo-2-indolinone |
| 10725 | B | 3 | 3-(2-bromo-hydroxy-5-methoxybenzylidenyl)-5-iodo-2-indolinone |
| 10725 | B | 4 | 3-[(2-methylfuran-5-yl)methylidenyl]-5-iodo-2-indolinone |
| 10725 | B | 5 | 3-[(3-methylpyrazol-5-yl)methylidenyl]-5-iodo-2-indolinone |
| 10725 | B | 6 | 3-(2-hydroxy-methoxy-4-methylbenzylidenyl)-5-iodo-2-indolinone |
| 10725 | B | 7 | 3-[4-(4-formylpiperazin-1-yl)benzylidenyl]-5-iodo-2-indolinone |
| 10725 | B | 8 | 3-[4-(morpholin-1-yl)benzylidenyl]-5-iodo-2-indolinone |
| 10725 | B | 9 | 3-[[2-chloro-4-methoxycarbonyl-3-(methoxycarbonylmethyl)pyrrol-5-yl]methylidenyl]-5-iodo-2-indolinone |
| 10725 | B | 10 | 3-[[4-bromo-2-(4-chlorophenyl)pyrazol-3-yl]methylidenyl]-5-iodo-2-indolinone |
| 10725 | B | 11 | 3-[(imidazol-4-yl)methylidenyl]-5-iodo-2-indolinone |
| 10725 | C | 2 | 3-[(3-bromothien-2-yl)methylidenyl]-5-bromo-4-methyl-2-indolinone |
| 10725 | C | 3 | 3-(2-bromo-hydroxy-5-methoxybenzylidenyl)-5-bromo-4-methyl-2-indolinone |
| 10725 | C | 4 | 3-[(2-methylfuran-5-yl)methylidenyl]-5-bromo-4-methyl-2-indolinone |
| 10725 | C | 5 | 3-[(3-methylpyrazol-5-yl)methylidenyl)-5-bromo-4-methyl-2-indolinone |
| 10725 | C | 6 | 3-(2-hydroxy-methoxy-4-methylbenzylidenyl)-5-bromo-4-methyl-2-indolinone |
| 10725 | C | 7 | 3-[4-(4-formylpiperazin-1-yl)benzylidenyl]-5-bromo-4-methyl-2-indolinone |
| 10725 | C | 8 | 3-[4-(morpholin-1-yl)benzylidenyl]-5-bromo-4-methyl-2-indolinone |
| 10725 | C | 9 | 3-[[2-chloro-4-methoxycarbonyl-3-(methoxycarbonylmethyl)pyrrol-5-yl]methylidenyl]-5-bromo-4-methyl-2-indolinone |
| 10725 | C | 10 | 3-[[4-bromo-2-(4-chlorophenyl)pyrazol-3-yl]methylidenyl]-5-bromo-4-methyl-2-indolinone |
| 10725 | C | 11 | 3-[(imidazol-4-yl)methylidenyl]-5-bromo-4-methyl-2-indolinone |
| 10725 | D | 2 | 3-[(3-bromothien-2-yl)methylidenyl]-5-methylaminosulfonyl-2-indolinone |
| 10725 | D | 3 | 3-(2-bromo-hydroxy-5-methoxybenzylidenyl)-5-methylaminosulfonyl-2-indolinone |
| 10725 | D | 4 | 3-[(2-methylfuran-5-yl)methylidenyl]-5-methylaminosulfonyl-2-indolinone |
| 10725 | D | 5 | 3-[(3-methylpyrazol-5-yl)methylidenyl]-5-methylaminosulfonyl-2-indolinone |
| 10725 | D | 6 | 3-(2-hydroxy-6-methoxy-4-methylbenzylidenyl)-5-methylaminosulfonyl-2-indolinone |
| 10725 | D | 7 | 3-[4-(4-formylpiperazin-1-yl)benzylidenyl]-5-methylaminosulfonyl-2-indolinone |
| 10725 | D | 8 | 3-[4-(morpholin-1-yl)benzylidenyl]-5-methylaminosulfonyl-2-indolinone |
| 10725 | D | 9 | 3-[[2-chloro-4-methoxycarbonyl-3-(methoxycarbonylmethyl)pyrrol-5-yl]methylidenyl]-5-methylaminosulfonyl-2-indolinone |
| 10725 | D | 10 | 3-[[4-bromo-2-(4-chlorophenyl)pyrazol-3-yl]methylidenyl]-5-methylaminosulfonyl-2-indolinone |
| 10725 | D | 11 | 3-[(imidazol-4-yl)methylidenyl]-5-methylaminosulfonyl-2-indolinone |
| 10725 | E | 2 | 3-[(3-bromothien-2-yl)methylidenyl]-5-[4-(trifluoromethyl)phenylaminosulfonyl]-2-indolinone |
| 10725 | E | 3 | 3-(2-bromo-6-hydroxy-5-methoxybenzylidenyl)-5-[4-(trifluoromethyl)phenylaminosulfonyl]-2-indolinone |
| 10725 | E | 4 | 3-[(2-methylfuran-5-yl)methylidenyl]-5-[4-(trifluoromethyl)phenylaminosulfonyl]-2-indolinone |
| 10725 | E | 5 | 3-[(3-methylpyrazol-5-yl)methylidenyl]-5-[4-(trifluoromethyl)phenylaminosulfonyl]-2-indolinone |
| 10725 | E | 6 | 3-(2-hydroxy-methoxy-4-methylbenzylidenyl)-5-[4-(trifluoromethyl)phenylaminosulfonyl]-2-indolinone |
| 10725 | E | 7 | 3-[4-(4-formylpiperazin-1-yl)benzylidenyl]-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10725 | E | 8 | 3-[4-(morpholin-1-yl)benzylidenyl]-5-[4-(trifluoromethyl)phenylaminosulfonyl]-2-indolinone |
| 10725 | E | 9 | 3-[[2-chloro-4-methoxycarbonyl-3-(methoxycarbonylmethyl)pyrrol-5-yl]methylidenyl]-5-[4-(trifluoromethyl)phenylaminosulfonyl]-2-indolinone |
| 10725 | E | 10 | 3-[[4-bromo-2-(4-chlorophenyl)pyrazol-3-yl]methylidenyl]-5-[4-(trifluoromethyl)phenylaminosulfonyl]-2-indolinone |
| 10725 | E | 11 | 3-[(imidazol-4-yl)methylidenyl]-5-[4-(trifluoromethyl)phenylaminosulfonyl]-2-indolinone |
| 10725 | F | 2 | 3-[(3-bromothien-2-yl)methylidenyl]-5-(morpholin-1-yl)sulfonyl-2-indolinone |
| 10725 | F | 3 | 3-(2-bromo-6-hydroxy-5-methoxybenzylidenyl)-5-(morpholin-1-yl)sulfonyl-2-indolinone |
| 10725 | F | 4 | 3-[(2-methylfuran-5-yl)methylidenyl]-5-(morpholin-1-yl)sulfonyl-2-indolinone |
| 10725 | F | 5 | 3-[(3-methylpyrazol-5-yl)methylidenyl]-5-(morpholin-1-yl)sulfonyl-2-indolinone |
| 10725 | F | 6 | 3-(2-hydroxy-6-methoxy-4-methylbenzylidenyl)-5-(morpholin-1-yl)sulfonyl-2-indolinone |
| 10725 | F | 7 | 3-[4-(4-formylpiperazin-1-yl)benzylidenyl]-5-(morpholin-1-yl)sulfonyl-2-indolinone |
| 10725 | F | 8 | 3-[4-(morpholin-1-yl)benzylidenyl]-5-(morpholin-1-yl)sulfonyl-2-indolinone |
| 10725 | F | 9 | 3-[[2-chloro-4-methoxycarbonyl-3-(methoxycarbonylmethyl)pyrrol-5-yl]methylidenyl]-5-(morpholin-1-yl)sulfonyl-2-indolinone |
| 10725 | F | 10 | 3-[[4-bromo-2-(4-chlorophenyl)pyrazol-3-yl]methylidenyl]-5-(morpholin-1-yl)sulfonyl-2-indolinone |
| 10725 | F | 11 | 3-[(imidazol-4-yl)methylidenyl]-5-(morpholin-1-yl)sulfonyl-2-indolinone |
| 10725 | G | 2 | 3-[(3-bromothien-2-yl)methylidenyl]-5-(2-chloroethyl)-2-indolinone |
| 10725 | G | 3 | 3-(2-bromo-hydroxy-5-methoxybenzylidenyl)-5-(2-chloroethyl)-2-indolinone |
| 10725 | G | 4 | 3-[(2-methylfuran-5-yl)methylidenyl]-5-(2-chloroethyl)-2-indolinone |
| 10725 | G | 5 | 3-[(3-methylpyrazol-5-yl)methylidenyl]-5-(2-chloroethyl)-2-indolinone |
| 10725 | G | 6 | 3-(2-hydroxy-methoxy-4-methylbenzylidenyl)-5-(2-chloroethyl)-2-indolinone |
| 10725 | G | 7 | 3-[4-(4-formylpiperazin-1-yl)benzylidenyl]-5-(2-chloroethyl)-2-indolinone |
| 10725 | G | 8 | 3-[4-(morpholin-1-yl)benzylidenyl]-5-(2-chloroethyl)-2-indolinone |
| 10725 | G | 9 | 3-[[2-chloro-4-methoxycarbonyl-3-(methoxycarbonylmethyl)pyrrol-5-yl]methylidenyl]-5-(2-chloroethyl)-2-indolinone |
| 10725 | G | 10 | 3-[[4-bromo-2-(4-chlorophenyl)pyrazol-3-yl]methylidenyl]-5-(2-chloroethyl)-2-indolinone |
| 10725 | G | 11 | 3-[(imidazol-4-yl)methylidenyl]-5-(2-chloroethyl)-2-indolinone |
| 10726 | A | 3 | 3-[(2-ethoxycarbonyl-4-methoxycarbonyl-3-methylpyrrol-5-yl)methylidenyl]-5,7-dibromo-2-indolinone |
| 10726 | A | 4 | 3-(3-t-butyl-4-hydroxy-5-methylbenzylidenyl)-5,7-dibromo-2-indolinone |
| 10726 | A | 5 | 3-[(2-bromofuran-5-yl)methylidenyl]-5,7-dibromo-2-indolinone |
| 10726 | A | 6 | 3-[(1,3-dimethylpyrrol-4-yl)methylidenyl]-5,7-dibromo-2-indolinone |
| 10726 | A | 7 | 3-[(5,8-dihydroxy-1,2,3,4-tetrahydronapth-yl)methylidenyl]-5,7-dibromo-2-indolinone |
| 10726 | A | 8 | 3-(5-fluoro-2-oxindol-3-idenyl)-5,7-dibromo-2-indolinone |
| 10726 | A | 9 | 3-(2-oxindol-3-idenyl)-5,7-dibromo-2-indolinone |
| 10726 | A | 10 | 3-[(2-ethylthien-5-yl)methylidenyl]-5,7-dibromo-2-indolinone |
| 10726 | A | 11 | 3-(4-methoxybenzylidenyl)-5,7-dibromo-2-indolinone |
| 10726 | B | 3 | 3-[(2-ethoxycarbonyl-4-methoxycarbonyl-3-methylpyrrol-5-yl)methylidenyl]-5-iodo-2-indolinone |
| 10726 | B | 4 | 3-(3-t-butyl-4-hydroxy-5-methylbenzylidenyl)-5-iodo-2-indolinone |

TABLE 13-continued

| MASTER BARCODE | PLATE ROW | PLATE COLUMN | NAME |
|---|---|---|---|
| 10726 | B | 5 | 3-[(2-bromofuran-5-yl)methylidenyl]-5-iodo-2-indolinone |
| 10726 | B | 6 | 3-[(1,3-dimethylpyrrol-4-yl)methylidenyl]-5-iodo-2-indolinone |
| 10726 | B | 7 | 3-[(5,8-dihydroxy-1,2,3,4-tetrahydronapth-6-yl)methylidenyl]-5-iodo-2-indolinone |
| 10726 | B | 8 | 3-(5-fluoro-2-oxindol-3-idenyl)-5-iodo-2-indolinone |
| 10726 | B | 9 | 3-[(2-oxindol-3-idenyl)methylidenyl]-5-iodo-2-indolinone |
| 10726 | B | 10 | 3-[(2-ethylthien-5-yl)methylidenyl]-5-iodo-2-indolinone |
| 10726 | B | 11 | 3-(4-methoxybenzylidenyl)-5-iodo-2-indolinone |
| 10726 | C | 3 | 3-[(2-ethoxycarbonyl-4-methoxycarbonyl-3-methylpyrrol-5-yl)methylidenyl]-5-bromo-4-methyl-2-indolinone |
| 10726 | C | 4 | 3-(3-t-butyl-4-hydroxy-5-methylbenzylidenyl)-5-bromo-4-methyl-2-indolinone |
| 10726 | C | 5 | 3-[(2-bromofuran-5-yl)methylidenyl]-5-bromo-4-methyl-2-indolinone |
| 10726 | C | 6 | 3-[(1,3-dimethylpyrrol-4-yl)methylidenyl]-5-bromo-4-methyl-2-indolinone |
| 10726 | C | 7 | 3-[(5,8-dihydroxy-1,2,3,4-tetrahydronapth-yl)methylidenyl]-5-bromo-4-methyl-2-indolinone |
| 10726 | C | 8 | 3-(5-fluoro-2-oxindol-3-idenyl)-5-bromo-4-methyl-2-indolinone |
| 10726 | C | 9 | 3-(2-oxindol-3-idenyl)-5-bromo-4-methyl-2-indolinone |
| 10726 | C | 10 | 3-[(2-ethylthien-5-yl)methylidenyl]-5-bromo-4-methyl-2-indolinone |
| 10726 | C | 11 | 3-(4-methoxybenzylidenyl)-5-bromo-4-methyl-2-indolinone |
| 10726 | D | 3 | 3-[(2-ethoxycarbonyl-4-methoxycarbonyl-3-methylpyrrol-5-yl)methylidenyl]-5-methylaminosulfonyl-2-indolinone |
| 10726 | D | 4 | 3-(3-t-butyl-4-hydroxy-5-methylbenzylidenyl)-5-methylaminosulfonyl-2-indolinone |
| 10726 | D | 5 | 3-[(2-bromofuran-5-yl)methylidenyl]-5-methylaminosulfonyl-2-indolinone |
| 10726 | D | 6 | 3-[(1,3-dimethylpyrrol-4-yl)methylidenyl]-5-methylaminosulfonyl-2-indolinone |
| 10726 | D | 7 | 3-[(5,8-dihydroxy-1,2,3,4-tetrahydronapth-6-yl)methylidenyl]-5-methylaminosulfonyl-2-indolinone |
| 10726 | D | 8 | 3-(5-fluoro-2-oxindol-3-idenyl)-5-methylaminosulfonyl-2-indolinone |
| 10726 | D | 9 | 3-(2-oxindol-3-idenyl)-5-methylaminosulfonyl-2-indolinone |
| 10726 | D | 10 | 3-[(2-ethylthien-5-yl)methylidenyl]-5-methylaminosulfonyl-2-indolinone |
| 10725 | D | 11 | 3-(4-methoxybenzylidenyl)-5-methylaminosulfonyl-2-indolinone |
| 10726 | E | 3 | 3-[(2-ethoxycarbonyl-4-methoxycarbonyl-3-methylpyrrol-5-yl)methylidenyl]-5-[4-(trifluoromethyl)phenylaminosulfonyl]-2-indolinone |
| 10726 | E | 4 | 3-(3-t-butyl-4-hydroxy-5-methylbenzylidenyl)-5-[4-(trifluoromethyl)phenylaminosulfonyl]-2-indolinone |
| 10726 | E | 5 | 3-[(2-bromofuran-5-yl)methylidenyl]-5-[4-(trifluoromethyl)phenylaminosulfonyl]-2-indolinone |
| 10726 | E | 6 | 3-[(1,3-dimethylpyrrol-4-yl)methylidenyl]-5-[4-(trifluoromethyl)phenylaminosulfonyl]-2-indolinone |
| 10726 | E | 7 | 3-[(5,8-dihydroxy-1,2,3,4-tetrahydronapth-6-yl)methylidenyl]-5-[4-(trifluoromethyl)phenylaminosulfonyl]-2-indolinone |
| 10726 | E | 8 | 3-(5-fluoro-2-oxindol-3-idenyl)-5-[4-(trifluoromethyl)phenylaminosulfonyl]-2-indolinone |
| 10726 | E | 9 | 3-(2-oxindol-3-idenyl)-5-[4-(trifluoromethyl)phenylaminosulfonyl]-2-indolinone |
| 10726 | E | 10 | 3-[(2-ethylthien-5-yl)methylidenyl]-5-[4-(trifluoromethyl)phenylaminosulfonyl]-2-indolinone |
| 10726 | E | 11 | 3-(4-methoxybenzylidenyl)-5-[4-(trifluoromethyl)phenylaminosulfonyl]-2-indolinone |
| 10726 | F | 3 | 3-[(2-ethoxycarbonyl-4-methoxycarbonyl-3-methylpyrrol-5-yl)methylidenyl]-5-(morpholin-1-yl)sulfonyl-2-indolinone |
| 10726 | F | 4 | 3-(3-t-butyl-4-hydroxy-5-methylbenzylidenyl)-5-(morpholin-1-yl)sulfonyl-2-indolinone |

TABLE 13-continued

| MASTER BARCODE | PLATE ROW | PLATE COLUMN | NAME |
|---|---|---|---|
| 10726 | F | 5 | 3-[(2-bromofuran-5-yl)methylidenyl]-5-(morpholin-1-yl)sulfonyl-2-indolinone |
| 10726 | F | 6 | 3-[(1,3-dimethylpyrrol-4-yl)methylidenyl]-5-(morpholin-1-yl)sulfonyl-2-indolinone |
| 10726 | F | 7 | 3-[(5,8-dihydroxy-1,2,3,4-tetrahydronapth-6-yl)methylidenyl]-5-(morpholin-1-yl)sulfonyl-2-indolinone |
| 10726 | F | 8 | 3-(5-fluoro-2-oxindol-3-idenyl)-5-(morpholin-1-yl)sulfonyl-2-indolinone |
| 10726 | F | 9 | 3-(2-oxindol-3-idenyl)-5-(morpholin-1-yl)sulfonyl-2-indolinone |
| 10726 | F | 10 | 3-[(2-ethylthien-5-yl)methylidenyl]-5-(morpholin-1-yl)sulfonyl-2-indolinone |
| 10726 | F | 11 | 3-(4-methoxybenzylidenyl)-5-(morpholin-1-yl)sulfonyl-2-indolinone |
| 10726 | G | 3 | 3-[(2-ethoxycarbonyl-4-methoxycarbonyl-3-methylpyrrol-5-yl)methylidenyl]-5-(2-chloroethyl)-2-indolinone |
| 10726 | G | 4 | 3-(3-t-butyl-4-hydroxy-5-methylbenzylidenyl)-5-(2-chloroethyl)-2-indolinone |
| 10726 | G | 5 | 3-[(2-bromofuran-5-yl)methylidenyl]-5-(2-chloroethyl)-2-indolinone |
| 10726 | G | 6 | 3-[(1,3-dimethylpyrrol-4-yl)methylidenyl]-5-(2-chloroethyl)-2-indolinone |
| 10726 | G | 7 | 3-[(5,8-dihydroxy-1,2,3,4-tetrahydronapth-6-yl)methylidenyl]-5-(2-chloroethyl)-2-indolinone |
| 10726 | G | 8 | 3-(5-fluoro-2-oxindol-3-idenyl)-5-(2-chloroethyl)-2-indolinone |
| 10726 | G | 9 | 3-(2-oxindol-3-idenyl)-5-(2-chloroethyl)-2-indolinane |
| 10726 | G | 10 | 3-[(2-ethylthien-5-yl)methylidenyl]-5-(2-chloroethyl)-2-indolinone |
| 10726 | G | 11 | 3-(4-methoxybenzylidenyl)-5-(2-chloroethyl)-2-indolinone |
| 10727 | A | 2 | 3-(4-diethylaminobenzylidenyl)-5,7-dibromo-2-indolinone |
| 10727 | A | 3 | 3-[(2,4-diethylpyrrol-5-yl)methylidenyl]-5,7-dibromo-2-indolinone |
| 10727 | A | 4 | 3-(3-bromo-5-chloro-2-hydroxybenzylidenyl)-5,7-dibromo-2-indolinone |
| 10727 | A | 5 | 3-[2-(4-chlorophenylmercapto)benzylidenyl]-5,7-dibromo-2-indolinone |
| 10727 | A | 6 | 3-[(5-chlorobenzodioxolan-6 yl)methylidenyl]-5,7-dibromo-2-indolinone |
| 10727 | A | 7 | 3-[(1,4-benzopyranon-3 yl)methylidenyl]-5,7-dibromo-2-indolinone |
| 10727 | A | 8 | 3-(3-cyanobenzylidenyl)-5,7-dibromo-2-indolinone |
| 10727 | A | 9 | 3-(4-cyanobenzylidenyl)-5,7-dibromo-2-indolinone |
| 10727 | A | 10 | 3-(2,5-dihydroxybenzylidenyl)-5,7-dibromo-2-indolinone |
| 10727 | A | 11 | 3-(2,3-dimethoxybenzylidenyl)-5,7-dibromo-2-indolinone |
| 10727 | 8 | 2 | 3-(4-diethylaminobenzylidenyl)-5-iodo-2-indolinone |
| 10727 | B | 3 | 3-[(2,4-diethylpyrrol-5-yl)methylidenyl]-5-iodo-2-indolinone |
| 10727 | 8 | 4 | 3-(3-bromo-5-chloro-2-hydroxybenzylidenyl)-5-iodo-2-indolinone |
| 10727 | 8 | 5 | 3-[2-(4-chlorophenylmercapto)benzylidenyl]-5-iodo-2-indolinone |
| 10727 | B | 6 | 3-[(5-chlorobenzodioxolan-6-yl)methylidenyl]-5-iodo-2-indolinone |
| 10727 | B | 7 | 3-[(1,4-benzopyranon-3-yl)methylidenyl]-5-iodo-2-indolinone |
| 10727 | B | 8 | 3-(3-cyanobenzylidenyl)-5-iodo-2-indolinone |
| 10727 | B | 9 | 3-(4-cyanobenzylidenyl)-5-iodo-2-indolinone |
| 10727 | B | 10 | 3-(2,5-dihydroxybenzylidenyl)-5-iodo-2-indolinone |
| 10727 | B | 11 | 3-(2,3-dimethoxybenzylidenyl)-5-iodo-2-indolinone |
| 10727 | C | 2 | 3-(4-diethylaminobenzylidenyl)-5-bromo-4-methyl-2-indolinone |
| 10727 | C | 3 | 3-[(2,4-diethylpyrrol-5-yl)methylidenyl]-5-bromo-4-metyl-2-indolinone |
| 10727 | G | 4 | 3-(3-bromo-5-chloro-2-hydroxybenzylidenyl)-5-bromo-4-methyl-2-indolinone |
| 10727 | C | 5 | 3-[2-(4-chlorophenylmercapto)benzylidenyl]-5-bromo-4-methyl-2-indolinone |
| 10727 | C | 6 | 3-[(5-chlorobenzodioxolan-yl)methylidenyl]-5-bromo-4-methyl-2-indolinone |

TABLE 13-continued

| MASTER BARCODE | PLATE ROW | PLATE COLUMN | NAME |
|---|---|---|---|
| 10727 | C | 7 | 3-[(1,4-benzopyranon-3-yl)methylidenyl]-5-bromo-4-methyl-2-indolinone |
| 10727 | C | 8 | 3-(3-cyanobenzylidenyl)-5-bromo-4-methyl-2-indolinone |
| 10727 | C | 9 | 3-(4-cyanobenzylidenyl)-5-bromo-4-methyl-2-indolinone |
| 10727 | C | 10 | 3-(2,5-dihydroxybenzylidenyl)-5-bromo-4-methyl-2-indolinone |
| 10727 | C | 11 | 3-(2,3-dimethoxybenzylidenyl)-5-bromo-4-methyl-2-indolinone |
| 10727 | D | 2 | 3-(4-diethylaminobenzylidenyl)-5-methylaminosulfonyl-2-indolinone |
| 10727 | D | 3 | 3-[(2,4-diethylpyrrol-5-yl)methylidenyl]-5-methylaninosulfonyl-2-indolinone |
| 10727 | D | 4 | 3-(3-bromo-5-chloro-2-hydroxybenzylidenyl)-5-methylaminosulfonyl-2-indolinone |
| 10727 | D | 5 | 3-[2-(4-chlorophenylmercapto)benzylidenyl]-5-methylaminosulfonyl-2-indolinone |
| 10727 | D | 6 | 3-[(5-chlorobenzodioxolan-yl)methylidenyl]-5-methylaminosulfonyl-2-indolinone |
| 10727 | D | 7 | 3-[(1,4-benzopyranon-3-yl)methylidenyl]-5-methylaminosulfonyl-2-indolinone |
| 10727 | D | 8 | 3-(3-cyanobenzylidenyl)-5-methylaminosulfonyl-2-indolinone |
| 10727 | D | 9 | 3-(4-cyanobenzylidenyl)-5-methylaminosulfonyl-2-indolinone |
| 10727 | D | 10 | 3-(2,5-dihydroxybenzylidenyl)-5-methylaminosulfonyl-2-indolinone |
| 10727 | D | 11 | 3-(2,3-dimethoxybenzylidenyl)-5-methylaminosulfonyl-2-indolinone |
| 10727 | E | 2 | 3-(4-diethylaminobenzylidenyl)-5-[4-(trifluoromethyl)phenylaminosulfonyl]-2-indolinone |
| 10727 | E | 3 | 3-[(2-4-diethylpyrrol-5-yl)methylidenyl]-5-[4-(trifluoromethyl)phenylaminosulfonyl]-2-indolinone |
| 10727 | E | 4 | 3-(3-bromo-5-chloro-2-hydroxybenzylidenyl)-5-[4-(trifluoromethyl)phenylaminosulfonyl]-2-indolinone |
| 10727 | E | 5 | 3-[2-(4-chlorophenylmercapto)benzylidenyl]-5-[4-(trifluoromethyl)phenylaminosulfonyl]-2-indolinone |
| 10727 | E | 6 | 3-[(5-chlorobenzodioxolan-6-yl)methylidenyl]-5-[4-(trifluoromethyl)phenylaminosulfonyl]-2-indolinone |
| 10727 | E | 7 | 3-[(1,4-benzopyranon-3-yl)methylidenyl]-5-[4-(trifluoromethyl)phenylaminosulfonyl]-2-indolinone |
| 10727 | E | 8 | 3-(3-cyanobenzylidenyl)-5-[4-(trifluoromethyl)phenylaminosulfonyl]-2-indolinone |
| 10727 | E | 9 | 3-(4-cyanobenzylidenyl)-5-[4-(trifluoromethyl)phenylaminosulfonyl]-2-indolinone |
| 10727 | E | 10 | 3-(2,5-dihydroxybenzylidenyl)-5-[4-(trifluoromethyl)phenylaminosulfonyl]-2-indolinone |
| 10727 | E | 11 | 3-(2,3-dimethoxybenzylidenyl)-5-[4-(trifluoromethyl)phenylaminosulfonyl]-2-indolinone |
| 10727 | F | 2 | 3-(4-diethylaminobenzylidenyl)-5-(morpholin-1-yl)sulfonyl-2-indolinone |
| 10727 | F | 3 | 3-[(2,4-diethylpyrrol-5-yl)methylidenyl]-5-(morpholin-1-yl)sulfonyl-2-indolinone |
| 10727 | F | 4 | 3-(3-bromo-5-chloro-2-hydroxybenzylidenyl)-5-(morpholin-1-yl)sulfonyl-2-indolinone |
| 10727 | F | 5 | 3-[2-(4-chlorophenylmercapto)benzylidenyl]-5-(morpholin-1-yl)sulfonyl-2-indolinone |
| 10727 | F | 6 | 3-[(5-chlorobenzodioxolan-6-yl)methylidenyl]-5-(morpholin-1-yl)sulfonyl-2-indolinone |
| 10727 | F | 7 | 3-[(1,4-benzopyranon-3-yl)methylidenyl]-5-(morpholin-1-yl)sulfonyl-2-indolinone |
| 10727 | F | 8 | 3-(3-cyanobenzylidenyl)-5-(morpholin-1-yl)sulfonyl-2-indolinone |
| 10727 | F | 9 | 3-(4-cyanobenzylidenyl)-5-(morpholin-1-yl)sulfonyl-2-indolinone |
| 10727 | F | 10 | 3-(2,5-dihydroxybenzylidenyl)-5-(morpholin-1-yl)sulfonyl-2-indolinone |
| 10727 | F | 11 | 3-(2,3-dimethoxybenzylidenyl)-5-(morpholin-1-yl)sulfonyl-2-indolinone |
| 10727 | G | 2 | 3-(4-diethylaminobenzylidenyl)-5-(2-chloroethyl)-2-indolinone |
| 10727 | G | 3 | 3-[(2,4-diethylpyrrol-5-yl)methylidenyl]-5-(2-chloroethyl)-2-indolinone |
| 10727 | G | 4 | 3-(3-bromo-5-chloro-2-hydroxybenzylidenyl)-5-(2-chloroethyl)-2-indolinone |

TABLE 13-continued

| MASTER BARCODE | PLATE ROW | PLATE COLUMN | NAME |
|---|---|---|---|
| 10727 | G | 5 | 3-[2-(4-chlorophenylmercapto)benzylidenyl]-5-(2-chloroethyl)-2-indolinone |
| 10727 | G | 6 | 3-[(5-chlorobenzodioxolan-6-yl)methylidenyl]-5-(2-chloroethyl)-2-indolinone |
| 10727 | G | 7 | 3-[(1,4-benzopyranon-3-yl)methylidenyl]-5-(2-chloroethyl)-2-indolinone |
| 10727 | G | 8 | 3-(3-cyanobenzylidenyl)-5-(2-chloroethyl)-2-indolinone |
| 10727 | G | 9 | 3-(4-cyanobenzylidenyl)-5-(2-chloroethyl)-2-indolinone |
| 10727 | G | 10 | 3-(2,5-dihydroxybenzylidenyl)-5-(2-chloroethyl)-2-indolinone |
| 10727 | G | 11 | 3-(2-3-dimethoxybenzylidenyl)-5-(2-chloroethyl)-2-indolinone |
| 10728 | A | 2 | 3-(2,5-dimethoxybenzylidenyl)-5,7-dibromo-2-indolinone |
| 10728 | A | 3 | 3-(2,6-dimethoxybenzylidenyl)-5,7-dibromo-2-indolinone |
| 10728 | A | 4 | 3-(3,5-dimethoxybenzylidenyl)-5,7-dibromo-2-indolinone |
| 10728 | A | 5 | 3-(4-dimethylamino-2-methoxybenzylidenyl)-5,7-dibromo-2-indolinone |
| 10728 | A | 6 | 3-[(fluoren-2-yl)methylidenyl]-5,7-dibromo-2-indolinone |
| 10728 | A | 7 | 3-[2-fluoro-3-(trifluoromethyl)benzylidenyl]-5,7-dibromo-2-indolinone |
| 10728 | A | 8 | 3-[2-fluoro-5-(trifluoromethyl)benzylidenyl]-5,7-dibromo-2-indolinone |
| 10728 | A | 9 | 3-[2-fluoro-(trifluoromethyl)benzylidenyl]-5,7-dibromo-2-indolinone |
| 10728 | A | 10 | 3-(2-carboxymethoxybenzylidenyl)-5,7-dibromo-2-indolinone |
| 10728 | A | 11 | 3-[(4-methoxybenzodioxolan-6-yl)methylidenyl]-5,7-dibromo-2-indolinone |
| 10728 | B | 2 | 3-(2,5-dimethoxybenzylidenyl)-5-iodo-2-indolinone |
| 10728 | B | 3 | 3-(2,6-dimethoxybenzylidenyl)-5-iodo-2-indolinone |
| 10728 | B | 4 | 3-(3,5-dimethoxybenzylidenyl)-5-iodo-2-inddiinone |
| 10728 | B | 5 | 3-(4-dimethylamino-2-methoxybenzylidenyl)-5-iodo-2-indolinone |
| 10728 | B | 6 | 3-[(fluoren-2-yl)methylidenyl]-5-iodo-2-indolinone |
| 10728 | B | 7 | 3-[2-fluoro-3-(trifluoromethyl)benzylidenyl]-5-iodo-2-indolinone |
| 10728 | B | 8 | 3-[2-fluoro-5-(trifluoromethyl)benzylidenyl]-5-iodo-2-indolinone |
| 10728 | B | 9 | 3-[2-fluoro-6-(trifluoromethyl)benzylidenyl]-5-iodo-2-indolinone |
| 10728 | B | 10 | 3-(2-carboxymethoxybenzylidenyl)-5-iodo-2-indolinone |
| 10728 | B | 11 | 3-[(4-methoxybenzodioxolan-6-yl)methylidenyl]-5-iodo-2-indolinone |
| 10728 | C | 2 | 3-(2,5-dimethoxybenzylidenyl)-5-bromo-4-methyl-2-indolinone |
| 10728 | C | 3 | 3-(2,6-dimethoxybenzylidenyl)-5-bromo-4-methyl-2-indolinone |
| 10728 | C | 4 | 3-(3,5-dimethoxybenzylidenyl)-5-bromo-4-methyl-2-indolinone |
| 10728 | C | 5 | 3-(4-dimethylamino-2-methoxybenzylidenyl)-5-bromo-4-methyl-2-indolinone |
| 10728 | C | 6 | 3-[(fluoren-2-yl)methylidenyl]-5-bromo-methyl-2-indolinone |
| 10728 | C | 7 | 3-[2-fluoro-3-(trifluoromethyl)benzylidenyl]-5-bromo-4-methyl-2-indolinone |
| 10728 | C | 8 | 3-[2-fluoro-5-(trifluoromethyl)benzylidenyl]-5-bromo-4-methyl-2-indolinone |
| 10728 | C | 9 | 3-[2-fluoro-(trifluoromethyl)benzylidenyl]-5-bromo-4-methyl-2-indolinone |
| 10728 | C | 10 | 3-(2-carboxymethoxybenzylidenyl)-5-bromo-methyl-2-indolinone |
| 10728 | C | 11 | 3-[(4-methoxybenzodioxolan-6-yl)methylidenyl]-5-bromo-4-methyl-2-indolinone |
| 10728 | D | 2 | 3-(2,5-dimethoxybenzylidenyl)-5-methylaminosulfonyl-2-indolinone |
| 10728 | D | 3 | 3-(2,6-dimethoxybenzylidenyl)-5-methylaminosulfonyl-2-indolinone |
| 10728 | D | 4 | 3-(3,5-dimethoxybenzylidenyl)-5-methylaminosulfonyl-2-indolinone |

TABLE 13-continued

| MASTER BARCODE | PLATE ROW | PLATE COLUMN | NAME |
|---|---|---|---|
| 10728 | D | 5 | 3-(4-dimethylamino-2-methoxybenzylidenyl)-5-methylaminosulfonyl-2-indolinone |
| 10728 | D | 6 | 3-[(fluoren-2-yl)methylidenyl]-5-methylaminosulfonyl-2-indolinone |
| 10728 | D | 7 | 3-[2-fluoro-3-(trifluoromethyl)benzylidenyl]-5-methylaminosulfonyl-2-indolinone |
| 10728 | D | 8 | 3-[2-fluoro-5-(trifluoromethyl)benzylidenyl]-5-methylaminosulfonyl-2-indolinone |
| 10728 | D | 9 | 3-[2-fluoro-6-(trifluoromethyl)benzylidenyl]-5-methylaminosulfonyl-2-indolinone |
| 10728 | D | 10 | 3-(2-carboxymethoxybenzylidenyl)-5-methylaminosulfonyl-2-indolinone |
| 10728 | D | 11 | 3-[(4-methoxybenzodioxolan-6-yl)methylidenyl]-5-methylaminosulfonyl-2-indolinone |
| 10728 | E | 2 | 3-(2,5-dimethoxybenzylidenyl)-5-[4-(trifluoromethyl)phenylaminosulfonyl]-2-indolinone |
| 10728 | E | 3 | 3-(2,6-dimethoxybenzylidenyl)-5-[4-(trifluoromethyl)phenylaminosulfonyl]-2-indolinone |
| 10728 | E | 4 | 3-(3,5-dimethoxybenzylidenyl)-5-[4-(trifluoromethyl)phenylaminosulfonyl]-2-indolinone |
| 10728 | E | 5 | 3-(4-dimethylamino-2-methoxybenzylidenyl)-5-[4-(trifluoromethyl)phenylaminosulfonyl]-2-indolinone |
| 10728 | E | 6 | 3-[(fluoren-2-yl)methylidenyl]-5-[4-(trifluoromethyl)phenylaminosulfonyl]-2-indolinone |
| 10728 | E | 7 | 3-[2-fluoro-3-(trifluoromethyl)benzylidenyl]-5-[4-(trifluoromethyl)phenylaminosulfonyl]-2-indolinone |
| 10728 | E | 8 | 3-[2-fluoro-5-(trifluoromethyl)benzylidenyl]-5-[4-(trifluoromethyl)phenylaminosulfonyl]-2-indolinone |
| 10728 | E | 9 | 3-[2-fluoro-(trifluoromethyl)benzylidenyl]-5-[4-(trifluoromethyl)phenylaminosulfonyl]-2-indolinone |
| 10728 | E | 10 | 3-(2-carboxymethoxybenzylidenyl)-5-[4-(trifluoromethyl)phenylaminosulfonyl]-2-indolinone |
| 10728 | E | 11 | 3-[(4-methoxybenzodioxolan-6-yl)methylidenyl]-5-[4-(trifluoromethyl)phenylaminosulfonyl]-2-indolinone |
| 10728 | F | 2 | 3-(2,5-dimethoxybenzylidenyl)-5-(morpholin-1-yl)aminosulfonyl-2-indolinone |
| 10728 | F | 3 | 3-(2,6-dimethoxybenzylidenyl)-5-(morpholin-1-yl)aminosulfonyl-2-indolinone |
| 10728 | F | 4 | 3-(3,5-dimethoxybenzylidenyl)-5-(morpholin-1-yl)aminosulfonyl-2-indolinone |
| 10728 | F | 5 | 3-(4-dimethylamino-2-methoxybenzylidenyl)-5-(morpholin-1-yl)aminosulfonyl-2-indolinone |
| 10728 | F | 6 | 3-[(fluoren-2-yl)methylidenyl]-5-(morpholin-1-yl)aminosulfonyl-2-indolinone |
| 10728 | F | 7 | 3-[2-fluoro-3-(trifluoromethyl)benzylidenyl]-5-(morpholin-1-yl)aminosulfonyl-2-indolinone |
| 10728 | F | 8 | 3-[2-fluoro-5-(trifluoromethyl)benzylidenyl]-5-(morpholin-1-yl)aminosulfonyl-2-indolinone |
| 10728 | F | 9 | 3-[2-fluoro-(trifluoromethyl)benzylidenyl]-5-(morpholin-1-yl)aminosulfonyl-2-indolinone |
| 10728 | F | 10 | 3-(2-carboxymethoxybenzylidenyl)-5-(morpholin-1-yl)aminosulfonyl-2-indolinone |
| 10728 | F | 11 | 3-[(4-methoxybenzodioxolan-6-yl)methylidenyl]-5-(morpholin-1-yl)aminosulfonyl-2-indolinone |
| 10728 | G | 2 | 3-(2,5-dimethoxybenzylidenyl)-5-(2-chloroethyl)-2-indolinone |
| 10728 | G | 3 | 3-(2,6-dimethoxybenzylidenyl)-5-(2-chloroethyl)-2-indolinone |
| 10728 | G | 4 | 3-(3,5-dimethoxybenzylidenyl)-5-(2-chloroethyl)-2-indolinone |
| 10728 | G | 5 | 3-(4-dimethylamino-2-methoxybenzylidenyl)-5-(2-chloroethyl)-2-indolinone |
| 10728 | G | 6 | 3-[(fluoren-2-yl)methylidenyl]-5-(2-chloroethyl)-2-indolinone |
| 10728 | G | 7 | 3-[2-fluoro-3-(trifluoromethyl)benzylidenyl]-5-(2-chloroethyl)-2-indolinone |
| 10728 | G | 8 | 3-[2-fluoro-5-(trifluoromethyl)benzylidenyl]-5-(2-chloroethyl)-2-indolinone |
| 10728 | G | 9 | 3-[2-fluoro-(trifluoromethyl)benzylidenyl]-5-(2-chloroethyl)-2-indolinone |
| 10728 | G | 10 | 3-(2-carboxymethoxybenzylidenyl)-5-(2-chloroethyl)-2-indolinone |
| 10728 | G | 11 | 3-[(4-methoxybenzodioxolan-6-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10729 | A | 2 | 3-[(2-methoxynapth-1-yl)methylidenyl]-5,7-dibromo-2-indolinone |
| 10729 | A | 3 | 3-[(1-methoxynapth-yl)methylidenyl]-5,7-dibromo-2-indolinone |
| 10729 | A | 4 | 3-(4-methylmercaptobenzylidenyl)-5,7-dibromo-2-indolinone |
| 10729 | A | 5 | 3-[(3-methylthien-2-yl)methylidenyl]-5,7-dibromo-2-indoinone |
| 10729 | A | 6 | 3-(3-phenoxybenzylidenyl)-5,7-dibromo-2-indolinone |
| 10729 | A | 7 | 3-[(pyrid-2-yl)methyliaenyl]-5,7-dibromo-2-indolinone |
| 10729 | A | 8 | 3-[(pyrid-3-yl)methyldenyl]-5,7-dibromo-2-indolinone |
| 10729 | A | 9 | 3-[(pyrid-4-yl)methylidenyl]-5,7-dibromo-2-indolinone |
| 10729 | A | 10 | 3-[4-(pyrrolidin-1-yl)benzylidenyl]-5,7-dibromo-2-indolinone |
| 10729 | A | 11 | 3-[(cyclohexen-3-yl)methylidenyl]-5,7-dibromo-2-indolinone |
| 10729 | B | 2 | 3-[(2-methoxynapth-1-yl)methylidenyl]-5-iodo-2-indolinone |
| 10729 | B | 3 | 3-[(1-methoxynapth-4-yl)methylidenyl])-5-iodo-2-indolinone |
| 10729 | B | 4 | 3-(4-methylmercaptobenzylidenyl)-5-iodo-2-indolinone |
| 10729 | B | 5 | 3-[(3-methylthien-2-yl)methylidenyl]-5-iodo-2-indolinone |
| 10729 | 8 | 6 | 3-(3-phenoxybenzylidenyl)-5-iodo-2-indolinone |
| 10729 | B | 7 | 3-[(pyrid-2-yl)methylidenyl]-5-iodo-2-indolinone |
| 10729 | B | 8 | 3-[(pyrid-3-yl)methylidenyl]-5-iodo-2-indolinone |
| 10729 | B | 9 | 3-[(pyrid-4-yl)methylidenyl]-5-iodo-2-indolinone |
| 10729 | B | 10 | 3-[4-(pyrrolidin-1-yl)benzylidenyl]-5-iodo-2-indolinone |
| 10729 | B | 11 | 3-[(cyclohexen-3-yl)methylidenyl]-5-iodo-2-indolinone |
| 10729 | C | 2 | 3-[(2-methoxynapth-1-yl)methylidenyl]-5-bromo-4-methyl-2-indolinone |
| 10729 | C | 3 | 3-[(1-methoxynapth-4-yl)methylidenyl]-5-bromo-4 methyl-2-indolinone |
| 10729 | C | 4 | 3-(4-methylmercaptobenzylidenyl)-5-bromo-4-methyl-2-indolinone |
| 10729 | C | 5 | 3-[(3-methylthien-2-yl)methylidenyl]-5-bromo-4-methyl-2-indolinone |
| 10729 | C | 6 | 3-(3-phenoxybenzylidenyl)-5-bromo-4-methyl-2-indolinone |
| 10729 | C | 7 | 3-[(pyrid-2-yl)methylidenyl]-5-bromo-4-methyl-2-indolinone |
| 10729 | C | 8 | 3-[(pyrid-3-yl)methylidenyl]-5-bromo-4-methyl-2-indolinone |
| 10729 | C | 9 | 3-[(pyrid-4-yl)methylidenyl)-5-bromo-4-methyl-2-indolinone |
| 10729 | C | 10 | 3-[4-(pyrrolidin-1-yl)benzylidenyl]-5-bromo-4-methyl-2-indolinone |
| 10729 | C | 11 | 3-[(cyclohexen-3-yl)methylidenyl]-5-bromo-4-methyl-2-indolinone |
| 10729 | D | 2 | 3-[(2-methoxynapth-1-yl)methylidenyl]-5-methylaminosulfonyl-2-indolinone |
| 10729 | D | 3 | 3-[(1-methoxynapth-4-yl)methylidenyl]-5-methylaminosulfonyl-2-indolinone |
| 10729 | D | 4 | 3-(4-methylmercaptobenzylidenyl)-5-methylaminosulfonyl-2-indolinone |
| 10729 | D | 5 | 3-[(3-methylthien-2-yl)methylidenyl]-5-methylaminosulfonyl-2-indolinone |
| 10729 | D | 6 | 3-(3-phenoxybenzylidenyl)-5-methylaminosulfonyl-2-indolinone |
| 10729 | D | 7 | 3-[(pyrid-2-yl)methylidenyl]-5-methylaminosulfonyl-2-indolinone |
| 10729 | D | 8 | 3-[(pyrid-3-yl)methylidenyl]-5-methylaminosulfonyl-2-indolinone |
| 10729 | A | 7 | 3-[(pyrid-2-yl)methylidenyl]-5,7-dibromo-2-indolinone |
| 10729 | A | 8 | 3-[(pyrid-3-yl)methylidenyl]-5,7-dibromo-2-indolinone |
| 10729 | A | 9 | 3-[(pyrid-4-yl)methylidenyl]-5,7-dibromo-2-indolinone |

TABLE 13-continued

| MASTER BARCODE | PLATE ROW | PLATE COLUMN | NAME |
|---|---|---|---|
| 10729 | A | 10 | 3-[4-(pyrrolidin-1-yl)benzylidenyl]-5,7-dibromo-2-indolinone |
| 10729 | A | 11 | 3-[(cyclohexen-3-yl)methylidenyl]-5,7-dibromo-2-indolinone |
| 10729 | B | 2 | 3-[(2-methoxynapth-1-yl)methylidenyl]-5-iodo-2-indolinone |
| 10729 | B | 3 | 3-[(1-methoxynapth-4-yl)methylidenyl]-5-iodo-2-indolinone |
| 10729 | B | 4 | 3-(4-methylmercaptobenzylidenyl)-5-iodo-2-indolinone |
| 10729 | B | 5 | 3-[3-methylthien-2-yl)methyldenyl]-5-iodo-2-indolinone |
| 10729 | B | 6 | 3-(3-phenoxybenzylidenyl)-5-iodo-2-indolinone |
| 10729 | B | 7 | 3-[(pyrid-2-yl)methylidenyl]-5-iodo-2-indolinone |
| 10729 | B | 8 | 3-[(pyrid-3-yl)methylidenyl]-5-iodo-2-indolinone |
| 10729 | B | 9 | 3-[(pyrid-4-yl)methylidenyl]-5-iodo-2-indolinone |
| 10729 | B | 10 | 3-[4-(pyrrolidin-1-yl)benzylidenyl]-5-iodo-2-indolinone |
| 10729 | B | 11 | 3-[(cyclohexen-3-yl)methylidenyl]-5-iodo-2-indolinone |
| 10729 | C | 2 | 3-[(2-methoxynapth-1-yl)methylidenyl]-5-bromo-4-methyl-2-indolinone |
| 10729 | C | 3 | 3-[(1-methoxynapth-4-yl)methylidenyl]-5-bromo-4-methyl-2-indolinone |
| 10729 | C | 4 | 3-(4-methylmercaptobenzylidenyl)-5-bromo-4-methyl-2-indolinone |
| 10729 | C | 5 | 3-[(3-methylthien-2-yl)methylidenyl]-5-bromo-4-methyl-2-indolinone |
| 10729 | C | 6 | 3-(3-phenoxybenzylidenyl)-5-bromo-4-methyl-2-indolinone |
| 10729 | C | 7 | 3-[(pyrid-2-yl)methylidenyl]-5-bromo-4-methyl-2-indolinone |
| 10729 | C | 8 | 3-[(pyrid-3-yl)methylidenyl]-5-bromo-4-methyl-2-indolinone |
| 10729 | C | 9 | 3-[(pyrid-4-yl)methylidenyl]-5-bromo-4-methyl-2-indolinone |
| 10729 | C | 10 | 3-[4-(pyrrolidin-1-yl)benzylidenyl]-5-bromo-4-methyl-2-indolinone |
| 10729 | C | 11 | 3-[(cyclohexen-3-yl)methylidenyl]-5-bromo-4-methyl-2-indolinone |
| 10729 | D | 2 | 3-[(2-methoxynapth-1-yl)methylidenyl]-5-methylaminosulfonyl-2-indolinone |
| 10729 | D | 3 | 3-[(1-methoxynapth-4-yl)methylidenyl]-5-methylaminosulfonyl-2-indolinone |
| 10729 | D | 4 | 3-(4-methylmercaptobenzylidenyl)-5-methylaminosulfonyl-2-indolinone |
| 10729 | D | 5 | 3-[(3-methylthien-2-yl)methylidenyl]-5-methylaminosulfonyl-2-indolinone |
| 10729 | D | 6 | 3-(3-phenoxybenzylidenyl)-5-methylaminosulfonyl 2-indolinone |
| 10729 | D | 7 | 3-[(pyrid-2-yl)methylidenyl]-5-methylaminosulfonyl-2-indolinone |
| 10729 | D | 8 | 3-[(pyrid-3-yl)methylidenyl]-5-methylaminosulfonyl-2-indolinone |
| 10729 | D | 9 | 3-[(pyrid-4-yl)methylidenyl]-5-methylaminosulfonyl-2-indolinone |
| 10729 | D | 10 | 3-[4-(pyrrolidin-1-yl)benzylidenyl]-5-methylaminosulfonyl-2-indolinone |
| 10729 | D | 11 | 3-[(cyclohexen-3-yl)methylidenyl]-5-methylaminosulfonyl-2-indolinone |
| 10729 | E | 2 | 3-[(2-methoxynapth-1-yl)methylidenyl]-5-[4-(trifluoromethyl)phenylaminosulfonyl]-2-indolinone |
| 10729 | E | 3 | 3-[(1-methoxynapth-4-yl)methylidenyl]-5-[4-(trifluoromethyl)phenylaminosulfonyl]-2-indolinone |
| 10729 | E | 4 | 3-(4-methylmercaptobenzylidenyl)-5-[4-(trifluoromethyl)phenylaminosulfonyl]-2-indolinone |
| 10729 | E | 5 | 3-[(3-methylthien-2-yl)methylidenyl]-5-[4-(trifluoromethyl)phenylaminosulfonyl]-2-indolinone |
| 10729 | E | 6 | 3-(3-phenoxybenzylidenyl)-5-[4-(trifluoromethyl)phenylaminosulfonyl]-2-indolinone |
| 10729 | E | 7 | 3-[(pyrid-2-yl)methylidenyl]-5-[4-(trifluoromethyl)phenylaminosulfonyl]-2-indolinone |
| 10729 | E | 8 | 3-[(pyrid-3-yl)methylidenyl]-5-[4-(trifluoromethyl)phenylaminosulfonyl]-2-indolinone |
| 10729 | E | 9 | 3-[(pyrid-4-yl)methylidenyl]-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10729 | E | 10 | 3-[4-(pyrrolidin-1-yl)benzylidenyl]-5-[4-(trifluoromethyl)phenylaminosulfonyl]-2-indolinone |
| 10729 | E | 11 | 3-[(cyclohexen-3-yl)methylidenyl]-5-[4-(trifluoromethyl)phenylaminosulfonyl]-2-indolinone |
| 10729 | F | 2 | 3-[(2-methoxynapth-1-yl)methylidenyl]-5-(morpholin-1-yl)aminosulfonyl-2-indolinone |
| 10729 | F | 3 | 3-[(1-methoxynapth-4-yl)methylidenyl]-5-(morpholin-1-yl)aminosulfonyl-2-indolinone |
| 10729 | F | 4 | 3-(4-methylmercaptobenzylidenyl)-5-(morpholin-1-yl)aminosulfonyl-2-indolinone |
| 10729 | F | 5 | 3-[(3-methylthien-2-yl)methylidenyl]-5-(morpholin-1-yl)aminosulfonyl-2-indolinone |
| 10729 | F | 6 | 3-(3-phenoxybenzylidenyl)-5-(morpholin-1-yl)aminosulfonyl-2-indolinone |
| 10729 | F | 7 | 3-[(pyrid-2-yl)methylidenyl]-5-(morpholin-1-yl)aminosulfonyl-2-indolinone |
| 10729 | F | 8 | 3-[(pyrid-3-yl)methylidenyl]-5-(morpholin-1-yl)aminosulfonyl-2-indolinone |
| 10729 | F | 9 | 3-[(pyrid-4-yl)methylidenyl]-5-(morpholin-1-yl)aminosulfonyl-2-indolinone |
| 10729 | F | 10 | 3-[4-(pyrrolidin-1-yl)benzylidenyl]-5-(morpholin-1-yl)aminosulfonyl-2-indolinone |
| 10729 | F | 11 | 3-[(cyclohexen-3-yl)methylidenyl]-5-(morpholin-1-yl)aminosulfonyl-2-indolinone |
| 10729 | G | 2 | 3-[(2-methoxynapth-1-yl)methylidenyl]-5-(2-chloroethyl)-2-indolinone |
| 10729 | G | 3 | 3-[(1-methoxynapth-4-yl)methylidenyl]-5-(2-chloroethyl)-2-indolinone |
| 10729 | G | 4 | 3-(4-methylmercaptobenzylidenyl)-5-(2-chloroethyl)-2-indolinone |
| 10729 | G | 5 | 3-[(3-methylthien-2-yl)methylidenyl]-5-(2-chloroethyl)-2-indolinone |
| 10729 | G | 6 | 3-(3-phenoxybenzylidenyl)-5-(2-chloroethyl)-2-indolinone |
| 10729 | G | 7 | 3-[(pyrid-2-yl)methylidenyl]-5-(2-chloroethyl)-2-indolinone |
| 10729 | G | 8 | 3-[(pyrid-3-yl)methylidenyl]-5-(2-chloroethyl)-2-indolinone |
| 10729 | G | 9 | 3-[(pyrid-4-yl)methylidenyl]-5-(2-chloroethyl)-2-indolinone |
| 10729 | G | 10 | 3-[4-(pyrrolidin-1-yl)benzylidenyl]-5-(2-chloroethyl)-2-indolinone |
| 10729 | G | 11 | 3-[(cyclohexen-3-yl)methylidenyl]-5-(2-chloroethyl)-2-indolinone |
| 10730 | A | 2 | 3-(2,3,4-trimethoxybenzylidenyl)-5,7-dibromo-2-indolinone |
| 10730 | A | 3 | 3-(2,4,5-trimethoxybenzylidenyl)-5,7-dibromo-2-indolinone |
| 10730 | A | 4 | 3-(3,4,5-trimethoxybenzylidenyl)-5,7-dibromo-2-indolinone |
| 10730 | A | 5 | 3-[(1-acetylindol-3-yl)methylidenyl]-5,7-dibromo-2-indolinone |
| 10730 | A | 6 | 3-[(6-chloro-1,4-benzofuranon-3-yl)methylidenyl]-5,7-dibromo-2-indolinone |
| 10730 | A | 7 | 3-[2-[(2-chlorophenyl)furan-5-yl]methylidenyl]-5,7-dibromo-2-indolinone |
| 10730 | A | 8 | 3-[2-chloroquinolin-3-yl)methylidenyl]-5,7-dibromo-2-indolinone |
| 10730 | A | 9 | 3-[(6,8-dibromo-1,4-benzofuranon-3-yl)methylidenyl]-5,7-dibromo-2-indolinone |
| 10730 | A | 10 | 3-[(2,5-dimethoxyletrahydrofuran-3-yl)methylidenyl]-5,7-dibromo-2-indolinone |
| 10730 | A | 11 | 3-[(2,3-dimethylfuran-5-yl)methylidenyl]-5,7-dibromo-2-indolinone |
| 10730 | B | 2 | 3-(2,3,4-trimethoxybenzylidenyl)-5-iodo-2-indolinone |
| 10730 | B | 3 | 3-(2,4,5-trimethoxybenzylidenyl)-5-iodo-2-indolinone |
| 10730 | B | 4 | 3-(3,4,5-trimethoxybenzylidenyl)-5-iodo-2-indolinone |
| 10730 | B | 5 | 3-[(1-acetylindol-3-yl)methylidenyl]-5-iodo-2-indolinone |
| 10730 | B | 6 | 3-[(6-chloro-1,4-benzofuranon-3-yl)methylidenyl]-5-iodo-2-indolinone |
| 10730 | B | 7 | 3-[2-[(2-chlorophenyl)furan-5-yl]methylidenyl]-5-iodo-2-indolinone |

TABLE 13-continued

| MASTER BARCODE | PLATE ROW | PLATE COLUMN | NAME |
|---|---|---|---|
| 10730 | B | 8 | 3-[(2-chloroquinolin-3-yl)methylidenyl]-5-iodo-2-indolinone |
| 10730 | B | 9 | 3-[(6,8-dibromo-1,4-benzofuranon-3-yl)methylidenyl]-5-iodo-2-indolinone |
| 10730 | B | 10 | 3-[(2,5-dimethoxyletrahydrofuran-3-yl)methylidenyl]-5-iodo-2-indolinone |
| 10730 | B | 11 | 3-[(2,3-dimethylfuran-5-yl)methylidenyl]-5-iodo-2-indolinone |
| 10730 | C | 2 | 3-(2,3,4-trimethoxybenzylidenyl)-5-bromo-4-methyl-2-indolinone |
| 10730 | C | 3 | 3-(2,4,5-trimethoxybenzylidenyl)-5-bromo-4-methyl-2-indolinone |
| 10730 | C | 4 | 3-(3,4,5-trimethoxybenzylidenyl)-5-bromo-4-methyl-2-indolinone |
| 10730 | C | 5 | 3-[(1-acetylindol-3-yl)methylidenyl]-5-bromo-4-methyl-2-indolinone |
| 10730 | C | 6 | 3-[(6-chloro-1,4-benzofuranon-3-yl)methylidenyl]-5-bromo-4-methyl-2-indolinone |
| 10730 | C | 7 | 3-[2-[(2-chlorophenyl)furan-5-yl]methylidenyl]-5-bromo-4-methyl-2-indolinone |
| 10730 | C | 8 | 3-[(2-chloroquinolin-3-yl)methylidenyl]-5-bromo-4-methyl-2-indolinone |
| 10730 | C | 9 | 3-[(6,8-dibromo-1,4-benzofuranon-3-yl)methylidenyl]-5-bromo-4-methyl-2-indolinone |
| 10730 | C | 10 | 3-[(2,5-dimethoxy-trahydrofuran-3-yl)methylidenyl)-5-bromo-4-methyl-2-indolinone |
| 10730 | C | 11 | 3-[(2,3-dimethylfuran-5-yl)methylidenyl]-5-bromo-4-methyl-2-indolinone |
| 10730 | D | 2 | 3-(2,3,4-trimethoxybenzylidenyl)-5-methylaminosulfonyl-2-indolinone |
| 10730 | D | 3 | 3-(2,4,5-trimethoxybenzylidenyl)-5-methylaminosulfonyl-2-indolinone |
| 10730 | D | 4 | 3-(3,4,5-trimethoxybenzylidenyl)-5-methylaminosulfonyl-2-indolinane |
| 10730 | D | 5 | 3-[(1-acetylindol-3-yl)methylidenyl]-5-methylaminosulfonyl-2-indolinone |
| 10730 | D | 6 | 3-[(6-chloro-1,4-benzofuranon-3-yl)methylidenyl]-5-methylaminosulfonyl-2-indolinone |
| 10730 | D | 7 | 3-[2-[(2-chlorophenyl)furan-5-yl]methylidenyl]-5-methylaminosulfonyl-2-indolinone |
| 10730 | D | 8 | 3-[(2-chloroquinolin-3-yl)methylidenyl)-5-methylaminosulfonyl-2-indolinone |
| 10730 | D | 9 | 3-[(6,8-dibromo-1,4-benzofuranon-3-yl)methylidenyl]-5-methylaminosulfonyl-2-indolinone |
| 10730 | D | 10 | 3-[(2,5-dimethoxyletrahydrofuran-3-yl)methylidenyl]-5-methylaminosulfonyl-2 indolinone |
| 10730 | D | 11 | 3-[(2,3-dimethylfuran-5-yl)methylidenyl]-5-methylaminosulfonyl-2-indolinone |
| 10730 | E | 2 | 3-(2,3,4-trimethoxybenzylidenyl)-5-[4-(trifluoromethyl)phenylaminosulfonyl]-2-indolinone |
| 10730 | E | 3 | 3-(2,4,5-trimethoxybenzylidenyl)-5-[4-(trifluoromethyl)phenylaminosulfonyl]-2-indolinone |
| 10730 | E | 4 | 3-(3,4,5-trimethoxybenzylidenyl)-5-[4-(trifluoromethyl)phenylaminosulfonyl]-2-indolinone |
| 10730 | E | 5 | 3-[(1-acetylindol-3-yl)methylidenyl]-5-[4-(trifluoromethyl)phenylaminosulfonyl]-2-indolinone |
| 10730 | E | 6 | 3-[(6-chloro-1,4-benzofuranon-3-yl)methylidenyl]-5-[4-(trifluoromethyl)phenylaminosulfonyl]-2-indolinone |
| 10730 | E | 7 | 3-[2-[(2-chlorophenyl)furan-5-yl]methylidenyl]-5-[4-(trifluoromethyl)phenylaminosulfonyl]-2-indolinone |
| 10730 | E | 8 | 3-[(2-chloroquinolin-3-yl)methylidenyl]-5-[4-(trifluoromethyl)phenylaminosulfonyl]-2-indolinone |
| 10730 | E | 9 | 3-[(6,8-dibromo-1,4-benzofuranon-3-yl)methylidenyl]-5-[4-(trifluoromethyl)phenylaminosulfonyl]-2-indolinone |
| 10730 | E | 10 | 3-[(2,5-dimethoxyletrahydrofuran-3-yl)methylidenyl)-5-[4-(trifluoromethyl)phenylaminosulfonyl]-2-indolinone |
| 10730 | E | 11 | 3-[(2,3-dimethylfuran-5-yl)methylidenyl]-5-[4-(trifluoromethyl)phenylaminosulfonyl]-2-indolinone |
| 10730 | F | 2 | 3-(2,3,4-trimethoxybenzylidenyl)-5-(morpholin-1-yl)sulfonyl-2-indolinone |

TABLE 13-continued

| MASTER BARCODE | PLATE ROW | PLATE COLUMN | NAME |
|---|---|---|---|
| 10730 | F | 3 | 3-(2,4,5-trimethoxybenzylidnyl)-5-(morpholin-1-yl)sulfonyl-2-indolinone |
| 10730 | F | 4 | 3-(3,4,5-trimethoxybenzylidenyl)-5-(morpholin-1-yl)sulfonyl-2-indolinone |
| 10730 | F | 5 | 3-[(1-acetylindol-3-yl)methylidenyl]-5-(morpholin-1-yl)sulfonyl-2-indolinone |
| 10730 | F | 6 | 3-[(6-chloro-1,4-benzofuranon-3-yl)methylidenyl]-5-(morpholin-1-yl)sulfonyl-2-indolinone |
| 10730 | F | 7 | 3-[2-[(2-chlorophenyl)furan-5-yl]methylidenyl]-5-(morpholin-1-yl)sulfonyl-2-indolinone |
| 10730 | F | 8 | 3-[(2-chloroquinolin-3-yl)methylidenyl]-5-(morpholin-1-yl)sulfonyl-2-indolinone |
| 10730 | F | 9 | 3-[(6,8-dibromo-1,4-benzofuranon-3-yl)methylidenyl]-5-(morpholin-1-yl)sulfonyl-2-indolinone |
| 10730 | F | 10 | 3-[(2,5-dimethoxyletrahydrofuran-3-yl)methylidenyl]-5-(morpholin-1-yl)sulfonyl-2-indolinone |
| 10730 | F | 11 | 3-[(2,3-dimethylfuran-5-yl)methylidenyl]-5-(morpholin-1-yl)sulfonyl-2-indolinone |
| 10730 | G | 2 | 3-(2,3,4-trimethoxybenzylidenyl)-5-(2-chloroethyl)-2-indolinone |
| 10730 | G | 3 | 3-(2,4,5-trimethoxybenzylidenyl)-5-(2-chloroethyl)-2-indolinone |
| 10730 | G | 4 | 3-(3,4,5-trimethoxybenzylidenyl)-5-(2-chloroethyl)-2-indolinone |
| 10730 | G | 5 | 3-[(1-acetylindol-3-yl)methylidenyl]-5-(2-chloroethyl)-2-indolinone |
| 10730 | G | 6 | 3-[(6-chloro-1,4-benzofuranon-3-yl)methylidenyl]-5-(2-chloroethyl)-2-indolinone |
| 10730 | G | 7 | 3-[2-[(2-chlorophenyl)furan-5-yl]methylidenyl]-5-(2-chloroethyl)-2-indolinone |
| 10730 | G | 8 | 3-[(2-chloroquinolin-3-yl)methylidenyl]-5-(2-chloroethyl)-2-indolinone |
| 10730 | G | 9 | 3-[(6,8-dibromo-1,4-benzofuranon-3-yl)methylidenyl]-5-(2-chloroethyl)-2-indolinone |
| 10730 | G | 10 | 3-[(2,5-dimethoxyletrahydrofuran-3-yl)methylidenyl]-5-(2-chloroethyl)-2-indolinone |
| 10730 | G | 11 | 3-[(2,3-dimethylfuran-5-yl)methylidenyl]-5-(2-chloroethyl)-2-indolinone |
| 10731 | A | 2 | 3-[(9-ethylcarbazol-3-yl)methylidenyl]-5,7-dibromo-2-indolinone |
| 10731 | A | 3 | 3-[(6,7-dimethyl-1,4-benzopyron-3-yl)methylidenyl]-5,7-dibromo-2-indolinone |
| 10731 | A | 4 | 3-[[4-(propen-2-yl)cyclohexen-1-yl]methylidenyl]-5,7-dibromo-2-indolinone |
| 10731 | A | 5 | 3-[6-isopropyl-1,4-benzopyron-3-yl)methylidenyl]-5,7-dibromo-2-indolinone |
| 10731 | A | 6 | 3-[(6-methyl-1,4-benzopyron-3-yl)methylidenyl]-5,7-dibromo-2-indolinone |
| 10731 | A | 7 | 3-[(6-nitro-1,4-benzopyron-3-yl)methylidenyl]-5,7-dibromo-2-indolinone |
| 10731 | A | 8 | 3-[(pyrimid-2,4-dion-5-yl)methylidenyl]-5,7-dibromo-2-indolinone |
| 10731 | A | 9 | 3-[(5-methoxyindol-3-yl)methylidenyl]-5,7-dibromo-2-indolinone |
| 10731 | A | 10 | 3-(1-methyl-2-oxindol-3-idenyl)-5,7-dibromo-2-indolinone |
| 10731 | A | 11 | 3-[2-[2-(nitrophenyl)furan-5-yl]methylidenyl]-5,7-dibromo-2-indolinone |
| 10731 | B | 2 | 3-[(9-ethylcarbazol-3-yl)methylidenyl]-5-iodo-2-indolinone |
| 10731 | B | 3 | 3-[(6,7-dimethyl-1,4-benzopyron-3-yl)methylidenyl]-5-iodo-2-indolinone |
| 10731 | B | 4 | 3-[[4-(propen-2-yl)cyclohexen-1-yl]methylidenyl]-5-iodo-2-indolinone |
| 10731 | B | 5 | 3-[(6-isopropyl-1,4-benzopyron-3-yl)methylidenyl]-5-iodo-2-indolinone |
| 10731 | B | 6 | 3-[(6-methyl-1,4-benzopyron-3-yl)methylidenyl]-5-iodo-2-indolinone |
| 10731 | B | 7 | 3-[(6-nitro-1,4-benzopyron-3-yl)methylidenyl]-5-iodo-2-indolinone |
| 10731 | B | 8 | 3-[(pyrimid-2,4-dion-5yl)methylidenyl]-5-iodo-2-indolinone |
| 10731 | B | 9 | 3-[(5-methoxyindol-3-yl)methylidenyl]-5-iodo-2-indolinone |

TABLE 13-continued

| MASTER BARCODE | PLATE ROW | PLATE COLUMN | NAME |
|---|---|---|---|
| 10731 | B | 10 | 3-(1-methyl-2-oxindol-3-idenyl)-5-iodo-2-indolinone |
| 10731 | B | 11 | 3-[2-[2-(nitrophenyl)furan-5-yl]methylidenyl]-5-iodo-2-indolinone |
| 10731 | C | 2 | 3-[(9-ethylcarbazol-3-yl)methylidenyl]-5-bromo-4-methyl-2-indolinone |
| 10731 | C | 3 | 3-[(6,7-dimethyl-1,4-benzopyron-3-yl)methylidenyl]-5-bromo-4-methyl-2-indolinone |
| 10731 | C | 4 | 3-[[4-(propen-2-yl)cyclohexen-1-yl]methylidenyl]-5-bromo-4-methyl-2-indolinone |
| 10731 | C | 5 | 3-[(6-isopropyl-1,4-benzopyron-3-yl)methylidenyl]-5-bromo-4-methyl-2-indolinone |
| 10731 | C | 6 | 3-[(6-methyl-1,4-benzopyron-3-yl)methylidenyl]-5-bromo-4-methyl-2-indolinone |
| 10731 | C | 7 | 3-[(6-nitro-1,4-benzopyron-3-yl)methylidenyl]-5-bromo-4-methyl-2-indolinone |
| 10731 | C | 8 | 3-[(pyrimid-2,4-dion-5-yl)methylidenyl]-5-bromo-4-methyl-2-indolinone |
| 10731 | C | 9 | 3-[(5-methoxyindol-3-yl)methylidenyl]-5-bromo-4-methyl-2-indolinone |
| 10731 | C | 10 | 3-(1-methyl-2-oxindol-3-idenyl)-5-bromo-4-methyl-2-indolinone |
| 10731 | C | 11 | 3-[2-[2-(nitrophenyl)furan-5-yl]methylidenyl]-5-bromo-4-methyl-2-indolinone |
| 10731 | D | 2 | 3-[(9-ethylcarbazol-3-yl)methylidenyl]-5-methylaminosulfonyl-2-indolinone |
| 10731 | D | 3 | 3-[(6,7-dimethyl-1,4-benzopyron-3-yl)methylidenyl]-5-methylaminosulfonyl-2-indolinone |
| 10731 | D | 4 | 3-[[4-(propen-2-yl)cyclohexen-1-yl]methylidenyl]-5-methylaminosulfonyl-2-indolinone |
| 10731 | D | 5 | 3-[(6-isopropyl-1,4-benzopyron-3-yl)methylidenyl]-5-methylaminosulfonyl-2-indolinone |
| 10731 | D | 6 | 3-[(6-methyl-1,4-benzopyron-3-yl)methylidenyl]-5-methylaminosulfonyl-2-indolinone |
| 10731 | D | 7 | 3-[(6-nitro-1,4-benzopyron-3-yl)methylidenyl]-5-methylaminosulfonyl-2-indolinone |
| 10731 | D | 8 | 3-[(pyrimid-2,4-dion-5-yl)methylidenyl]-5-methylaminosulfonyl-2-indolinone |
| 10731 | D | 9 | 3-[(5-methoxyindol-3-yl)methylidenyl]-5-methylaminosulfonyl-2-indolinone |
| 10731 | D | 10 | 3-(1-methyl-2-oxindol-3-idenyl)-5-methylaminosulfonyl-2-indolinone |
| 10731 | D | 11 | 3-[2-[2-(nitrophenyl)furan-5-yl]methylidenyl]-5-methylaminosulfonyl-2-indolinone |
| 10731 | E | 2 | 3-[(9-ethylcarbazol-3-yl)methylidenyl]-5-[4-(trifluoromethyl)phenylaminosulfonyl]-2-indolinone |
| 10731 | E | 3 | 3-[(6,7-dimethyl-1,4-benzopyron-3-yl)methylidenyl]-5-[4-(trifluoromethyl)phenylaminosulfonyl]-2-indolinone |
| 10731 | E | 4 | 3-[[4-(propen-2-yl)cyclohexen-1-yl]methylidenyl]-5-[4-(trifluoromethyl)phenylaminosulfonyl]-2-indolinone |
| 10731 | E | 5 | 3-[(6-isopropyl-1,4-benzopyron-3-yl)methylidenyl]-5-[4-(trifluoromethyl)phenylaminosulfonyl]-2-indolinone |
| 10731 | E | 6 | 3-[(6-methyl-1,4-benzopyron-3-yl)methylidenyl]-5-[4-(trifluoromethyl)phenylaminosulfonyl]-2-indolinone |
| 10731 | E | 7 | 3-[(6-nitro-1,4-benzopyron-3-yl)methylidenyl]-5-[4-(trifluoromethyl)phenylaminosulfonyl]-2-indolinone |
| 10731 | E | 8 | 3-[(pyrimid-2,4-ion-5-yl)methylidenyl]-5-[4-(trifluoromethyl)phenylaminosulfonyl]-2-indolinone |
| 10731 | E | 9 | 3-[(5-methoxyindol-3-yl)methylidenyl]-5-[4-(trifluoromethyl)phenylaminosulfonyl]-2-indolinone |
| 10731 | E | 10 | 3-(1-methyl-2-oxindol-3-idenyl)-5-[4-(trifluoromethyl)phenylaminosulfonyl]-2-indolinone |
| 10731 | E | 11 | 3-[2-[2-(nitrophenyl)furan-5-yl]methylidenyl]-5-[4-(trifluoromethyl)phenylaminosulfonyl]-2-indolinone |
| 10731 | F | 2 | 3-[(9-ethylcarbazol-3-yl)methylidenyl]-5-(morpholin-1-yl)sulfonyl-2-indolinone |
| 10731 | F | 3 | 3-[(6,7-dimethyl-1,4-benzopyron-3-yl)methylidenyl]-5-(morpholin-1-yl)sulfonyl-2-indolinone |
| 10731 | F | 4 | 3-[[4-(propen-2-yl)cyclohexen-1-yl]methylidenyl]-5-(morpholin-1-yl)sulfonyl-2-indolinone |
| 10731 | F | 5 | 3-[(6-isopropyl-1,4-benzopyron-3-yl)methylidenyl]-5-(morpholin-1-yl)sulfonyl-2-indolinone |

TABLE 13-continued

| MASTER BARCODE | PLATE ROW | PLATE COLUMN | NAME |
|---|---|---|---|
| 10731 | F | 6 | 3-[(6-methyl-1,4-benzopyron-3-yl)methylidenyl]-5-(morpholin-1-yl)sulfonyl-2-indolinone |
| 10731 | F | 7 | 3-[(6-nitro-1,4-benzopyron-3-yl)methylidenyl]-5-(morpholin-1-yl)sulfonyl-2-indolinone |
| 10731 | F | 8 | 3-[(pyrimid-2,4-dion-5-yl)methylidenyl]-5-(morpholin-1-yl)sulfonyl-2-indolinone |
| 10731 | F | 9 | 3-[(5-methoxyindol-3-yl)methylidenyl]-5-(morpholin-1-yl)sulfonyl-2-indolinone |
| 10731 | F | 10 | 3-(1-methyl-2-oxindol-3-idenyl)-5-(morpholin-1-yl)sulfonyl-2-indolinone |
| 10731 | F | 11 | 3-[2-[2-(nitrophenyl)furan-5-yl]methylidenyl]-5-(morpholin-1-yl)sulfonyl-2-indolinone |
| 10731 | G | 2 | 3-[(9-ethylcarbazol-3-yl)methylidenyl]-5-(2-chloroethyl)-2-indolinone |
| 10731 | G | 3 | 3-[(6,7-dimethyl-1,4-benzopyron-3-yl)methylidenyl]-5-(2-chloroethyl)-2-indolinone |
| 10731 | G | 4 | 3-[[4-(propen-2-yl)cyclohexen-1-yl]methylidenyl]-5-(2-chloroethyl)-2-indolinone |
| 10731 | G | 5 | 3-[(6-isopropyl-1,4-benzopyron-3-yl)methylidenyl]-5-(2-chloroethyl)-2-indolinone |
| 10731 | G | 6 | 3-[(6-methyl-1,4-benzopyron-3-yl)methylidenyl]-5-(2-chloroethyl)-2-indolinone |
| 10731 | G | 7 | 3-[(6-nitro-1,4-benzopyron-3-yl)methylidenyl]-5-(2-chloroethyl)-2-indolinone |
| 10731 | G | 8 | 3-[(pyrimid-2,4-dion-5-yl)methylidenyl]-5-(2-chloroethyl)-2-indolinone |
| 10731 | G | 9 | 3-[(5-methoxyindol-3-yl)methylidenyl]-5-(2-chloroethyl)-2-indolinone |
| 10731 | G | 10 | 3-(1-methyl-2-oxindol-3-idenyl)-5-(2-chloroethyl)-2-indolinone |
| 10731 | G | 11 | 3-[2-[2-(nitrophenyl)furan-5-yl]methylidenyl]-5-(2-chloroethyl)-2-indolinone |
| 10732 | A | 2 | 3-[2-(thien-2-yl)-2-(trifluoromethyl)ethylidenyl]-5,7-dibromo-2-indolinone |
| 10732 | A | 3 | 3-(3,5-diisopropyl-4-methoxybenzylidenyl)-5,7-dibromo-2-indolinone |
| 10732 | A | 4 | 3-(3,5-diisopropyl-4-phenoxybenzylidenyl)-5,7-dibromo-2-indolinone |
| 10732 | A | 5 | 3-(3-t-butyl-4-methoxybenzylidenyl)-5,7-dibromo-2-indolinone |
| 10732 | A | 6 | 3-(4-benzyloxy-3-t-butylbenzylidenyl)-5,7-dibromo-2-indolinone |
| 10732 | A | 7 | 3-(3-bromo-5-t-butyl-4-methoxybenzylidenyl)-5,7-dibromo-2-indolinone |
| 10732 | A | 8 | 3-(4-benzyloxy-3-bromo-5-t-butylbenzylidenyl)-5,7-dibromo-2-indolinone |
| 10732 | A | 9 | 3-(3-t-butyl-5-chloro-4-methoxybenzylidenyl)-5,7-dibromo-2-indolinone |
| 10732 | A | 10 | 3-(4-benzyloxy-5-t-butyl-3-chlorobenzylidenyl)-5,7-dibromo-2-indolinone |
| 10732 | A | 11 | 3-(3-t-butyl-5-iodo-4-methoxybenzylidenyl)-5,7-dibromo-2-indolinone |
| 10732 | B | 2 | 3-[2-(thien-2-yl)-2-(trifluoromethyl)ethylidenyl]-5-iodo-2-indolinone |
| 10732 | B | 3 | 3-(3,5-diisopropyl-4-methoxybenzylidenyl)-5-iodo-2-indolinone |
| 10732 | B | 4 | 3-(3,5-diisopropyl-4-phenoxybenzylidenyl)-5-iodo-2-indolinone |
| 10732 | B | 5 | 3-(3-t-butyl-4-methoxybenzylidenyl)-5-iodo-2-indolinone |
| 10732 | B | 6 | 3-(4-benzyloxy-3-t-butylbenzylidenyl)-5-iodo-2-indolinone |
| 10732 | B | 7 | 3-(3-bromo-5-t-butyl-4-methoxybenzylidenyl)-5-iodo-2-indolinone |
| 10732 | B | 8 | 3-(4-benzyloxy-3-bromo-5-t-butylbenzylidenyl)-5-iodo-2-indolinone |
| 10732 | B | 9 | 3-(3-t-butyl-5-chloro-4-methoxybenzylidenyl)-5-iodo-2-indolinone |
| 10732 | B | 10 | 3-(4-benzyloxy-5-t-butyl-3-chlorobenzylidenyl)-5-iodo-2-indolinone |
| 10732 | B | 11 | 3-(3-t-butyl-5-iodo-4-methoxybenzylidenyl)-5-iodo-2-indolinone |
| 10732 | C | 2 | 3-[2-(thien-2-yl)-2-(trifluoromethyl)ethylidenyl]-5-bromo-4-methyl-2-indolinone |
| 10732 | C | 3 | 3-(3,5-diisopropyl-4-methoxybenzylidenyl)-5-bromo-4-methyl-2-indolinone |

TABLE 13-continued

| MASTER BARCODE | PLATE ROW | PLATE COLUMN | NAME |
|---|---|---|---|
| 10732 | C | 4 | 3-(3,5-diisopropyl-4-phenoxybenzylidenyl)-5-bromo-4-methyl-2-indolinone |
| 10732 | C | 5 | 3-(3-t-butyl-4-methoxybenzylidenyl)-5-bromo-4-methyl-2-indolinone |
| 10732 | C | 6 | 3-(4-benzyloxy-3-t-butylbenzylidenyl)-5-bromo-4-methyl-2-indolinone |
| 10732 | C | 7 | 3-(3-bromo-5-t-butyl-4-methoxybenzylidenyl)-5-bromo-4-methyl-2-indolinone |
| 10732 | C | 8 | 3-(4-benzyloxy-3-bromo-5-t-butylbenzylidenyl)-5-bromo-4-methyl-2-indolinone |
| 10732 | C | 9 | 3-(3-t-butyl-5-chloro-4-methoxybenzylidenyl)-5-bromo-4-methyl-2-indolinbne |
| 10732 | C | 10 | 3-(4-benzyloxy-5-t-butyl-3-chlorobenzylidenyl)-5-bromo-4-methyl-2-indolinone |
| 10732 | C | 11 | 3-(3-t-butyl-5-iodo-4-methoxybenzylidenyl)-5-bromo-4-methyl-2-indolinone |
| 10732 | D | 2 | 3-[2-(thien-2-yl)-2-(trifluoromethyl)ethylidenyl]-5-methylaminosulfonyl-2-indolinone |
| 10732 | D | 3 | 3-(3,5-diisopropyl-4-methoxybenzylidenyl)-5-methylaminosulfonyl-2-indolinone |
| 10732 | D | 4 | 3-(3,5-diisopropyl-4-phenoxybenzylidenyl)-5-methylaminosulfonyl-2-indolinone |
| 10732 | D | 5 | 3-(3-t-butyl-4-methoxybenzylidenyl)-5-methylaminosulfonyl-2-indolinone |
| 10732 | D | 6 | 3-(4-benzyloxy-3-t-butylbenzylidenyl)-5-methylaminosulfonyl-2-indolinone |
| 10732 | D | 7 | 3-(3-bromo-5-t-butyl-4-methoxybenzylidenyl)-5-methylaminosulfonyl-2-indolinone |
| 10732 | D | 8 | 3-(4-benzyloxy-3-bromo-5-t-butylbenzylidenyl)-5-methylaminosulfonyl-2-indolinone |
| 10732 | D | 9 | 3-(3-t-butyl-5-chloro-4-methoxybenzylidenyl)-5-methylaminosulfonyl-2-indolinone |
| 10732 | D | 10 | 3-(4-benzyloxy-5-t-butyl-3-chlorobenzylidenyl)-5-methylaminosulfonyl-2-indolinone |
| 10732 | D | 11 | 3-(3-t-butyl-5-iodo-4-methoxybenzylidenyl)-5-methylaminosulfonyl-2-indolinone |
| 10732 | E | 2 | 3-[2-(thien-2-yl)-2-(trifluoromethyl)ethylidenyl]-5-[4-(trifluoromethyl)phenylaminosulfonyl]-2-indolinone |
| 10732 | E | 3 | 3-(3,5-diisopropyl-4-methoxybenzylidenyl)-5-[4-(trifluoromethyl)phenylaminosulfonyl]-2-indolinone |
| 10732 | E | 4 | 3-(3,5-diisopropyl-4-phenoxybenzylidenyl)-5-[4-(trifluoromethyl)phenylaminosulfonyl)-2-indolinone |
| 10732 | E | 5 | 3-(3-t-butyl-4-methoxybenzylidenyl)-5-[4-(trifluoromethyl)phenylaminosulfonyl)-2-indolinone |
| 10732 | E | 6 | 3-(4-benzyloxy-3-t-butylbenzylidenyl)-5-[4-(trifluoromethyl)phenylaminosulfonyl)-2-indolinone |
| 10732 | E | 7 | 3-(3-bromo-5-t-butyl-4-methoxybenzylidenyl)-5-[4-(trifluoromethyl)phenylaminosulfonyl)-2-indolinone |
| 10732 | E | 8 | 3-(4-benzyloxy-3-bromo-5-t-butylbenzylidenyl)-5-[4-(trifluoromethyl)phenylaminosulfonyl)-2-indolinone |
| 10732 | E | 9 | 3-(3-t-butyl-5-chloro-4-methoxybenzylidenyl)-5-[4-(trifluoromethyl)phenylaminosulfonyl]-2-indolinone |
| 10732 | E | 10 | 3-(4-benzyloxy-5-t-butyl-3-chlorobenzylidenyl)-5-[4-(trifluoromethyl)phenylaminosulfonyl]-2-indolinone |
| 10732 | E | 11 | 3-(3-t-butyl-5-iodo-4-methoxybenzylidenyl)-5-[4-(trifluoromethyl)phenylaminosulfonyl]-2-indolinone |
| 10732 | F | 2 | 3-[2-(thien-2-yl)-2-(trifluoromethyl)ethylidenyl]-5-(morpholin-1-yl)sulfonyl-2-indolinone |
| 10732 | F | 3 | 3-(3,5-diisopropyl-4-methoxybenzylidenyl)-5-(morpholin-1-yl)sulfonyl-2-indolinone |
| 10732 | F | 4 | 3-(3,5-diisopropyl-4-phenoxybenzylidenyl)-5-(morpholin-1-yl)sulfonyl-2-indoinone |
| 10732 | F | 5 | 3-(3-t-butyl-4-methoxybenzylidenyl)-5-(morpholin-1-yl)sulfonyl-2-indolinone |
| 10732 | F | 6 | 3-(4-benzyloxy-3-t-butylbenzylidenyl)-5-(morpholin-1-yl)sulfonyl-2-indolinone |
| 10732 | F | 7 | 3-(3-bromo-5-t-butyl-4-methoxybenzylidenyl)-5-(morpholin-1-yl)sulfonyl-2-indolindne |
| 10732 | F | 8 | 3-(4-benzyloxy-3-bromo-5-t-butylbenzylidenyl)-5-(morpholin-1-yl)sulfonyl-2-indolinone |
| 10732 | F | 9 | 3-(3-t-butyl-5-chloro-4-methoxybenzylidenyl)-5-(morpholin-1-yl)sulfonyl-2-indolinone |
| 10732 | F | 10 | 3-(4-benzyloxy-5-t-butyl-3-chloro-benzylidenyl)-5-(morpholin-1-yl)sulfonyl-2-indolinone |
| 10732 | F | 11 | 3-(3-t-butyl-5-iodo-4-methoxybenzylidenyl)-5-(morpholin-1-yl)sulfonyl-2-indolinone |

TABLE 13-continued

| MASTER BARCODE | PLATE ROW | PLATE COLUMN | NAME |
|---|---|---|---|
| 10732 | G | 2 | 3-[2-(thien-2-yl)-2-(trifluoromethyl)ethylidenyl]-5-(2-chloroethyl)-2-indolinone |
| 10732 | G | 3 | 3-(3,5-diisopropyl-4-methoxybenzylidenyl]-5-(2-chloroethyl)-2-indolinone |
| 10732 | G | 4 | 3-(3,5-diisopropyl-4-phenoxybenzylidenyl]-5-(2-chloroethyl)-2-indolinone |
| 10732 | G | 5 | 3-(3-t-butyl-4-methoxybenzylidenyl)-5-(2-chloroethyl)-2-indolinone |
| 10732 | G | 6 | 3-(4-benzyloxy-3-t-butylbenzylidenyl)-5-(2-chloroethyl)-2-indolinone |
| 10732 | G | 7 | 3-(3-bromo-5-t-butyl-4-methoxybenzylidenyl)-5-(2-chloroethyl)-2-indolinone |
| 10732 | G | 8 | 3-(4-benzyloxy-3-bromo-5-t-butylbenzylidenyl)-5-(2-chloroethyl)-2-indolinone |
| 10732 | G | 9 | 3-(3-t-butyl-5-chloro-4-methoxybenzylidenyl)-5-(2-chloroethyl)-2-indolinone |
| 10732 | G | 10 | 3-(4-benzyloxy-5-t-butyl-3-chlorobenzylidenyl)-5-(2-chloroethyl)-2-indolinone |
| 10732 | G | 11 | 3-(3-t-butyl-5-iodo-4-methoxybenzylidenyl)-5-(2-chloroethyl)-2-indolinone |
| 10733 | A | 2 | 3-(4-benzyloxy-3-t-butyl-5-iodobenzylidenyl)-5,7-dibromo-2-indolinone |
| 10733 | A | 3 | 3-(3-t-butyl-4-methoxy-5-nitrobenzylidenyl)-5,7-dibromo-2-indolinone |
| 10733 | A | 4 | 3-(3,5-di-t-butyl-4-methoxybenzylidenyl)-5,7-dlbromo-2-indolinone |
| 10733 | A | 5 | 3-(4-benzyloxy-3,5-di-t-butylbenzylidenyl)-5,7-dibromo-2-indolinone |
| 10733 | A | 6 | 3-(3,5-dimethylA-methoxybenzylidenyl)-5,7-dibromo-2-indolinone |
| 10733 | A | 7 | 3-(4-benzyloxy-3,5-dimethylbenzylidenyl)-5,7-dibromo-2-indolinone |
| 10733 | A | 8 | 3-(5-bromo-2-hydroxy-3-methoxybenzylidenyl)-5,7-dibromo-2-indolinone |
| 10733 | A | 9 | 3-(5-bromo-2-hydroxybenzylidenyl)-5,7-dibromo-2-indolinone |
| 10733 | A | 10 | 3-(2-hydroxy-5-nitrobenzylidenyl)-5,7-dibromo-2-indolinone |
| 10733 | A | 11 | 3-(4-hydroxy-3-methoxy-2-nitrobenzylidenyl)-5,7-dibromo-2-indolinone |
| 10733 | B | 2 | 3-(4-benzyloxy-3-t-butyl-5-iodobenzylidenyl)-5-iodo-2-indolinone |
| 10733 | B | 3 | 3-(3-t-butyl-4-methoxy-5-nitrobenzylidenyl)-5-iodo-2-indolinone |
| 10733 | B | 4 | 3-(3,5-di-t-butyl-4-methoxybenzylidenyl)-5-iodo-2-indolinone |
| 10733 | B | 5 | 3-(4-benzyloxy-3,5-di-t-butylbenzylidenyl)-5-iodo-2-indolinone |
| 10733 | 8 | 6 | 3-(3,5-dimethyl-4-methoxybenzylidenyl)-5-iodo-2-indolinone |
| 10733 | 8 | 7 | 3-(4-benzyloxy-3,5-dimethylbenzylidenyl)-5-iodo-2-indolinone |
| 10733 | B | 8 | 3-(5-bromo-2-hydroxy-3-methoxybenzylidenyl)-5-iodo-2-indolinone |
| 10733 | B | 9 | 3-(5-bromo-2-hydroxybenzlidenyl)-5-iodo-2-indolinone |
| 10733 | B | 10 | 3-(2-hydroxy-5-nitrobenzylidenyl)-5-iodo-2-indolinone |
| 10733 | B | 11 | 3-(4-hydroxy-3-methoxy-2-nitrobenzylidenyl)-5-iodo-2-indolinone |
| 10733 | C | 2 | 3-(4-benzyloxy-3-t-butyl-5-iodobenzylidenyl)-5-bromo-4-methyl-2-indolinone |
| 10733 | C | 3 | 3-(3-t-butyl-4-methoxy-5-nitrobenzylidenyl)-5-bromo-4-methyl-2-indolinone |
| 10733 | C | 4 | 3-(3,5-di-t-butyl-4-methoxybenzylidenyl)-5-bromo-4-methyl-2-indolinone |
| 10733 | C | 5 | 3-(4-benzyloxy-3,5-di-t-butylbenzylidenyl)-5-bromo-4-methyl-2-indolinone |
| 10733 | C | 6 | 3-(3,5-dimethyl-4-ethoxybenzylidenyl)-5-bromo-4-methyl-2-indolinone |
| 10733 | C | 7 | 3-(4-benzyloxy-3,5-dimethylbenzylidenyl)-5-bromo-4-methyl-2-indolinone |
| 10733 | C | 8 | 3-(5-bromo-2-hydroxy-3-methoxybenzylidenyl)-5-bromo-4-methyl-2-indolinone |
| 10733 | C | 9 | 3-(5-bromo-2-hydroxybenzylidenyl)-5-bromo-4-methyl-2-indolinone |

TABLE 13-continued

| MASTER BARCODE | PLATE ROW | PLATE COLUMN | NAME |
|---|---|---|---|
| 10733 | C | 10 | 3-(2-hydroxy-5-nitrobenzylidenyl)-5-bromo-4-methyl-2-indolinone |
| 10733 | C | 11 | 3-(4-hydroxy-3-methoxy-2-nitrobenzylidenyl)-5-bromo-4-methyl-2-indolinone |
| 10733 | D | 2 | 3-(4-benzyloxy-3-t-butyl-5-iodobenzylidenyl)-5-methylaminosulfonyl-2-indolinone |
| 10733 | D | 3 | 3-(3-tbutyl-methoxy-5-nitrobenzylidenyl)-5-methylaminosulfonyl-2-indolinone |
| 10733 | D | 4 | 3-(3,5-di-t-butyl-methoxybenzylidenyl)-5-methylaminosulfonyl-2-indolinone |
| 10733 | D | 5 | 3-(4-benzyloxy-3,5-di-t-butylbenzylidenyl)-5-methylaminosulfonyl-2-indolinone |
| 10733 | D | 6 | 3-(3,5-dimethyl-methoxybenzylidenyl)-5-methylaminosulfonyl-2-indolinone |
| 10733 | D | 7 | 3-(4-benzyloxy-3,5-dimethylbenzylidenyl)-5-methylaminosulfonyl-2-indolinone |
| 10733 | D | 8 | 3-(5-bromo-2-hydroxy-3-methoxybenzylidenyl)-5-methylaminosulfonyl-2-indolinone |
| 10733 | D | 9 | 3-(5-bromo-2-hydroxybenzylidenyl)-5-methylaminosulfonyl-2-indolinone |
| 10733 | D | 10 | 3-(2-hydroxy-5-nitrobenzylidenyl)-5-methylaminosulfonyl-2-indolinone |
| 10733 | D | 11 | 3-(4-hydroxy-3-methoxy-2-nitrobenzylidenyl)-5-methylaminosulfonyl-2-indolinone |
| 10733 | E | 2 | 3-(4-benzyloxy-3-t-butyl-5-iodobenzylidenyl)-5-[4-(trifluoromethyl)phenylaminosulfonyl]-2-indolinone |
| 10733 | E | 3 | 3-(3-t-butyl-methoxy-5-nitrobenzylidenyl)-5-[4-(trifluoromethyl)phenylaminosulfonyl]-2-indolinone |
| 10733 | E | 4 | 3-(3,5-di-t-butyl-methoxybenzylidenyl)-5-[4-(trifluoromethyl)phenylaminosulfonyl]-2-indolinone |
| 10733 | E | 5 | 3-(4-benzyloxy-3,5-di-t-butylbenzylidenyl)-5-[4-(trifluoromethyl)phenylaminosulfonyl]-2-indolinone |
| 10733 | E | 6 | 3-(3,5-dimethyl-4-methoxybenzylidenyl)-5-[4-(trifluoromethyl)phenylaminosulfonyl]-2-indolinone |
| 10733 | E | 7 | 3-(4-benzyloxy-3,5-dimethylbenzylidenyl)-5-[4-(trifluoromethyl)phenylaminosulfonyl]-2-indolinone |
| 10733 | E | 8 | 3-(5-bromo-2-hydrosy-3-methoxybenzylidenyl)-5-[4-(trifluoromethyl)phenylaminosulfonyl]-2-indolinone |
| 10733 | E | 9 | 3-(5-bromo-2-hydroxybenzylidenyl)-5-[4-(trifluoromethyl)phenylaminosulfonyl]-2-indolinone |
| 10733 | E | 10 | 3-(2-hydroxy-5-nitrobenzylidenyl)-5-[4-(trifluoromethyl)phenylaminosulfonyl]-2-indolinone |
| 10733 | E | 11 | 3-(4-hydroxy-3-methoxy-2-nitrobenzylidenyl)-5-[4-(trifluoromethyl)phenylaminosulfonyl]-2-indolinone |
| 10733 | F | 2 | 3-(4-benzyloxy-3-t-butyl-5-iodobenzylidenyl)-5-(morpholin-1yl)sulfonyl-2-indolinone |
| 10733 | F | 3 | 3-(3-t-butyl-4-methoxy-5-nitrobenzylidenyl)-5-(morpholin-1-yl)sulfonyl-2-indolinone |
| 10733 | F | 4 | 3-(3,5-di-t-butyl-4-methoxybenzylidenyl)-5-(morpholin-1-yl)sulfonyl-2-indolinone |
| 10733 | F | 5 | 3-(4-benzyloxy-3,5-di-t-butylbenzylidenyl)-5-(morpholin-1-yl)sulfonyl-2-indolinone |
| 10733 | F | 6 | 3-(3,5-dimethyl-4-methoxybenzylidenyl)-5-(morpholin-1-yl)sulfonyl-2-indolinone |
| 10733 | F | 7 | 3-(4-benzyloxy-3,5-dimethylbenzylidenyl)-5-(morpholin-1-yl)sulfonyl-2-indolinone |
| 10733 | F | 8 | 3-(5-bromo-2-hydroxy-3-methoxybenzylidenyl)-5-(morpholin-1-yl)sulfonyl-2-indolinone |
| 10733 | F | 9 | 3-(5-bromo-2-hydroxybenzylidenyl)-5-(morpholin-1-yl)sulfonyl-2-indolinone |
| 10733 | F | 10 | 3-(2-hydroxy-5-nitrobenzylidenyl)-5-(morpholin-1-yl)sulfonyl-2-indolinone |
| 10733 | F | 11 | 3-(4-hydroxy-3-methoxy-2-nitrobenzylidenyl)-5-(morpholin-1-yl)sulfonyl-2-indolinone |
| 10733 | G | 2 | 3-(4-benzyloxy-3-t-butyl-5-iodobenzylidenyl)-5-(2-chloroethyl)-2-indolinone |
| 10733 | G | 3 | 3-(3-t-butyl-4-methoxy-5-nitrobenzylidenyl)-5-(2-chloroethyl)-2-indolinone |
| 10733 | G | 4 | 3-(3-5-di-t-butyl-4-methoxybenzylidenyl)-5-(2-chloroethyl)-2-indolinone |
| 10733 | G | 5 | 3-(4-benzyloxy-3,5-di-t-butylbenzylidenyl)-5-(2-chloroethyl)-2-indolinone |
| 10733 | G | 6 | 3-(3,5-dimethyl-methoxybenzylidenyl)-5-(2-chloroethyl)-2-indolinone |
| 10733 | G | 7 | 3-(4-benzyloxy-3,5-dimethylbenzylidenyl)-5-(2-chloroethyl)-2-indolinone |

TABLE 13-continued

| MASTER BARCODE | PLATE ROW | PLATE COLUMN | NAME |
| --- | --- | --- | --- |
| 10733 | G | 8 | 3-(5-bromo-2-hydroxy-3-methoxybenzylidenyl)-5-(2-chloroethyl)-2-indolinone |
| 10733 | G | 9 | 3-(5-bromo-2-hydroxybenzylidenyl)-5-(2-chloroethyl)-2-indolinone |
| 10733 | G | 10 | 3-(2-hydroxy-5-nitrobenzylidenyl)-5-(2-chloroethyl)-2-indolinone |
| 10733 | G | 11 | 3-(4-hydroxy-3-methoxy-2-nitrobenzylidenyl)-5-(2-chloroethyl)-2-indolinone |
| 10734 | A | 2 | 3-(-ethoxy-2-hydroxybenzylidenyl)-5,7-dibromo-2-indolinone |
| 10734 | A | 3 | 3-(3,5-dichloro-2-hydroxybenzylidenyl)-5,7-dibromo-2-indolinone |
| 10734 | A | 4 | 3-(5-chloro-2-hydroxybenzylidenyl)-5,7-dibromo-2-indolinone |
| 10734 | A | 5 | 3-(4-diethylamino-2-hydroxybenzylidenyl)-5,7-dibromo-2-indolinone |
| 10734 | A | 6 | 3-(4-nitrobenzylidenyl)-5,7-dibromo-2-indolinone |
| 10734 | A | 7 | 3-(3,5-dibromo-2-hydroxybenzylidenyl)-5,7-dibromo-2-indolinone |
| 10734 | A | 8 | 3-(3-fluoro-2-hydroxybenzylidenyl)-5,7-dibromo-2-indolinone |
| 10734 | A | 9 | 3-(3-bromo-4-hydroxybenxylidenyl)-5,7-dibromo-2-indolinone |
| 10734 | A | 10 | 3-(4-t-butylbenzylidenyl)-5,7-dibromo-2-indolinone |
| 10734 | A | 11 | 3-[(2-bromothien-5-yl)methylidenyl]-5,7-dibromo-2-indolinone |
| 10734 | B | 2 | 3-(3-ethoxy-2-hydroxybenzylidenyl)-5-iodo-2-indolinone |
| 10734 | B | 3 | 3-(3,5-dichloro-2-hydroxybenzylidenyl)-5-iodo-2-indolinone |
| 10734 | B | 4 | 3-(5-chloro-2-hydroxybenzylidenyl)-5-iodo-2-indolinone |
| 10734 | B | 5 | 3-(4-diethylamino-2-hydroxybenzylidenyl)-5-iodo-2-indolinone |
| 10734 | B | 6 | 3-(4-nitrobenzylidenyl)-5-iodo-2-indolinone |
| 10734 | B | 7 | 3-(3,5-dibromo-2-hydroxybenzylidenyl)-5-iodo-2-indolinone |
| 10734 | B | 8 | 3-(3-fluoro-2-hydroxybenzylidenyl)-5-iodo-2-indolinone |
| 10734 | B | 9 | 3-(3-bromo-4-hydroxybenzylidenyl)-5-iodo-2-indolinone |
| 10734 | B | 10 | 3-(4-t-butylbenzylidenyl)-5-iodo-2-indolinone |
| 10734 | B | 11 | 3-[(2-bromothien-5-yl)methylidenyl]-5-iodo-2-indolinone |
| 10734 | C | 2 | 3-(3-ethoxy-2-hydroxybenzylidenyl)-5-bromo-4-methyl-2-indolinone |
| 10734 | C | 3 | 3-(3,5-dichloro-2-hydroxybenzylidenyl)-5-bromo-4-methyl-2-indolinone |
| 10734 | C | 4 | 3-(5-chloro-2-hydroxybenzylidenyl)-5-bromo-4-methyl-2-indolinone |
| 10734 | C | 5 | 3-(4-diethylamino-2-hydroxybenzylidenyl)-5-bromo-4-methyl-2-indolinone |
| 10734 | C | 6 | 3-(4-nitrobenzylidenyl)-5-bromo-4-methyl-2-indolinone |
| 10734 | C | 7 | 3-(3,5-dibromo-2-hydroxybenzylidenyl)-5-bromo-4-methyl-2-indolinone |
| 10734 | C | 8 | 3-(3-fluoro-2-hydroxybenzylidenyl)-5-bromo-4-methyl-2-indolinone |
| 10734 | C | 9 | 3-(3-bromo-4-hydroxybenzylidenyl)-5-bromo-4-methyl-2-indolinone |
| 10734 | C | 10 | 3-(4-t-butylbenzylidenyl)-5-bromo-4-methyl-2-indolinone |
| 10734 | C | 11 | 3-[(2-bromothien-5-yl)methylidenyl]-5-bromo-4-methyl-2-indolinone |
| 10734 | D | 2 | 3-(3-ethoxy-2-hydroxybenzylidenyl)-5-methylaminosulfonyl-2-indolinone |
| 10734 | D | 3 | 3-(3,5-dichloro-2-hydroxybenzylidenyl)-5-methylaminosulfonyl-2-indolinone |
| 10734 | D | 4 | 3-(5-chloro-2-hydroxybenzylidenyl)-5-methylaminosulfonyl-2-indolinone |
| 10734 | D | 5 | 3-(4-diethylamino-2-hydroxybenzylidenyl)-5-methylaminosulfonyl-2-indolinone |
| 10734 | D | 6 | 3-(4-nitrobenzylidenyl)-5-methylaminosulfonyl-2-indolinone |
| 10734 | D | 7 | 3-(3,5-dibromo-2-hydroxybenzylidenyl)-5-methylaminosulfonyl-2-indolinone |

TABLE 13-continued

| MASTER BARCODE | PLATE ROW | PLATE COLUMN | NAME |
|---|---|---|---|
| 10734 | D | 8 | 3-(3-fluoro-2-hydroxybenzylidenyl)-5-methylaminosulfonyl-2-indolinone |
| 10734 | D | 9 | 3-(3-bromo-4-hydroxybenzylidenyl)-5-methylaminosulfonyl-2-indolinone |
| 10734 | D | 10 | 3-(4-t-butylbenzylidenyl)-5-methylaminosulfonyl-2-indolinone |
| 10734 | D | 11 | 3-[(2-bromothien-5-yl)methylidenyl]-5-methylaminosulfonyl-2-indolinone |
| 10734 | E | 2 | 3-(3-ethoxy-2-hydroxybenzylidenyl)-5-[4-(trifluoromethyl)phenylaminosulfonyl]-2-indolinone |
| 10734 | E | 3 | 3-(3,5-dichloro-2-hydroxybenzylidenyl)-5-[4-(trifluoromethyl)phenylaminosulfonyl]-2-indolinone |
| 10734 | E | 4 | 3-(5-chloro-2-hydroxybenzylidenyl)-5-[4-(tflfluoromethyl)phenylaminosulfonyl]-2-indolinone |
| 10734 | E | 5 | 3-(4-diethylamino-2-hydroxybenzylidenyl)-5-[4-(trifluoromethyl)phenylaminosulfonyl]-2-indolinone |
| 10734 | E | 6 | 3-(4-nitrobenzylidenyl)-5-[4-(trifluoromethyl)phenylaminosulfonyl]-2-indolinone |
| 10734 | E | 7 | 3-(3,5-dibromo-2-hydroxybenzylidenyl)-5-[4-(trifluoromethyl)phenylaminosulfonyl)-2-indoinone |
| 10734 | E | 8 | 3-(3-fluoro-2-hydroxybenzylidenyl)-5-[4-(trifluoromethyl)phenylaminosulfonyl)-2-indolinone |
| 10734 | E | 9 | 3-(3-bromo-4-hydroxybenzylidenyl)-5-[4-(trifluoromethyl)phenylaminosulfonyl]-2-indolinone |
| 10734 | E | 10 | 3-(4-t-butylbenzylidenyl)-5-[4-(trifluoromethyl)phenylaminosulfonyl]-2-indolinone |
| 10734 | E | 11 | 3-[(2-bromothien-5-yl)methylidenyl]-5-[4-(trifluoromethyl)phenylaminosulfonyl]-2-indolinone |
| 10734 | F | 2 | 3-(3-fluoro-2-hydroxybenzylidenyl)-5-(morpholin-1-yl)sulfonyl-2-indolinone |
| 10734 | F | 3 | 3-(3,5-dichloro-2-hydroxybenzylidenyl)-5-(morpholin-1-yl)sulfonyl-2-indolinone |
| 10734 | F | 4 | 3-(5-chloro-2-hydroxybenzylidenyl)-5-(morpholin-1-yl)sulfonyl-2-indolinone |
| 10734 | F | 5 | 3-(4-diethylamino-2-hydroxybenzylidenyl)-5-(morpholin-1-yl)sulfonyl-2-indolinone |
| 10734 | F | 6 | 3-(4-nitrobenzylidenyl)-5-(morpholin-1-yl)sulfonyl-2-indolinone |
| 10734 | F | 7 | 3-(3,5-dibromo-2-hydroxybenzylidenyl)-5-(morpholin-1-yl)sulfonyl-2-indolinone |
| 10734 | F | 8 | 3-(3-fluoro-2-hydroxybenzylidenyl)-5-(mornholin-1-yl)sulfonyl-2-indolinone |
| 10734 | F | 9 | 3-(3-bromo-4-hydroxybenzylidenyl)-5-(morpholin-1-yl)sulfonyl-2-indolinone |
| 10734 | F | 10 | 3-(4-t-butylbenzylidenyl)-5-(morpholin-1-yl)sulfonyl-2-indolinone |
| 10734 | F | 11 | |
| 10734 | F | 2 | 3-(3-ethoxy-2-hydroxybenzylidenyl)-5-(2-chloroethyl)-2-indolinone |
| 10734 | G | 3 | 3-(3,5-dichloro-2-hydroxybenzylidenyl)-5-(2-chloroethyl)-2-indolinone |
| 10734 | G | 4 | 3-(5-chloro-2-hydroxybenzylidenyl)-5-(2-chloroethy-)-2-indolinone |
| 10734 | G | 5 | 3-(4-diethylamino-2-hydroxybenzylidenyl)-5-(2-chloroethyl)-2-indolinone |
| 10734 | G | 6 | 3-(4-nitrobenzylidenyl)-5-(2-chloroethyl)-2-indolinone |
| 10734 | G | 7 | 3-(3,5-dibromo-2-hydroxybenzylidenyl)-5-(2-chloroethyl)-2-indolinone |
| 10734 | G | 8 | 3-(3-fluoro-2-hydroxybenzylidenyl)-5-(2-chloroethyl)-2-indolinone |
| 10734 | G | 9 | 3-(3-bromo-4-hydroxybenzylidenyl)-5-(2-chloroethyl)-2-indolinone |
| 10734 | G | 10 | 3-(4-t-butylbenzylidenyl)-5-(2-chloroethyl)-2-indolinone |
| 10734 | G | 11 | 3-[(2-bromothien-5-yl)methylidenyl]-5-(2-chloroethyl)-2-indolinone |

TABLE 14

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10717/A02 | 0.1 | 24.3 | | 46.1 |
| 10717/A03 | 2.9 | 1.0 | | 54.6 |
| 10717/A04 | −4.5 | 29.0 | | 37.4 |
| 10717/A05 | −2.6 | 16.6 | | 35.6 |
| 10717/A06 | −10.8 | −7.8 | | 31.7 |
| 10717/A07 | −6.4 | 20.2 | | 29.2 |
| 10717/A08 | −5.2 | 39.1 | | 21.7 |
| 10717/A09 | −3.9 | 37.7 | | 9.4 |
| 10717/A10 | −3.3 | 8.1 | | 71.6 |
| 10717/A11 | −5.8 | 59.9 | | 64.8 |
| 10717/B02 | 5.0 | 31.7 | | 87.5 |
| 10717/B03 | −8.8 | 7.3 | | 90.5 |
| 10717/B04 | −18.3 | 10.3 | | 70.0 |
| 10717/B05 | 1.0 | 31.7 | | 87.4 |
| 10717/B06 | 5.4 | −30.8 | | 89.5 |
| 10717/B07 | −18.3 | 58.3 | | 90.0 |
| 10717/B08 | −0.9 | 60.5 | | 88.8 |
| 10717/B09 | −40.7 | 78.3 | | 88.8 |
| 10717/B10 | −2.3 | 16.1 | | 56.1 |
| 10717/B11 | 11.4 | 82.7 | | 91.0 |
| 10717/C02 | 4.1 | −0.4 | | 29.7 |
| 10717/C03 | −7.7 | 18.0 | | 25.3 |
| 10717/C04 | −0.8 | 14.4 | | 25.0 |
| 10717/C05 | −2.3 | 13.1 | | 44.6 |
| 10717/C06 | 7.6 | −49.7 | | 44.1 |
| 10717/C07 | 1.6 | 28.7 | | 16.5 |
| 10717/C08 | 7.0 | 24.3 | | 27.3 |
| 10717/C09 | 77.1 | 8.1 | | 47.7 |
| 10717/C10 | −8.0 | 17.5 | | 22.8 |
| 10717/C11 | 4.6 | 67.3 | | 71.8 |
| 10717/D02 | 5.1 | 10.1 | | 28.6 |
| 10717/D03 | 1.1 | −1.4 | | 11.1 |
| 10717/D04 | −2.1 | 4.9 | | 21.0 |
| 10717/D05 | −3.8 | −2.8 | | 23.8 |
| 10717/D06 | 1.0 | −23.4 | | 33.8 |
| 10717/D07 | −8.4 | −4.5 | | 16.8 |
| 10717/D08 | 6.8 | −7.8 | | 16.0 |
| 10717/D09 | −55.0 | 6.8 | | 29.1 |
| 10717/D10 | −6.0 | 3.5 | | 15.6 |
| 10717/D11 | 11.6 | 59.1 | | 55.3 |
| 10717/E02 | 17.9 | 17.2 | | 24.0 |
| 10717/E03 | 19.0 | 11.7 | | 52.2 |
| 10717/E04 | 6.1 | −28.3 | | 29.4 |
| 10717/E05 | 13.2 | 22.4 | | 39.1 |
| 10717/E06 | 7.5 | −26.1 | | 24.8 |
| 10717/E07 | 15.3 | −7.8 | | 41.0 |
| 10717/E08 | 13.2 | 28.2 | | 51.7 |
| 10717/E09 | −1.1 | −5.8 | | 19.2 |
| 10717/E10 | 4.7 | −6.1 | | 35.9 |
| 10717/E11 | 8.9 | 44.9 | | 75.1 |
| 10717/F02 | 2.2 | 6.2 | | 30.4 |
| 10717/F03 | 0.5 | −4.7 | | 42.8 |
| 10717/F04 | −0.1 | −15.7 | | 11.4 |
| 10717/F05 | 3.2 | −20.1 | | 21.5 |
| 10717/F06 | 8.9 | −22.8 | | 49.0 |
| 10717/F07 | 2.0 | −14.3 | | 37.6 |
| 10717/F08 | −0.7 | −23.4 | | 64.0 |
| 10717/F09 | −13.3 | 1.8 | | 41.4 |
| 10717/F10 | −4.4 | −26.4 | | 54.6 |
| 10717/F11 | 1.4 | 91.2 | | 81.5 |
| 10717/G02 | 14.9 | 32.3 | | 30.7 |
| 10717/G03 | 1.8 | 18.8 | | 4.5 |
| 10717/G04 | 0.8 | 6.0 | | 10.9 |
| 10717/G05 | 5.3 | −0.1 | | 4.7 |
| 10717/G06 | 4.3 | −3.4 | | 34.0 |
| 10717/G07 | −17.0 | 13.1 | | 7.5 |
| 10717/G08 | 1.9 | 36.4 | | 10.9 |
| 10717/G09 | −29.7 | 24.9 | | 19.1 |
| 10717/G10 | 4.8 | 2.4 | | 30.9 |
| 10717/G11 | 16.4 | 71.7 | | 73.8 |
| 10718/A02 | 3.0 | 11.3 | | 54.6 |
| 10718/A03 | 7.6 | −6.1 | | 92.7 |
| 10718/A04 | 6.9 | 27.3 | | 81.7 |
| 10718/A05 | 3.2 | −6.9 | | 36.1 |
| 10718/A06 | 7.8 | 19.4 | | 61.3 |
| 10718/A07 | 16.2 | −10.6 | | 58.6 |
| 10718/A08 | 3.2 | 5.8 | | 36.8 |
| 10718/A09 | −18.4 | −4.1 | | 67.7 |
| 10718/A10 | 23.4 | 41.5 | | 77.9 |
| 10718/A11 | 2.7 | 21.2 | | 58.9 |
| 10718/B02 | 7.0 | 24.9 | | 52.9 |
| 10718/B03 | 1.7 | −0.2 | | 77.9 |
| 10718/B04 | 11.8 | 8.5 | | 63.9 |
| 10718/B05 | 11.5 | 56.3 | | 76.0 |
| 10718/B06 | 16.5 | 28.5 | | 78.4 |
| 10718/B07 | 17.7 | 9.9 | | 53.7 |
| 10718/B08 | 5.4 | 28.9 | | 63.4 |
| 10718/B09 | −14.7 | −0.8 | | 52.9 |
| 10718/B10 | 20.1 | 13.7 | | 83.6 |
| 10718/B11 | 4.5 | 30.3 | | 69.6 |
| 10718/C02 | 26.2 | −21.9 | | 29.6 |
| 10718/C03 | −13.9 | 41.3 | | 95.7 |
| 10718/C04 | 15.3 | 14.8 | | 93.1 |
| 10718/C05 | 20.5 | 10.9 | | 8.7 |
| 10718/C06 | 16.8 | 5.6 | | 3.9 |
| 10718/C07 | 6.3 | −4.9 | | 29.6 |
| 10718/C08 | 19.6 | 13.1 | | 22.7 |
| 10718/C09 | 5.3 | 26.5 | | 38.2 |
| 10718/C10 | −11.9 | −18.7 | | 4.4 |
| 10718/C11 | 11.4 | −0.2 | | 10.1 |
| 10718/D02 | 13.3 | 14.4 | | 32.0 |
| 10718/D03 | 1.1 | 61.9 | | 92.9 |
| 10718/D04 | 6.4 | 52.0 | | 92.9 |
| 10718/D05 | 11.5 | 2.8 | | 10.6 |
| 10718/D06 | 15.8 | 20.0 | | 11.1 |
| 10718/D07 | 7.8 | 5.6 | | 26.1 |
| 10718/D08 | 3.9 | 3.0 | | 2.3 |
| 10718/D09 | −9.1 | 6.0 | | 9.9 |
| 10718/D10 | 15.0 | 12.3 | | 55.3 |
| 10718/D11 | 13.3 | 5.4 | | 11.3 |
| 10718/E02 | 19.7 | 1.0 | | 46.3 |
| 10718/E03 | 10.0 | 50.4 | | 95.3 |
| 10718/E04 | 15.1 | 16.4 | | 87.7 |
| 10718/E05 | 16.1 | −3.1 | | 32.2 |
| 10718/E06 | 15.4 | 2.0 | | 33.4 |
| 10718/E07 | 15.6 | 13.9 | | 80.5 |
| 10718/E08 | 9.2 | 9.3 | | 69.6 |
| 10718/E09 | 0.9 | 17.0 | | 80.8 |
| 10718/E10 | 15.2 | −7.5 | | 60.8 |
| 10718/E11 | 12.1 | −15.2 | | 37.5 |
| 10718/F02 | 20.1 | 17.8 | | 66.7 |
| 10718/F03 | −0.2 | 22.5 | | 87.9 |
| 10718/F04 | 9.4 | 1.2 | | 78.1 |
| 10718/F05 | 19.5 | −4.9 | | 53.7 |
| 10718/F06 | 18.3 | −9.1 | | 42.5 |
| 10718/F07 | 16.5 | −6.3 | | 67.9 |
| 10718/F08 | 15.3 | −8.7 | | 28.4 |
| 10718/F09 | −3.0 | −9.5 | | 52.7 |
| 10718/F10 | 17.9 | −12.0 | | 23.7 |
| 10718/F11 | 10.1 | −3.9 | | 31.3 |
| 10718/G02 | −2.5 | 49.2 | | 67.7 |
| 10718/G03 | −4.7 | 57.3 | | 77.9 |
| 10718/G04 | 1.8 | 15.8 | | 78.1 |
| 10718/G05 | 3.7 | 2.8 | | 60.3 |
| 10718/G06 | 9.8 | −18.7 | | 61.0 |
| 10718/G07 | 11.4 | −21.3 | | 52.0 |
| 10718/G08 | 6.1 | −8.3 | | 17.5 |
| 10718/G09 | −12.8 | −15.4 | | 27.0 |
| 10718/G10 | 7.1 | −7.5 | | 10.8 |
| 10718/G11 | 15.6 | −4.9 | | 3.0 |
| 10719/A02 | 21.4 | 43.0 | | 40.9 |
| 10719/A03 | 3.9 | 67.7 | | 84.1 |
| 10719/A04 | 19.2 | 43.7 | | 22.9 |
| 10719/A05 | 10.0 | 23.1 | | 39.6 |
| 10719/A06 | 14.0 | 18.2 | | −7.0 |
| 10719/A07 | 21.3 | 15.5 | | 68.1 |
| 10719/A08 | 11.9 | 47.3 | | 75.5 |
| 10719/A09 | 12.3 | 2.2 | | 47.0 |
| 10719/A10 | 10.9 | 8.2 | | 13.4 |
| 10719/A11 | 7.4 | 10.5 | | 34.9 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10719/B02 | 11.5 | 29.0 | | 47.0 |
| 10719/B03 | 14.2 | 59.5 | | 85.8 |
| 10719/B04 | 24.9 | 29.9 | | 38.4 |
| 10719/B05 | 17.7 | 35.9 | | 33.6 |
| 10719/B06 | 21.3 | −0.5 | | 22.5 |
| 10719/B07 | 12.5 | 23.7 | | 52.2 |
| 10719/B08 | 4.0 | 42.3 | | 33.2 |
| 10719/B09 | 11.3 | −17.7 | | 23.5 |
| 10719/B10 | 1.1 | −1.2 | | 53.4 |
| 10719/B11 | 11.2 | −23.9 | | 36.5 |
| 10719/C02 | 4.1 | 10.2 | | 41.3 |
| 10719/C03 | 15.3 | 60.6 | | 69.1 |
| 10719/C04 | 59.9 | 14.4 | | 14.7 |
| 10719/C05 | 25.6 | 27.4 | | 35.5 |
| 10719/C06 | 47.7 | −14.3 | | 18.4 |
| 10719/C07 | 31.2 | 14.4 | | 7.7 |
| 10719/C08 | 15.0 | −10.2 | | 57.5 |
| 10719/C09 | 23.5 | −0.1 | | 8.9 |
| 10719/C10 | 11.8 | 10.7 | | 7.9 |
| 10719/C11 | 9.9 | −25.7 | | −5.1 |
| 10719/D02 | 9.7 | 9.8 | | 27.5 |
| 10719/D03 | 4.8 | 95.7 | | 93.2 |
| 10719/D04 | 27.8 | 15.3 | | 28.9 |
| 10719/D05 | 16.3 | 18.5 | | 71.8 |
| 10719/D06 | 25.8 | −12.2 | | 11.2 |
| 10719/D07 | −123.5 | 13.7 | | 41.5 |
| 10719/D08 | 8.2 | −12.2 | | 45.2 |
| 10719/D09 | 7.8 | −3.1 | | 13.0 |
| 10719/D10 | 8.3 | −11.8 | | 22.3 |
| 10719/D11 | −8.7 | −11.1 | | 12.8 |
| 10719/E02 | 26.1 | 40.0 | | 35.7 |
| 10719/E03 | 17.1 | 73.0 | | 87.2 |
| 10719/E04 | 31.2 | −7.4 | | 3.1 |
| 10719/E05 | 21.5 | 21.2 | | 39.0 |
| 10719/E06 | 17.1 | −42.0 | | −4.5 |
| 10719/E07 | 26.7 | −18.4 | | 55.5 |
| 10719/E08 | 21.8 | 36.8 | | 80.0 |
| 10719/E09 | 13.5 | −33.1 | | 36.1 |
| 10719/E10 | 17.6 | −32.4 | | 40.2 |
| 10719/E11 | 26.3 | −51.8 | | 28.5 |
| 10719/F02 | 28.6 | 14.8 | | 28.1 |
| 10719/F03 | 11.2 | −30.8 | | 89.5 |
| 10719/F04 | 26.6 | −6.0 | | 3.3 |
| 10719/F05 | 20.7 | 35.0 | | 63.1 |
| 10719/F06 | 13.5 | −26.0 | | −22.0 |
| 10719/F07 | 18.7 | 20.1 | | 36.7 |
| 10719/F08 | 15.1 | 90.9 | | 75.7 |
| 10719/F09 | −6.5 | −17.7 | | 19.2 |
| 10719/F10 | 10.4 | −17.7 | | 30.8 |
| 10719/F11 | 11.6 | −66.3 | | 8.7 |
| 10719/G02 | 27.3 | −12.2 | | −2.4 |
| 10719/G03 | −25.8 | 89.5 | | 87.6 |
| 10719/G04 | 11.5 | −4.7 | | −8.2 |
| 10719/G05 | 18.0 | 4.0 | | 15.9 |
| 10719/G06 | 23.2 | −45.7 | | −18.1 |
| 10719/G07 | 20.1 | −8.1 | | 24.0 |
| 10719/G08 | 3.2 | 65.4 | | 39.4 |
| 10719/G09 | 18.1 | −32.8 | | 1.3 |
| 10719/G10 | 9.7 | −27.6 | | 35.5 |
| 10719/G11 | 6.9 | −44.1 | | 24.0 |
| 10720/A02 | 4.7 | 11.3 | | 45.2 |
| 10720/A03 | 17.7 | −5.3 | | 58.2 |
| 10720/A04 | 12.3 | −1.8 | | 62.3 |
| 10720/A05 | 8.0 | −4.4 | | 43.4 |
| 10720/A06 | 5.6 | 44.7 | | 63.6 |
| 10720/A07 | 6.6 | 42.5 | | 57.2 |
| 10720/A08 | −2.2 | −23.2 | | 77.9 |
| 10720/A09 | 8.1 | 8.6 | | 75.4 |
| 10720/A10 | −5.2 | −2.7 | | 68.4 |
| 10720/A11 | −0.6 | −23.2 | | 58.7 |
| 10720/B02 | 6.5 | 18.4 | | 38.8 |
| 10720/B03 | 6.4 | 32.3 | | 53.3 |
| 10720/B04 | 9.8 | 50.5 | | 61.8 |
| 10720/B05 | 11.6 | 58.4 | | 51.8 |
| 10720/B06 | 7.3 | 21.2 | | 55.1 |
| 10720/B07 | 12.0 | 52.0 | | 61.5 |
| 10720/B08 | 3.6 | −12.6 | | 27.7 |
| 10720/B09 | 10.1 | 37.6 | | 57.4 |
| 10720/B10 | −5.5 | 50.2 | | 45.2 |
| 10720/B11 | −20.3 | 22.4 | | 42.1 |
| 10720/C02 | 18.0 | 23.5 | | 63.6 |
| 10720/C03 | 15.1 | 0.9 | | 50.3 |
| 10720/C04 | 15.3 | −13.1 | | 29.0 |
| 10720/C05 | −36.1 | −15.3 | | 72.5 |
| 10720/C06 | 12.2 | −9.7 | | 36.7 |
| 10720/C07 | 20.7 | −25.4 | | 26.7 |
| 10720/C08 | 10.9 | −1.1 | | 65.6 |
| 10720/C09 | 12.1 | 44.7 | | 47.5 |
| 10720/C10 | −21.1 | 2.0 | | 62.6 |
| 10720/C11 | 52.5 | −21.9 | | 30.0 |
| 10720/D02 | 12.1 | 11.1 | | 17.8 |
| 10720/D03 | 17.0 | 0.9 | | 61.5 |
| 10720/D04 | 15.6 | −7.7 | | 23.6 |
| 10720/D05 | 4.8 | −24.1 | | 9.8 |
| 10720/D06 | 10.1 | −35.0 | | 31.8 |
| 10720/D07 | 11.8 | 14.8 | | 36.2 |
| 10720/D08 | 3.3 | −13.3 | | 42.1 |
| 10720/D09 | 5.8 | 2.4 | | 62.8 |
| 10720/D10 | −6.6 | −10.2 | | 51.0 |
| 10720/D11 | 9.8 | −5.5 | | 23.9 |
| 10720/E02 | 5.7 | 25.2 | | 18.0 |
| 10720/E03 | 34.3 | 54.4 | | 54.9 |
| 10720/E04 | 18.4 | −2.7 | | 46.7 |
| 10720/E05 | −13.8 | 40.7 | | 55.4 |
| 10720/E06 | 25.5 | 30.1 | | 33.1 |
| 10720/E07 | 18.8 | 55.1 | | 30.3 |
| 10720/E08 | 2.5 | 37.4 | | 55.1 |
| 10720/E09 | 11.5 | 56.4 | | 43.4 |
| 10720/E10 | −4.1 | 49.1 | | 23.1 |
| 10720/E11 | 9.3 | −65.5 | | −10.4 |
| 10720/F02 | 9.1 | −19.3 | | 17.8 |
| 10720/F03 | 10.6 | 7.1 | | 44.1 |
| 10720/F04 | 10.6 | −11.7 | | 43.1 |
| 10720/F05 | −3.6 | −14.2 | | 39.8 |
| 10720/F06 | 11.9 | −24.3 | | 21.9 |
| 10720/F07 | 4.6 | 35.2 | | 64.6 |
| 10720/F08 | −4.1 | −39.6 | | 36.2 |
| 10720/F09 | 5.9 | 6.4 | | 49.2 |
| 10720/F10 | −2.6 | 6.0 | | 42.8 |
| 10720/F11 | 5.0 | −61.1 | | 1.6 |
| 10720/G02 | 5.0 | −13.1 | | 20.1 |
| 10720/G03 | 2.6 | 10.0 | | 42.1 |
| 10720/G04 | 2.4 | −34.1 | | 5.0 |
| 10720/G05 | −2.9 | 27.0 | | 37.0 |
| 10720/G06 | −3.4 | −10.4 | | 21.6 |
| 10720/G07 | 5.1 | −8.0 | | 12.9 |
| 10720/G08 | −17.9 | −9.5 | | 26.7 |
| 10720/G09 | 2.1 | −19.7 | | 49.5 |
| 10720/G10 | −36.6 | 20.4 | | 55.9 |
| 10720/G11 | −18.0 | −56.7 | | 36.2 |
| 10721/A02 | 10.6 | 17.8 | | 41.1 |
| 10721/A03 | 11.4 | 25.5 | | 56.2 |
| 10721/A04 | 6.5 | 59.0 | | 85.0 |
| 10721/A05 | 12.5 | 41.4 | | 52.9 |
| 10721/A06 | 6.4 | 32.7 | | 81.3 |
| 10721/A07 | −4.7 | 35.2 | | 29.7 |
| 10721/A08 | 4.8 | 24.0 | | 29.9 |
| 10721/A09 | 10.9 | 28.0 | | 23.0 |
| 10721/A10 | 5.2 | 31.1 | | 68.9 |
| 10721/A11 | 4.8 | 24.6 | | 23.9 |
| 10721/B02 | 19.5 | 58.6 | | 82.6 |
| 10721/B03 | 19.9 | 38.9 | | 70.8 |
| 10721/B04 | 13.8 | 79.3 | | 93.1 |
| 10721/B05 | 45.9 | 76.8 | | 70.8 |
| 10721/B06 | 3.4 | 71.5 | | 92.4 |
| 10721/B07 | 11.2 | 47.6 | | 47.1 |
| 10721/B08 | 18.5 | 64.0 | | 64.5 |
| 10721/B09 | 9.0 | 38.9 | | 28.3 |
| 10721/B10 | 20.9 | 42.9 | | 30.4 |
| 10721/B11 | −2.1 | 34.6 | | 6.7 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10721/C02 | 9.7 | 68.3 | | 59.2 |
| 10721/C03 | 16.5 | 64.6 | | 6.2 |
| 10721/C04 | 21.8 | 77.7 | | 88.7 |
| 10721/C05 | 56.4 | 68.1 | | 48.7 |
| 10721/C06 | 14.4 | 80.2 | | 56.4 |
| 10721/C07 | 10.9 | 24.6 | | 25.7 |
| 10721/C08 | 55.8 | 38.3 | | 24.8 |
| 10721/C09 | 17.5 | 39.8 | | -4.7 |
| 10721/C10 | 21.1 | 17.4 | | 44.6 |
| 10721/C11 | 13.9 | 14.1 | | 3.7 |
| 10721/D02 | 15.1 | 21.5 | | 22.5 |
| 10721/D03 | 17.8 | 11.6 | | 19.5 |
| 10721/D04 | 15.2 | 5.0 | | 35.3 |
| 10721/D05 | -25.1 | 47.0 | | 91.9 |
| 10721/D06 | 1.6 | 44.5 | | 9.0 |
| 10721/D07 | 6.4 | 23.0 | | -6.8 |
| 10721/D08 | 3.9 | 31.7 | | 45.3 |
| 10721/D09 | 17.6 | 15.3 | | -4.9 |
| 10721/D10 | 23.7 | 3.3 | | 13.4 |
| 10721/D11 | 20.6 | 22.2 | | 23.2 |
| 10721/E02 | 17.2 | -9.5 | | 38.8 |
| 10721/E03 | 10.9 | 25.1 | | 12.3 |
| 10721/E04 | 16.0 | 48.5 | | 87.3 |
| 10721/E05 | 10.8 | 61.3 | | 69.9 |
| 10721/E06 | 40.4 | 91.5 | | 81.0 |
| 10721/E07 | 15.6 | 37.7 | | 43.6 |
| 10721/E08 | 15.7 | 29.8 | | 39.5 |
| 10721/E09 | 36.9 | 42.5 | | 0.7 |
| 10721/E10 | 9.3 | 19.9 | | 55.7 |
| 10721/E11 | 0.7 | 32.1 | | 31.3 |
| 10721/F02 | 17.0 | 11.0 | | 27.8 |
| 10721/F03 | 9.1 | 7.0 | | 40.6 |
| 10721/F04 | 7.4 | 0.0 | | 26.0 |
| 10721/F05 | 8.1 | 20.5 | | 67.8 |
| 10721/F06 | 2.2 | 21.7 | | 80.3 |
| 10721/F07 | 4.8 | 3.5 | | 55.7 |
| 10721/F08 | -6.4 | 37.3 | | 76.1 |
| 10721/F09 | 65.2 | 7.0 | | 52.5 |
| 10721/F10 | 49.6 | 7.5 | | 79.9 |
| 10721/F11 | 29.7 | 95.9 | | 78.2 |
| 10721/G02 | 16.4 | 23.6 | | 7.9 |
| 10721/G03 | 12.1 | 23.4 | | 25.3 |
| 10721/G04 | 3.2 | 64.6 | | 90.3 |
| 10721/G05 | -15.1 | 7.7 | | 8.6 |
| 10721/G06 | 18.9 | 23.2 | | 39.5 |
| 10721/G07 | 3.3 | 14.7 | | 10.0 |
| 10721/G08 | 5.4 | 12.8 | | -2.4 |
| 10721/G09 | 20.4 | 14.9 | | 5.1 |
| 10721/G10 | 24.4 | 2.1 | | 12.0 |
| 10721/G11 | -7.1 | 0.4 | | -0.0 |
| 10722/A02 | 0.8 | 23.7 | 28.9 | 44.9 |
| 10722/A03 | 6.7 | 0.8 | 29.5 | 90.3 |
| 10722/A04 | 13.4 | 21.0 | -0.9 | 51.4 |
| 10722/A05 | 10.5 | 22.4 | 33.5 | 90.5 |
| 10722/A06 | 9.6 | 28.4 | 19.8 | 71.6 |
| 10722/A07 | 9.4 | 29.9 | 23.8 | 64.1 |
| 10722/A08 | 13.7 | 23.9 | 15.2 | 70.5 |
| 10722/A09 | 7.3 | 16.8 | 21.5 | 86.5 |
| 10722/A10 | 6.6 | -4.2 | 15.2 | 79.0 |
| 10722/A11 | 6.7 | -0.1 | 21.5 | 68.6 |
| 10722/B02 | 10.1 | 16.3 | 28.9 | 44.3 |
| 10722/B03 | 13.6 | 19.6 | 3.7 | 40.1 |
| 10722/B04 | 14.7 | 10.6 | 3.1 | 53.4 |
| 10722/B05 | 18.5 | 9.3 | 21.5 | 67.2 |
| 10722/B06 | 13.9 | -4.9 | 21.5 | 72.6 |
| 10722/B07 | 6.6 | 6.2 | 20.9 | 48.2 |
| 10722/B08 | 11.2 | 0.5 | 27.8 | 72.0 |
| 10722/B09 | 8.7 | 7.8 | 14.6 | 59.7 |
| 10722/B10 | -0.9 | -11.3 | 20.3 | 56.4 |
| 10722/B11 | 5.2 | -15.5 | 25.5 | 83.0 |
| 10722/C02 | 29.1 | 32.1 | 30.6 | 34.5 |
| 10722/C03 | 16.7 | 42.3 | 22.6 | 73.6 |
| 10722/C04 | 10.7 | 26.7 | 8.9 | 70.7 |
| 10722/C05 | 23.5 | 19.1 | 26.6 | 44.9 |
| 10722/C06 | 24.5 | -11.0 | 24.9 | 45.1 |
| 10722/C07 | 15.8 | -15.5 | 31.2 | 61.2 |
| 10722/C08 | 17.8 | 14.8 | 31.2 | 80.1 |
| 10722/C09 | 25.9 | -3.1 | 32.4 | 45.1 |
| 10722/C10 | 2.3 | 22.8 | 18.0 | 33.9 |
| 10722/C11 | 13.8 | -14.2 | 36.4 | 52.6 |
| 10722/D02 | 30.7 | 26.1 | 31.8 | 26.4 |
| 10722/D03 | 15.0 | 31.0 | -9.4 | 52.8 |
| 10722/D04 | 23.5 | 20.3 | 15.7 | 63.4 |
| 10722/D05 | 21.4 | -3.8 | 22.0 | 35.8 |
| 10722/D06 | 21.9 | -2.5 | 8.9 | 32.4 |
| 10722/D07 | 14.1 | -2.8 | 25.5 | 42.6 |
| 10722/D08 | 29.1 | -2.6 | 41.5 | 60.5 |
| 10722/D09 | 14.7 | -17.2 | 30.6 | 52.2 |
| 10722/D10 | 8.2 | -0.6 | 41.5 | 40.5 |
| 10722/D11 | 9.6 | -10.1 | 15.2 | 41.0 |
| 10722/E02 | 17.0 | 22.2 | 23.2 | 71.1 |
| 10722/E03 | 10.7 | 33.0 | -7.2 | 88.4 |
| 10722/E04 | 38.6 | 1.4 | 30.6 | 52.6 |
| 10722/E05 | 19.2 | -7.0 | 19.2 | 73.0 |
| 10722/E06 | 21.4 | 7.6 | 32.9 | 71.6 |
| 10722/E07 | 24.3 | 28.7 | 40.9 | 71.6 |
| 10722/E08 | 18.6 | 10.4 | 38.7 | 82.8 |
| 10722/E09 | 16.2 | 4.1 | 26.6 | 55.1 |
| 10722/E10 | 3.1 | -13.3 | 31.8 | 86.6 |
| 10722/E11 | 15.3 | 4.2 | 28.3 | 84.0 |
| 10722/F02 | 5.3 | 9.2 | 12.9 | 33.9 |
| 10722/F03 | 12.0 | 13.7 | -14.0 | 59.7 |
| 10722/F04 | 27.5 | 16.8 | -2.0 | 58.9 |
| 10722/F05 | 15.0 | -2.8 | 6.0 | 6.4 |
| 10722/F06 | 11.0 | 6.5 | 2.6 | 6.0 |
| 10722/F07 | 15.5 | -3.7 | -6.6 | 63.0 |
| 10722/F08 | 66.3 | -5.4 | 25.5 | 89.3 |
| 10722/F09 | 15.3 | -35.8 | 26.6 | 65.7 |
| 10722/F10 | 3.3 | 10.7 | 24.9 | 67.8 |
| 10722/F11 | 4.5 | -6.5 | 15.7 | 73.2 |
| 10722/G02 | 15.1 | 27.3 | 14.6 | 43.0 |
| 10722/G03 | 5.3 | 4.1 | -3.7 | 52.2 |
| 10722/G04 | 7.2 | -13.3 | 11.7 | 63.2 |
| 10722/G05 | 10.8 | -9.0 | -6.0 | 9.7 |
| 10722/G06 | 7.4 | -5.2 | -6.0 | 12.2 |
| 10722/G07 | 8.0 | -32.5 | -3.7 | 41.2 |
| 10722/G08 | 8.2 | -8.5 | 12.9 | 66.1 |
| 10722/G09 | 6.1 | -5.9 | 0.9 | 51.0 |
| 10722/G10 | -1.7 | 3.3 | 16.9 | 27.0 |
| 10722/G11 | 0.6 | -39.4 | 0.3 | 35.3 |
| 10723/A02 | -5.5 | 97.8 | 64.4 | 100.8 |
| 10723/A03 | 1.2 | 38.5 | 11.7 | 76.5 |
| 10723/A04 | 27.2 | 30.8 | 13.1 | 97.9 |
| 10723/A05 | -17.8 | 26.4 | 17.9 | 75.7 |
| 10723/A06 | 8.6 | 20.1 | 43.6 | 79.1 |
| 10723/A07 | -6.1 | 3.9 | 22.1 | 63.2 |
| 10723/A08 | -12.9 | -2.1 | 29.7 | 77.3 |
| 10723/A09 | -1.0 | -4.5 | 42.9 | 85.9 |
| 10723/A10 | -3.1 | -24.8 | 34.6 | 62.1 |
| 10723/A11 | 42.9 | -4.0 | 41.5 | 60.0 |
| 10723/B02 | -0.3 | 91.0 | 29.0 | 100.3 |
| 10723/B03 | 7.1 | -5.0 | 14.5 | 82.5 |
| 10723/B04 | 18.7 | 5.1 | 40.1 | 90.6 |
| 10723/B05 | -15.4 | 36.4 | 15.2 | 85.1 |
| 10723/B06 | 31.8 | 11.9 | 58.8 | 90.6 |
| 10723/B07 | 6.5 | 28.8 | 24.9 | 86.7 |
| 10723/B08 | 1.0 | -0.4 | 56.1 | 82.8 |
| 10723/B09 | 2.7 | -12.0 | 27.6 | 57.7 |
| 10723/B10 | 5.8 | 1.8 | 17.2 | 88.5 |
| 10723/B11 | 6.3 | -26.0 | 22.8 | 62.6 |
| 10723/C02 | 9.6 | 73.6 | 39.4 | 100.6 |
| 10723/C03 | -3.1 | 5.9 | 42.9 | 88.8 |
| 10723/C04 | 8.8 | 23.5 | 36.7 | 91.9 |
| 10723/C05 | 5.6 | 35.2 | 22.8 | 73.1 |
| 10723/C06 | 17.8 | -4.5 | 26.3 | 63.4 |
| 10723/C07 | 20.9 | -4.0 | 27.6 | 44.3 |
| 10723/C08 | -35.5 | 45.0 | 29.0 | 83.0 |
| 10723/C09 | -22.3 | 62.7 | 62.3 | 84.6 |
| 10723/C10 | 9.5 | -7.2 | 25.6 | 43.8 |
| 10723/C11 | 9.5 | -1.1 | 8.9 | 47.0 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10723/D02 | 2.0 | 63.2 | 22.1 | 93.0 |
| 10723/D03 | −14.7 | 33.5 | 8.2 | 69.4 |
| 10723/D04 | 15.2 | 45.1 | 31.8 | 97.7 |
| 10723/D05 | −6.1 | 3.7 | 8.2 | 54.5 |
| 10723/D06 | 17.6 | −7.4 | 6.2 | 60.0 |
| 10723/D07 | 15.8 | 13.4 | 16.6 | 21.9 |
| 10723/D08 | −4.5 | 4.9 | 31.1 | 53.5 |
| 10723/D09 | 50.4 | −3.8 | 21.4 | 62.6 |
| 10723/D10 | 6.5 | −9.3 | 21.4 | 38.1 |
| 10723/D11 | 14.8 | −6.2 | 24.9 | 42.0 |
| 10723/E02 | 8.1 | 91.0 | 46.4 | 97.9 |
| 10723/E03 | 8.7 | 8.3 | 47.1 | 76.8 |
| 10723/E04 | 30.7 | 59.8 | 36.0 | 94.5 |
| 10723/E05 | 8.9 | −15.6 | −4.9 | 63.7 |
| 10723/E06 | 19.3 | 11.5 | 18.6 | 74.4 |
| 10723/E07 | 17.4 | 38.1 | 14.5 | 47.7 |
| 10723/E08 | −0.4 | 52.6 | 26.3 | 89.3 |
| 10723/E09 | 7.9 | 29.1 | 22.1 | 91.7 |
| 10723/E10 | 5.2 | −7.9 | 44.3 | 59.5 |
| 10723/E11 | 8.9 | −44.6 | 32.5 | 50.1 |
| 10723/F02 | 10.3 | 70.4 | 1.3 | 99.0 |
| 10723/F03 | 4.4 | 9.3 | 1.3 | 78.3 |
| 10723/F04 | 12.3 | 17.5 | 21.4 | 94.0 |
| 10723/F05 | −6.4 | −3.8 | −7.7 | 45.6 |
| 10723/F06 | 20.4 | 5.4 | −30.6 | 84.1 |
| 10723/F07 | 20.7 | −4.1 | 6.8 | 26.6 |
| 10723/F08 | −0.5 | 5.7 | 20.7 | 75.5 |
| 10723/F09 | 1.2 | 14.1 | 3.4 | 78.6 |
| 10723/F10 | 9.1 | 4.2 | −2.2 | 74.1 |
| 10723/F11 | −1.2 | −41.3 | 36.7 | 72.3 |
| 10723/G02 | −1.6 | 90.8 | 13.8 | 99.2 |
| 10723/G03 | 4.3 | 18.5 | 6.2 | 74.7 |
| 10723/G04 | 8.7 | 16.7 | 21.4 | 85.9 |
| 10723/G05 | −9.4 | 1.3 | 2.0 | 79.9 |
| 10723/G06 | 14.1 | −26.7 | −0.8 | 64.5 |
| 10723/G07 | 14.2 | 15.5 | −5.6 | 43.0 |
| 10723/G08 | −22.9 | 0.1 | 7.5 | 79.9 |
| 10723/G09 | −1.8 | −32.6 | −2.9 | 80.7 |
| 10723/G10 | 3.5 | 4.1 | −27.8 | 40.7 |
| 10723/G11 | −4.1 | −35.0 | −7.7 | 39.4 |
| 10724/A02 | 1.8 | 36.7 | 6.3 | 61.7 |
| 10724/A03 | −7.8 | 17.2 | 0.1 | 30.7 |
| 10724/A04 | −15.9 | 15.4 | 5.0 | 62.6 |
| 10724/A05 | −15.2 | 20.3 | 5.0 | 68.4 |
| 10724/A06 | −3.7 | 1.4 | 30.7 | 46.8 |
| 10724/A07 | 3.7 | 18.3 | 16.1 | 58.7 |
| 10724/A09 | −5.2 | 1.6 | 19.6 | 37.5 |
| 10724/A10 | 1.6 | 40.0 | 28.6 | 83.8 |
| 10724/A11 | 12.8 | −16.6 | 29.3 | 27.2 |
| 10724/B02 | −6.2 | 34.9 | −21.5 | 48.8 |
| 10724/B03 | −48.9 | 14.9 | 14.7 | 51.0 |
| 10724/B04 | −20.5 | 50.2 | 42.5 | 81.2 |
| 10724/B05 | −2.2 | 21.2 | 12.6 | 45.6 |
| 10724/B06 | 13.4 | 30.9 | 43.2 | 52.1 |
| 10724/B07 | −1.8 | 44.0 | 27.2 | 57.9 |
| 10724/B09 | 3.5 | 8.7 | 25.8 | 43.8 |
| 10724/B10 | 8.5 | 76.2 | 9.8 | 95.0 |
| 10724/B11 | 9.0 | −23.2 | 23.0 | 43.0 |
| 10724/C02 | −0.3 | 53.6 | −9.0 | 40.7 |
| 10724/C03 | −20.3 | 16.5 | 4.3 | 68.7 |
| 10724/C04 | −18.6 | 13.2 | 24.4 | 84.3 |
| 10724/C05 | −18.6 | −0.8 | 20.3 | 67.7 |
| 10724/C06 | −1.5 | −2.4 | 34.9 | 15.4 |
| 10724/C07 | −1.2 | 9.4 | 22.3 | 14.2 |
| 10724/C09 | 9.3 | 1.0 | 20.3 | 5.3 |
| 10724/C10 | −2.3 | 13.8 | 27.2 | 91.2 |
| 10724/C11 | 10.3 | 0.7 | 23.0 | 4.9 |
| 10724/D02 | 12.4 | 40.5 | −9.6 | 37.5 |
| 10724/D03 | 0.1 | 2.5 | −15.2 | 18.2 |
| 10724/D04 | 0.5 | 5.4 | −1.3 | 70.5 |
| 10724/D05 | −1.6 | −8.4 | 35.6 | 36.1 |
| 10724/D06 | 12.4 | −12.4 | 40.4 | 23.0 |
| 10724/D07 | −2.6 | 25.6 | 7.0 | 38.1 |
| 10724/D09 | 0.9 | −15.3 | 18.9 | 16.1 |
| 10724/D10 | 3.7 | 12.7 | 38.3 | 59.6 |
| 10724/D11 | 14.9 | 12.9 | 29.3 | 20.3 |
| 10724/E02 | 17.7 | 39.8 | −54.2 | 55.4 |
| 10724/E03 | 10.6 | 33.1 | 14.7 | 85.8 |
| 10724/E04 | 55.2 | 8.9 | −32.6 | 93.3 |
| 10724/E05 | 13.3 | 0.5 | −7.6 | 70.3 |
| 10724/E06 | 8.3 | 1.6 | 6.3 | 25.8 |
| 10724/E07 | −3.6 | 9.4 | 0.1 | 46.8 |
| 10724/E09 | 14.3 | 6.3 | 21.0 | 27.0 |
| 10724/E10 | 7.3 | 41.4 | 34.9 | 84.0 |
| 10724/E11 | 5.1 | −26.8 | 5.0 | 39.3 |
| 10724/F02 | 9.7 | 27.4 | 0.8 | 73.0 |
| 10724/F03 | −12.5 | 9.8 | −45.8 | 44.2 |
| 10724/F04 | 10.2 | 2.9 | −52.1 | 81.9 |
| 10724/F05 | −7.2 | −16.4 | −0.6 | 67.0 |
| 10724/F06 | 13.8 | −3.5 | −5.5 | 51.2 |
| 10724/F07 | −6.0 | 8.9 | −6.2 | 47.3 |
| 10724/F09 | 17.1 | −14.6 | −17.3 | 20.5 |
| 10724/F10 | 2.7 | −10.4 | 1.5 | 55.6 |
| 10724/F11 | 4.5 | 3.8 | −6.9 | 49.3 |
| 10724/G02 | 15.1 | 42.5 | −7.6 | 44.9 |
| 10724/G03 | −8.4 | 7.8 | −2.7 | 36.7 |
| 10724/G04 | −7.9 | 12.9 | −12.4 | 71.0 |
| 10724/G05 | −0.1 | −20.8 | −10.3 | 61.0 |
| 10724/G06 | 0.1 | 3.2 | −6.9 | 20.3 |
| 10724/G07 | −1.9 | −11.7 | 41.6 | 2.3 |
| 10724/G09 | 9.1 | −21.7 | −18.0 | −2.8 |
| 10724/G10 | 7.0 | −10.6 | −15.9 | 62.8 |
| 10724/G11 | 6.8 | −29.5 | −29.1 | 11.2 |
| 10725/A02 | −2.0 | 3.9 | −14.2 | 46.6 |
| 10725/A03 | 3.6 | −38.2 | 5.9 | 68.0 |
| 10725/A04 | −8.6 | 26.2 | −3.2 | 55.3 |
| 10725/A05 | −13.9 | 7.9 | 13.1 | 47.5 |
| 10725/A06 | −7.3 | −9.5 | 40.9 | 71.7 |
| 10725/A07 | −12.3 | 18.2 | 17.9 | 59.3 |
| 10725/A08 | −2.9 | 10.9 | 14.1 | 45.3 |
| 10725/A09 | −13.9 | 4.9 | 29.4 | 44.3 |
| 10725/A10 | −3.2 | 14.0 | 33.7 | 43.2 |
| 10725/A11 | −21.9 | 14.6 | 18.9 | 49.1 |
| 10725/B02 | −2.8 | 2.5 | −7.5 | 66.9 |
| 10725/B03 | 4.9 | −15.3 | 7.8 | 70.8 |
| 10725/B04 | 1.1 | 76.9 | 9.3 | 90.4 |
| 10725/B05 | −61.0 | 20.4 | 44.7 | 68.3 |
| 10725/B06 | −0.5 | −13.7 | 31.3 | 53.3 |
| 10725/B07 | 24.6 | 45.8 | 100.8 | 74.0 |
| 10725/B08 | −24.1 | 41.8 | −29.4 | 66.7 |
| 10725/B09 | 0.4 | 72.3 | −43.8 | 65.7 |
| 10725/B10 | 5.1 | 53.3 | −26.0 | 69.9 |
| 10725/B11 | −42.3 | 43.0 | 66.3 | 76.3 |
| 10725/C02 | 7.0 | −43.4 | −5.1 | 6.3 |
| 10725/C03 | 2.0 | −12.7 | 19.3 | 72.9 |
| 10725/C04 | −27.3 | 31.8 | 25.1 | 75.9 |
| 10725/C05 | −37.0 | −21.9 | 28.9 | 31.7 |
| 10725/C06 | −9.3 | −11.5 | 46.6 | 54.7 |
| 10725/C07 | 65.0 | −16.5 | 107.0 | 38.8 |
| 10725/C08 | −8.7 | −11.9 | 101.7 | 28.0 |
| 10725/C09 | 11.2 | 23.6 | 34.7 | 24.1 |
| 10725/C10 | 8.7 | 5.3 | 38.5 | −0.6 |
| 10725/C11 | 104.5 | −22.1 | 80.7 | 48.4 |
| 10725/D02 | −3.6 | −23.9 | −8.4 | 14.0 |
| 10725/D03 | −11.3 | −2.5 | 5.4 | 72.9 |
| 10725/D04 | 3.6 | 4.3 | 12.2 | 55.1 |
| 10725/D05 | 2.3 | −19.7 | 10.7 | 24.5 |
| 10725/D06 | −0.5 | −26.4 | 21.7 | 24.7 |
| 10725/D07 | 2.6 | −25.8 | 18.4 | 37.0 |
| 10725/D08 | 1.8 | 20.0 | 38.5 | 39.2 |
| 10725/D09 | −0.9 | 4.3 | 35.6 | 28.0 |
| 10725/D10 | 9.0 | 11.7 | 43.8 | 27.8 |
| 10725/D11 | 13.6 | −12.5 | 23.2 | 100.5 |
| 10725/E02 | −5.6 | 4.3 | −8.9 | 40.2 |
| 10725/E03 | −0.8 | −10.3 | 10.7 | 60.9 |
| 10725/E04 | −38.8 | 31.2 | 3.1 | 59.0 |
| 10725/E05 | −0.2 | −5.5 | 27.5 | 28.2 |
| 10725/E06 | −1.8 | −17.7 | 39.0 | 36.7 |
| 10725/E07 | 9.7 | 12.5 | 28.9 | 45.3 |
| 10725/E08 | 12.1 | 14.2 | 48.6 | 39.7 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10725/E09 | 7.0 | 31.4 | 37.5 | 22.4 |
| 10725/E10 | 9.3 | 6.1 | 28.4 | -4.7 |
| 10725/E11 | 18.9 | -36.0 | 20.8 | 9.6 |
| 10725/F02 | 5.8 | -3.7 | -15.1 | 27.8 |
| 10725/F03 | 4.3 | -36.2 | -27.1 | 63.2 |
| 10725/F04 | -6.9 | -49.6 | -4.6 | 38.1 |
| 10725/F05 | -0.8 | -18.9 | -5.6 | 15.5 |
| 10725/F06 | -1.0 | -37.8 | 14.1 | 41.8 |
| 10725/F07 | 6.9 | 16.4 | 15.0 | 67.8 |
| 10725/F08 | 8.9 | 15.4 | 28.9 | 72.2 |
| 10725/F09 | 6.8 | 32.2 | 28.4 | 48.5 |
| 10725/F10 | 4.8 | 3.7 | 17.9 | 14.2 |
| 10725/F11 | 9.9 | 20.8 | 20.3 | 25.7 |
| 10725/G02 | -3.7 | -20.5 | -11.8 | 30.8 |
| 10725/G03 | -6.9 | -2.5 | -6.5 | 58.6 |
| 10725/G04 | 6.1 | -12.3 | -8.9 | 47.1 |
| 10725/G05 | -18.3 | 68.7 | 7.4 | 15.6 |
| 10725/G06 | 21.7 | -19.9 | 27.5 | 35.8 |
| 10725/G07 | 4.8 | -25.8 | 23.7 | 39.7 |
| 10725/G08 | -14.8 | -13.7 | 8.3 | 47.3 |
| 10725/G09 | 15.2 | 6.5 | 43.8 | 4.7 |
| 10725/G10 | 11.1 | 17.8 | 44.7 | 27.7 |
| 10725/G11 | -28.0 | -32.4 | 22.2 | 25.7 |
| 10726/A03 | -2.6 | -12.5 | 4.3 | 70.1 |
| 10726/A04 | 7.6 | 40.8 | 44.2 | 85.7 |
| 10726/A05 | -7.1 | -28.4 | 22.1 | 75.2 |
| 10726/A06 | -4.6 | 0.2 | 22.1 | 54.7 |
| 10726/A07 | -72.3 | 88.7 | -36.8 | 101.4 |
| 10726/A08 | -4.0 | -28.4 | 10.7 | 63.1 |
| 10726/A09 | -4.5 | -6.3 | 16.4 | 70.8 |
| 10726/A10 | 3.7 | 26.5 | 8.1 | 58.9 |
| 10726/A11 | 0.5 | 6.2 | 23.3 | 70.8 |
| 10726/B03 | 11.1 | 3.5 | 16.4 | 81.1 |
| 10726/B04 | 16.8 | 71.1 | 39.1 | 78.9 |
| 10726/B05 | 13.2 | 49.0 | 27.1 | 96.8 |
| 10726/B06 | 11.3 | 6.6 | 34.1 | 76.1 |
| 10726/B07 | -36.5 | 72.4 | -59.5 | 98.5 |
| 10726/B08 | 12.2 | 23.6 | 24.6 | 60.2 |
| 10726/B09 | 7.5 | 28.9 | 22.7 | 72.3 |
| 10726/B10 | 3.7 | 40.8 | 6.2 | 58.5 |
| 10726/B11 | 7.4 | 39.4 | 23.3 | 64.4 |
| 10726/C03 | 24.9 | 29.8 | 28.4 | 38.9 |
| 10726/C04 | 12.3 | 58.4 | 36.6 | 91.7 |
| 10726/C05 | 4.0 | 16.7 | 25.2 | 58.0 |
| 10726/C06 | 23.8 | -0.9 | 36.0 | 42.6 |
| 10726/C07 | -17.0 | 40.8 | -67.7 | 84.9 |
| 10726/C08 | 3.4 | 7.5 | 21.4 | 46.8 |
| 10726/C09 | 12.9 | -14.3 | 26.5 | 48.5 |
| 10726/C10 | 5.5 | 2.8 | 16.4 | 36.7 |
| 10726/C11 | -32.2 | 4.8 | 51.1 | 34.7 |
| 10726/D03 | 21.6 | -5.4 | 21.4 | 52.1 |
| 10726/D04 | 7.8 | -20.1 | 34.1 | 62.9 |
| 10726/D05 | 8.2 | -8.1 | 39.1 | 51.2 |
| 10726/D06 | 16.3 | -24.4 | 28.4 | 42.8 |
| 10726/D07 | -26.9 | 18.5 | -81.0 | 84.6 |
| 10726/D08 | 12.1 | -11.4 | 22.1 | 39.5 |
| 10726/D09 | 14.4 | -6.5 | 22.1 | 45.7 |
| 10726/D10 | 14.7 | -6.5 | 32.2 | 35.3 |
| 10726/D11 | 10.5 | -6.3 | 30.9 | 9.6 |
| 10726/E03 | -5.5 | -15.9 | 20.2 | 62.4 |
| 10726/E04 | 8.1 | 53.0 | 12.6 | 85.5 |
| 10726/E05 | 8.1 | 5.5 | 4.3 | 71.0 |
| 10726/E06 | 6.2 | -20.6 | 41.7 | -7.4 |
| 10726/E07 | -40.0 | 20.5 | -12.1 | 84.0 |
| 10726/E08 | 4.1 | -8.5 | 34.1 | 58.9 |
| 10726/E09 | 9.9 | 10.0 | 34.7 | 50.3 |
| 10726/E10 | 16.5 | -9.0 | 37.9 | 41.5 |
| 10726/E11 | 16.2 | -14.1 | 30.3 | 34.5 |
| 10726/F03 | 8.3 | -17.4 | 5.6 | 54.1 |
| 10726/F04 | 31.5 | 33.4 | 18.3 | 93.5 |
| 10726/F05 | 8.9 | -26.8 | -17.8 | 51.2 |
| 10726/F06 | 17.7 | -24.1 | 17.0 | 16.2 |
| 10726/F07 | 9.6 | 76.2 | -99.4 | 96.1 |
| 10726/F08 | 15.3 | -21.5 | 28.4 | 67.3 |
| 10726/F09 | 9.6 | -22.8 | -2.6 | 66.8 |
| 10726/F10 | 7.0 | -17.4 | 9.4 | 51.4 |
| 10726/F11 | 13.6 | -16.8 | 25.2 | 57.6 |
| 10726/G03 | 11.3 | -17.2 | 4.3 | 26.8 |
| 10726/G04 | 9.7 | 60.6 | 14.5 | 72.8 |
| 10726/G05 | 14.9 | 5.1 | 6.2 | 61.1 |
| 10726/G06 | 7.0 | -37.5 | -26.6 | 19.9 |
| 10726/G07 | -13.7 | 54.4 | -107.6 | 94.8 |
| 10726/G08 | 2.9 | -2.7 | 14.5 | 39.1 |
| 10726/G09 | 3.6 | 3.3 | 13.2 | 42.4 |
| 10726/G10 | 10.5 | 6.0 | -7.0 | 26.8 |
| 10726/G11 | 9.1 | 1.3 | -7.7 | 11.8 |
| 10727/A02 | -1.3 | 3.2 | -10.3 | 52.0 |
| 10727/A03 | 6.3 | -19.2 | -4.5 | 40.7 |
| 10727/A04 | -4.6 | 28.2 | 12.3 | 80.9 |
| 10727/A05 | 4.2 | -3.0 | 5.7 | 29.0 |
| 10727/A06 | -17.1 | -6.3 | 13.7 | 32.7 |
| 10727/A07 | -10.7 | -3.7 | 12.3 | 61.1 |
| 10727/A08 | -0.6 | 9.7 | 15.2 | 9.7 |
| 10727/A09 | -16.8 | 12.7 | 16.6 | 44.2 |
| 10727/A10 | -6.4 | 89.0 | 18.1 | 95.2 |
| 10727/A11 | 7.4 | 6.2 | 10.8 | 16.5 |
| 10727/B02 | 2.4 | -18.4 | -10.3 | 90.5 |
| 10727/B03 | -13.4 | -2.8 | -7.4 | 84.5 |
| 10727/B04 | 46.0 | 47.4 | 21.0 | 87.1 |
| 10727/B05 | 10.5 | 39.0 | 9.4 | 83.3 |
| 10727/B06 | -3.9 | 40.7 | 6.4 | 91.0 |
| 10727/B07 | 8.4 | 46.5 | 0.6 | 83.5 |
| 10727/B08 | 4.0 | 47.4 | 14.4 | 90.7 |
| 10727/B09 | 6.7 | 31.7 | 18.1 | 81.9 |
| 10727/B10 | 3.9 | 94.0 | 29.7 | 99.2 |
| 10727/B11 | 16.8 | 6.9 | 15.9 | 69.8 |
| 10727/C02 | -2.0 | -28.5 | -12.5 | 73.8 |
| 10727/C03 | -3.2 | 14.6 | 11.5 | 11.9 |
| 10727/C04 | 0.2 | 27.6 | 23.2 | 81.7 |
| 10727/C05 | 13.7 | 11.8 | 7.9 | 8.9 |
| 10727/C06 | 5.2 | 5.6 | 12.3 | 45.2 |
| 10727/C07 | 15.9 | 8.4 | 13.0 | 36.7 |
| 10727/C08 | 4.9 | 3.6 | 23.2 | 47.8 |
| 10727/C09 | -13.5 | 16.6 | 21.7 | 37.9 |
| 10727/C10 | -35.3 | 85.3 | 45.7 | 94.4 |
| 10727/C11 | -25.6 | -15.6 | 22.4 | 14.5 |
| 10727/D02 | 3.2 | 22.6 | 5.7 | 51.6 |
| 10727/D03 | 3.1 | 39.4 | -3.0 | 24.0 |
| 10727/D04 | 25.9 | 39.6 | 6.4 | 76.0 |
| 10727/D05 | 8.5 | 3.4 | -0.1 | 39.9 |
| 10727/D06 | 13.1 | 8.6 | 10.8 | 24.4 |
| 10727/D07 | 19.7 | 10.5 | -14.7 | 50.6 |
| 10727/D08 | 14.1 | -0.5 | 5.0 | 8.5 |
| 10727/D09 | 8.2 | 15.1 | 7.2 | 17.9 |
| 10727/D10 | 11.4 | 86.2 | 9.4 | 79.9 |
| 10727/D11 | 10.5 | -23.7 | 17.4 | 17.3 |
| 10727/E02 | 9.3 | 22.4 | -6.7 | 28.0 |
| 10727/E03 | 11.1 | 35.5 | 5.7 | 28.8 |
| 10727/E04 | 46.1 | 82.1 | -7.4 | 98.4 |
| 10727/E05 | 17.1 | 12.9 | -7.4 | 12.1 |
| 10727/E06 | 14.2 | -9.3 | 9.4 | -2.2 |
| 10727/E07 | 20.1 | 7.1 | 10.1 | 45.2 |
| 10727/E08 | 14.2 | 25.6 | 23.9 | 27.0 |
| 10727/E09 | 9.3 | 15.1 | 15.9 | 28.4 |
| 10727/E10 | 9.7 | 85.1 | 5.0 | 96.6 |
| 10727/E11 | 37.3 | -33.4 | 7.9 | -5.4 |
| 10727/F02 | 15.9 | -0.5 | 11.5 | 52.0 |
| 10727/F03 | 8.9 | 36.8 | -3.7 | 22.0 |
| 10727/F04 | 15.3 | 17.9 | -10.3 | 92.0 |
| 10727/F05 | 21.8 | -9.1 | -3.7 | 6.0 |
| 10727/F06 | 14.5 | 4.9 | 8.6 | 37.7 |
| 10727/F07 | 21.4 | -8.9 | 2.1 | 17.9 |
| 10727/F08 | 12.5 | -5.4 | 10.1 | 36.9 |
| 10727/F09 | -45.2 | -2.0 | 21.7 | 9.3 |
| 10727/F10 | 15.9 | 74.1 | 9.4 | 93.4 |
| 10727/F11 | 17.3 | -2.6 | 18.1 | -3.0 |
| 10727/G02 | 7.1 | 37.5 | -20.5 | 81.5 |
| 10727/G03 | -3.5 | 19.4 | -10.3 | 40.5 |
| 10727/G04 | 27.2 | 80.6 | -27.0 | 94.0 |
| 10727/G05 | 8.0 | 11.2 | -2.3 | 7.1 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10727/G06 | 2.9 | −12.1 | −12.5 | 31.1 |
| 10727/G07 | 7.2 | 5.4 | −24.1 | 29.6 |
| 10727/G08 | 15.7 | −19.6 | −7.4 | 21.8 |
| 10727/G09 | 5.7 | −9.7 | 10.8 | 18.8 |
| 10727/G10 | −5.6 | 85.1 | 10.8 | 99.2 |
| 10727/G11 | 6.9 | −3.5 | 15.9 | −0.8 |
| 10728/A02 | −12.3 | 9.2 | −7.9 | 25.6 |
| 10728/A03 | −7.3 | −25.8 | −7.9 | 29.2 |
| 10728/A04 | −3.5 | 28.0 | 15.6 | 28.5 |
| 10728/A05 | −10.8 | 17.7 | 4.5 | 31.8 |
| 10728/A06 | −10.4 | 17.2 | −3.1 | 19.7 |
| 10728/A07 | −21.6 | 59.6 | 31.1 | 28.5 |
| 10728/A08 | −1.4 | 24.1 | 0.5 | 40.2 |
| 10728/A09 | −5.5 | 19.3 | 10.3 | 53.1 |
| 10728/A10 | −16.3 | −3.4 | 1.8 | 77.2 |
| 10728/A11 | −2.3 | −0.6 | −9.3 | 58.8 |
| 10728/B02 | −11.1 | −10.5 | −0.4 | 61.2 |
| 10728/B03 | −1.3 | −36.6 | 10.3 | 74.4 |
| 10728/B04 | −6.0 | −2.0 | 9.8 | 67.2 |
| 10728/B05 | −12.3 | 26.9 | 9.4 | 60.4 |
| 10728/B06 | 4.7 | 38.1 | 7.6 | 56.0 |
| 10728/B07 | 31.4 | 11.1 | 20.9 | 82.2 |
| 10728/B08 | 14.8 | 34.7 | −6.6 | 77.0 |
| 10728/B09 | 1.7 | 31.7 | −0.4 | 81.7 |
| 10728/B10 | 3.9 | 16.8 | 2.7 | 79.3 |
| 10728/B11 | −1.0 | 48.2 | −12.4 | 80.3 |
| 10728/C02 | −32.1 | −35.4 | 42.3 | 15.5 |
| 10728/C03 | 10.5 | 9.7 | 24.9 | 16.9 |
| 10728/C04 | −0.0 | 16.1 | 27.2 | 33.6 |
| 10728/C05 | −21.7 | 16.1 | 23.2 | 33.7 |
| 10728/C06 | 8.4 | 4.2 | 2.7 | 22.9 |
| 10728/C07 | −7.2 | 8.3 | 8.9 | 46.3 |
| 10728/C08 | −2.2 | 17.5 | 9.4 | 25.5 |
| 10728/C09 | 14.5 | −6.8 | 8.1 | 31.6 |
| 10728/C10 | 6.1 | 4.4 | 11.2 | 28.7 |
| 10728/C11 | −10.1 | 21.8 | 8.5 | 45.2 |
| 10728/D02 | −0.3 | 9.9 | 9.8 | 21.4 |
| 10728/D03 | 10.2 | 10.8 | 32.0 | 13.5 |
| 10728/D04 | 6.8 | −1.1 | 26.7 | 23.1 |
| 10728/D05 | 4.9 | 12.7 | 7.2 | 29.5 |
| 10728/D06 | 10.4 | 5.8 | 5.8 | 23.2 |
| 10728/D07 | 8.1 | 2.4 | 2.3 | 21.8 |
| 10728/D08 | 13.5 | 6.9 | 2.7 | 34.7 |
| 10728/D09 | 10.5 | −2.9 | −3.9 | 27.6 |
| 10728/D10 | 17.9 | 18.6 | −3.9 | 30.5 |
| 10728/D11 | 15.9 | 22.1 | −10.2 | 52.5 |
| 10728/E02 | 5.4 | 7.4 | 15.2 | 5.4 |
| 10728/E03 | 13.2 | 9.5 | 12.0 | 11.9 |
| 10728/E04 | 5.5 | 10.1 | 23.2 | 25.6 |
| 10728/E05 | 17.4 | 7.4 | 5.8 | 53.4 |
| 10728/E06 | 6.6 | −4.7 | 12.0 | 26.4 |
| 10728/E07 | 9.6 | 21.8 | 28.0 | 79.8 |
| 10728/E08 | 15.2 | 5.1 | 29.4 | 46.3 |
| 10728/E09 | 9.0 | 0.1 | 22.3 | 40.0 |
| 10728/E10 | 24.7 | −20.8 | 13.8 | 57.2 |
| 10728/E11 | 16.3 | −5.9 | 8.9 | 53.1 |
| 10728/F02 | 2.9 | 4.4 | 7.2 | 25.6 |
| 10728/F03 | 6.8 | −0.2 | −9.3 | 18.7 |
| 10728/F04 | 14.2 | 5.1 | 7.2 | 47.9 |
| 10728/F05 | 6.0 | −5.9 | −0.4 | 53.3 |
| 10728/F06 | 14.4 | −1.5 | 1.8 | 28.2 |
| 10728/F07 | 2.4 | −2.2 | −0.8 | 62.6 |
| 10728/F08 | 14.5 | −13.5 | 8.9 | 62.8 |
| 10728/F09 | 5.9 | −13.0 | 1.4 | 23.4 |
| 10728/F10 | 18.0 | −6.3 | 4.9 | 48.7 |
| 10728/F11 | 16.7 | 0.8 | −12.4 | 72.5 |
| 10728/G02 | 2.3 | −10.2 | 0.9 | 7.1 |
| 10728/G03 | 14.3 | −2.0 | −8.4 | 8.8 |
| 10728/G04 | 21.8 | −8.2 | 0.5 | 20.9 |
| 10728/G05 | 9.4 | 7.2 | −4.4 | 63.1 |
| 10728/G06 | 13.5 | −14.1 | −13.3 | 25.3 |
| 10728/G07 | 22.6 | −12.3 | −17.3 | 42.4 |
| 10728/G08 | 21.4 | −5.7 | −11.9 | 42.3 |
| 10728/G09 | 6.8 | −8.0 | 6.3 | 22.2 |
| 10728/G10 | 10.4 | −12.5 | −0.8 | 27.9 |
| 10728/G11 | 3.2 | 16.1 | −12.8 | 71.4 |
| 10729/A02 | 15.5 | 10.0 | −25.7 | 28.1 |
| 10729/A03 | 4.7 | 27.0 | 1.9 | 27.5 |
| 10729/A04 | −4.0 | 58.8 | −16.6 | 45.4 |
| 10729/A05 | −17.7 | 23.4 | −6.8 | 38.8 |
| 10729/A06 | −10.9 | 36.5 | −8.6 | 29.8 |
| 10729/A07 | −10.0 | 49.0 | −36.7 | 51.1 |
| 10729/A08 | −13.3 | 37.8 | −23.4 | 48.1 |
| 10729/A09 | 0.4 | 25.7 | 11.0 | 80.3 |
| 10729/A10 | 0.7 | 28.7 | −12.8 | 34.8 |
| 10729/A11 | 4.9 | 15.5 | −11.7 | 49.9 |
| 10729/B02 | 13.8 | 34.9 | −10.2 | 77.2 |
| 10729/B03 | 11.2 | 38.2 | −9.4 | 57.3 |
| 10729/B04 | 0.1 | 63.7 | −22.7 | 43.8 |
| 10729/B05 | −5.2 | 50.6 | −25.7 | 51.0 |
| 10729/B06 | 2.0 | 56.9 | −19.2 | 61.1 |
| 10729/B07 | −13.4 | 69.0 | −33.2 | 58.2 |
| 10729/B08 | −14.7 | 53.2 | −13.6 | 66.0 |
| 10729/B09 | −16.0 | 51.6 | −6.4 | 47.2 |
| 10729/B10 | −0.7 | 68.3 | −13.9 | 32.6 |
| 10729/B11 | 7.8 | 18.8 | 4.2 | 36.6 |
| 10729/C02 | 6.0 | 16.9 | 9.1 | 18.2 |
| 10729/C03 | 11.0 | 25.7 | 13.7 | 13.5 |
| 10729/C04 | −2.5 | 35.9 | 4.2 | 20.7 |
| 10729/C05 | 5.8 | 21.8 | −5.6 | 15.5 |
| 10729/C06 | 3.8 | 38.2 | 3.1 | 15.2 |
| 10729/C07 | −22.4 | 60.8 | −1.8 | 58.4 |
| 10729/C08 | −20.3 | 25.4 | −13.6 | 55.7 |
| 10729/C09 | −26.4 | 33.2 | −34.8 | 60.4 |
| 10729/C10 | 2.5 | 45.7 | 3.5 | 15.8 |
| 10729/C11 | 10.4 | 35.9 | −17.4 | 41.3 |
| 10729/D02 | 12.2 | 5.7 | 15.6 | 31.7 |
| 10729/D03 | 15.3 | 15.5 | 14.1 | 22.6 |
| 10729/D04 | −5.7 | 18.8 | −12.8 | 33.1 |
| 10729/D05 | 2.2 | 22.1 | 2.3 | 28.1 |
| 10729/D06 | 0.2 | 45.7 | 2.7 | 30.2 |
| 10729/D07 | −15.3 | 21.4 | −20.0 | 25.5 |
| 10729/D08 | −26.2 | 10.3 | −21.1 | 27.6 |
| 10729/D09 | −9.6 | 22.1 | −12.1 | 34.8 |
| 10729/D10 | 4.1 | 11.3 | −11.3 | 36.1 |
| 10729/D11 | −2.0 | 19.2 | 0.1 | 18.8 |
| 10729/E02 | 26.6 | 8.0 | 28.4 | 11.7 |
| 10729/E03 | 6.9 | 20.1 | 29.2 | 27.5 |
| 10729/E04 | 9.7 | 19.5 | 26.5 | 9.8 |
| 10729/E05 | 46.8 | 12.6 | 29.9 | 13.4 |
| 10729/E06 | 12.1 | 43.7 | 24.7 | −0.7 |
| 10729/E07 | 4.1 | 26.7 | 29.6 | 21.6 |
| 10729/E08 | 10.9 | 40.1 | 11.0 | 73.7 |
| 10729/E09 | 6.9 | 29.6 | −11.7 | 85.0 |
| 10729/E10 | 5.7 | 50.3 | 11.8 | 7.5 |
| 10729/E11 | 70.9 | 25.7 | 22.4 | 50.8 |
| 10729/F02 | 18.9 | −14.0 | 20.1 | 19.5 |
| 10729/F03 | 30.0 | 10.6 | 33.7 | 27.8 |
| 10729/F04 | 16.0 | 13.3 | 25.4 | 44.9 |
| 10729/F05 | 15.4 | −4.8 | 31.5 | 33.8 |
| 10729/F06 | 36.4 | 15.9 | 29.6 | 44.3 |
| 10729/F07 | −5.8 | 6.7 | 6.1 | 37.3 |
| 10729/F08 | −3.4 | 10.3 | 0.8 | 44.6 |
| 10729/F09 | −2.6 | 13.3 | 8.8 | 38.2 |
| 10729/F10 | 20.0 | 58.5 | 15.2 | 39.0 |
| 10729/F11 | −1.5 | 25.4 | 7.2 | 15.2 |
| 10729/G02 | 18.8 | −4.8 | 16.7 | 31.3 |
| 10729/G03 | 10.4 | 14.6 | 13.7 | 20.1 |
| 10729/G04 | 12.2 | 52.9 | 1.6 | 18.2 |
| 10729/G05 | 8.7 | 4.4 | 9.9 | 22.6 |
| 10729/G06 | 10.9 | 15.2 | 11.8 | 26.0 |
| 10729/G07 | −2.5 | −0.8 | 14.4 | 38.2 |
| 10729/G08 | −1.0 | 6.0 | 0.8 | 39.9 |
| 10729/G09 | −3.3 | 20.8 | 1.9 | 49.6 |
| 10729/G10 | −9.1 | 60.1 | −13.2 | 26.7 |
| 10729/G11 | −0.5 | 23.4 | 3.8 | 15.4 |
| 10730/A02 | −3.7 | 27.5 | −23.1 | 39.5 |
| 10730/A03 | −3.2 | 34.4 | −11.2 | 62.3 |
| 10730/A04 | −9.9 | 37.2 | −5.1 | 70.6 |
| 10730/A05 | −10.8 | 18.6 | 2.8 | 42.7 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10730/A06 | −7.0 | 6.7 | 6.3 | 61.0 |
| 10730/A07 | −18.9 | 10.4 | −23.9 | 55.4 |
| 10730/A08 | −2.9 | 10.4 | −6.0 | 69.0 |
| 10730/A09 | 1.9 | 1.1 | −4.7 | 69.5 |
| 10730/A10 | 0.5 | 56.1 | 1.0 | 68.7 |
| 10730/A11 | 6.8 | 56.4 | −6.4 | 91.0 |
| 10730/B02 | 5.0 | 10.4 | 5.4 | 66.3 |
| 10730/B03 | −0.5 | 46.8 | 17.3 | 78.3 |
| 10730/B04 | 12.8 | 36.5 | 7.2 | 73.2 |
| 10730/B05 | −0.5 | 8.5 | −2.9 | 71.1 |
| 10730/B06 | 2.4 | 25.0 | 7.6 | 71.3 |
| 10730/B07 | 0.6 | 57.1 | 2.4 | 63.1 |
| 10730/B08 | 4.4 | 48.4 | 0.2 | 91.8 |
| 10730/B09 | 9.4 | 14.2 | 15.1 | 70.6 |
| 10730/B10 | 15.2 | 15.8 | 19.0 | 69.5 |
| 10730/B11 | 1.9 | 70.2 | −13.9 | 81.7 |
| 10730/C02 | 48.8 | 2.7 | 26.5 | 31.2 |
| 10730/C03 | 25.5 | −12.1 | 36.5 | 43.2 |
| 10730/C04 | 46.1 | 0.1 | 15.5 | 43.2 |
| 10730/C05 | 11.4 | −9.8 | 8.5 | 46.1 |
| 10730/C06 | 5.3 | 8.5 | 7.6 | 34.7 |
| 10730/C07 | 7.3 | 20.3 | 1.0 | 37.4 |
| 10730/C08 | −2.3 | 24.3 | 8.5 | 56.5 |
| 10730/C09 | 14.0 | 28.2 | 18.1 | 42.9 |
| 10730/C10 | 15.4 | 20.5 | 44.4 | 40.3 |
| 10730/C11 | −8.0 | 38.4 | 16.4 | 66.6 |
| 10730/D02 | 12.4 | 18.6 | 24.3 | 34.7 |
| 10730/D03 | 8.4 | 9.9 | 19.0 | 34.2 |
| 10730/D04 | 9.1 | 10.4 | 20.8 | 33.6 |
| 10730/D05 | 11.9 | 12.6 | −1.6 | 38.1 |
| 10730/D06 | 5.8 | 35.3 | −2.0 | 55.9 |
| 10730/D07 | 8.8 | 43.0 | 5.0 | 52.5 |
| 10730/D08 | 8.6 | 44.9 | 12.9 | −13.6 |
| 10730/D09 | 9.8 | 45.1 | −1.6 | 59.1 |
| 10730/D10 | −15.3 | 16.7 | −3.3 | 18.5 |
| 10730/D11 | 7.7 | 2.0 | −0.7 | 9.7 |
| 10730/E02 | 24.8 | 17.7 | 16.4 | 18.8 |
| 10730/E03 | 34.5 | 65.3 | 14.6 | 53.3 |
| 10730/E04 | 22.1 | 13.5 | 18.6 | 35.2 |
| 10730/E05 | 8.7 | 15.8 | 28.7 | 49.0 |
| 10730/E06 | 11.1 | 1.5 | 26.0 | 52.8 |
| 10730/E07 | 12.0 | 18.8 | 30.0 | 37.1 |
| 10730/E08 | 25.1 | 6.2 | 48.4 | 40.3 |
| 10730/E09 | 21.8 | 21.7 | 20.3 | 33.9 |
| 10730/E10 | 26.0 | 9.3 | 39.6 | 63.6 |
| 10730/E11 | 29.1 | 19.1 | 31.7 | 77.2 |
| 10730/F02 | 18.4 | 2.9 | 20.3 | −6.2 |
| 10730/F03 | 11.7 | 10.4 | 1.5 | −0.6 |
| 10730/F04 | 18.3 | −4.8 | 28.7 | 36.0 |
| 10730/F05 | 19.6 | −16.3 | 19.5 | 23.5 |
| 10730/F06 | 21.9 | −0.6 | 3.2 | 56.5 |
| 10730/F07 | 67.5 | 27.3 | −2.0 | 60.7 |
| 10730/F08 | 2.1 | 0.8 | −0.3 | 46.4 |
| 10730/F09 | 14.4 | 17.9 | 13.3 | 71.1 |
| 10730/F10 | 13.4 | 6.2 | 1.9 | 42.1 |
| 10730/F11 | −1.3 | −24.1 | 4.5 | 53.6 |
| 10730/G02 | 23.3 | 20.8 | 18.1 | 41.1 |
| 10730/G03 | 15.2 | −6.9 | 44.0 | 43.2 |
| 10730/G04 | 7.4 | −6.7 | 21.6 | 47.7 |
| 10730/G05 | 22.3 | −18.2 | 65.0 | 35.8 |
| 10730/G06 | 8.2 | −2.7 | 0.2 | 17.7 |
| 10730/G07 | 8.3 | 6.4 | 19.9 | 26.2 |
| 10730/G08 | 23.3 | 9.5 | 20.3 | 16.6 |
| 10730/G09 | 18.7 | −20.3 | 23.0 | 16.4 |
| 10730/G10 | 11.3 | 3.1 | 22.1 | 42.1 |
| 10730/G11 | −1.4 | 26.2 | −0.3 | 46.1 |
| 10731/A02 | 2.7 | 14.8 | −3.9 | 23.9 |
| 10731/A03 | 2.5 | 10.8 | 7.5 | 54.8 |
| 10731/A04 | 5.0 | 20.2 | 5.1 | 43.6 |
| 10731/A05 | −6.5 | 34.3 | 14.1 | 85.8 |
| 10731/A06 | −5.5 | 30.1 | 1.3 | 53.0 |
| 10731/A07 | −4.3 | 39.4 | 4.6 | 49.5 |
| 10731/A08 | −13.8 | 25.7 | −2.5 | 59.9 |
| 10731/A09 | −2.7 | 21.9 | −14.4 | 46.7 |
| 10731/A10 | −5.3 | 26.3 | −3.5 | 41.2 |
| 10731/A11 | 3.1 | 16.1 | −0.1 | 53.4 |
| 10731/B02 | 6.5 | 15.5 | 13.2 | 71.6 |
| 10731/B03 | 1.9 | 12.3 | 9.9 | 60.9 |
| 10731/B04 | 12.0 | 31.3 | 0.3 | 71.0 |
| 10731/B05 | 3.8 | 35.9 | 17.9 | 86.0 |
| 10731/B06 | 6.2 | 37.5 | 5.6 | 56.2 |
| 10731/B07 | 11.7 | 29.1 | 6.0 | 41.6 |
| 10731/B08 | 6.2 | 37.2 | −23.4 | 57.4 |
| 10731/B09 | −0.5 | 15.0 | 0.3 | 29.6 |
| 10731/B10 | 1.3 | 50.5 | 4.6 | 72.9 |
| 10731/B11 | 6.9 | 55.2 | −13.0 | 58.2 |
| 10731/C02 | 3.1 | −6.9 | −2.5 | 11.1 |
| 10731/C03 | 4.5 | 9.1 | 11.3 | 38.7 |
| 10731/C04 | 10.5 | 31.0 | 15.1 | 32.5 |
| 10731/C05 | 14.9 | 35.5 | 22.7 | 78.3 |
| 10731/C06 | 13.8 | 23.1 | 7.0 | 18.2 |
| 10731/C07 | 70.4 | 35.5 | 31.3 | −11.6 |
| 10731/C08 | 10.2 | 23.6 | −3.0 | 25.8 |
| 10731/C09 | 15.1 | 16.8 | −6.3 | 22.7 |
| 10731/C10 | 19.7 | 20.9 | 6.5 | 23.3 |
| 10731/C11 | 5.5 | 29.6 | −9.2 | 16.2 |
| 10731/D02 | −8.4 | 4.9 | 17.9 | 8.7 |
| 10731/D03 | 17.3 | 16.3 | 28.4 | 40.2 |
| 10731/D04 | 9.3 | 15.8 | 6.5 | 24.5 |
| 10731/D05 | 32.7 | 53.9 | 46.0 | 92.7 |
| 10731/D06 | 16.1 | 23.2 | 8.0 | 59.7 |
| 10731/D07 | 12.3 | 25.9 | 2.7 | 45.9 |
| 10731/D08 | 25.8 | 16.8 | −8.7 | 44.2 |
| 10731/D09 | 6.1 | 12.6 | −2.0 | 23.9 |
| 10731/D10 | 13.0 | 15.8 | 9.9 | 21.1 |
| 10731/D11 | 15.2 | 43.6 | 8.4 | 56.6 |
| 10731/E02 | 11.2 | 7.9 | 13.7 | 49.1 |
| 10731/E03 | −1.4 | 10.4 | 15.6 | 20.7 |
| 10731/E04 | 23.8 | 13.6 | 30.8 | 55.6 |
| 10731/E05 | 7.0 | 17.7 | 27.0 | 82.2 |
| 10731/E06 | 2.6 | 10.4 | −12.0 | 37.7 |
| 10731/E07 | 12.6 | 38.4 | 3.7 | 45.9 |
| 10731/E08 | 10.5 | 40.1 | 8.9 | 59.0 |
| 10731/E09 | 52.5 | 17.2 | 23.2 | 27.0 |
| 10731/E10 | 33.1 | 25.1 | 21.7 | 35.5 |
| 10731/E11 | 17.9 | 26.4 | 27.9 | 60.7 |
| 10731/F02 | 11.1 | 17.7 | 14.1 | 47.5 |
| 10731/F03 | 7.9 | 8.4 | 11.8 | 40.6 |
| 10731/F04 | 24.5 | 5.0 | 3.2 | 17.0 |
| 10731/F05 | 17.6 | 19.5 | 20.3 | 84.4 |
| 10731/F06 | 2.2 | 7.2 | −23.4 | 20.9 |
| 10731/F07 | 13.3 | 37.7 | 1.3 | 34.7 |
| 10731/F08 | 9.2 | 7.1 | 4.1 | 23.5 |
| 10731/F09 | 2.3 | −0.7 | 15.6 | 20.5 |
| 10731/F10 | 11.0 | 7.9 | 28.4 | 48.1 |
| 10731/F11 | 19.7 | 42.3 | 20.3 | 60.1 |
| 10731/G02 | 16.8 | 4.7 | −10.1 | 15.2 |
| 10731/G03 | 12.9 | 7.7 | 6.5 | 33.7 |
| 10731/G04 | 14.5 | 7.1 | 0.3 | 23.3 |
| 10731/G05 | 17.5 | 18.5 | 8.0 | 72.4 |
| 10731/G06 | 10.8 | 2.3 | −0.6 | 33.3 |
| 10731/G07 | 31.6 | 0.7 | 40.8 | 10.9 |
| 10731/G08 | 18.2 | 13.3 | −13.9 | 19.5 |
| 10731/G09 | 13.3 | 8.9 | −8.7 | 4.4 |
| 10731/G10 | −9.0 | 5.5 | 5.6 | 10.3 |
| 10731/G11 | 1.5 | 67.2 | 16.0 | 64.3 |
| 10732/A02 | −12.5 | 5.1 | 10.8 | 53.7 |
| 10732/A03 | −9.9 | 0.8 | −3.8 | 37.4 |
| 10732/A04 | −14.1 | −10.6 | −9.4 | 34.8 |
| 10732/A05 | −3.9 | 4.6 | −12.9 | 20.5 |
| 10732/A06 | −0.0 | −1.4 | 12.3 | 5.7 |
| 10732/A07 | −19.8 | −0.3 | 0.7 | 26.1 |
| 10732/A08 | −10.0 | 12.1 | 31.0 | 32.7 |
| 10732/A09 | −11.2 | 39.7 | 8.8 | 60.3 |
| 10732/A10 | 10.2 | 6.1 | 7.3 | 20.3 |
| 10732/A11 | −0.6 | 1.8 | 40.1 | 65.3 |
| 10732/B02 | 2.9 | −26.0 | 23.5 | 78.0 |
| 10732/B03 | 8.2 | −15.3 | 17.4 | 58.1 |
| 10732/B04 | −1.3 | −22.1 | 16.9 | 79.5 |
| 10732/B05 | 2.8 | 17.0 | 21.9 | 71.2 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10732/B06 | 8.1 | 12.8 | −12.4 | 74.3 |
| 10732/B07 | 1.6 | 15.8 | 21.4 | 75.1 |
| 10732/B08 | 8.0 | 7.8 | 16.9 | 64.4 |
| 10732/B09 | 14.0 | 2.0 | 18.4 | 69.2 |
| 10732/B10 | 12.1 | 0.6 | 0.7 | 51.5 |
| 10732/B11 | 9.0 | 9.3 | 70.9 | 73.7 |
| 10732/C02 | 11.9 | −6.5 | 7.3 | 40.1 |
| 10732/C03 | 14.7 | 1.4 | 7.3 | 14.0 |
| 10732/C04 | 12.8 | −14.7 | 3.8 | 30.6 |
| 10732/C05 | 11.2 | −22.8 | −17.0 | 18.5 |
| 10732/C06 | 11.8 | −43.2 | 5.3 | 21.6 |
| 10732/C07 | 15.4 | −28.6 | 4.3 | 26.5 |
| 10732/C08 | 7.6 | 1.6 | 17.9 | 54.5 |
| 10732/C09 | 8.0 | −3.9 | 15.4 | 37.9 |
| 10732/C10 | 15.1 | 1.2 | 5.8 | 43.0 |
| 10732/C11 | 18.2 | −5.0 | 16.4 | 31.9 |
| 10732/D02 | 9.2 | 8.7 | −24.0 | 50.2 |
| 10732/D03 | 22.5 | −18.7 | 26.0 | 24.9 |
| 10732/D04 | 24.6 | −11.4 | 50.7 | 40.7 |
| 10732/D05 | 15.7 | −36.7 | 4.3 | 30.2 |
| 10732/D06 | 16.3 | 3.6 | 16.4 | 24.3 |
| 10732/D07 | 14.7 | −19.1 | −3.8 | 43.2 |
| 10732/D08 | 33.3 | −20.6 | 30.5 | 49.4 |
| 10732/D09 | 15.2 | −9.9 | 15.9 | 40.3 |
| 10732/D10 | 25.5 | −16.6 | 24.5 | 33.1 |
| 10732/D11 | 18.8 | −13.4 | 18.9 | 48.6 |
| 10732/E02 | 13.1 | 0.8 | 4.8 | 33.3 |
| 10732/E03 | 16.7 | −1.6 | 48.7 | 3.9 |
| 10732/E04 | 15.8 | −10.6 | 29.5 | 8.2 |
| 10732/E05 | 18.7 | −17.0 | 41.1 | 2.2 |
| 10732/E06 | 2.8 | −11.0 | 16.9 | −2.1 |
| 10732/E07 | 21.3 | −8.5 | 42.2 | 15.2 |
| 10732/E08 | 13.6 | −21.7 | 32.6 | 29.4 |
| 10732/E09 | 15.3 | −7.2 | 46.7 | 18.1 |
| 10732/E10 | 16.7 | −3.3 | 35.6 | 1.6 |
| 10732/E11 | 16.2 | −32.2 | 47.7 | 41.4 |
| 10732/F02 | 7.0 | 23.1 | −9.4 | 55.6 |
| 10732/F03 | 31.9 | 54.1 | 51.8 | 68.6 |
| 10732/F04 | 16.2 | −0.1 | 23.5 | 57.2 |
| 10732/F05 | 37.3 | −30.7 | 12.8 | 58.9 |
| 10732/F06 | 11.6 | −8.0 | 0.2 | 45.7 |
| 10732/F07 | 31.0 | −12.5 | 38.6 | 65.5 |
| 10732/F08 | 12.6 | −11.9 | 14.9 | 76.6 |
| 10732/F09 | 25.6 | −13.4 | 25.5 | 79.7 |
| 10732/F10 | 14.1 | 0.8 | 15.9 | 65.1 |
| 10732/F11 | 21.9 | −21.5 | 77.5 | 75.2 |
| 10732/G02 | 8.1 | −0.7 | 10.3 | 39.5 |
| 10732/G03 | 0.8 | −20.0 | 36.1 | 38.1 |
| 10732/G04 | 12.6 | 8.0 | 25.0 | 24.9 |
| 10732/G05 | 17.2 | 3.8 | 15.4 | 15.2 |
| 10732/G06 | 26.5 | −12.1 | 0.2 | 16.2 |
| 10732/G07 | 4.6 | −21.9 | 21.4 | 23.9 |
| 10732/G08 | 10.0 | −20.4 | 37.6 | 44.7 |
| 10732/G09 | 16.9 | −34.8 | 9.8 | 33.9 |
| 10732/G10 | 14.0 | −38.2 | 20.4 | 45.7 |
| 10732/G11 | 10.9 | −33.7 | 38.6 | 63.0 |
| 10733/A02 | −5.2 | 25.9 | 11.5 | 74.6 |
| 10733/A03 | 45.0 | 33.6 | 23.2 | 24.9 |
| 10733/A04 | −11.2 | 32.8 | −14.1 | 24.0 |
| 10733/A05 | −23.3 | 55.2 | −4.0 | 18.2 |
| 10733/A06 | −16.6 | 45.1 | −24.3 | 33.7 |
| 10733/A07 | −27.4 | 28.5 | −12.9 | 27.2 |
| 10733/A08 | −17.1 | 19.5 | −10.1 | 27.2 |
| 10733/A09 | −11.9 | 25.9 | −7.6 | 22.1 |
| 10733/A10 | −9.3 | 14.2 | −13.3 | 21.1 |
| 10733/A11 | 15.0 | 23.0 | 4.2 | 43.5 |
| 10733/B02 | −7.4 | 31.6 | 14.7 | 74.6 |
| 10733/B03 | 3.1 | 14.4 | 35.8 | 62.2 |
| 10733/B04 | −3.3 | 28.5 | 24.9 | 56.3 |
| 10733/B05 | −1.1 | 26.7 | 27.3 | 61.3 |
| 10733/B06 | 4.6 | 43.6 | −9.2 | 71.4 |
| 10733/B07 | 1.2 | 32.7 | 4.2 | 73.5 |
| 10733/B08 | −16.0 | 32.5 | −15.7 | 65.5 |
| 10733/B09 | −2.6 | 21.1 | 7.0 | 64.5 |
| 10733/B10 | 5.7 | 11.8 | −59.6 | 65.1 |
| 10733/B11 | 22.5 | 12.5 | 23.7 | 36.6 |
| 10733/C02 | 5.8 | 31.6 | 15.1 | 71.8 |
| 10733/C03 | 17.0 | 14.4 | 28.1 | 29.3 |
| 10733/C04 | 8.4 | 29.0 | 19.2 | 18.4 |
| 10733/C05 | 11.5 | 17.2 | 11.1 | 23.2 |
| 10733/C06 | 4.7 | 22.7 | 20.0 | 4.1 |
| 10733/C07 | 1.2 | 16.7 | 4.6 | 10.2 |
| 10733/C08 | −28.5 | 65.8 | −3.6 | 85.7 |
| 10733/C09 | −18.0 | 46.0 | 91.9 | 16.3 |
| 10733/C10 | −7.6 | 36.0 | −6.4 | 20.5 |
| 10733/C11 | 42.8 | 15.8 | 62.2 | 35.1 |
| 10733/D02 | 3.1 | 12.5 | 17.6 | 63.4 |
| 10733/D03 | 33.2 | 11.2 | 40.7 | 32.8 |
| 10733/D04 | 15.5 | 19.9 | 26.5 | 37.7 |
| 10733/D05 | 16.5 | 10.6 | 16.8 | 25.1 |
| 10733/D06 | 17.9 | 30.8 | 1.3 | −19.4 |
| 10733/D07 | −1.4 | 37.4 | 0.9 | −6.8 |
| 10733/D08 | −8.3 | 38.3 | 42.3 | 80.0 |
| 10733/D09 | 9.8 | 48.3 | 33.8 | 38.7 |
| 10733/D10 | 2.9 | 46.8 | −10.1 | 22.8 |
| 10733/D11 | 1.0 | 33.7 | −4.0 | 31.6 |
| 10733/E02 | 0.8 | −1.3 | 20.8 | 60.5 |
| 10733/E03 | 42.6 | 10.7 | 43.1 | 26.8 |
| 10733/E04 | 2.1 | 45.4 | −13.7 | 17.5 |
| 10733/E05 | 10.6 | 58.3 | −33.2 | 2.9 |
| 10733/E06 | 13.5 | 37.3 | 22.4 | 10.4 |
| 10733/E07 | 13.2 | 19.9 | 29.3 | −10.1 |
| 10733/E08 | −5.1 | 54.2 | 75.2 | 81.1 |
| 10733/E09 | 13.4 | 72.4 | 35.8 | 62.6 |
| 10733/E10 | 5.5 | 31.3 | 10.3 | 52.8 |
| 10733/E11 | 5.5 | 31.6 | 15.9 | 71.8 |
| 10733/F02 | −15.7 | 11.3 | 3.8 | 71.6 |
| 10733/F03 | 17.5 | −3.6 | 24.5 | 24.2 |
| 10733/F04 | 21.4 | 76.3 | −28.7 | 65.1 |
| 10733/F05 | 26.2 | 84.6 | −25.1 | 65.1 |
| 10733/F06 | 19.3 | 17.8 | −4.8 | 20.9 |
| 10733/F07 | 16.4 | 19.2 | 1.7 | −16.4 |
| 10733/F08 | −13.2 | 17.2 | −32.4 | 66.6 |
| 10733/F09 | −2.1 | 30.1 | −0.3 | 52.8 |
| 10733/F10 | 8.5 | 21.9 | −5.6 | 24.4 |
| 10733/F11 | 4.1 | 0.6 | −17.8 | 44.4 |
| 10733/G02 | 8.3 | −6.2 | −7.6 | 64.5 |
| 10733/G03 | 24.7 | 0.7 | 12.7 | 30.5 |
| 10733/G04 | 11.5 | 10.6 | 11.9 | 20.3 |
| 10733/G05 | 19.2 | 1.5 | −1.1 | 1.8 |
| 10733/G06 | 37.0 | 5.2 | 0.1 | 0.8 |
| 10733/G07 | 19.5 | 18.1 | −6.8 | 8.5 |
| 10733/G08 | 2.5 | 44.2 | 68.7 | 79.0 |
| 10733/G09 | 77.8 | 38.7 | −17.0 | 41.4 |
| 10733/G10 | 12.7 | 18.2 | −58.0 | 41.9 |
| 10733/G11 | 3.3 | −1.0 | −4.4 | 32.6 |
| 10734/A02 | 4.1 | 0.0 | −3.8 | 51.1 |
| 10734/A03 | 10.1 | 18.5 | 22.3 | 87.8 |
| 10734/A04 | 0.6 | 11.4 | 11.7 | 68.0 |
| 10734/A05 | 9.1 | 22.6 | 2.9 | 69.9 |
| 10734/A06 | −6.4 | −6.4 | −9.9 | 46.9 |
| 10734/A07 | −9.4 | 15.2 | 21.9 | 89.3 |
| 10734/A08 | 0.1 | 6.8 | 9.1 | 71.5 |
| 10734/A09 | −7.9 | 27.3 | −9.5 | 88.4 |
| 10734/A10 | 4.4 | 27.8 | 26.3 | 55.4 |
| 10734/A11 | 6.3 | 12.5 | 5.5 | 51.9 |
| 10734/B02 | 8.5 | −8.9 | −2.9 | 61.9 |
| 10734/B03 | 21.7 | 45.1 | 13.0 | 90.1 |
| 10734/B04 | 2.8 | 38.7 | 14.4 | 88.4 |
| 10734/B05 | −2.3 | 17.8 | 56.3 | 67.8 |
| 10734/B06 | −0.9 | 54.0 | 0.2 | 91.2 |
| 10734/B07 | 9.1 | 65.5 | 18.8 | 93.2 |
| 10734/B08 | −0.5 | 19.3 | −2.4 | 56.1 |
| 10734/B09 | −32.3 | 34.9 | 12.6 | 94.3 |
| 10734/B10 | 15.7 | 60.7 | 7.7 | 82.6 |
| 10734/B11 | 12.6 | 50.9 | −5.5 | 83.6 |
| 10734/C02 | −3.9 | −6.7 | 36.0 | 78.6 |
| 10734/C03 | −5.6 | 48.6 | 24.5 | 88.2 |
| 10734/C04 | −37.6 | 38.1 | 24.5 | 90.7 |
| 10734/C05 | −10.3 | 9.3 | 3.8 | 52.7 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10734/C06 | −1.7 | 18.4 | −0.2 | 48.3 |
| 10734/C07 | −2.7 | 41.0 | 32.0 | 96.8 |
| 10734/C08 | −34.2 | 35.1 | 5.5 | 93.2 |
| 10734/C09 | −13.3 | 36.2 | 11.3 | 88.6 |
| 10734/C10 | 10.1 | 24.4 | 17.4 | 11.6 |
| 10734/C11 | 6.3 | 18.0 | 9.1 | 23.9 |
| 10734/D02 | −11.5 | 5.2 | 6.4 | 46.0 |
| 10734/D03 | 17.4 | 19.6 | 24.1 | 78.6 |
| 10734/D04 | 6.1 | −10.7 | 13.5 | 46.9 |
| 10734/D05 | 2.4 | −9.6 | 8.2 | 55.0 |
| 10734/D06 | 0.0 | 1.3 | −9.1 | 30.6 |
| 10734/D07 | 14.7 | 51.1 | 28.1 | 92.0 |
| 10734/D08 | 2.5 | −13.7 | 2.0 | 49.8 |
| 10734/D09 | −11.6 | 21.0 | 42.2 | 88.0 |
| 10734/D10 | 11.1 | −4.4 | 9.9 | 20.6 |
| 10734/D11 | 9.8 | 14.6 | 17.0 | 33.9 |
| 10734/E02 | 7.9 | −10.8 | 50.1 | 66.9 |
| 10734/E03 | 26.9 | 55.0 | 27.2 | 99.3 |
| 10734/E04 | 10.7 | −7.8 | 26.7 | 88.9 |
| 10734/E05 | 10.6 | 7.9 | 17.9 | 63.6 |
| 10734/E06 | 28.4 | 6.3 | 13.5 | 50.6 |
| 10734/E07 | 27.9 | 82.4 | 8.2 | 100.8 |
| 10734/E08 | 26.6 | 24.2 | 13.0 | 89.1 |
| 10734/E09 | 8.0 | 73.0 | 1.1 | 96.2 |
| 10734/E10 | 18.5 | −5.0 | 29.8 | 27.9 |
| 10734/E11 | 19.2 | −8.0 | 16.1 | 67.1 |
| 10734/F02 | 6.2 | 0.7 | 10.4 | 55.0 |
| 10734/F03 | 4.2 | 24.8 | −24.1 | 86.8 |
| 10734/F04 | −2.6 | 3.9 | 25.0 | 76.5 |
| 10734/F05 | 9.8 | −15.6 | −1.1 | 73.8 |
| 10734/F06 | 11.0 | −17.1 | −21.4 | 64.2 |
| 10734/F07 | 6.6 | 33.7 | −5.1 | 95.7 |
| 10734/F08 | 4.8 | −23.6 | −6.0 | 66.3 |
| 10734/F09 | −3.7 | 3.1 | −17.4 | 93.9 |
| 10734/F10 | 14.8 | −8.3 | 25.8 | 44.8 |
| 10734/F11 | 13.3 | −15.6 | 16.1 | 47.3 |
| 10734/G02 | 1.5 | 3.4 | 14.8 | 63.6 |
| 10734/G03 | 18.7 | 82.8 | −3.8 | 93.4 |
| 10734/G04 | −1.1 | 62.9 | 16.1 | 72.1 |
| 10734/G05 | 7.4 | −0.3 | 2.9 | 57.7 |
| 10734/G06 | 16.5 | 12.5 | −18.8 | 43.1 |
| 10734/G07 | 21.9 | 51.1 | −25.0 | 96.6 |
| 10734/G08 | 11.6 | 33.7 | 0.2 | 82.2 |
| 10734/G09 | 8.5 | 21.4 | −7.7 | 84.7 |
| 10734/G10 | 10.8 | 3.8 | 9.9 | 19.3 |
| 10734/G11 | 8.7 | 4.1 | −25.4 | 20.2 |

What is claimed is:

1. An indolinone compound of formula I or II,

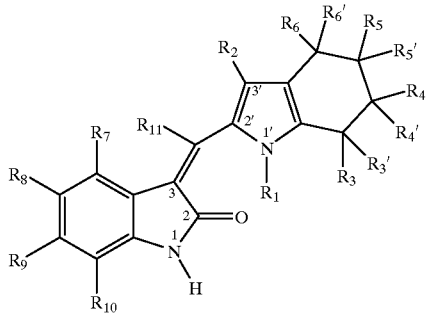

I

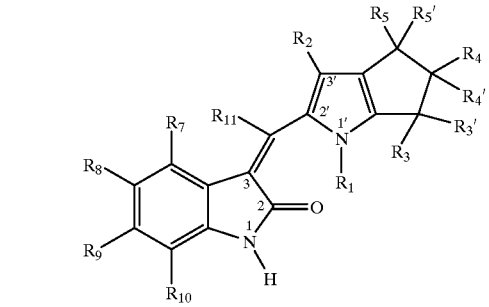

II or the pharmaceutically acceptable salt thereof where
(a) $R_1$ is selected from the group consisting of,
(i) alkyl that is optionally substituted with a monocyclic or bicyclic five, six, eight, nine, or ten membered heterocyclic ring, where the ring is optionally substituted with one or more halogen, or trihalomethyl substituents;
(ii) five, six, eight, nine, or ten membered monocyclic or bicyclic heterocyclic ring, where the ring is optionally substituted with one or more halogen or trihalomethyl substituents;
(iii) ketone of formula —CO—$R_{12}$, where $R_{12}$ is selected from the group consisting of hydrogen, alkyl, or a five or six membered heterocyclic ring;
(iv) a carboxylic acid of formula -$(R_{13})_n$—COOH or ester of formula -$(R_{14})_m$—COO—$R_{15}$, where $R_{13}$, $R_{14}$, and $R_{15}$ and are independently selected from the group consisting of alkyl or a five or six membered heterocyclic ring and n and m are independently 0 or 1;
(v) a sulfone of formula —(SO$_2$)—$R_{16}$, where $R_{16}$ is selected from the group consisting of alkyl or a five or six membered heterocyclic ring, where the ring is optionally substituted with an alkyl moiety;
(vi) -$(R_{17})_n$-(indole-1-yl) or -$(R_{18})_m$—CHOH—$(R_{19})_p$-(indole-1-yl), where the indole moiety is optionally substituted with an aldehyde and $R_{17}$, $R_{18}$, and $R_{19}$ are alkyl and n, m, and p are independently 0 or 1;
(vii) taken together with a 2' substituent of the indole ring forms a tricyclic moiety, where each ring in the tricyclic moiety is a five or six membered heterocyclic ring; and
(viii) hydrogen;
(b) $R_2$, $R_3$, $R_{3'}$, $R_4$, $R_{4'}$, $R_5$, $R_{5'}$, $R_6$, and $R_{6'}$ are selected from the group consisting of,
(i) hydrogen;
(ii) alkyl that is optionally substituted with a monocyclic or bicyclic five, six, eight, nine, or ten membered heterocyclic ring, where the ring is optionally substituted with one or more halogen, or trihalomethyl substituents;
(iii) five, six, eight, nine, or ten membered monocyclic or bicyclic heterocyclic ring, where the ring is optionally substituted with one or more halogen or trihalomethyl substituents;
(iv) ketone of formula —CO—$R_{20}$, where $R_{20}$ is selected from the group consisting of hydrogen, alkyl, or a five or six membered heterocyclic ring;
(v) a carboxylic acid of formula -$(R_{21})_n$—COOH or ester of formula -$(R_{22})_m$—COO—$R_{23}$, where $R_{21}$, $R_{22}$, and $R_{23}$ and are independently selected from the group consisting of alkyl or a five or six membered heterocyclic ring and m and n are independently 0 or 1;

(vi) halogen;
(vii) an alcohol of formula $(R_{24})_m$—OH or an ether of formula -$(R_{24})_n$—O—$R_{25}$, where $R_{24}$ and $R_{25}$ are independently selected from the group consisting of alkyl and a five or six membered heterocyclic ring and m and n are independently 0 or 1;
(viii) —$NR_{26}R_{27}$, where $R_{26}$ and $R_{27}$ are independently selected from the group consisting of hydrogen, oxygen, alkyl, and a five or six membered heterocyclic ring;
(ix) —$NHCOR_{28}$, where $R_{28}$ is selected from the group consisting of hydroxyl, alkyl, and a five or six membered heterocyclic ring, where the ring is optionally substituted with alkyl, halogen, carboxylate, or ester;
(x) —$SO_2NR_{29}R_{30}$, where $R_{29}$ and $R_{30}$ are selected from the group consisting of hydrogen, oxygen, alkyl, and a five or six membered heterocyclic ring;
(xi) any two of $R_3$, $R_{3'}$, $R_4$, $R_{4'}$, $R_5$, $R_{5'}$, $R_6$, or $R_{6'}$ taken together form a bicyclic or tricyclic heterocyclic moiety fused to the six membered ring of the indole, where each ring in the multicyclic moiety is a five or six membered heterocyclic ring;

(c) $R_7$, $R_8$, $R_9$, and $R_{10}$ are independently selected from the group consisting of,
(i) hydrogen;
(ii) alkyl that is optionally substituted with a monocyclic or bicyclic five, six, eight, nine, or ten membered heterocyclic ring, where the ring is optionally substituted with one or more halogen, or trihalomethyl substituents;
(iii) five, six, eight, nine, or ten membered monocyclic or bicyclic heterocyclic ring, where the ring is optionally substituted with one or more halogen or trihalomethyl substituents;
(iv) ketone of formula —CO—$R_{31}$, where $R_{31}$ is selected from the group consisting of hydrogen, alkyl, or a five or six membered heterocyclic ring;
(v) a carboxylic acid of formula -$(R_{32})_n$—COOH or ester of formula -$(R_{33})_m$—COO—$R_{34}$, where $R_{32}$, $R_{33}$, and $R_{34}$ and are independently selected from the group consisting of alkyl or a five or six membered heterocyclic ring and n and m are independently 0 or 1;
(vi) halogen;
(vii) an alcohol of formula $(R_{35})_m$—OH or an ether of formula -$(R_{35})_n$—O—$R_{36}$, where $R_{35}$ and $R_{36}$ are independently chosen from the group consisting of alkyl or a five or six membered heterocyclic ring and m and n are independently 0 or 1;
(viii) —$NR_{37}R_{38}$, where $R_{37}$ and $R_{38}$ are independently selected from the group consisting of hydrogen, oxygen, alkyl, and a five or six membered heterocyclic ring;
(ix) —$NHCOR_{39}$, where $R_{39}$ is selected from the group consisting of hydroxyl, alkyl, and a five or six membered heterocyclic ring, where the ring is optionally substituted with alkyl, halogen, carboxylate, or ester;
(x) —$SO_2NR_{40}R_{41}$, where $R_{40}$ and $R_{41}$ are selected from the group consisting of hydrogen, oxygen, alkyl, and a five or six membered heterocyclic ring;
(xi) any two of $R_7$, $R_8$, $R_9$, or $R_{10}$ taken together form a bicyclic or tricyclic heterocyclic moiety fused to the six membered ring of the indole, where each ring in the multicyclic moiety is a five or six membered heterocyclic ring; and (d) $R_{11}$ is hydrogen or alkyl or a pharmaceutically acceptable salt thereof.

2. The compound or salt of claim 1, wherein $R_3$, $R_{3'}$, $R_4$, $R_{4'}$, $R_5$, $R_{5'}$, $R_6$, and $R_{6'}$ are hydrogen.

3. The compound or salt of claim 1, wherein $R_1$ and $R_{11}$ are hydrogen.

4. The compound or salt of claim 1, wherein $R_7$, $R_8$, $R_9$, and $R_{10}$ are independently selected from the group consisting of lower alkyl, halogen and $NH_2$.

5. The compound or salt of formula I of claim 1, wherein $R_1$, $R_2$, $R_3$, $R_{3'}$, $R_4$, $R_{4'}$, $R_5$, $R_{5'}$, $R_6$, $R_{6'}$, $R_7$, $R_8$, $R_9$, $R_{10}$, and $R_{11}$ are hydrogen.

6. The compound or salt of formula I of claim 1, where $R_8$ is bromine, chlorine, or $NH_2$ and $R_1$, $R_2$, $R_3$, $R_{3'}$, $R_4$, $R_{4'}$, $R_5$, $R_{5'}$, $R_6$, $R_{6'}$, $R_7$, $R_9$, $R_{10}$, and $R_{11}$ are hydrogen.

7. The compound or salt of formula I of claim 1, where $R_7$ is methyl and $R_1$, $R_2$, $R_3$, $R_{3'}$, $R_4$, $R_{4'}$, $R_5$, $R_{5'}$, $R_6$, $R_{6'}$, $R_7$, $R_9$, $R_{10}$, and $R_{11}$ are hydrogen.

8. A pharmaceutical composition comprising a compound of any one of claims 1–7 and a physiologically acceptable carrier or diluent.

9. A method of treating an abnormal condition in an organism, where the abnormal condition is associated with an aberration in a signal transduction pathway characterized by an interaction between a protein kinase and a natural binding partner, where the method comprises the following steps:
(a) administering a compound of any one of claims 1–7 to an organism; and
(b) promoting or disrupting the abnormal interaction.

10. The method of claim 9, where the organism is a mammal.

11. The method of claim 9, where the protein kinase is a FLK protein kinase.

12. The method of claim 9, where the protein kinase is a platelet derived growth factor receptor protein kinase.

13. A method of modulating the catalytic activity of a protein kinase with an indolinone compound or salt of claim 1.

14. The method of claim 13, where the protein kinase is a FLK protein kinase.

15. The method of claim 13, where the protein kinase is a platelet derived growth factor receptor protein kinase.

* * * * *